United States Patent
Naji et al.

(10) Patent No.: US 12,110,515 B2
(45) Date of Patent: Oct. 8, 2024

(54) MODIFIED THERMOCOCCUS POLYMERASES

(71) Applicant: Singular Genomics Systems, Inc., San Diego, CA (US)

(72) Inventors: Souad Naji, La Jolla, CA (US); Carl W. Fuller, Berkley Heights, NJ (US); Eli N. Glezer, Del Mar, CA (US); Andrew Spaventa, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 36 days.

(21) Appl. No.: 18/048,388

(22) Filed: Oct. 20, 2022

(65) Prior Publication Data

US 2023/0227798 A1    Jul. 20, 2023

Related U.S. Application Data

(63) Continuation of application No. 17/017,578, filed on Sep. 10, 2020, now Pat. No. 11,512,295.

(60) Provisional application No. 62/899,644, filed on Sep. 12, 2019.

(51) Int. Cl.
  *C12N 9/12* (2006.01)
  *C12N 15/10* (2006.01)
  *C12Q 1/6874* (2018.01)

(52) U.S. Cl.
  CPC ......... *C12N 9/1252* (2013.01); *C12N 15/102* (2013.01); *C12Q 1/6874* (2013.01); *C12Y 207/07007* (2013.01)

(58) Field of Classification Search
  None
  See application file for complete search history.

(56) References Cited

U.S. PATENT DOCUMENTS

| | | |
|---|---|---|
| 5,034,506 A | 7/1991 | Summerton et al. |
| 5,235,033 A | 8/1993 | Summerton et al. |
| 5,756,334 A | 5/1998 | Perler et al. |
| 5,763,594 A | 6/1998 | Hiatt et al. |
| 5,808,045 A | 9/1998 | Hiatt et al. |
| 5,872,244 A | 2/1999 | Hiatt et al. |
| 6,232,465 B1 | 5/2001 | Hiatt et al. |
| 6,255,475 B1 | 7/2001 | Kwiatkowski |
| 6,664,079 B2 | 12/2003 | Ju et al. |
| 7,057,026 B2 | 6/2006 | Barnes et al. |
| 7,541,170 B2 | 6/2009 | Wang et al. |
| 7,541,444 B2 | 6/2009 | Milton et al. |
| 8,114,973 B2 | 2/2012 | Siddiqi et al. |
| 8,460,910 B2 | 6/2013 | Smith et al. |
| 8,852,910 B2 | 10/2014 | Smith et al. |
| 9,085,762 B2 | 7/2015 | Hogrefe et al. |
| 9,447,389 B2 | 9/2016 | Smith et al. |
| 9,765,309 B2 | 9/2017 | Chen et al. |
| 10,017,750 B2 | 7/2018 | Smith et al. |
| 10,041,115 B2 | 8/2018 | Stupi et al. |
| 10,421,996 B2 | 9/2019 | Bomati et al. |
| 10,738,072 B1 | 8/2020 | Graham et al. |
| 11,034,942 B1 | 6/2021 | Naji et al. |
| 11,136,565 B2 | 10/2021 | Naji et al. |
| 11,512,295 B2 | 11/2022 | Naji et al. |
| 11,845,923 B2 | 12/2023 | Naji et al. |
| 11,851,687 B2 | 12/2023 | Naji et al. |
| 11,884,943 B2 | 1/2024 | Naji et al. |
| 11,891,633 B2 | 2/2024 | Naji et al. |
| 2003/0157483 A1 | 8/2003 | Sorge et al. |
| 2004/0191825 A1 | 9/2004 | Wang et al. |
| 2006/0199214 A1 | 9/2006 | Jack et al. |
| 2006/0240439 A1 | 10/2006 | Smith et al. |
| 2011/0045489 A1 | 2/2011 | Gardner et al. |
| 2015/0140561 A1 | 5/2015 | Bergmann et al. |
| 2016/0090579 A1 | 3/2016 | Bomati et al. |
| 2017/0130051 A1 | 5/2017 | Marma et al. |
| 2017/0298327 A1 | 10/2017 | Bomati et al. |
| 2018/0274024 A1 | 9/2018 | Ju et al. |
| 2019/0077726 A1 | 3/2019 | Graham et al. |
| 2020/0080065 A1 | 3/2020 | Fuller et al. |
| 2021/0079364 A1 | 3/2021 | Naji et al. |
| 2021/0284975 A1 | 9/2021 | Naji et al. |
| 2022/0119779 A1 | 4/2022 | Naji et al. |
| 2022/0119780 A1 | 4/2022 | Naji et al. |
| 2022/0282230 A1 | 9/2022 | Naji et al. |
| 2023/0011240 A1 | 1/2023 | Fuller et al. |
| 2024/0101979 A1 | 3/2024 | Naji et al. |

FOREIGN PATENT DOCUMENTS

| | | |
|---|---|---|
| WO | WO-1996/07669 A1 | 3/1996 |
| WO | WO-2004/018497 A2 | 3/2004 |
| WO | WO-2004/018497 A3 | 3/2004 |
| WO | WO-2005/024010 A1 | 3/2005 |
| WO | WO-2008/083393 A2 | 7/2008 |

(Continued)

OTHER PUBLICATIONS

Guo et al. (PNAS, vol. 101, No. 25, pp. 9205-9210, Jun. 2004).*
Ngo et al. in The Protein Folding Problem and Tertiary Structure Prediction, 1994, Merz et al. (ed.), Birkhauser, Boston, MA, pp. 433 and 492-495).*
Arezi, B. et al. (Sep. 27, 2002). "Efficient and high fidelity incorporation of dye-terminators by a novel archaeal DNA polymerase mutant," *J Mol Biol* 322(4): 719-729.

(Continued)

*Primary Examiner* — Richard G Hutson
(74) *Attorney, Agent, or Firm* — Mintz, Levin, Cohn, Ferris, Glovesky, Popeo, P.C.; Zachary L. Terranova

(57) ABSTRACT

Provided herein are modified Archaeal family B polymerases derived from the Archaeal microorganism *Thermococcus* sp. EP1 that exhibit improved incorporation of nucleotide analogues utilized in DNA sequences.

18 Claims, 10 Drawing Sheets

Specification includes a Sequence Listing.

(56) References Cited

FOREIGN PATENT DOCUMENTS

| WO | WO-2008/083393 A3 | 7/2008 |
|---|---|---|
| WO | WO-2014/142921 A1 | 9/2014 |
| WO | WO-2015/200693 A1 | 12/2015 |
| WO | WO-2017/058953 A1 | 4/2017 |
| WO | WO-2017/205336 A1 | 11/2017 |
| WO | WO-2018/148723 A1 | 8/2018 |
| WO | WO-2019/164977 A1 | 8/2019 |
| WO | WO-2020/056044 A1 | 3/2020 |
| WO | WO-2021/173711 A2 | 9/2021 |
| WO | WO-2021/173711 A3 | 9/2021 |

OTHER PUBLICATIONS

Bentley, D.R. et al. (Nov. 6, 2008). "Accurate whole human genome sequencing using reversible terminator chemistry," *Nature* 456(7218): 53-59, 55 pages of Supplementary material.

Bergen, K. et al. (Jun. 17, 2013, e-published Jun. 3, 2013). "Structures of KOD and 9° N DNA polymerases complexed with primer template duplex," *ChemBioChem* 14(9): 1058-1062.

Canard, B. et al. (Oct. 11, 1994). "DNA polymerase fluorescent substrates with reversible 3'-tags," *Gene* 148(1): 1-6.

Canard, B. et al. (Nov. 21, 1995). "Catalytic editing properties of DNA polymerases," *PNAS USA* 92(24): 10859-10863.

Chen, F. et al. (Feb. 2, 2010, e-published Jan. 11, 2010). "Reconstructed evolutionary adaptive paths give polymerases accepting reversible terminators for sequencing and SNP detection," *PNAS USA* 107(5): 1948-1953.

Cohen, G.N. et al. (Mar. 5, 2003). "An integrated analysis of the genome of the hyperthermophilic archaeon Pyrococcus abyssi," *Mol Microbiol* 47(6): 1495-1512.

Dietrich, J. et al. (Nov. 19, 2002). "PCR performance of the highly thermostable proof-reading B-type DNA polymerase from Pyrococcus abyssi," *FEMS Microbial Lett* 217(1): 89-94.

Evans, S.J. et al. (Mar. 1, 2000). " Improving dideoxynucleotide-triphosphate utilisation by the hyper-thermophilic DNA polymerase from the archaeon Pyrococcus furiosus," *Nucleic Acids Res* 28(5): 1059-1066.

Filée, J. et al. (Jun. 2002, e-published Feb. 25, 2014). "Evolution of DNA polymerase families: evidences for multiple gene exchange between cellular and viral proteins," *J Mol Evol* 54(6): 763-773.

Földesi, A. et al. (e-published Apr. 4, 2007). "The fluoride cleavable 2-(cyanoethoxy)methyl (CEM) group as reversible 3'-O-terminator for DNA sequencing-by-synthesis—synthesis, incorporation, and cleavage," *Nucleosides, Nucleotides Nucleic Acids* 26(3): 271-275.

Fuller, C.W. et al. (Nov. 2009, e-published Nov. 6, 2009). "The challenges of sequencing by synthesis," *Nat Biotechnol* 27(11): 1013-1023.

Fuller, C.W. et al. (May 10, 2016, e-published Apr. 18, 2016). "Real-time single-molecule electronic DNA sequencing by synthesis using polymer-tagged nucleotides on a nanopore array," *PNAS USA* 113(19): 5233-5238.

Gardner, A.F. et al. (Jun. 15, 1999). "Determinants of nucleotide sugar recognition in an archaeon DNA polymerase," *Nucleic Acids Res* 27(12): 2545-2553.

Gardner, A.F. et al. (Jan. 15, 2002). "Acyclic and dideoxy terminator preferences denote divergent sugar recognition by archaeon and Taq DNA polymerases," *Nucleic Acids Res* 30(2): 605-613.

Gueguen, Y. et al. (Dec. 20, 2001). "Characterization of two DNA polymerases from the hyperthermophilic euryarchaeon *Pyrococcus abyssi*," *Eur J Biochem* 268(22): 5961-5969.

Guo, J. et al. (Jul. 8, 2008, e-published Jun. 30, 2008). "Four-color DNA sequencing with 3'- O-modified nucleotide reversible terminators and chemically cleavable fluorescent dideoxynucleotides," *PNAS USA* 105(27): 9145-9150.

Guo, J. et al. (Apr. 20, 2010). "An integrated system for DNA sequencing by synthesis using novel nucleotide analogues," *Acc Chem Res* 43(4): 551-563.

Horhota, A. et al. (May 25, 2005). "Kinetic analysis of an efficient DNA-dependent TNA polymerase," *J Am Chem Soc* 127(20): 7427-7434.

Hutter, D. et al. (Nov. 2010, e-published Dec. 1, 2010). "Labeled nucleoside triphosphates with reversibly terminating aminoalkoxyl groups," *Nucleosides, Nucleotides, Nucleic Acids* 29(11): 879-895.

International Search Report mailed on Jan. 28, 2020 for PCT Application No. PCT/US2019/50678, filed Sep. 11, 2019, 6 pages.

Ishino, S. et al. (Aug. 29, 2014). "DNA polymerases as useful reagents for biotechnology—the history of developmental research in the field," *Front Microbiol* 5: 465.

Ju, J. et al. (Dec. 26, 2006, e-published Dec. 14, 2006). "Four-color DNA sequencing by synthesis using cleavable fluorescent nucleotide reversible terminators," *PNAS USA* 103(52): 19635-19640.

Kim, T.S. et al. (Jan. 4, 2010). "Novel 3'-O-fluorescently modified nucleotides for reversible termination of DNA synthesis," *ChemBioChem* 11(10): 75-78.

Knapp, D.C. et al. (Mar. 1, 2011, e-published Feb. 3, 2011). "Fluoride-Cleavable, Fluorescently Labelled Reversible Terminators: Synthesis and Use in Primer Extension," *Chem Eur J* 17: 2903-2915.

Kumar, S. et al. (Sep. 21, 2012). "PEG-labeled nucleotides and nanopore detection for single molecule DNA sequencing by synthesis," *Sci Rep* 2: 684.

Metzker, M.L. et al. (Oct. 11, 1994). "Termination of DNA synthesis by novel 3'-modified-deoxyribonucleoside 5'-triphosphates," *Nucleic Acids Res* 22(20): 4259-4267.

Needleman, S. B. et al. (Mar. 28, 1970, e-published Oct. 28, 2004). "A general method applicable to the search for similarities in the amino acid sequence of two proteins," *J Mol Biol* 48(3): 443-453.

Nikiforov, T.T. (May 15, 2011, e-published Feb. 26, 2011). "Fluorogenic polymerase, endonuclease, and ligase assays based on DNA substrates labeled with a single fluorophore," *Anal Biochem* 412(2): 229-236.

Nikiforov, T.T. (Sep. 15, 2014, e-published Jun. 5, 2014). "Generic assay format for endo- and exonucleases based on fluorogenic substrates labeled with single fluorophores," *Anal Biochem* 461: 67-73.

Pearson, W.R. et al. (Apr. 1, 1988). "Improved tools for biological sequence comparison," *PNAS USA* 85(8): 2444-2448.

Rosenblum, B.B. et al. (Nov. 1, 1997). "New dye-labeled terminators for improved DNA sequencing patterns," *Nucleic Acids Res* 25(22): 4500-4504.

Ruparel, H. et al. (Apr. 26, 2005). "Design and synthesis of a 3'-O-allyl photocleavable fluorescent nucleotide as a reversible terminator for DNA sequencing by synthesis," *PNAS USA* 102(17): 5932-5937.

Seo, T.S. et al. (Jan. 24, 2003). "Click chemistry to construct fluorescent oligonucleotides for DNA sequencing," *J Org Chem* 68(2): 609-612.

Smith T.F. et al. (Dec. 1981, e-published Sep. 3, 2004). "Comparison of biosequences," *Advances in Applied Math* 2(4): 482-489.

Southworth, M.W. et al. (May 28, 1996). "Cloning of thermostable DNA polymerases from hyperthermophilic marine Archaea with emphasis on *Thermococcus* sp. 9 degrees N-7 and mutations artectInq a-s' exonuclease activity," *PNAS USA* 93(11): 5281-5285.

Tabor, S. et al. (Apr. 15, 1989). "Selective inactivation of the exonuclease activity of bacteriophage T7 DNA polymerase by in vitro mutagenesis," *J Biol Chem* 264(11): 6447-6458.

Truniger, V. et al. (Jan. 16, 2004). "Function of the C-terminus of phi29 DNA polymerase in DNA and terminal protein binding," *Nucleic Acids Research* 32(1): 361-370.

Uniprot Accession No. E2D778 (Nov. 2010). Located at https://www.uniprot.org/uniprotkb/E2D778/entry. Last accessed Jan. 20, 2023.

Welch, M.B. et al. (1999, e-published Oct. 4, 2006). "Synthesis of Nucleosides Designed for Combinatorial DNA Sequencing," *Chem Eur J* 5(3): 951-960.

Welch, M.B. et al. (Feb. 1999). "Synthesis of fluorescent, photolabile 3'-O-protected nucleoside triphosphates for the base addition sequencing scheme," *Nucleosides Nucleotides* 18(2): 197-201.

(56) References Cited

OTHER PUBLICATIONS

Whisstock, J.C. et al. (Aug. 2003). "Prediction of protein function from protein sequence and structure," *Quarterly Reviews of Biophysics* 36(3): 307-340.

Witkowski, A. et al. (Sep. 7, 1999). "Conversion of a beta-ketoacyl synthase to a malonyl decarboxylase by replacement of the active-site cysteine with glutamine," *Biochemistry* 38(36): 11643-11650.

Written Opinion mailed on Jan. 28, 2020 for PCT Application No. PCT/US2019/50678, filed Sep. 11, 2019, 10 pages.

Wu, J. et al. (Oct. 16, 2007, e-published Oct. 8, 2007). "3'-O-modified nucleotides as reversible terminators for pyrosequencing," *PNAS USA* 104(42): 16462-16467.

Zhu, Z. et al. (Aug. 25, 1994). "Directly labeled DNA probes using fluorescent nucleotides with different length linkers," *Nucleic Acids Res* 22(16): 3418-3422.

Dong, Q. et al. (Nov. 15, 1993) "Mutational studies of human DNA polymerase alpha. Identification of residues critical for deoxynucleotide binding and misinsertion fidelity of DNA synthesis," *Journal of Biological Chemistry* 268(32): 24163-24174.

Fogg, M. J. et al. (Dec. 1, 2002, e-published Nov. 4, 2022). "Structural basis for uracil recognition by archaeal family B DNA polymerases," *Nature structural & Molecular biology* 9(12): 922-927.

Killelea, T. et al. (Jun. 14, 2011, e-published May 20, 2011). "Role of Disulfide Bridges in Archaeal Family-B DNA Polymerases," *ChemBioChem* 12(9): 1330-1336.

Kisselev, L. (Jan. 2002, e-published Jan. 17, 2002). "Polypeptide release factors in prokaryotes and eukaryotes: same function, different structure," *Structure* 10(1): 8-9.

Lasken, R. S. et al. (Jul. 26, 1996). "Archaebacterial DNA polymerases tightly bind uracilcontaining DNA," *J Bio Chem* 271 (30): 17692-17696.

Liu, H. et al. (Dec. 15, 2000). "Identification of conserved residues contributing to the activities of adenovirus DNA polymerase," *Journal of Virology* 74(24): 11681-11689.

Nørholm, M. H. (Mar. 16, 2010). "A mutant Pfu DNA polymerase designed for advanced uracil-excision DNA engineering," *BMC biotechnology* 10: Article 21, pp. 1-7.

Pavlov, Y. I. et al. (Sep. 1, 2001). "In vivo consequences of putative active site mutations in yeast DNA polymerases α, ε, δ, and ξ," *Genetics* 159(1): 47-64.

Yang, G. et al. (Aug. 1, 2002, e-published Jul. 16, 2002). "A conserved Tyr residue is required for sugar selectivity in a Pol α DNA polymerase," *Biochemistry* 41(32): 10256-10261.

\* cited by examiner

| | 601 | | | | | | | | | 610 | | | | | | | | | | 620 | | | | | | | | | | 630 | | | | | | | | | | 640 | | | | | | | | | | 650 | | | | | | | | | | 660 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 9°N-7 | G | K | I | – | T | T | R | G | L | E | – | V | R | R | D | W | S | E | – | A | K | E | T | Q | A | R | V | L | E | A | I | – | L | K | H | G | D | V | E | E | A | V | R | I | V | K | E | V | T | E | K | L | S | K | Y | E | V | P | P | E | K | L |
| Therminator | G | K | I | – | T | T | R | G | L | E | – | V | R | R | D | W | S | E | – | A | K | E | T | Q | A | R | V | L | E | A | I | – | L | K | H | G | D | V | E | E | A | V | R | I | V | K | E | V | T | E | K | L | S | K | Y | E | V | P | P | E | K | L |
| Therminator II | G | K | I | – | T | T | R | G | L | E | – | V | R | R | D | W | S | E | – | A | K | E | T | Q | A | R | V | L | E | A | I | – | L | K | H | G | D | V | E | E | A | V | R | I | V | K | E | V | T | E | K | L | S | K | Y | E | V | P | P | E | K | L |
| Therminator III | G | K | I | – | T | T | R | G | L | E | – | V | R | R | D | W | S | E | – | A | K | E | T | Q | A | R | V | L | E | A | I | – | L | K | H | G | D | V | E | E | A | V | R | I | V | K | E | V | T | E | K | L | S | K | Y | E | V | P | P | E | K | L |
| Pol812 | G | K | I | – | T | T | R | G | L | E | – | V | R | R | D | W | S | E | – | A | K | E | T | Q | A | R | V | L | E | A | I | – | L | K | H | G | D | V | E | E | A | V | R | I | V | K | E | V | T | E | K | L | S | K | Y | E | V | P | P | E | K | L |

| | 661 | | | | | | | | | 670 | | | | | | | | | | 680 | | | | | | | | | | 690 | | | | | | | | | | 700 | | | | | | | | | | 710 | | | | | | | | | | 720 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 9°N-7 | V | I | H | E | Q | I | – | T | R | D | L | R | D | – | Y | K | A | T | G | P | H | V | A | V | A | K | R | L | A | A | R | G | V | K | I | R | P | G | T | V | – | S | Y | I | – | V | L | K | G | S | G | R | I | G | D | R | A | I | – | P | A | D | E | F |
| Therminator | V | I | H | E | Q | I | – | T | R | D | L | R | D | – | Y | K | A | T | G | P | H | V | A | V | A | K | R | L | A | A | R | G | V | K | I | R | P | G | T | V | – | S | Y | I | – | V | L | K | G | S | G | R | I | G | D | R | A | I | – | P | A | D | E | F |
| Therminator II | V | I | H | E | Q | I | – | T | R | D | L | R | D | – | Y | K | A | T | G | P | H | V | A | V | A | K | R | L | A | A | R | G | V | K | I | R | P | G | T | V | – | S | Y | I | – | V | L | K | G | S | G | R | I | G | D | R | A | I | – | P | A | D | E | F |
| Therminator III | V | I | H | E | Q | I | – | T | R | D | L | R | D | – | Y | K | A | T | G | P | H | V | A | V | A | K | R | L | A | A | R | G | V | K | I | R | P | G | T | V | – | S | Y | I | – | V | L | K | G | S | G | R | I | G | D | R | A | I | – | P | A | D | E | F |
| Pol812 | V | I | H | E | Q | I | – | T | R | D | L | R | D | – | Y | K | A | T | G | P | H | V | A | V | A | K | R | L | A | A | R | G | V | K | I | R | P | G | T | V | – | S | Y | I | – | V | L | K | G | S | G | R | I | G | D | R | A | I | – | P | A | D | E | F |

| | 721 | | | | | | | | | 730 | | | | | | | | | | 740 | | | | | | | | | | 750 | | | | | | | | | | 760 | | | | | | | | | | 770 | | | | | 775 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 9°N-7 | D | P | T | K | H | R | Y | D | A | E | Y | Y | I | E | N | Q | V | L | P | A | V | E | R | I | L | K | A | F | G | Y | R | K | E | D | L | R | Y | Q | K | T | K | Q | V | G | L | G | A | W | L | K | V | V | K | G | K |
| Therminator | D | P | T | K | H | R | Y | D | A | E | Y | Y | I | E | N | Q | V | L | P | A | V | E | R | I | L | K | A | F | G | Y | R | K | E | D | L | R | Y | Q | K | T | K | Q | V | G | L | G | A | W | L | K | V | V | K | G | K |
| Therminator II | D | P | T | K | H | R | Y | D | A | E | Y | Y | I | E | N | Q | V | L | P | A | V | E | R | I | L | K | A | F | G | Y | R | K | E | D | L | R | Y | Q | K | T | K | Q | V | G | L | G | A | W | L | K | V | V | K | G | K |
| Therminator III | D | P | T | K | H | R | Y | D | A | E | Y | Y | I | E | N | Q | V | L | P | A | V | E | R | I | L | K | A | F | G | Y | R | K | E | D | L | R | Y | Q | K | T | K | Q | V | G | L | G | A | W | L | K | V | V | K | G | K |
| Pol812 | D | P | T | K | H | R | Y | D | A | E | Y | Y | I | E | N | Q | V | L | P | A | V | E | R | I | L | K | A | F | G | Y | R | K | E | D | L | R | Y | Q | K | T | K | Q | V | G | L | G | A | W | L | K | V | V | K | G | K |

FIG. 2A

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 9°N-7 | M | I | L | D | T | D | Y | I | T | E | N | G | K | P | V | - | R | V | F | K | K | E | N | G | E | F | K | I | E | Y | D | R | T | F | E | P | Y | F | Y | A | L | L | K | D | D | S | A | I | E | D | V | K | K | V | T | A | K | R | H | G |
| SG2000 | M | I | L | G | A | D | Y | I | T | K | D | G | K | P | I | V | R | L | F | K | K | E | N | G | E | F | K | I | E | L | D | P | H | F | R | P | Y | I | Y | A | L | L | R | D | D | S | A | I | E | E | I | M | Q | I | K | G | E | R | H | G |
| SG2100 | M | I | L | G | A | D | Y | I | T | K | D | G | K | P | I | V | R | L | F | K | K | E | N | G | E | F | K | I | E | L | D | P | H | F | R | P | Y | I | Y | A | L | L | R | D | D | S | A | I | E | E | I | M | Q | I | K | G | E | R | H | G |
| SG2105 | M | I | L | G | A | D | Y | I | T | K | D | G | K | P | I | V | R | L | F | K | K | E | N | G | E | F | K | I | E | L | D | P | H | F | R | P | Y | I | Y | A | L | L | R | D | D | S | A | I | E | E | I | M | Q | I | K | G | E | R | H | G |
| SG2200 | M | I | L | G | A | D | Y | I | T | K | D | G | K | P | I | V | R | L | F | K | K | E | N | G | E | F | K | I | E | L | D | P | H | F | R | P | Y | I | Y | A | L | L | R | D | D | S | A | I | E | E | I | M | Q | I | K | G | E | R | H | G |

| | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 9°N-7 | T | V | V | K | V | K | R | A | E | K | V | Q | K | K | F | L | G | R | P | I | E | V | W | K | L | Y | F | N | H | P | Q | D | V | P | A | I | R | D | R | - | R | A | H | P | A | V | V | D | I | Y | E | Y | D | I | P | F | A | K | R | Y |
| SG2000 | K | T | V | R | I | V | D | A | I | K | V | K | K | K | F | L | R | R | P | V | E | V | W | K | L | I | F | E | E | H | P | Q | D | V | P | A | M | R | G | K | I | R | S | H | P | A | V | V | D | I | Y | E | Y | D | I | P | F | A | K | R | Y |
| SG2100 | K | T | V | R | I | V | D | A | I | K | V | K | K | K | F | L | R | R | P | V | E | V | W | K | L | I | F | E | E | H | P | Q | D | V | P | A | M | R | G | K | I | R | S | H | P | A | V | V | D | I | Y | E | Y | D | I | P | F | A | K | R | Y |
| SG2105 | K | T | V | R | I | V | D | A | I | K | V | K | K | K | F | L | R | R | P | V | E | V | W | K | L | - | F | E | E | H | P | Q | D | V | P | A | M | R | G | K | I | R | S | H | P | A | V | V | D | I | Y | E | Y | D | I | P | F | A | K | R | Y |
| SG2200 | K | T | V | R | I | V | D | A | I | K | V | K | K | K | F | L | R | R | P | V | E | V | W | K | L | - | F | E | E | H | P | Q | D | V | P | A | M | R | G | K | I | R | S | H | P | A | V | V | D | I | Y | E | Y | D | I | P | F | A | K | R | Y |

| | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 9°N-7 | L | I | D | K | G | L | - | - | P | M | E | G | D | E | E | L | T | M | L | A | F | D | I | E | T | L | Y | H | E | G | E | E | F | G | T | G | P | I | L | M | I | S | Y | A | D | G | S | E | A | R | V | I | T | W | K | K | I | D | L | P |
| SG2000 | L | - | D | K | G | L | - | - | P | M | E | G | E | E | D | L | K | L | L | A | F | A | I | A | T | F | Y | H | E | G | D | E | F | G | K | G | E | I | I | M | I | S | Y | A | D | E | E | E | A | G | V | I | T | W | K | R | I | N | L | P | Y |
| SG2100 | L | - | D | K | G | L | - | - | P | M | E | G | E | E | D | L | K | L | L | A | F | A | I | A | T | F | Y | H | E | G | D | E | F | G | K | G | E | I | I | M | I | S | Y | A | D | E | E | E | A | G | V | I | T | W | K | R | I | N | L | P | Y |
| SG2105 | L | - | D | K | G | L | - | - | P | M | E | G | E | E | D | L | K | L | L | A | F | A | I | A | T | F | Y | H | E | G | D | E | F | G | K | G | E | I | I | M | I | S | Y | A | D | E | E | E | A | G | V | I | T | W | K | R | I | N | L | P | Y |
| SG2200 | L | - | D | K | G | L | - | - | P | A | E | G | E | E | D | L | K | L | L | A | F | A | I | A | T | F | Y | H | E | G | D | E | F | G | K | G | E | I | I | M | I | S | Y | A | D | E | E | E | A | G | V | I | T | W | K | R | I | N | L | P | Y |

FIG. 2B

|  | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 209 | 210 | 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 | 235 | 236 | 237 | 238 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 9°N-7 | V | D | V | V | S | T | E | K | E | M | I | K | R | F | L | R | V | V | R | E | K | D | P | D | V | L | – | T | Y | N | G | D | N | F | D | F | A | Y | L | K | K | R | C | E | E | L | G | I | K | F | T | L | G | R | D | G | S | E |
| SG2000 | V | H | V | V | S | N | E | R | E | M | I | K | R | F | V | Q | I | – | K | E | K | D | P | D | V | I | – | T | Y | N | G | D | N | F | D | L | P | Y | I | I | K | R | A | E | K | L | G | V | R | L | L | L | G | R | D | K | E | H |
| SG2100 | V | H | V | V | S | N | E | R | E | M | I | K | R | F | V | Q | I | – | K | E | K | D | P | D | V | I | – | T | Y | N | G | D | N | F | D | L | P | Y | I | I | K | R | A | E | K | L | G | V | R | L | L | L | G | R | D | K | E | H | P |
| SG2105 | V | H | V | V | S | N | E | R | E | M | I | K | R | F | V | Q | I | – | K | E | K | D | P | D | V | I | – | T | Y | N | G | D | N | F | D | L | P | Y | I | I | K | R | A | E | K | L | G | V | R | L | L | L | G | R | D | K | E | H | P |
| SG2200 | V | H | V | V | S | N | E | R | E | M | I | K | R | F | V | Q | I | – | K | E | K | D | P | D | V | I | – | T | Y | N | G | D | N | F | D | L | P | Y | I | I | K | R | A | E | K | L | G | V | R | L | L | L | G | R | D | K | E | H | P |

|  | 239 | 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 | 268 | 269 | 270 | 271 | 272 | 273 | 274 | 275 | 276 | 277 | 278 | 279 | 280 | 281 | 282 | 283 | 284 | 285 | 286 | 287 | 288 | 289 | 290 | 291 | 292 | 293 | 294 | 295 | 296 | 297 | 298 | 299 | 300 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 9°N-7 | P | K | I | Q | R | M | G | D | R | F | A | V | E | V | K | G | R | I | H | F | D | L | Y | P | V | I | R | R | T | – | N | L | P | T | Y | T | L | E | A | V | Y | E | T | V | L | F | G | K | P | K | E | K | V | Y | A | E | E | I | A | Q | A |
| SG2000 | P | K | I | Q | R | M | G | D | S | F | A | V | E | V | K | G | R | I | H | F | D | L | F | P | V | V | R | R | T | – | N | L | P | T | Y | T | L | E | A | V | Y | E | T | V | L | G | K | Q | K | T | K | L | G | A | E | E | I | A | A | I |
| SG2100 | P | K | I | Q | R | M | G | D | S | F | A | V | E | V | K | G | R | – | H | F | D | L | F | P | V | V | R | R | T | – | N | L | P | T | Y | T | L | E | A | V | Y | E | T | V | L | G | K | Q | K | T | K | L | G | A | E | E | I | A | A | I |
| SG2105 | P | K | I | Q | R | M | G | D | S | F | A | V | E | V | K | G | R | – | H | F | D | L | F | P | V | V | R | R | T | – | N | L | P | T | Y | T | L | E | A | V | Y | E | T | V | L | G | K | Q | K | T | K | L | G | A | E | E | I | A | A | I |
| SG2200 | P | K | I | Q | R | M | G | D | S | F | A | V | E | V | K | G | R | – | H | F | D | L | F | P | V | V | R | R | T | – | N | L | P | T | Y | T | L | E | A | V | Y | E | T | V | L | G | K | Q | K | T | K | L | G | A | E | E | I | A | A | I |

SEQUENCE LISTING

```
Sequence total quantity: 20
SEQ ID NO: 1            moltype = AA  length = 774
FEATURE                 Location/Qualifiers
source                  1..774
                        mol_type = protein
                        organism = Thermococcus sp.
SEQUENCE: 1
MILGADYITK DGKPIVRLFK KENGEFKIEL DPHFRPYIYA LLRDDSAIEE IMQIKGERHG   60
KTVRIVDAIK VKKKFLRRPV EVWKLIFEHP QDVPAMRGKI RSHPAVVDIY EYDIPFAKRY  120
LIDKGLIPME GEEDLKLLAF DIETFYHEGD EFGKGEIIMI SYADDEEAGV ITWKRINLPY  180
VHVVSNEREM IKRFVQIIKE KDPDVIITYN GDNFDLPYII KRAEKLGVRL LLGRDKEHPE  240
PKIQRMGDSF AVEIKGRIHF DLFPVVRRTI NLPTYTLEAV YETVLGKQKT KLGAEEIAAI  300
WETEEGMKKL AQYSMEDAKA TYELGREFFP MEAELAKVIG QSVWDVSRSS TGNLVEWYML  360
RVAYERNELA PNKPSDEEYK RRLRSTYLGG YVKEPERGLW GNIVYLDFRS LYPSIIVTHN  420
VSPDTLEREG CQDYEVAPIV GYRFCKDFPG FIPSILENLI ETRQEVKKRM KSTTDPVERK  480
MLDYRQRALK ILANSYYGYQ GYPKARWYSK ECAESVTAWG RHYIEMSIRE IEEKFGFKVL  540
YADTDGFYAT LPGETPETIK KKAKEFLDYI NSKLPGLLEL EYEGFYLRGF FVTKKRYAVI  600
DEDGRITTRG LEVVRRDWSE IAKETQAKVL EAILREGSVE KAVEIVKSVV ERIAKYKVPL  660
EKLVIHEQIT RELKDYKAIG PHVAIAKRLA AKGIKVKPGT IISYIVLKGG GKISDRVVLL  720
TEYDPRKHKY DPDYYIENQV LPAVLRILEA FGYKKEDLKY QRSKQTGLEA WLRR        774

SEQ ID NO: 2            moltype = AA  length = 775
```

```
FEATURE                 Location/Qualifiers
source                  1..775
                        mol_type = protein
                        organism = Thermococcus sp.
SEQUENCE: 2
MILDTDYITE NGKPVIRVFK KENGEFKIEY DRTFEPYFYA LLKDDSAIED VKKVTAKRHG    60
TVVKVKRAEK VQKKFLGRPI EVWKLYFNHP QDVPAIRDRI RAHPAVVDIY EYDIPFAKRY   120
LIDKGLIPME GDEELTMLAF DIETLYHEGE EFGTGPILMI SYADGSEARV ITWKKIDLPY   180
VDVVSTEKEM IKRFLRVVRE KDPDVLITYN GDNFDFAYLK KRCEELGIKF TLGRDGSEPK   240
IQRMGDRFAV EVKGRIHFDL YPVIRRTINL PTYTLEAVYE AVFGKPKEKV YAEEIAQAWE   300
SGEGLERVAR YSMEDAKVTY ELGREFFPME AQLSRLIGQS LWDVSRSSTG NLVEWFLLRK   360
AYKRNELAPN KPDERELARR RGGYAGGYVK EPERGLWDNI VYLDFRSLYP SIIITHNVSP   420
DTLNREGCKE YDVAPEVGHK FCKDFPGFIP SLLGDLLEER QKIKRKMKAT VDPLEKKLLD   480
YRQRAIKILA NSFYGYYGYA KARWYCKECA ESVTAWGREY IEMVIRELEE KFGFKVLYAD   540
TDGLHATIPG ADAETVKKKA KEFLKYINPK LPGLLELEYE GFYVRGFFVT KKKYAVIDEE   600
GKITTRGLEI VRRDWSEIAK ETQARVLEAI LKHGDVEEAV RIVKEVTEKL SKYEVPPEKL   660
VIHEQITRDL RDYKATGPHV AVAKRLAARG VKIRPGTVIS YIVLKGSGRI GDRAIPADEF   720
DPTKHRYDAE YYIENQVLPA VERILKAFGY RKEDLRYQKT KQVGLGAWLK VKGKK        775

SEQ ID NO: 3            moltype = AA  length = 783
FEATURE                 Location/Qualifiers
source                  1..783
                        mol_type = protein
                        organism = Thermococcus sp.
SEQUENCE: 3
MRFWPLDATY SVVGGVPEVR VFGVDGEGRR VVLVDRRFRP YFYAKCDKCD ASLAKSYLSR    60
VAPVEAVEVV ERRFFGRPTI FLKVVAKVPE DVRKLREAAL GAPGVVDVYE ADIRYYMRYM   120
IDKGVVPCAW NVVEAREAGK LGPLPLYEVV EWAGVEEGFP PPLRVLAFDI EVYNERGSPD   180
PLRDPVVMLA VKTSDGREEV FEAEGRDDRR VIRGFVDFVK EFDPDVIVGY NSNGFDWPYL   240
SERAKALGVP LRVDRLGGVP QQSVYGHWSV VGRANVDLYN IVDEFPEIKV KTLDRVAEYF   300
GVMKRSERVL IPGHKVYEYW NDPAKRPTLM RYVLDDVRST LGLAEKLLPF LIQLSSVSGL   360
PLDQVAAASV GNRVEWMLLR YAYRMGEVAP NREEREYEPY KGAIVLEPKP GLYSDVLVLD   420
FSSMYPNIMM KYNLSPDTYL EPHEPDPPEG VVVAPEVGHR FRKAPTGFIP AVLKHLVELR   480
RAVREEAKKY PPDSPEYRLL DERQRALKVM ANAMYGYLGW VGARWYKKEV AESVTAFARA   540
ILLDVVEYAK RLGIEVIYGD TDSLFVKKSG AVDRLVKYVE ERHGIEIKVD KDYERVLFTE   600
AKKRYAGLLR DGRIDIVGFE VVRGDWCELA KEVQLNVVEL ILKSKSVGEA RERVVKYVRE   660
VVERLKAYKF DLDDLIIWKT LDKELDEYKA YGPHVHAALE LKRRGYKVGK GTTVGYVIVR   720
GPGKVSERAM PYIFVDDASK VDVDYYIEKQ VIPAALRIAE VLGVKESDLK TGRVEKSLLD   780
FLG                                                                783

SEQ ID NO: 4            moltype = AA  length = 774
FEATURE                 Location/Qualifiers
source                  1..774
                        mol_type = protein
                        organism = Thermococcus sp.
SEQUENCE: 4
MILGADYITK DGKPIVRLFK KENGEFKIEL DPHFRPYIYA LLRDDSAIEE IMQIKGERHG    60
KTVRIVDAIK VKKKFLRRPV EVWKLIFEHP QDVPAMRGKI RSHPAVVDIY EYDIPFAKRY   120
LIDKGLIPME GEEDLKLLAF AIATFYHEGD EFGKGEIIMI SYADDEEAGV ITWKRINLPY   180
VHVVSNEREM IKRFVQIIKE KDPDVIITYN GDNFDLPYII KRAEKLGVRL LLGRDKEHPE   240
PKIQRMGDSF AVEIKGRIHF DLFPVVRRTI NLPTYTLEAV YETVLGKQKT KLGAEEIAAI   300
WETEEGMKKL AQYSMEDAKA TYELGREFFP MEAELAKVIG QSVWDVSRSS TGNLVEWYML   360
RVAYERNELA PNKPSDEEYK RRLRSTYLGG YVKEPERGLW GNIVYLDFRS SAVSIIVTHN   420
VSPDTLEREG CQDYEVAPIV GYRFCKDFPG FIPSILENLI ETRQEVKKRM KSTTDPVERK   480
MLDYRQRALK ILANSYYGYQ GYPKARWYSK ECAESVTAWG RHYIEMSIRE IEEKFGFKVL   540
YADTDGFYAT LPGETPETIK KKAKEFLDYI NSKLPGLLEL EYEGFYLRGF FVTKKRYAVI   600
DEDGRITTRG LEVVRRDWSE IAKETQAKVL EAILREGSVE KAVEIVKSVV ERIAKYKVPL   660
EKLVIHEQIT RELKDYKAIG PHVAIAKRLA AKGIKVKPGT IISYIVLKGG GKISDRVVLL   720
TEYDPRKHKY DPDYYIENQV LPAVLRILEA FGYKKEDLKY QRSKQTGLEA WLRR         774

SEQ ID NO: 5            moltype = AA  length = 774
FEATURE                 Location/Qualifiers
source                  1..774
                        mol_type = protein
                        organism = Thermococcus sp.
SEQUENCE: 5
MILGADYITK DGKPIVRLFK KENGEFKIEL DPHFRPYIYA LLRDDSAIEE IMQIKGERHG    60
KTVRIVDAIK VKKKFLRRPV EVWKLIFEHP QDVPAMRGKI RSHPAVVDIY EYDIPFAKRY   120
LIDKGLIPME GEEDLKLLAF AIATFYHEGD EFGKGEIIMI SYADDEEAGV ITWKRINLPY   180
VHVVSNEREM IKRFVQIIKE KDPDVIITYN GDNFDLPYII KRAEKLGVRL LLGRDKEHPE   240
PKIQRMGDSF AVEIKGRIHF DLFPVVRRTI NLPTYTLEAV YETVLGKQKT KLGAEEIAAI   300
WETEEGMKKL AQYSMEDAKA TYELGREFFP MEAELAKVIG QSVWDVSRSS TGNLVEWYML   360
RVAYERNELA PNKPSDEEYK RRLRSTYLGG YVKEPERGLW GNIVYLDFRS SAVSIIVTHN   420
VSPDTLEREG CQDYEVAPIV GYRFCKDFPG FIPSILENLI ETRQEVKKRM KSTTDPVERK   480
MLDYRQRVLK ILANSYYGYQ GYPKARWYSK ECAESVTAWG RHYIEMSIRE IEEKFGFKVL   540
YADTDGFYAT LPGETPETIK KKAKEFLDYI NSKLPGLLEL EYEGFYLRGF FVTKKRYAVI   600
DEDGRITTRG LEVVRRDWSE IAKETQAKVL EAILREGSVE KAVEIVKSVV ERIAKYKVPL   660
EKLVIHEQIT RELKDYKAIG PHVAIAKRLA AKGIKVKPGT IISYIVLKGG GKISDRVVLL   720
TEYDPRKHKY DPDYYIENQV LPAVLRILEA FGYKKEDLKY QRSKQTGLEA WLRR         774
```

```
SEQ ID NO: 6             moltype = AA  length = 774
FEATURE                  Location/Qualifiers
source                   1..774
                         mol_type = protein
                         organism = Thermococcus sp.
SEQUENCE: 6
MILGADYITK DGKPIVRLFK KENGEFKIEL DPHFRPYIYA LLRDDSAIEE IMQIKGERHG    60
KTVRIVDAIK VKKKFLRRPV EVWKLIFEHP QDVPAMRGKI RSHPAVVDIY EYDIPFAKRY   120
LIDKGLIPAE GEEDLKLLAF AIATFYHEGD EFGKGEIIMI SYADDEEAGV ITWKRINLPY   180
VHVVSNEREM IKRFVQIIKE KDPDVIITYN GDNFDLPYII KRAEKLGVRL LLGRDKEHPE   240
PKIQRMGDSF AVEIKGRIHF DLFPVVRRTI NLPTYTLEAV YETVLGKQKT KLGAEEIAAI   300
WETEEGMKKL AQYSMEDAKA TYELGREFFP MEAELAKVIG QSVWDVSRSS TGNLVEWYML   360
RVAYERNELA PNKPSDEEYK RRLRSTYLGG YVKEPERGLW GNIVYLDFRS AAISIIVTHN   420
VSPDTLEREG CQDYEVAPIV GYRFCKDFPG FIPSILENLI ETRQEVKKRM KSTTDPVERK   480
MLDYRQRVLK ILANSYYGYQ GYPKARWYSK ECAESVTAWG RHYIEMSIRE IEEKFGFKVL   540
YADTDGFYAT LPGETPETIK KKAKEFLDYI NSKLPGLLEL EYEGFYLRGF FVTKKRYAVI   600
DEDGRITTRG LEVVRRDWSE IAKETQAKVL EAILREGSVE KAVEIVKSVV ERIAKYKVPL   660
EKLVIHEQIT RELKDYKAIG PHVAIAKRLA AKGIKVKPGT IISYIVLKGG GKISDRVVLL   720
TEYDPRKHKY DPDYYIENQV LPAVLRILEA FGYKKEDLKY QRSKQTGLEA WLRR         774

SEQ ID NO: 7             moltype = AA  length = 775
FEATURE                  Location/Qualifiers
source                   1..775
                         mol_type = protein
                         organism = Thermococcus sp.
SEQUENCE: 7
MILDTDYITE NGKPVIRVFK KENGEFKIEY DRTFEPYFYA LLKDDSAIED VKKVTAKRHG    60
TVVKVKRAEK VQKKFLGRPI EVWKLYFNHP QDVPAIRDRI RAHPAVVDIY EYDIPFAKRY   120
LIDKGLIPME GDEELTMLAF AIATLYHEGE EFGTGPILMI SYADGSEARV ITWKKIDLPY   180
VDVVSTEKEM IKRFLRVVRE KDPDVLITYN GDNFDFAYLK KRCEELGIKF TLGRDGSEPK   240
IQRMGDRFAV EVKGRIHFDL YPVIRRTINL PTYTLEAVYE AVFGKPKEKV YAEEIAQAWE   300
SGEGLERVAR YSMEDAKVTY ELGREFFPME AQLSRLIGQS LWDVSRSSTG NLVEWFLLRK   360
AYKRNELAPN KPDERELARR RGGYAGGYVK EPERGLWDNI VYLDFRSLYP SIIITHNVSP   420
DTLNREGCKE YDVAPEVGHK FCKDFPGFIP SLLGDLLEER QKIKRKMKAT VDPLEKKLLD   480
YRQRLIKILA NSFYGYYGYA KARWYCKECA ESVTAWGREY IEMVIRELEE KFGFKVLYAD   540
TDGLHATIPG ADAETVKKKA KEFLKYINPK LPGLLELEYE GFYVRGFFVT KKKYAVIDEE   600
GKITTRGLEI VRRDWSEIAK ETQARVLEAI LKHGDVEEAV RIVKEVTEKL SKYEVPPEKL   660
VIHEQITRDL RDYKATGPHV AVAKRLAARG VKIRPGTVIS YIVLKGSGRI GDRAIPADEF   720
DPTKHRYDAE YYIENQVLPA VERILKAFGY RKEDLRYQKT KQVGLGAWLK VKGKK        775

SEQ ID NO: 8             moltype = AA  length = 775
FEATURE                  Location/Qualifiers
source                   1..775
                         mol_type = protein
                         organism = Thermococcus sp.
SEQUENCE: 8
MILDTDYITE NGKPVIRVFK KENGEFKIEY DRTFEPYFYA LLKDDSAIED VKKVTAKRHG    60
TVVKVKRAEK VQKKFLGRPI EVWKLYFNHP QDVPAIRDRI RAHPAVVDIY EYDIPFAKRY   120
LIDKGLIPME GDEELTMLAF AIATLYHEGE EFGTGPILMI SYADGSEARV ITWKKIDLPY   180
VDVVSTEKEM IKRFLRVVRE KDPDVLITYN GDNFDFAYLK KRCEELGIKF TLGRDGSEPK   240
IQRMGDRFAV EVKGRIHFDL YPVIRRTINL PTYTLEAVYE AVFGKPKEKV YAEEIAQAWE   300
SGEGLERVAR YSMEDAKVTY ELGREFFPME AQLSRLIGQS LWDVSRSSTG NLVEWFLLRK   360
AYKRNELAPN KPDERELARR RGGYAGGYVK EPERGLWDNI VYLDFRSLVP SIIITHNVSP   420
DTLNREGCKE YDVAPEVGHK FCKDFPGFIP SLLGDLLEER QKIKRKMKAT VDPLEKKLLD   480
YRQRLIKILA NSFYGYYGYA KARWYCKECA ESVTAWGREY IEMVIRELEE KFGFKVLYAD   540
TDGLHATIPG ADAETVKKKA KEFLKYINPK LPGLLELEYE GFYVRGFFVT KKKYAVIDEE   600
GKITTRGLEI VRRDWSEIAK ETQARVLEAI LKHGDVEEAV RIVKEVTEKL SKYEVPPEKL   660
VIHEQITRDL RDYKATGPHV AVAKRLAARG VKIRPGTVIS YIVLKGSGRI GDRAIPADEF   720
DPTKHRYDAE YYIENQVLPA VERILKAFGY RKEDLRYQKT KQVGLGAWLK VKGKK        775

SEQ ID NO: 9             moltype = AA  length = 775
FEATURE                  Location/Qualifiers
source                   1..775
                         mol_type = protein
                         organism = Thermococcus sp.
SEQUENCE: 9
MILDTDYITE NGKPVIRVFK KENGEFKIEY DRTFEPYFYA LLKDDSAIED VKKVTAKRHG    60
TVVKVKRAEK VQKKFLGRPI EVWKLYFNHP QDVPAIRDRI RAHPAVVDIY EYDIPFAKRY   120
LIDKGLIPME GDEELTMLAF AIATLYHEGE EFGTGPILMI SYADGSEARV ITWKKIDLPY   180
VDVVSTEKEM IKRFLRVVRE KDPDVLITYN GDNFDFAYLK KRCEELGIKF TLGRDGSEPK   240
IQRMGDRFAV EVKGRIHFDL YPVIRRTINL PTYTLEAVYE AVFGKPKEKV YAEEIAQAWE   300
SGEGLERVAR YSMEDAKVTY ELGREFFPME AQLSRLIGQS LWDVSRSSTG NLVEWFLLRK   360
AYKRNELAPN KPDERELARR RGGYAGGYVK EPERGLWDNI VYLDFRSSAV SIIITHNVSP   420
DTLNREGCKE YDVAPEVGHK FCKDFPGFIP SLLGDLLEER QKIKRKMKAT VDPLEKKLLD   480
YRQRAIKILA NSFYGYYGYA KARWYCKECA ESVTAWGREY IEMVIRELEE KFGFKVLYAD   540
TDGLHATIPG ADAETVKKKA KEFLKYINPK LPGLLELEYE GFYVRGFFVT KKKYAVIDEE   600
GKITTRGLEI VRRDWSEIAK ETQARVLEAI LKHGDVEEAV RIVKEVTEKL SKYEVPPEKL   660
VIHEQITRDL RDYKATGPHV AVAKRLAARG VKIRPGTVIS YIVLKGSGRI GDRAIPADEF   720
```

```
DPTKHRYDAE YYIENQVLPA VERILKAFGY RKEDLRYQKT KQVGLGAWLK VKGKK          775

SEQ ID NO: 10              moltype = AA   length = 775
FEATURE                    Location/Qualifiers
source                     1..775
                           mol_type = protein
                           organism = Thermococcus sp.
SEQUENCE: 10
MILDTDYITE NGKPVIRVFK KENGEFKIEY DRTFEPYFYA LLKDDSAIED VKKVTAKRHG    60
TVVKVKRAEK VQKKFLGRPI EVWKLYFNHP QDVPAIRDRI RAHPAVVDIY EYDIPFAKRY   120
LIDKGLIPAE GDEELTMLAF AIATLYHEGE EFGTGPILMI SYADGSEARV ITWKKIDLPY   180
VDVVSTEKEM IKRFLRVVRE KDPDVLITYN GDNFDFAYLK KRSEELGIKF TLGRDGSEPK   240
IQRMGDRFAV EVKGRIHFDL YPVIRRTINL PTYTLEAVYE AVFGKPKEKV YAEEIAQAWE   300
SGEGLERVAR YSMEDAKVTY ELGREFFPME AQLSRLIGQS LWDVSRSSTG NLVEWFLLRK   360
AYKRNELAPN KPDERELARR RGGYAGGYVK EPERGLWDNI VYLDFRSAAI SIIITHNVSP   420
DTLNREGCKE YDVAPEVGHK FCKDFPGFIP SLLGDLLEER QKIKRKMKAT VDPLEKKLLD   480
YRQRVIKILA NSFYGYYGYA KARWYCKECA ESVTAWGREY IEMVIRELEE KFGFKVLYAD   540
TDGLHATIPG ADAETVKKKA KEFLKYINPK LPGLLELEYE GFYVRGFFVT KKKYAVIDEE   600
GKITTRGLEI VRRDWSEIAK ETQARVLEAI LKHGDVEEAV RIVKEVTEKL SKYEVPPEKL   660
VIHEQITRDL RDYKATGPHV AVAKRLAARG VKIRPGTVIS YIVLKGSGRI GDRAIPADEF   720
DPTKHRYDAE YYIENQVLPA VERILKAFGY RKEDLRYQKT KQVGLGAWLK VKGKK          775

SEQ ID NO: 11              moltype = DNA   length = 60
FEATURE                    Location/Qualifiers
misc_feature               1..60
                           note = Synthetic construct
misc_difference            60
                           note = Dideoxycytidine (ddC)
source                     1..60
                           mol_type = other DNA
                           organism = synthetic construct
SEQUENCE: 11
gactcacatg aatcagtgca gcatcagatg tatgaccgaa gcggacgaag gtgcgtggac    60

SEQ ID NO: 12              moltype = DNA   length = 60
FEATURE                    Location/Qualifiers
misc_feature               1..60
                           note = Synthetic construct
misc_difference            60
                           note = Dideoxycytidine (ddC)
source                     1..60
                           mol_type = other DNA
                           organism = synthetic construct
SEQUENCE: 12
gtggttcatc gcgtccgata tcaaacttcg tcaagtcgaa gcggacgaag gtgcgtggac    60

SEQ ID NO: 13              moltype = DNA   length = 60
FEATURE                    Location/Qualifiers
misc_feature               1..60
                           note = Synthetic construct
misc_difference            60
                           note = Dideoxycytidine (ddC)
source                     1..60
                           mol_type = other DNA
                           organism = synthetic construct
SEQUENCE: 13
tactaggttg tacgatccct gcacttcagc taagcacgaa gcggacgaag gtgcgtggac    60

SEQ ID NO: 14              moltype = DNA   length = 60
FEATURE                    Location/Qualifiers
misc_feature               1..60
                           note = Synthetic construct
misc_difference            60
                           note = Dideoxycytidine (ddC)
source                     1..60
                           mol_type = other DNA
                           organism = synthetic construct
SEQUENCE: 14
agctaccaat atttagtttc cgagtctcag ctcatgcgaa gcggacgaag gtgcgtggac    60

SEQ ID NO: 15              moltype = DNA   length = 36
FEATURE                    Location/Qualifiers
misc_feature               1..36
                           note = Synthetic construct
source                     1..36
                           mol_type = other DNA
                           organism = synthetic construct
SEQUENCE: 15
aaaaaaaaaa aagtccacgc accttcgtcc gcttcg                               36
```

```
SEQ ID NO: 16          moltype = DNA  length = 2328
FEATURE                Location/Qualifiers
source                 1..2328
                       mol_type = other DNA
                       organism = Thermococcus sp.
SEQUENCE: 16
atgattctgg gcgccgacta tatcaccaaa gacggtaaac cgattgttcg tctgttcaaa   60
aaagaaaatg gtgagttcaa gatcgagctg gacccgcatt tccgtccgta catttacgca   120
ctcttgcgtg acgacagcgc gattgaagaa atcatgcaga tcaaaggtga acgccatggc   180
aagactgtcc gcattgtcga tgcgatcaag gtcaagaaaa agttcctgcg tcgccctgtc   240
gaagtgtgga agctgatttt cgagcacccg caagacgtcc cggcaatgcg tggcaagatt   300
cgcagccatc cggctgtggt cgatatttac gagtacgaca tcccgttcgc aaagcgctac   360
ctgattgaca agggcctgat cccgatggag ggtgaagaag atctgaagct gttagcctct   420
gacatcgaaa cgttctatca cgagggcgat gaatttggta aaggtgagat tatcatgatt   480
agctacgcgg acgacgaaga ggccggtgtg atcacctgga agcgcatcaa tctgccgtat   540
gttcatgttg tgtcgaatga acgcgagatg attaagcgtt tcgtgcaaat catcaaagaa   600
aaagacccgg acgttatcat tacctacaat ggtgataact ttgatttgcc gtacatcatt   660
aagcgcgcag aaaaactggg tgtccgtctg ctgctgggtc gcgacaaaga cacccggag    720
cctaagatcc agcgtatggg tgatagcttc gcggtggaaa ttaagggtcg tatccacttt   780
gatctgttcc cggtcgttcg ccgcaccatc aatctgccga cgtacaccct ggaagcggtt   840
tacgagactg tgttgggtaa gcaaaaaact aaactgggcg ctgaagaaat cgccgccatt   900
tgggaaaccg aagagggcat gaagaaactg gcgcaatata gcatggaaga tgcgaaggct   960
acctatgaac tgggtcgtga gttcttcccg atggaagctg agctggcaaa ggttattggt   1020
cagagcgtct gggacgtttc tcgttctagc accggcaacc tggtcgagtg gtacatgctg   1080
cgtgtggcgt atgagcgtaa gaactggca ccgaataagc cgagcgacga agagtacaaa    1140
cgtcgtctgc gctccactta cttgggcggc tacgtaaaag aaccggagcg cggtctgtgg   1200
ggtaacattg tgtatctgga cttcgtagcc ttgtatccaa gcattatcgt gacgcacaac   1260
gttagcccga atacgttgga gcgcgagggc tgccaggact acgaggttgc cccaattgtg   1320
ggttaccgct tctgcaaaga ttttccaggt ttcatccctt cgattctgga gaatctgatc   1380
gaaacccgtc aagaggttaa gaaacgcatg aaaagcacca cggatccggt cgaacgtaaa   1440
atgctggact atcgtcagcg tgcgctgaaa atcttggcta attcctatta tggttaccag   1500
ggctacccga aagctcgttg gtatagcaaa gagtgtgctg agtccgtgac ggcgtggggc   1560
cgtcactaca ttgagatgag cattcgtgag atttggttt caaggttctg   1620
tatgccgaca ccgatggttt ttatgcgacc ctgccggtg aaacgccgga aacgattaag    1680
aaaaagcaa aagaatttct ggactatatc aactccaagt taccgggtct gcttgagctg   1740
gagtatgagg gcttttactt gcgtggtttc tttgtcacca aaaaacgcta cgcagtgatc   1800
gatgaagatg gtcgtattac cacccgcggc ctggaagtcg ttcgtcgtga ctggagcgaa   1860
atcgcaaaag aaaccaagc aaaagtcctg gaagcgatcc tgcgtgaggg ctccgttgag   1920
aaagccgtgg aaatcgttaa gagcgttggt gagcgcattg cgaagtataa agttccactg   1980
gagaaattgg tcattcacga gcaaattacg cgcgaactga aagattacaa ggcaatcggt   2040
ccacatgttg cgatcgcgaa gcgtctggca gccaaaggta tcaaggttaa accgggtacc   2100
attatctcat atattgtgct gaaaggcggc ggcaagatca gcgatcgtgt ggttctgctg   2160
accgagtatg atccgcgtaa gcacaaatac gatccggatt actatatcga gaatcaagtg   2220
ctgccggccg ttttgagaat tctggaagca tttggctaca aaaaagagga cctgaaatac   2280
cagcgtagca agcaaaccgg cttggaagct tggctgcgtc gctaatga                2328

SEQ ID NO: 17          moltype = DNA  length = 6285
FEATURE                Location/Qualifiers
misc_feature           1..6285
                       note = Synthetic construct
source                 1..6285
                       mol_type = other DNA
                       organism = synthetic construct
SEQUENCE: 17
cccgtagaaa agatcaaagg atcttcttga gatccttttt ttctgcgcgt aatctgctgc   60
ttgcaaacaa aaaaccacc gctaccagcg gtggtttgtt tgccggatca agagctacca   120
actctttttc cgaaggtaac tggcttcagc agagcgcaga taccaaatac tgttcttcta   180
gtgtagccgt agttagccca ccacttcaag aactctgtag caccgcctac atacctcgct   240
ctgctaatcc tgttaccagt ggctgctgcc agtggcgata gtcgtgtct taccgggttg   300
gactcaagac gatagttacc ggataaggcg cagcggtcgg gctgaacggg gggttcgtgc   360
acacagccca gcttggagcg aacgacctac accgaactga tacctaca gcgtgagcta    420
tgagaaagcg ccacgcttcc cgaagggaga aaggcggaca ggtatccggt aagcggcagg   480
gtcggaacag gagagcgcac gagggagctt ccaggggaa agccctggta tcttatagt    540
cctgtcgggt ttcgccacct ctgacttgag cgtcgatttt tgtgatgctc gtcagggggg   600
cggagcctat ggaaaaacgc cagcaacgcg gcctttttac ggttcctggc cttttgctgg   660
cctttgctc acatgttctt tcctgcgtta tcccctgatt ctgtggataa ccgtattacc   720
gcctttgagt gagctgatac cgctcgccgc agccgaacga ccgagcgcag cgagtcagtg   780
agcgaggaag cggaaggcga agcgagggcg tcaaactaag cagaaggccc   840
ctgacggatg cctttttgc gtttctacaa actctttctg tgttgtaaaa cgacggccag   900
tcttaagctc gggcccctg gcggttctg ataacgagta atcgttaatc cgcaaataac    960
gtaaaaaccc gcttcggcgg gtttttttat gggggagtt tagggaaaga gcatttgtca   1020
gaatatttaa gggcgcctgt cactttgctt gatatatgag aattatttaa ccttataaat   1080
gagaaaaaag caacgcactt taaataagat acgttgcttt ttcgattgat gaacacctat   1140
aattaaacta ttcatctatt attatgatt ttttgtatat acaatatttc tagtttgtta   1200
aagagaatta agaaataa tctcgaaaat aataagga aatcagttt ttgatatcaa       1260
aattatacat gtcaacgata tacaaaaata taatacaaac tataagatgt tatcagtatt   1320
tattatgcat ttagaataaa ttttgtgtcg cccttccgcg aaattaatac gactcactat   1380
aggggaattg tgagcggata caattcccc tctagaaata attttgttta actttttgag    1440
```

-continued

```
accttaagga ggtaaaaaat gattctgggc gccgactata tcaccaaaga cggtaaaccg  1500
attgttcgtc tgttcaaaaa agaaaatggt gagttcaaga tcgagctgga cccgcatttc  1560
cgtccgtaca tttacgcact cttgcgtgac gacagcgcga ttgaagaaat catgcagatc  1620
aaaggtgaac gccatggcaa gactgtccgc attgtcgatg cgatcaaggt caagaaaaag  1680
ttcctgcgtc gccctgtcga agtgtggaag ctgattttcg agcacccgca agacgtcccg  1740
gcaatgcgtg gcaagattcg cagccatccg gctgtggtcg atatttacga gtacgacatc  1800
ccgttcgcaa agcgctacct gattgacaag ggcctgatcc cgatggaggg tgaagaagat  1860
ctgaagctgt tagcctttga catcgaaacg ttctatcacg agggcgatga atttggtaaa  1920
ggtgagatta tcatgattag ctacgcggac gacgaagagg ccggtcgtgat cacctggaag  1980
cgcatcaatc tgccgtatgt tcatgttgtg tcgaatgaac gcgagatgat taagcgtttc  2040
gtgcaaatca tcaaagaaaa agacccggac gttatcatta cctacaatgg tgataacttt  2100
gatttgccgt acatcattaa gcgcgcagaa aaactgggtg tccgtctgct gctgggtcgc  2160
gacaaagaac acccggagcc taagatccag cgtatgggtg atagcttcgc ggtggaaatt  2220
aagggtcgta tccactttga tctgttcccg gtcgttcgcc gcaccatcga tctgccgacg  2280
tacaccctgg aagcggttta cgagactgtg ttgggtaagc aaaaaactaa actgggcgct  2340
gaagaaatcg ccgccatttg ggaaaccgaa gagggcatga agaaactggc gcaatatagc  2400
atggaagatg cgaaggctac ctatgaactg ggtcgtgagt tcttcccgat ggaagctgag  2460
ctggcaaagg ttattggtca gagcgtctgg gacgtttctc gttctagcac cggcaacctg  2520
gtcgagtggt acatgctgcg tgtgcgtat gagcgtaacg aactggcacc gaataagccg  2580
agcgacgaag agtacaaacg tcgtctgcgc tccacttact tgggcggcta cgtaaaagaa  2640
ccggagcgcg gtctgtgggg taacattgtg tatctggact ttcgtagctt gtatccaagc  2700
attatcgtga cgcacaacgt tagcccggat acgttggagc gcgaggggctg ccaggactac  2760
gaggttgccc caattgtggg ttaccgcttc tgcaaagatt ttccaggttt catcccttcg  2820
attctggaga atctgatcga aacccgtcaa gaggttaaga aacgcatgaa aagcaccacg  2880
gatccggtcg aacgtaaaat gctggactat cgtcagcgtg cgctgaaaat cttggctaat  2940
tcctattatg gttaccaggg ctacccgaaa gctcgttgt atagcaaaga gtgtgctgag  3000
tccgtgacgg cgtggggccg tcactacatt gagatgagca ttcgtgagat tgaagagaaa  3060
tttggtttca aggttctgta tgccgacacc gatggttttt atgcgaccct gccgggtgaa  3120
acgccggaaa cgattaagaa aaagcaaaa gaatttctgg actatatcaa ctccaagtta  3180
ccgggtctgc ttgagctgga gtatgagggc ttttacttgc gtggtttctt tgtcaccaaa  3240
aaacgctacg cagtgatcga tgaagatggt cgtattacca cccgcggcct ggaagtcgtt  3300
cgtcgtgact ggagcgaaat cgcaaaagaa acccaagcaa aagtcctgga agcgatcctg  3360
cgtgagggct ccgttgagaa agccgtgaaa atcgttaaga gcgtggtcga gcgcattgcg  3420
aagtataaag ttccactgga gaaattggtc attcacgagc aaattacgcg cgaactgaaa  3480
gattacaagg caatcggtcc acatgttgcg atcgcgaagc gtctggcagc caaaggtatc  3540
aaggttaaac cgggtaccat tatctcatat attgtgctga aaggcggcgg caagatcagc  3600
gatcgtgtgt tctgctgac cgagtatgat ccgcgtaagc acaaatacga tccggattac  3660
tatatcgaga atcaagtgct gccggccgtt ttgagaattc tggaagcatt tggctacaaa  3720
aaagagacc tgaaatacca gcgtagcaag caaaccggct tggaagcttg gctgcgtcgg  3780
taatgaggtt gaggtctcac cccctagcat aaccccttgg ggcctctaaa cgggtcttga  3840
gggggttttt gccccctgaga cgcgtcaatc gagttcgtac ctaagggcga cacccccctaa  3900
ttagcccggg cgaaaggccc agtctttcga ctgagccttt cgttttattt gatgcctggc  3960
agttccctac tctcgcatcg ggagtcccca cactaccatc gccgccaggc cgtttcactt  4020
ctgagttcgg catgggggtca ggtgggacca ccgcgctact gccgccaggc aaacaagggg  4080
tgttatgagc catattcagg tataaatggg ctcgcgataa tgttcagaat tggttaattg  4140
gttgtaacac tgaccctat ttgttttattt ttctaaatac attcaaatat gtatccgctc  4200
atgagacaat aaccctgata aatgcttcaa taatattgaa aaaggaagaa tatgagccat  4260
attcaacggg aaacgtcgag gccgcgatta aattccaaca tggatgctga tttatatggg  4320
tataaatggg ctcgcgataa tgtcgggcaa tcaggtgcga caatctatcg cttgtatggg  4380
aagcccgatg cgccagagtt gttctgaaa catggcaaag gtagcgttgc caatgatgtt  4440
acagatgaga tggtcagact aaactggctg acggaattta tgccacttcc gaccatcaaa  4500
catttatcc gtactcctga tgatgcatgg ttactcacca ctgcgatccc cggaaaaaca  4560
gcgttccagg tattagaaga atatcctgat tcaggtgaaa atattgttga tgcgctggca  4620
gtgttcctgc gccggttgca ctcgattcct gtttgtaatt gtccttttaa cagcgatcgc  4680
gtatttcgcc tcgctcaggc gcaatcacga atgaataacg gtttggttga tgcgagtgat  4740
tttgatgacg agcgtaatgg ctggcctgtt gaacaagtct ggaaagaaat gcataaactt  4800
ttgccattct caccggattc agtcgtcact catggtgatt tctcacttga taaccttatt  4860
tttgacgagg ggaaattaat aggttgtatt gatgttggac gagtcggaat cgcagaccga  4920
taccaggatc ttgccatcct atggaactgc ctcggtgagt tttctccttc attacagaaa  4980
cggcttttc aaaaatatgg tattgataat cctgatatga ataaattgca gtttcatttg  5040
atgctcgatg agtttttcta gcggcgcgc catcgaatgg cgcaaaacct ttcgcggtat  5100
ggcatgatag cgcccggaag agagtcaatt cagggtggtg aatatgaaac cagtaacgtt  5160
atacgatgtc gcagagtatg ccggtgtctc ttatcagacc gtttcccgcg tggtgaacca  5220
ggccagccac gtttctgcga aaacgcggga aaaagtggaa gcggcgatgg cggagctgaa  5280
ttacattccc aaccgcgtgg cacaacaact ggcgggcaaa cagtcgttgc tgattggcgt  5340
tgccacctcc agtctggccc tgcacgcgcc gtcgcaaatt gtcgcggcga ttaaatctcg  5400
cgccgatcaa ctgggtgcca gcgtggtggt gtcgatggta gaacgaagcg cgtcgaagc  5460
ctgtaaagcg gcggtgcaca atcttctcgc gcaacgcgtc agtgggctga tcattaacta  5520
tccgctggat gaccaggatg ccattgctgt ggaagctgcc tgcactaatg ttccggcgtt  5580
atttcttgat gtctctgacc agacacccat caacagtatt attttctccc atgaggacgg  5640
tacgcgactg ggcgtggagc atctggtcgc attgggtcac cagcaaatcg cgctgttagc  5700
gggcccatta agttctgtct cggcgcgtct gcgtctggct ggctggcata atatctcac  5760
tcgcaatcaa attcagccga tagcggaacg ggaaggcgac tggagtgcca tgtccggttt  5820
tcaacaaacc atgcaaatgc tgaatgaggg catcgttccc actgcgatgc tggttgccaa  5880
cgatcagatg gcgctgggcg caatgcgcgc cattaccgag tccgggctgc gcgttggtgc  5940
ggatatctcg gtagtgggat acgacgtac cgaagatagc tcatgttata tcccgccgtt  6000
aaccaccatc aaacaggatt ttcgcctgct ggggcaaacc agcgtggacc gcttgctgca  6060
actctctcag ggccaggcgg tgaagggcaa tcagctgttg ccagtctcac tggtgaaaag  6120
aaaaaccacc ctggcgccca atacgcaaac cgcctctccc cgcgcgttgg ccgattcatt  6180
```

```
aatgcagctg gcacgacagg tttcccgact ggaaagcggg cagtgactca tgaccaaaat   6240
cccttaacgt gagttacgcg cgcgtcgttc cactgagcgt cagac                   6285

SEQ ID NO: 18          moltype = AA   length = 774
FEATURE                Location/Qualifiers
source                 1..774
                       mol_type = protein
                       organism = Thermococcus sp.
SEQUENCE: 18
MILGADYITK DGKPIVRLFK KENGEFKIEL DPHFRPYIYA LLRDDSAIEE IMQIKGERHG    60
KTVRIVDAIK VKKKFLRRPV EVWKLIFEHP QDVPAMRGKI RSHPAVVDIY EYDIPFAKRY   120
LIDKGLIPAE GEEDLKLLAF AIATFYHEGD EFGKGEIIMI SYADDEEAGV ITWKRINLPY   180
VHVVSNEREM IKRFVQIIKE KDPDVIITYN GDNFDLPYII KRAEKLGVRL LLGRDKEHPE   240
PKIQRMGDSF AVEIKGRIHF DLFPVVRRTI NLPTYTLEAV YETVLGKQKT KLGAEEIAAI   300
WETEEGMKKL AQYSMEDAKA TYELGREFFP MEAELAKVIG QSVWDVSRSS TGNLVEWYML   360
RVAYERNELA PNKPSDEEYK RRLRSTYLGG YVKEPERGLW GNIVYLDFRS AGPSIIVTHN   420
VSPDTLEREG CQDYEVAPIV GYRFCKDFPG FIPSILENLI ETRQEVKKRM KSTTDPVERK   480
MLDYRQRVLK ILANSYYGYQ GYPKARWYSK ECAESVTAWG RHYIEMSIRE IEEKFGFKVL   540
YADTDGFYAT LPGETPETIK KKAKEFLDYI NSKLPGLLEL EYEGFYLRGF FVTKKRYAVI   600
DEDGRITTRG LEVVRRDWSE IAKETQAKVL EAILREGSVE KAVEIVKSVV ERIAKYKVPL   660
EKLVIHEQIT RELKDYKAIG PHVAIAKRLA AKGIKVKPGT IISYIVLKGG GKISDRVVLL   720
TEYDPRKHKY DPDYYIENQV LPAVLRILEA FGYKKEDLKY QRSKQTGLEA WLRR         774

SEQ ID NO: 19          moltype = DNA   length = 43
FEATURE                Location/Qualifiers
misc_feature           1..43
                       note = Synthetic construct
misc_difference        43
                       note = Dideoxycytidine (ddC)
source                 1..43
                       mol_type = other DNA
                       organism = synthetic construct
SEQUENCE: 19
cgtacggcta cggctacggc tacggctacg gctacggcta cgc                      43

SEQ ID NO: 20          moltype = DNA   length = 43
FEATURE                Location/Qualifiers
misc_feature           1..43
                       note = Synthetic construct
misc_difference        43
                       note = Dideoxycytidine (ddC)
source                 1..43
                       mol_type = other DNA
                       organism = synthetic construct
SEQUENCE: 20
cgtagccgta gccgtagccg tagccgtagc cgtagccgta gcc                      43
```

MODIFIED *THERMOCOCCUS* POLYMERASES

CROSS-REFERENCES TO RELATED APPLICATIONS

This application claims the benefit of U.S. Provisional Application No. 62/899,644, filed Sep. 12, 2019, which is incorporated herein by reference in its entirety and for all purposes.

SEQUENCE LISTING

The instant application contains a Sequence Listing which has been submitted electronically in ASCII format and is hereby incorporated by reference in its entirety. Said ASCII copy, created on Sep. 8, 2020, is named 051385-512001US_SL.txt and is 84.9 kilobytes in size.

BACKGROUND

The present disclosure generally relates to modified polymerase enzymes that exhibit improved incorporation of nucleotide analogues utilized in DNA sequencing.

DNA-polymerases add nucleotide triphosphate (dNTP) residues to the 3'-end of the growing DNA chain, using a complementary DNA as template. Three motifs, A, B and C, are seen to be conserved across all DNA-polymerases. Initial experiments with native DNA polymerases revealed difficulties incorporating modified nucleotides. There are several examples in which DNA polymerases have been modified to increase the rates of incorporation of nucleotide analogues. For example, as described in WO 2005/024010, modification to the amino acids at positions 408, 409, 410 of a 9°N polymerase modifies the ability of polymerases to incorporate nucleotide analogues having a substituent at the 3' position which is larger than a hydroxyl group (i.e., a reversible terminator).

Despite ongoing research, current modifications to the DNA polymerase still do not show sufficiently high incorporation rates of modified nucleotides. In nucleic acid sequencing applications, the modified nucleotide typically has a reversible terminator at the 3' position and a modified base (e.g., a base linked to a fluorophore via a cleavable linker). In case of cleavable linkers attached to the base, there is usually a residual spacer arm left after the cleavage. This residual modification may interfere with incorporation of subsequent nucleotides by polymerase. Therefore, it is highly desirable to have polymerases for carrying out sequencing by synthesis process (SBS) that are tolerable of these scars. In addition to rapid incorporation, the enzyme needs to be stable and have high incorporation fidelity. Balancing incorporation kinetics and fidelity can be a challenge. If the mutations in the polymerase result in a rapid average incorporation half time but is too promiscuous such that the inappropriate nucleotide is incorporated into the primer, this will result in a large source of error in sequencing applications. It is also desirable to design a polymerase capable to incorporating a variety of reversible terminators. Discovering a polymerase that has suitable kinetics and low misincorporation error remains a challenge. Disclosed herein, inter alia, are solutions to these and other problems in the art.

BRIEF SUMMARY

Provided herein are modified Archaeal family B polymerases and methods of using the same. In an aspect, provided herein are modified Archaeal family B polymerases derived from the Archaeal microorganism *Thermococcus* sp. EP1.

In an aspect, a modified *Thermococcus* sp. EP1 polymerase is provided. In an aspect is provided a polymerase including an amino acid sequence that is at least 80% identical to SEQ ID NO: 1; including the following amino acids: an alanine or serine at amino acid position 411 or an amino acid functionally equivalent to amino acid position 411; a glycine or alanine at amino acid position 412 or an amino acid functionally equivalent to amino acid position 412; and a proline, valine, or isoleucine at amino acid position 413 or an amino acid functionally equivalent to amino acid position 413.

In an aspect is provided a method of incorporating a modified nucleotide into a nucleic acid sequence including allowing the following components to interact: (i) a nucleic acid template, (ii) a nucleotide solution, and (iii) a polymerase, wherein the polymerase is a polymerase as described herein, including embodiments.

In an aspect is provided a method of sequencing a nucleic acid sequence including: a. hybridizing a nucleic acid template with a primer to form a primer-template hybridization complex; b. contacting the primer-template hybridization complex with a DNA polymerase and nucleotides, wherein the DNA polymerase is a polymerase of claim 1 and the nucleotides include a modified nucleotide, wherein the modified nucleotide includes a detectable label; c. subjecting the primer-template hybridization complex to conditions which enable the polymerase to incorporate the modified nucleotide into the primer-template hybridization complex to form a modified primer-template hybridization complex; and d. detecting the detectable label; thereby sequencing the nucleic acid sequence.

Provided herein are methods of using modified Archaeal family B polymerases for improved incorporation of modified nucleotides into a nucleic acid sequence.

BRIEF DESCRIPTION OF THE DRAWINGS

FIGS. 1A-1C depict a sequence alignment of DNA polymerase from *Thermococcus* sp. 9°N-7 e.g., "Therminator™ DNA polymerase" (New England Biolabs) and Pol812. All variations from the wild-type sequence are shown in boldface and underlined.

Figure 2C:
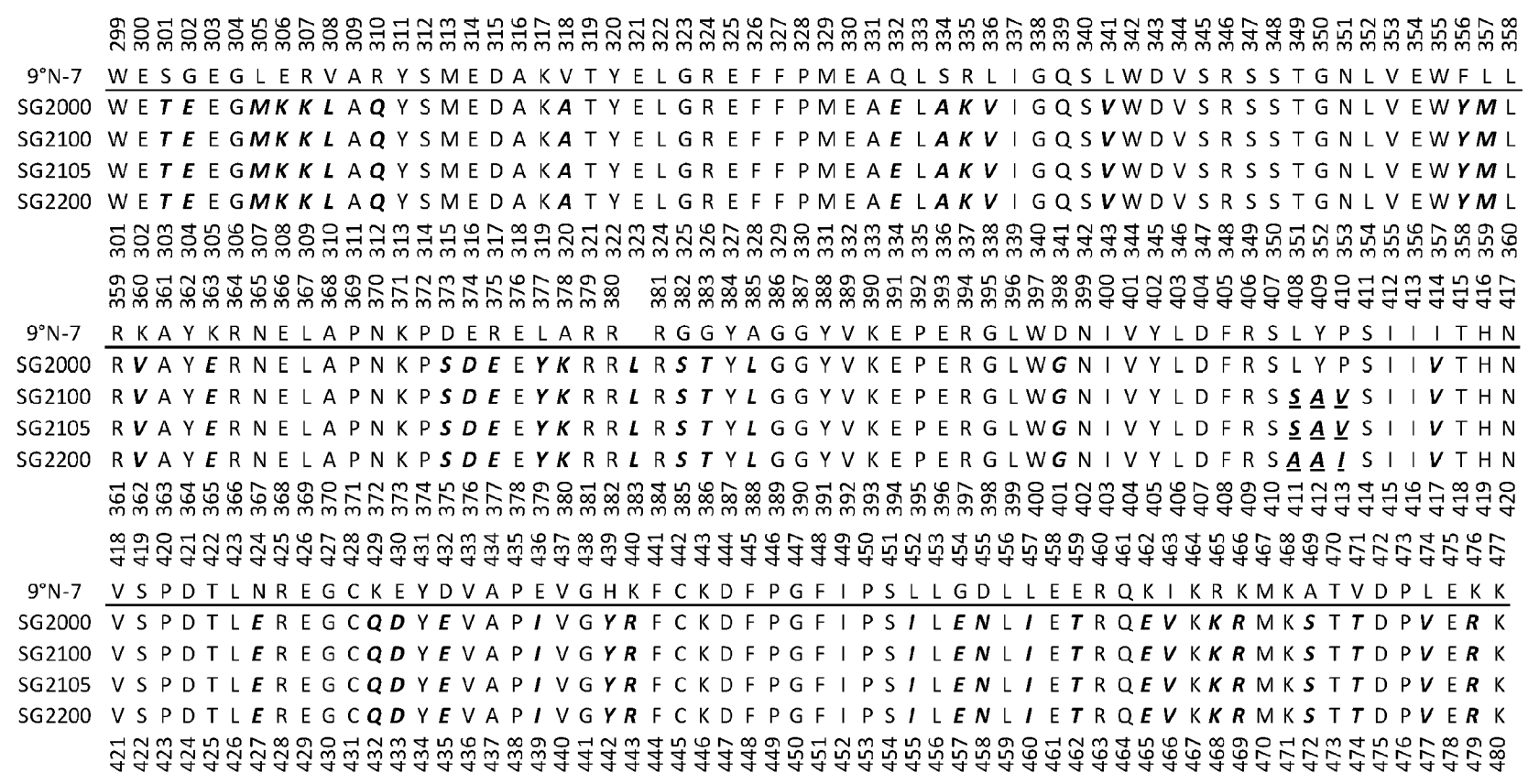
Figure 2D:
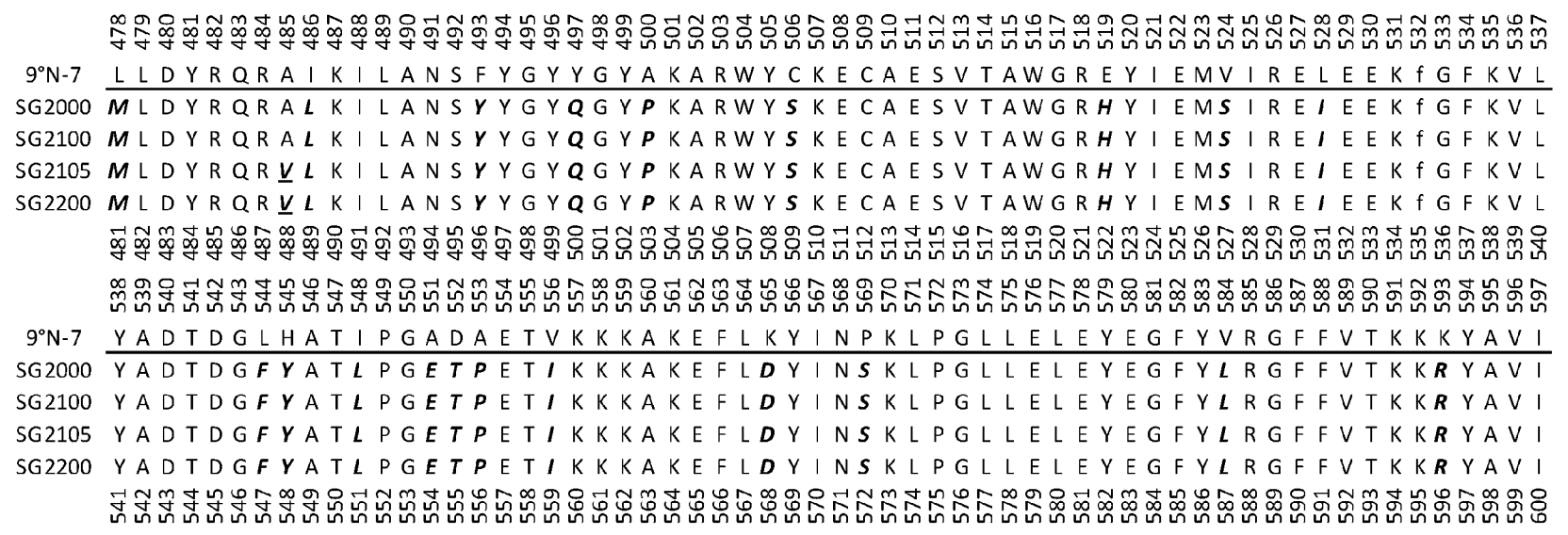
Figure 2E:
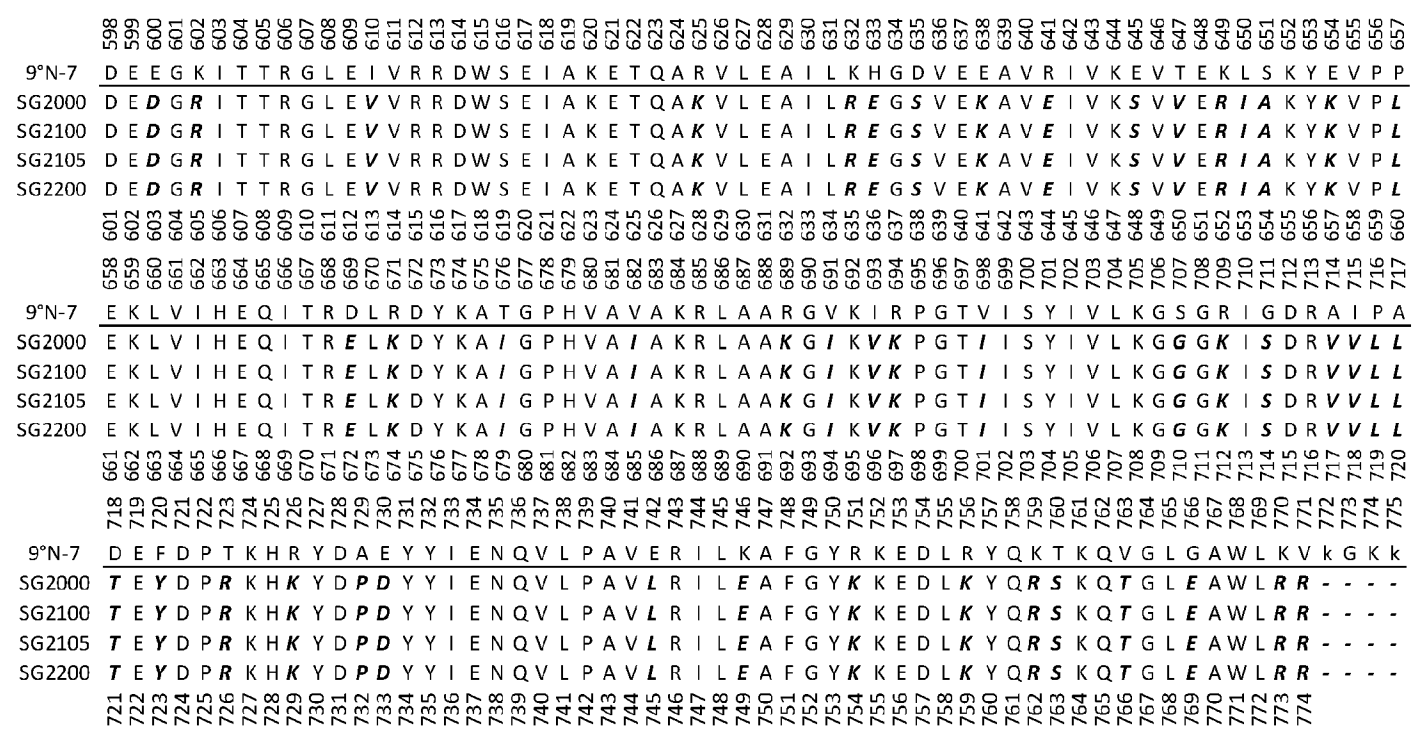

FIGS. 2A-2E provide a sequence alignment of the DNA polymerase from *Thermococcus* sp. 9°N-7 (GenBank AAA88769.1) with that of *Thermococcus* sp. EP1 (TspEP1) (GenBank WP_055286465.1). All differences between the 9°N-7 and that of TspEP1 are shown in italic boldface. Numbers at the top refer to the 9°N-7 sequence; numbers at the bottom refer to the TspEP1 sequence. Non-limiting examples of positions where mutations may be introduced into the wild type sequence (SEQ ID NO:1) to improve activity with modified are underlined. For example, these positions include 129, 141, 143, 411, 412, 413, 488 (relative to SEQ ID NO:1).

Figure 3B:
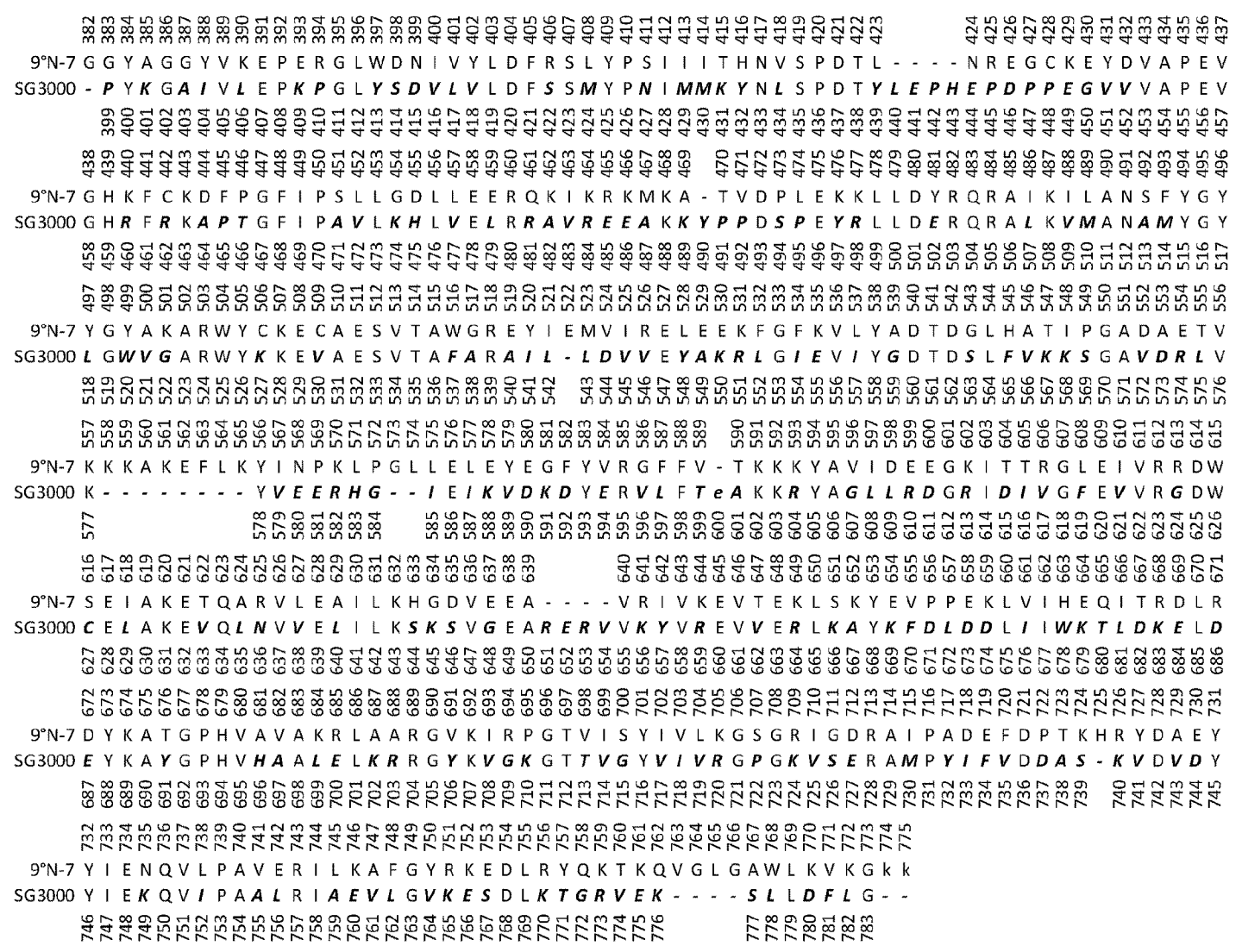

FIGS. 3A-3B provide a sequence Alignment of the DNA polymerase from *Thermococcus* sp. 9°N-7 (GenBank AAA88769.1) with that of *Pyrobaculum calidifontis* JCM 11548 (Pca) (GenBank ABO08474.1). All differences between the 9°N-7 and that of Pca are shown in italic boldface. Numbers at the top refer to the 9°N-7 sequence; numbers at the bottom refer to the Pca sequence. The purified Pca protein exhibited less than 5% specific activities for both DNA polymerase and exonuclease activities compared with 9°N-7 polymerase.

DETAILED DESCRIPTION

Provided herein, are, for example, family B polymerases derived from Archaea modified for improved incorporation of modified nucleotides into a nucleic acid sequence and methods of using the same.

I. Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein might be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

As used herein, the singular forms "a", "an", and "the" include plural references unless the context clearly dictates otherwise.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like. Different polynucleotides may have different three-dimensional structures, and may perform various functions, known or unknown.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms "monophosphate" is used in accordance with its ordinary meaning in the arts and refers to a moiety having the formula:

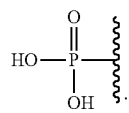

The term "polyphosphate" refers to at least two phosphate groups, having the formula:

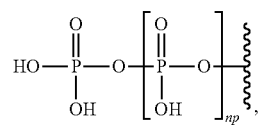

wherein np is an integer of 1 or greater and includes "diphosphate" and "triphosphate" with np=1 or 2 respectively. In embodiments, np is an integer from 0 to 5. In embodiments, np is an integer from 0 to 2. In embodiments, np is 2.

The term "base" as used herein refers to a purine or pyrimidine compound or a derivative thereof, that may be a constituent of nucleic acid (i.e. DNA or RNA, or a derivative thereof). In embodiments, the base is a derivative of a naturally occurring DNA or RNA base (e.g., a base analogue). In embodiments, the base is a base-pairing base. In embodiments, the base pairs to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), guanosine or a derivative thereof (e.g., 7-methylguanosine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is thymine, cytosine, uracil, adenine, guanine, hypoxanthine, xanthine, theobromine, caffeine, uric acid, or isoguanine. In embodiments, the base is

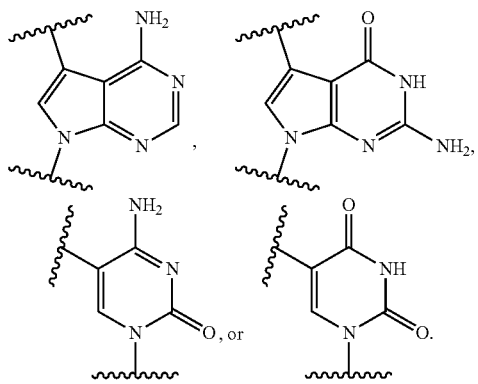

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "isolated", when applied to a nucleic acid or protein, denotes that the nucleic acid or protein is essentially free of other cellular components with which it is associated in the natural state. It can be, for example, in a homogeneous state and may be in either a dry or an aqueous solution. Purity and homogeneity are typically determined using analytical chemistry techniques such as polyacrylamide gel electrophoresis or high-performance liquid chromatography. A protein that is the predominant species present in a preparation is substantially purified.

The term "analogue", in reference to a chemical compound, refers to compound having a structure similar to that of another one, but differing from it in respect of one or more different atoms, functional groups, or substructures that are replaced with one or more other atoms, functional groups, or substructures. In the context of a nucleotide useful in practicing the invention, a nucleotide analog refers to a compound that, like the nucleotide of which it is an analog, can be incorporated into a nucleic acid molecule (e.g., an extension product) by a suitable polymerase, for example, a DNA polymerase in the context of a dNTP analogue. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; nonionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleoside of adenosine is thymidine and the complementary (matching) nucleoside of guanosine is cytidine. Thus, a complement may include a sequence of nucleotides that base pair with corresponding complementary nucleotides of a second nucleic acid sequence. The nucleotides of a complement may match, partially or completely, the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence, only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other may have a specified percentage of nucleotides that are complementary (i.e., about 60% identity, preferably 65%, 70%, 75%, 80%, 85%, 90%, 91%, 92%, 93%, 94%, 95%, 96%, 97%, 98%, 99%, or higher complementarity over a specified region).

"DNA" refers to deoxyribonucleic acid, a polymer of deoxyribonucleotides (e.g., dATP, dCTP, dGTP, dTTP, dUTP, etc.) linked by phosphodiester bonds. DNA can be single-stranded (ssDNA) or double-stranded (dsDNA), and can include both single and double-stranded (or "duplex") regions. "RNA" refers to ribonucleic acid, a polymer of ribonucleotides linked by phosphodiester bonds. RNA can be single-stranded (ssRNA) or double-stranded (dsRNA), and can include both single and double-stranded (or "duplex") regions. Single-stranded DNA (or regions thereof) and ssRNA can, if sufficiently complementary, hybridize to form double-stranded DNA/RNA complexes (or regions).

The term "DNA primer" refers to any DNA molecule that may hybridize to a DNA template and be bound by a DNA polymerase and extended in a template-directed process for nucleic acid synthesis.

The term "DNA template" refers to any DNA molecule that may be bound by a DNA polymerase and utilized as a template for nucleic acid synthesis.

The term "dATP analogue" refers to an analogue of deoxyadenosine triphosphate (dATP) that is a substrate for a DNA polymerase. The term "dCTP analogue" refers to an analogue of deoxycytidine triphosphate (dCTP) that is a substrate for a DNA polymerase. The term "dGTP analogue" refers to an analogue of deoxyguanosine triphosphate (dGTP) that is a substrate for a DNA polymerase. The term "dNTP analogue" refers to an analogue of deoxynucleoside triphosphate (dNTP) that is a substrate for a DNA polymerase. The term "dTTP analogue" refers to an analogue of deoxythymidine triphosphate (dUTP) that is a substrate for a DNA polymerase. The term "dUTP analogue" refers to an analogue of deoxyuridine triphosphate (dUTP) that is a substrate for a DNA polymerase.

The term "extendible" means, in the context of a nucleotide, primer, or extension product, that the 3'-OH group of the particular molecule is available and accessible to a DNA polymerase for extension or addition of nucleotides derived from dNTPs or dNTP analogues.

The term "modified nucleotide" refers to nucleotide modified in some manner. Typically, a nucleotide contains a single 5-carbon sugar moiety, a single nitrogenous base moiety and 1 to three phosphate moieties. In particular embodiments, a nucleotide can include a blocking moiety or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both.

A "removable" group, e.g., a label or a blocking group or protecting group, refers to a chemical group that can be removed from a dNTP analogue such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that the entire removable group be removed, only that a sufficient portion of it be removed such that a DNA polymerase can extend a nucleic acid by incorporation of at least one additional nucleotide using a dNTP of dNTP analogue.

"Reversible blocking groups" or "reversible terminators" include a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Suitable nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabelled. They may be modified with reversible terminators useful in methods provided herein and may be 3'-O-blocked reversible or 3'-unblocked reversible terminators. In nucleotides with 3'-O-blocked reversible terminators, the blocking group —OR [reversible terminating (capping) group] is linked to the oxygen atom of the 3'-OH of the pentose, while the label is linked to the base, which acts as a reporter and can be cleaved. The 3'-O-blocked reversible terminators are known in the art, and may be, for instance, a 3'-$ONH_2$ reversible terminator, a 3'-O-allyl reversible terminator, or a 3'-O-azidomethy reversible terminator.

3'-O-blocked reversible terminator

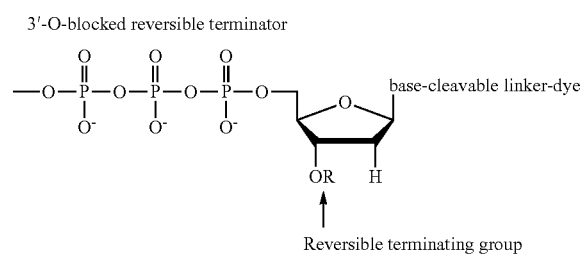

Reversible terminating group

In embodiments, provided herein are polymerases capable of incorporating differently sized reversible terminator probes linked to the 3' oxygen: e.g., an A-Term, S-Term, and i-term. A-Term refers to azide-containing terminators (Guo J, et al. PNAS 2008); for example having the formula:

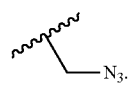

S-Term refers to sulfide-containing terminators (WO 2017/058953); for example having the formula

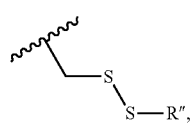

wherein R" is unsubstituted $C_1$-$C_4$ alkyl. The i-Term probe refers to an isomeric reversible terminator For example, an i-term probe has the formula:

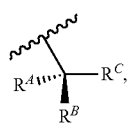

wherein $R^A$ and $R^B$ are hydrogen or alkyl, wherein at least one of $R^A$ or $R^B$ are hydrogen to yield a stereoisomeric probe, and $R^C$ is the remainder of the reversible terminator. In embodiments, the nucleotide is

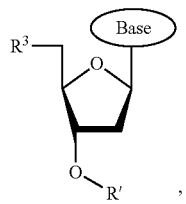

wherein Base is a Base as described herein, $R^3$ is —OH, monophosphate, or polyphosphate or a nucleic acid, and R' is a reversible terminator having the formula:

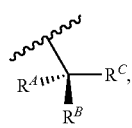

wherein $R^A$ and $R^B$ are hydrogen or alkyl and $R^C$ is the remainder of the reversible terminator. In embodiments, the reversible terminator is

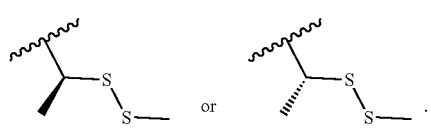

In embodiments, the reversible terminator is

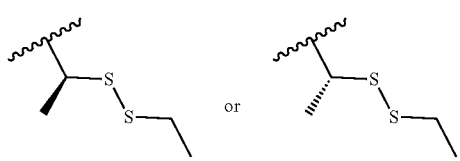

In embodiments, the reversible terminator is

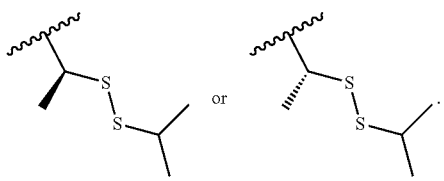

In embodiments, the reversible terminator is

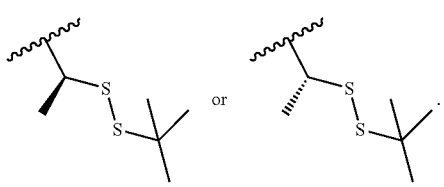

In embodiments, the reversible terminator is

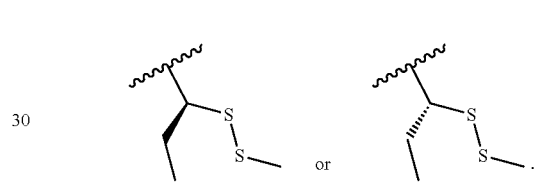

In embodiments, the reversible terminator is

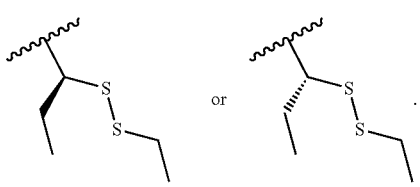

In embodiments, the reversible terminator is

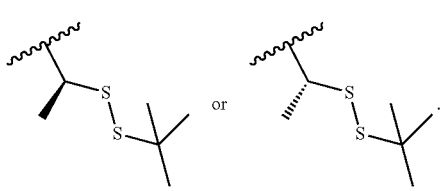

In embodiments, the reversible terminator is

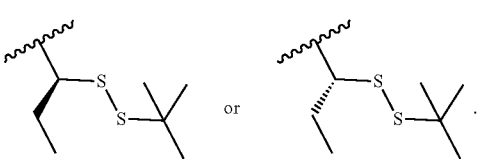

In embodiments, the reversible terminator is

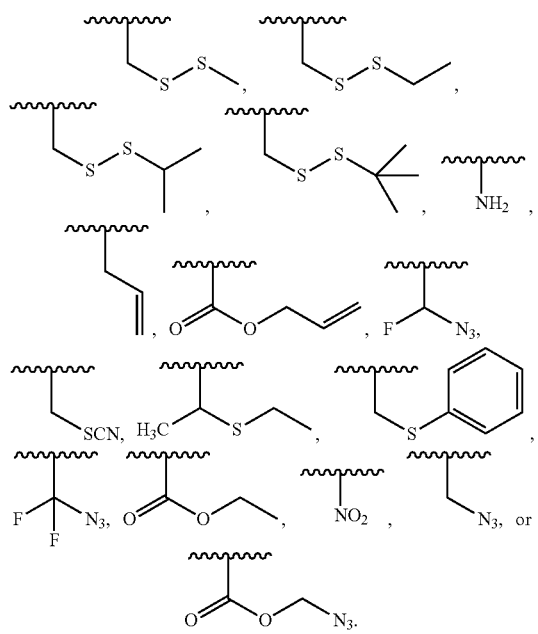

In nucleotides with 3'-unblocked reversible terminators, the termination group is linked to the base of the nucleotide as well as the label and functions not only as a reporter by as part of the reversible terminating group for termination of primer extension during sequencing. The 3'-unblocked reversible terminators are known in the art and include for example, the "virtual terminator" as described in U.S. Pat. No. 8,114,973 and the "Lightening terminator" as described in U.S. Pat. No. 10,041,115, the contents of which are incorporated herein by reference in their entirety.

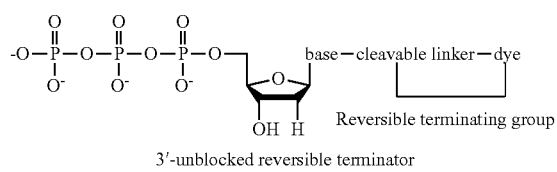

3'-unblocked reversible terminator

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers thereof, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, CH$_3$, —O—CH$_2$—CH$_3$, and —CN. Two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NR'R", —OR', —SR', and/or —SO₂R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

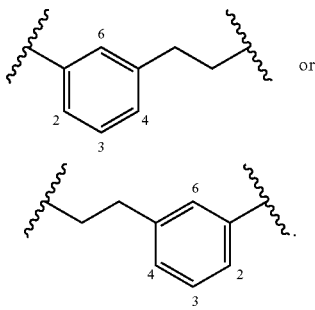

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), and silicon (Si).

The term "non-covalent linker" is used in accordance with its ordinary meaning and refers to a divalent moiety which includes at least two molecules that are not covalently linked to each other but are capable of interacting with each other via a non-covalent bond (e.g. electrostatic interactions (e.g. ionic bond, hydrogen bond, halogen bond) or van der Waals interactions (e.g. dipole-dipole, dipole-induced dipole, London dispersion). In embodiments, the non-covalent linker is the result of two molecules that are not covalently linked to each other that interact with each other via a non-covalent bond.

The term "anchor moiety" as used herein refers to a chemical moiety capable of interacting (e.g., covalently or non-covalently) with a second, optionally different, chemical moiety (e.g., complementary anchor moiety binder). In embodiments, the anchor moiety is a bioconjugate reactive group capable of interacting (e.g., covalently) with a complementary bioconjugate reactive group (e.g., complementary anchor moiety reactive group). In embodiments, an anchor moiety is a click chemistry reactant moiety. In embodiments, the anchor moiety (an "affinity anchor moiety") is capable of non-covalently interacting with a second chemical moiety (e.g., complementary affinity anchor moiety binder). Non-limiting examples of an anchor moiety include biotin, azide, trans-cyclooctene (TCO) and phenyl boric acid (PBA). In embodiments, an affinity anchor moiety (e.g., biotin moiety) interacts non-covalently with a complementary affinity anchor moiety binder (e.g., streptavidin moiety). In embodiments, an anchor moiety (e.g., azide moiety, trans-cyclooctene (TCO) moiety, phenyl boric acid (PBA) moiety) covalently binds a complementary anchor moiety binder (e.g., dibenzocyclooctyne (DBCO) moiety, tetrazine (TZ) moiety, salicylhydroxamic acid (SHA) moiety).

The terms "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(O), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is sodium dithionite ($Na_2S_2O_4$), weak acid, hydrazine ($N_2H_4$), Pd(O), or light-irradiation (e.g., ultraviolet radiation).

A photocleavable linker (e.g., including or consisting of a o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of an reducing agent (e.g., Tris(3-hydroxypropyl)phosphine). In embodiments, the cleavable linker is a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

The term "orthogonally cleavable linker" or "orthogonal cleavable linker" as used herein refer to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent. In embodiments, an orthogonally is a cleavable linker that following cleavage the two separated entities (e.g., fluorescent dye, bioconjugate reactive group) do not further react and form a new orthogonally cleavable linker.

The term "orthogonal binding group" or "orthogonal binding molecule" as used herein refer to a binding group (e.g. anchor moiety or complementary anchor moiety binder) that is capable of binding a first complementary binding group (e.g., complementary anchor moiety binder or anchor moiety) in a mixture of two or more different complementary binding groups and is unable to bind any other different complementary binding group in the mixture of two or more complementary binding groups. For example, two different binding groups are both orthogonal binding groups when a mixture of the two different binding groups are reacted with two complementary binding groups and each binding group binds only one of the complementary binding groups and not the other complementary binding group. An example of a set of four orthogonal binding groups and a set of orthogonal complementary binding groups are the binding groups biotin, azide, trans-cyclooctene (TCO) and phenyl boric acid (PBA), which specifically and efficiently bind or react with the complementary binding groups streptavidin, dibenzocyclooctyne (DBCO), tetrazine (TZ) and salicylhydroxamic acid (SHA) respectively.

The term "orthogonal detectable label" or "orthogonal detectable moiety" as used herein refer to a detectable label (e.g. fluorescent dye or detectable dye) that is capable of being detected and identified (e.g., by use of a detection means (e.g., emission wavelength, physical characteristic measurement)) in a mixture or a panel (collection of separate samples) of two or more different detectable labels. For example, two different detectable labels that are fluorescent dyes are both orthogonal detectable labels when a panel of the two different fluorescent dyes is subjected to a wavelength of light that is absorbed by one fluorescent dye but not the other and results in emission of light from the fluorescent dye that absorbed the light but not the other fluorescent dye. Orthogonal detectable labels may be separately identified by different absorbance or emission intensities of the orthogonal detectable labels compared to each other and not only be the absolute presence of absence of a signal. An example of a set of four orthogonal detectable labels is the set of Rox-Labeled Tetrazine, Alexa488-Labeled SHA, Cy5-Labeled Streptavidin, and R6G-Labeled Dibenzocyclooctyne.

The term "polymerase-compatible cleavable moiety" as used herein refers a cleavable moiety which does not interfere with the function of a polymerase (e.g., DNA polymerase, modified DNA polymerase). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible cleavable moiety includes an azido moiety or a dithiol linking moiety. In embodiments, the polymerase-compatible cleavable moiety is —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, the polymerase-compatible cleavable moiety comprises a disulfide moiety.

The term "allyl" as described herein refers to an unsubstituted methylene attached to a vinyl group (i.e. —CH=CH$_2$), having the formula

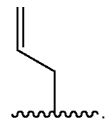 [SMILES: *CC=C]

An "allyl linker" refers to a divalent unsubstituted methylene attached to a vinyl group, having the formula

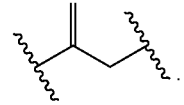 [SMILES: *CC(*)=C]

A "detectable agent" or "detectable compound" or "detectable label" or "detectable moiety" is a composition detectable by spectroscopic, photochemical, biochemical, immunochemical, chemical, magnetic resonance imaging, or other physical means. For example, detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lb, $^{177}$Lb, $^{186}$Re, $^{188}$Re, $^{189}$Re, $^{194}$Ir, $^{198}$Au, $^{199}$Ab, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), modified oligonucleotides (e.g., moieties described in PCT/US2015/022063, which is incorporated herein by reference), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lb, $^{177}$Lb, $^{186}$Re, $^{188}$Re, $^{189}$Re, $^{194}$Ir, $^{198}$Au, $^{199}$Ab, $^{211}$At, $^{211}$Pb, $^{212}$Bi, $^{212}$Pb, $^{213}$Bi, $^{223}$Ra, $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Examples of detectable agents include imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescein isothiocyanate moiety, tetramethylrhodamine-5-(and 6)-isothiocyanate moiety, Cy2 moeity, Cy3 moiety, Cy5 moiety, Cy7 moiety, 4',6-diamidino-2-phenylindole moiety, Hoechst 33258 moiety, Hoechst 33342 moiety, Hoechst 34580 moiety, propidium-iodide moiety, or acridine orange moiety. In embodiments, the detectable moiety is a Indo-1, Ca saturated moiety, Indo-1 Ca2+ moiety, Cascade Blue BSA pH 7.0 moiety, Cascade Blue moiety, LysoTracker Blue moiety, Alexa 405 moiety, LysoSensor Blue pH 5.0 moiety, LysoSensor Blue moiety, DyLight 405 moiety, DyLight 350 moiety, BFP (Blue Fluorescent Protein) moiety, Alexa 350 moiety, 7-Amino-4-methylcoumarin pH 7.0 moiety, Amino Coumarin moiety, AMCA conjugate moiety, Coumarin moiety, 7-Hydroxy-4-methylcoumarin moiety, 7-Hydroxy-4-methylcoumarin pH 9.0 moiety, 6,8-Difluoro-7-hydroxy-4-methylcoumarin pH 9.0 moiety, Hoechst 33342 moiety, Pacific Blue moiety, Hoechst 33258 moiety, Hoechst 33258-DNA moiety, Pacific Blue antibody conjugate pH 8.0 moiety, PO-PRO-1 moiety, PO-PRO-1-DNA moiety, POPO-1 moiety, POPO-1-DNA moiety, DAPI-DNA moiety, DAPI moiety, Marina Blue moiety, SYTOX Blue-DNA moiety, CFP (Cyan Fluorescent Protein) moiety, eCFP (Enhanced Cyan Fluorescent Protein) moiety, 1-Anilinonaphthalene-8-sulfonic acid (1,8-ANS) moiety, Indo-1, Ca free moiety, 1,8-ANS (1-Anilinonaphthalene-8-sulfonic acid) moiety, BO-PRO-1-DNA moiety, BOPRO-1 moiety, BOBO-1-DNA moiety, SYTO 45-DNA moiety, evoglow-Pp1 moiety, evoglow-Bs1 moiety, evoglow-Bs2 moiety, Auramine O moiety, DiO moiety, LysoSensor Green pH 5.0 moiety, Cy 2 moiety, LysoSensor Green moiety, Fura-2, high Ca moiety, Fura-2 Ca2+sup> moiety, SYTO 13-DNA moiety, YO-PRO-1-DNA moiety, YOYO-1-DNA moiety, eGFP (Enhanced Green Fluorescent Protein) moiety, LysoTracker Green moiety, GFP (S65T) moiety, BODIPY FL, MeOH moiety, Sapphire moiety, BODIPY FL conjugate moiety, MitoTracker Green moiety, MitoTracker Green F M, MeOH moiety, Fluorescein 0.1 M NaOH moiety, Calcein pH 9.0 moiety, Fluorescein pH 9.0 moiety, Calcein moiety, Fura-2, no Ca moiety, Fluo-4 moiety, FDA moiety, DTAF moiety, Fluorescein moiety, CFDA moiety, FITC moiety, Alexa Fluor 488 hydrazide-water moiety, DyLight 488 moiety, 5-FAM pH 9.0 moiety, Alexa 488 moiety, Rhodamine 110 moiety, Rhodamine 110 pH 7.0 moiety, Acridine Orange moiety, BCECF pH 5.5 moiety, PicoGreendsDNA quantitation reagent moiety, SYBR Green I moiety, Rhodaminen Green pH 7.0 moiety, CyQUANT GR-DNA moiety, NeuroTrace 500/525, green fluorescent Nissl stain-RNA moiety, DansylCadaverine moiety, Fluoro-Emerald moiety, Nissl moiety, Fluorescein dextran pH 8.0 moiety, Rhodamine Green moiety, 5-(and-6)-Carboxy-2',7'-dichlorofluorescein pH 9.0 moiety, DansylCadaverine, MeOH moiety, eYFP (Enhanced Yellow Fluorescent Protein) moiety, Oregon Green 488 moiety, Fluo-3 moiety, BCECF pH 9.0 moiety, SBFI-Na+ moiety, Fluo-3 Ca2+ moiety, Rhodamine 123 MeOH moiety, FlAsH moiety, Calcium Green-1 Ca2+ moiety, Magnesium Green moiety, DM-NERF pH 4.0 moiety, Calcium Green moiety, Citrine moiety, LysoSensor Yellow pH 9.0 moiety, TO-PRO-1-DNA moiety, Magnesium Green Mg2+ moiety, Sodium Green Na+ moiety, TOTO-1-DNA moiety, Oregon Green 514 moiety, Oregon Green 514 antibody conjugate pH 8.0 moiety, NBD-X moiety, DM-NERF pH 7.0 moiety, NBD-X, MeOH moiety, CI-NERF pH 6.0 moiety, Alexa 430 moiety, CI-NERF pH 2.5 moiety, Lucifer Yellow, CH moiety, LysoSensor Yellow pH 3.0 moiety, 6-TET, SE pH 9.0 moiety, Eosin antibody conjugate pH 8.0 moiety, Eosin moiety, 6-Carboxyrhodamine 6G pH 7.0 moiety, 6-Carboxyrhodamine 6G, hydrochloride moiety, Bodipy R6G SE moiety, BODIPY R6G MeOH moiety, 6 JOE moiety, Cascade Yellow moiety, mBanana moiety, Alexa 532 moiety, Erythrosin-5-isothiocyanate pH 9.0 moiety, 6-HEX, SE pH 9.0 moiety, mOrange moiety, mHoneydew moiety, Cy 3 moiety, Rhodamine B moiety, DiI moiety, 5-TAMRA-MeOH moiety, Alexa 555 moiety, DyLight 549 moiety, BODIPY TMR-X, SE moiety, BODIPY TMR-X MeOH moiety, PO-PRO-3-DNA moiety, PO-PRO-3 moiety, Rhodamine moiety, POPO-3 moiety, Alexa 546 moiety, Calcium Orange Ca2+ moiety, TRITC moiety, Calcium Orange moiety, Rhodaminephalloidin pH 7.0 moiety, MitoTracker Orange moiety, MitoTracker Orange MeOH moiety, Phycoerythrin moiety, Magnesium Orange moiety, R-Phycoerythrin pH 7.5 moiety, 5-TAMRA pH 7.0 moiety, 5-TAMRA moiety, Rhod-2 moiety, FM 1-43 moiety, Rhod-2 Ca2+ moiety, FM 1-43 lipid moiety, LOLO-1-DNA moiety, dTomato moiety, DsRed moiety, Dapoxyl (2-aminoethyl) sulfonamide moiety, Tetramethylrhodamine dextran pH 7.0 moiety, Fluor-Ruby moiety, Resorufin moiety, Resorufin pH 9.0 moiety, mTangerine moiety, LysoTracker Red moiety, Lissaminerhodamine moiety, Cy 3.5 moiety, Rhodamine Red-X antibody conjugate pH 8.0 moiety, Sulforhodamine 101 EtOH moiety, JC-1 pH 8.2 moiety, JC-1 moiety, mStrawberry moiety, MitoTracker Red moiety, MitoTracker Red, MeOH moiety, X-Rhod-1 Ca2+ moiety, Alexa 568 moiety, 5-ROX pH 7.0 moiety, 5-ROX (5-Carboxy-X-rhodamine, triethylammonium salt) moiety, BO-PRO-3-DNA moiety, BOPRO-3 moiety, BOBO-3-DNA moiety, Ethidium Bromide moiety, ReAsH moiety, Calcium Crimson moiety, Calcium Crimson Ca2+ moiety, mRFP moiety, mCherry moiety, HcRed moiety, DyLight 594 moiety, Ethidium homodimer-1-DNA moiety, Ethidiumhomodimer moiety, Propidium Iodide moiety, SYPRO Ruby moiety, Propidium Iodide-DNA moiety, Alexa 594 moiety, BODIPY TR-X, SE moiety, BODIPY TR-X, MeOH moiety, BODIPY TR-X phallacidin pH 7.0 moiety, Alexa Fluor 610 R-phycoerythrin streptavidin pH 7.2 moiety, YO-PRO-3-DNA moiety, Di-8 ANEPPS moiety, Di-8-ANEPPS-lipid moiety, YOYO-3-DNA moiety, Nile Red-lipid moiety, Nile Red moiety, DyLight 633 moiety, mPlum moiety, TO-PRO-3-DNA moiety, DDAO pH 9.0 moiety, Fura Red high Ca moiety, Allophycocyanin pH 7.5 moiety, APC (allophycocyanin) moiety, Nile Blue, EtOH moiety, TOTO-3-DNA moiety, Cy 5 moiety, BODIPY 650/665-X, MeOH moiety, Alexa Fluor 647 R-phycoerythrin streptavidin pH 7.2 moiety, DyLight 649 moiety, Alexa 647 moiety, Fura Red Ca2+ moiety, Atto 647 moiety, Fura Red, low Ca moiety, Carboxynaphthofluorescein pH 10.0 moiety, Alexa 660 moiety, Cy 5.5 moiety, Alexa 680 moiety, DyLight 680 moiety, Alexa 700 moiety, FM 4-64, 2% CHAPS moiety, or FM 4-64 moiety. In embodiments, the dectable moiety is a moiety of 1,1-Diethyl-4,4-carbocyanine iodide, 1,2-Diphenylacetylene, 1,4-Diphenylbutadiene, 1,4-Diphenylbutadiyne, 1,6-Diphenylhexatriene, 1,6-Diphenylhexatriene, 1-anilinonaphthalene-8-sulfonic acid, 2,7-Dichlorofluorescein, 2,5-DIPHENYLOXAZOLE, 2-Di-1-ASP, 2-dodecylresorufin, 2-Methylbenzoxazole, 3,3-Diethylthiadicarbocyanine iodide, 4-Dimethyl amino-4-Nitrostilbene, 5(6)-Carboxyfluorescein, 5(6)-Carboxynaphtofluorescein, 5(6)-Carboxytetramethylrhodamine B, 5-(and-6)-carboxy-2',7'-dichlorofluorescein, 5-(and-6)-carboxy-2,7-dichlorofluorescein, 5-(N-hexadecanoyl)aminoeosin, 5-(N-hexadecanoyl)aminoeosin, 5-chloromethylfluorescein, 5-FAM, 5-ROX, 5-TAMRA, 5-TAMRA, 6,8-difluoro-7-hydroxy-4-methylcoumarin, 6,8-difluoro-7-hydroxy-4-methylcoumarin, 6-carboxyrhodamine 6G, 6-HEX, 6-JOE, 6-JOE, 6-TET, 7-aminoactinomycin D, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline, 9,10-Bis(Phenylethynyl) Anthracene, 9,10-Diphenylanthracene, 9-METHYLCARBAZOLE, (CS)2Ir(µ-Cl)2Ir(CS)2, AAA, Acridine Orange, Acridine Orange, Acridine Yellow, Acridine Yellow, Adams Apple Red 680, Adirondack Green 520, Alexa Fluor 350, Alexa Fluor 405, Alexa Fluor 430, Alexa Fluor 430, Alexa Fluor 480, Alexa Fluor 488, Alexa Fluor 488, Alexa Fluor 488 hydrazide, Alexa Fluor 500, Alexa Fluor 514, Alexa Fluor 532, Alexa Fluor 546, Alexa Fluor 546, Alexa Fluor 555, Alexa Fluor 555, Alexa Fluor 568, Alexa Fluor 594, Alexa Fluor 594, Alexa Fluor 594, Alexa Fluor 610, Alexa Fluor 610-R-PE, Alexa Fluor 633, Alexa Fluor 635, Alexa Fluor 647, Alexa Fluor 647, Alexa Fluor 647-R-PE, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyan1, Aminomethylcoumarin, Amplex Gold (product), Amplex Red Reagent, Amplex UltraRed, Anthracene, APC, APC-Seta-750, AsRed2, ATTO 390, ATTO 425, ATTO 430LS, ATTO 465, ATTO 488, ATTO 490LS, ATTO 495, ATTO 514, ATTO 520, ATTO 532, ATTO 550, ATTO 565, ATTO 590, ATTO 594, ATTO 610, ATTO 620, ATTO 633, ATTO 635, ATTO 647, ATTO 647N, ATTO 655, ATTO 665, ATTO 680, ATTO 700, ATTO 725, ATTO 740, ATTO Oxa12, ATTO Rho3B, ATTO Rho6G, ATTO Rho11, ATTO Rho12, ATTO Rho13, ATTO Rho14, ATTO Rho101, ATTO Thio12, Auramine O, Azami Green, Azami Green monomeric, B-phycoerythrin, BCECF, BCECF, Bex1, Biphenyl, Birch Yellow 580, Blue-green algae, BO-PRO-1, BO-PRO-3, BOBO-1, BOBO-3, BODIPY 630 650-X, BODIPY 650/665-X, BODIPY FL, BODIPY FL, BODIPY R6G, BODIPY TMR-X, BODIPY TR-X, BODIPY TR-X Ph 7.0, BODIPY TR-X phallacidin, BODIPY-DiMe, BODIPY-Phenyl, BODIPY-TMSCC, C3-Indocyanine, C3-Indocyanine, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, C545T, C-Phycocyanin, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxynaphthofluorescein, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, CF405M, CF405S, CF488A, CF543, CF555, CFP, CFSE, CF™ 350, CF™ 485, Chlorophyll A, Chlorophyll B, Chromeo 488, Chromeo 494, Chromeo 505, Chromeo 546, Chromeo 642, Citrine, Citrine, ClOH butoxy aza-BODIPY, ClOH C12 aza-BODIPY, CM-H2DCFDA, Coumarin 1, Coumarin 6, Coumarin 6, Coumarin 30, Coumarin 314, Coumarin 334, Coumarin 343, Coumarine 545T, Cresyl Violet Perchlorate, CryptoLight CF1, CryptoLight CF2, CryptoLight CF3, CryptoLight CF4, CryptoLight CFS, CryptoLight CF6, Crystal Violet, Cumarin153, Cy2, Cy3, Cy3, Cy3.5, Cy3B, Cy3B, Cy3Cy5 ET, Cy5, Cy5, Cy5.5, Cy7, Cyanine3 NHS ester, Cyanine5 carboxylic acid, Cyanine5 NHS ester, Cyclotella meneghiniana Kützing, CypHer5, CypHer5 pH 9.15, CyQUANT GR, CyTrak Orange, Dabcyl SE, DAF-FM, DAMC (Weiss), dansyl cadaverine, Dansyl Glycine (Dioxane), DAPI, DAPI, DAPI, DAPI, DAPI (DMSO), DAPI (H2O), Dapoxyl (2-aminoethyl)sulfonamide, DCI, DCM, DCM, DCM (acetonitrile), DCM (MeOH), DDAO, Deep Purple, di-8-ANEPPS, DiA, Dichlorotris(1,10-phenanthroline) ruthenium(II), DiClOH C12 aza-BODIPY, DiClOHbutoxy aza-BODIPY, DiD, DiI, DiIC18(3), DiO, DiR, Diversa Cyan-FP, Diversa Green-FP, DM-NERF pH 4.0, DOCI, Doxorubicin, DPP pH-Probe 590-7.5, DPP pH-Probe 590-9.0, DPP pH-Probe 590-11.0, DPP pH-Probe 590-11.0, Dragon Green, DRAQ5, DsRed, DsRed, DsRed, DsRed-Express, DsRed-Express2, DsRed-Express T1, dTomato, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-557, DY-557, DY-590, DY-590, DY-615, DY-630, DY-631, DY-633, DY-635, DY-636, DY-647, DY-649P1, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-28, Dye-33, Dye-45, Dye-304, Dye-1041, DyLight 488, DyLight 549, DyLight 594, DyLight 633, DyLight 649, DyLight 680, E2-Crimson, E2-Orange, E2-Red/Green, EBFP, ECF, ECFP, ECL Plus, eGFP, ELF 97, Emerald, Envy Green, Eosin, Eosin Y, epicocconone, EqFP611, Erythrosin-5-isothiocyanate, Ethidium bromide, ethidium homodimer-1, Ethyl Eosin, Ethyl Eosin, Ethyl Nile Blue A, Ethyl-p-Dimethylaminobenzoate, Ethyl-p-Dimethylaminobenzoate, Eu2O3 nanoparticles, Eu (Soini), Eu(tta) 3DEADIT, EvaGreen, EVOblue-30, EYFP, FAD, FITC, FITC, FlAsH (Adams), Flash Red EX, FlAsH-CCPGCC, FlAsH-CCXXCC, Fluo-3, Fluo-4, Fluo-5F, Fluorescein, Fluorescein 0.1 NaOH, Fluorescein-Dibase, fluoro-emerald, Fluorol 5G, FluoSpheres blue, FluoSpheres crimson, FluoSpheres dark red, FluoSpheres orange, FluoSpheres red, FluoSpheres yellow-green, FM4-64 in CTC, FM4-64 in SDS, FM 1-43, FM 4-64, Fort Orange 600, Fura Red, Fura Red Ca free, fura-2, Fura-2 Ca free, Gadodiamide, Gd-Dtpa- Bma, Gadodiamide, Gd-Dtpa-Bma, GelGreen™, GelRed™, H9-40, HcRed1, Hemo Red 720, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hoechst-33258, Hoechst-33258, Hops Yellow 560, HPTS, HPTS, HPTS, HPTS, HPTS, indo-1, Indo-1 Ca free, Ir(Cn)2(acac), Ir(Cs)2(acac), IR-775 chloride, IR-806, Ir-OEP-CO-Cl, IRDye® 650 Alkyne, IRDye® 650 Azide, IRDye® 650 Carboxylate, IRDye® 650 DBCO, IRDye® 650 Maleimide, IRDye® 650 NHS Ester, IRDye® 680LT Carboxylate, IRDye® 680LT Maleimide, IRDye® 680LT NHS Ester, IRDye® 680RD Alkyne, IRDye® 680RD Azide, IRDye® 680RD Carboxylate, IRDye® 680RD DBCO, IRDye® 680RD Maleimide, IRDye® 680RD NHS Ester, IRDye® 700 phosphoramidite, IRDye® 700DX, IRDye® 700DX, IRDye® 700DX Carboxylate, IRDye® 700DX NHS Ester, IRDye® 750 Carboxylate, IRDye® 750 Maleimide, IRDye® 750 NHS Ester, IRDye® 800 phosphoramidite, IRDye® 800CW, IRDye® 800CW Alkyne, IRDye® 800CW Azide, IRDye® 800CW Carboxylate, IRDye® 800CW DBCO, IRDye® 800CW Maleimide, IRDye® 800CW NHS Ester, IRDye® 800RS, IRDye® 800RS Carboxylate, IRDye® 800RS NHS Ester, IRDye® QC-1 Carboxylate, IRDye® QC-1 NHS Ester, Isochrysis galbana—Parke, JC-1, JC-1, JOJO-1, Jonamac Red Evitag T2, Kaede Green, Kaede Red, kusabira orange, Lake Placid 490, LDS 751, Lissamine Rhodamine (Weiss), LOLO-1, lucifer yellow CH, Lucifer Yellow CH, lucifer yellow CH, Lucifer Yellow CH Dilitium salt, Lumio Green, Lumio Red, Lumogen F Orange, Lumogen Red F300, Lumogen Red F300, LysoSensor Blue DND-192, LysoSensor Green DND-153, LysoSensor Green DND-153, LysoSensor Yellow/Blue DND-160 pH 3, LysoSensor YellowBlue DND-160, LysoTracker Blue DND-22, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 10GN, Macrolex Fluorescence Yellow 10GN, Magnesium Green, Magnesium Octaethylporphyrin, Magnesium Orange, Magnesium Phthalocyanine, Magnesium Phthalocyanine, Magnesium Tetramesitylporphyrin, Magnesium Tetraphenylporphyrin, malachite green isothiocyanate, Maple Red-Orange 620, Marina Blue, mBanana, mBBr, mCherry, Merocyanine 540, Methyl green, Methyl green, Methyl green, Methylene Blue, Methylene Blue, mHoneyDew, MitoTracker Deep Red 633, MitoTracker Green FM, MitoTracker Orange CMTMRos, MitoTracker Red CMXRos, monobromobimane, Monochlorobimane, Monoraphidium, mOrange, mOrange2, mPlum, mRaspberry, mRFP, mRFP1, mRFP1.2 (Wang), mStrawberry (Shaner), mTangerine (Shaner), N,N-Bis(2,4,6-trimethylphenyl)-3,4:9,10-perylenebis(dicarboximide), NADH, Naphthalene, Naphthalene, Naphthofluorescein, Naphthofluorescein, NBD-X, NeuroTrace 500525, Nilblau perchlorate, nile blue, Nile Blue, Nile Blue (EtOH), nile red, Nile Red, Nile Red, Nile red, Nileblue A, NIR1, NIR2, NIR3, NIR4, NIR820, Octaethylporphyrin, OH butoxy aza-BODIPY, OHC12 aza-BODIPY, Orange Fluorescent Protein, Oregon Green 488, Oregon Green 488 DHPE, Oregon Green 514, Oxazin1, Oxazin 750, Oxazine 1, Oxazine 170, P4-3, P-Quaterphenyl, P-Terphenyl, PA-GFP (post-activation), PA-GFP (pre-activation), Pacific Orange, Palladium (II) meso-tetraphenyltetrabenzoporphyrin, PdOEPK, PdTFPP, PerCP-Cy5.5, Perylene, Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, Perylenediimid, Perylne Green pH-Probe 740-5.5, Phenol, Phenylalanine, pHrodo, succinimidyl ester, Phthalocyanine, PicoGreen dsDNA quantitation reagent, Pinacyanol-Iodide, Piroxicam, Platinum(II) tetraphenyltetrabenzoporphyrin, Plum Purple, PO-PRO-1, PO-PRO-3, POPO-1, POPO-3, POPOP, Porphin, PPO, Proflavin, PromoFluor-350, PromoFluor-405, PromoFluor-415, PromoFluor-488, PromoFluor-488 Premium, PromoFluor-488LSS, PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor-770, PromoFluor-780, PromoFluor-840, propidium iodide, Protoporphyrin IX, PTIR475/UF, PTIR545/UF, PtOEP, PtOEPK, PtTFPP, Pyrene, QD525, QD565, QD585, QD605, QD655, QD705, QD800, QD903, QD PbS 950, QDot 525, QDot 545, QDot 565, Qdot 585, Qdot 605, Qdot 625, Qdot 655, Qdot 705, Qdot 800, QpyMe2, QSY 7, QSY 7, QSY 9, QSY 21, QSY 35, quinine, Quinine Sulfate, Quinine sulfate, R-phycoerythrin, R-phycoerythrin, ReAsH-CCPGCC, ReAsH-CCXXCC, Red Beads (Weiss), Redmond Red, Resorufin, resorufin, rhod-2, Rhodamin 700 perchlorate, rhodamine, Rhodamine 6G, Rhodamine 6G, Rhodamine 101, rhodamine 110, Rhodamine 123, rhodamine 123, Rhodamine B, Rhodamine B, Rhodamine Green, Rhodamine pH-Probe 585-7.0, Rhodamine pH-Probe 585-7.5, Rhodamine phalloidin, Rhodamine Red-X, Rhodamine Red-X, Rhodamine Tag pH-Probe 585-7.0, Rhodol Green, Riboflavin, Rose Bengal, Sapphire, SBFI, SBFI Zero Na, Scenedesmus sp., SensiLight PBXL-1, SensiLight PBXL-3, Seta 633-NHS, Seta-633-NHS, SeTau-380-NHS, SeTau-647-NHS, Snake-Eye Red 900, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains All, Stilben derivate, Stilbene, Styryl8 perchlorate, Sulfo-Cyanine3 carboxylic acid, Sulfo-Cyanine3 carboxylic acid, Sulfo-Cyanine3 NHS ester, Sulfo-Cyanine5 carboxylic acid, Sulforhodamine 101, sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYPRO Ruby, SYTO 9, SYTO 11, SYTO 13, SYTO 16, SYTO 17, SYTO 45, SYTO 59, SYTO 60, SYTO 61, SYTO 62, SYTO 82, SYTO RNASelect, SYTO RNASelect, SYTOX Blue, SYTOX Green, SYTOX Orange, SYTOX Red, T-Sapphire, Tb (Soini), tCO, tdTomato, Terrylen, Terrylendiimid, testdye, Tetra-t-Butylazaporphine, Tetra-t-Butylnaphthalocyanine, Tetracen, Tetrakis(o-Aminophenyl)Porphyrin, Tetramesitylporphyrin, Tetramethylrhodamine, tetramethylrhodamine, Tetraphenylporphyrin, Tetraphenylporphyrin, Texas Red, Texas Red DHPE, Texas Red-X, ThiolTracker Violet, Thionin acetate, TMRE, TO-PRO-1, TO-PRO-3, Toluene, Topaz (Tsien1998), TOTO-1, TOTO-3, Tris(2,2-Bipyridyl)Ruthenium(II) chloride. Tris(4,4-diphenyl-2,2-bipyridine) ruthenium(II) chloride, Tris(4,7-diphenyl-1,10-phenanthroline) ruthenium(II) TMS, TRITC (Weiss), TRITC Dextran (Weiss), Tryptophan, Tyrosine, Vex1, Vybrant DyeCycle Green stain, Vybrant DyeCycle Orange stain, Vybrant DyeCycle Violet stain, WEGFP (post-activation), WellRED D2, WellRED D3, WellRED D4, WtGFP, WtGFP (Tsien1998), X-rhod-1, Yakima Yellow, YFP, YO-PRO-1, YO-PRO-3, YOYO-1, YoYo-1, YoYo-1 dsDNA, YoYo-1 ssDNA, YOYO-3, Zinc Octaethylporphyrin, Zinc Phthalocyanine, Zinc Tetramesitylporphyrin, Zinc Tetraphenylporphyrin, ZsGreen1, or ZsYellow1.

In embodiments, the detectable label is a fluorescent dye. In embodiments, the detectable label is a fluorescent dye capable of exchanging energy with another fluorescent dye (e.g., fluorescence resonance energy transfer (FRET) chromophores).

In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein.

The term "cyanine" or "cyanine moiety" as described herein refers to a detectable moiety containing two nitrogen groups separated by a polymethine chain. In embodiments, the cyanine moiety has 3 methine structures (i.e. cyanine 3 or Cy3). In embodiments, the cyanine moiety has 5 methine structures (i.e. cyanine 5 or Cy5). In embodiments, the cyanine moiety has 7 methine structures (i.e. cyanine 7 or Cy7).

Descriptions of nucleotide analogues of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics, which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein, which encodes a polypeptide, also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following groups each contain amino acids that are conservative substitutions for one another: 1) Non-polar—Alanine (A), Leucine (L), Isoleucine (I), Valine (V), Glycine (G), Methionine (M); 2) Aliphatic—Alanine (A), Leucine (L), Isoleucine (I), Valine (V); 3) Acidic—Aspartic acid (D), Glutamic acid (E); 4) Polar—Asparagine (N), Glutamine (Q); Serine (S), Threonine (T); 5) Basic—Arginine (R), Lysine (K); 7) Aromatic—Phenylalanine (F), Tyrosine (Y), Tryptophan (W), Histidine (H); 8) Other—Cysteine (C) and Proline (P).

The term "amino acid side chain" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the amino acid side chain may be a non-natural amino acid side chain. In embodiments, the amino acid side chain is H,

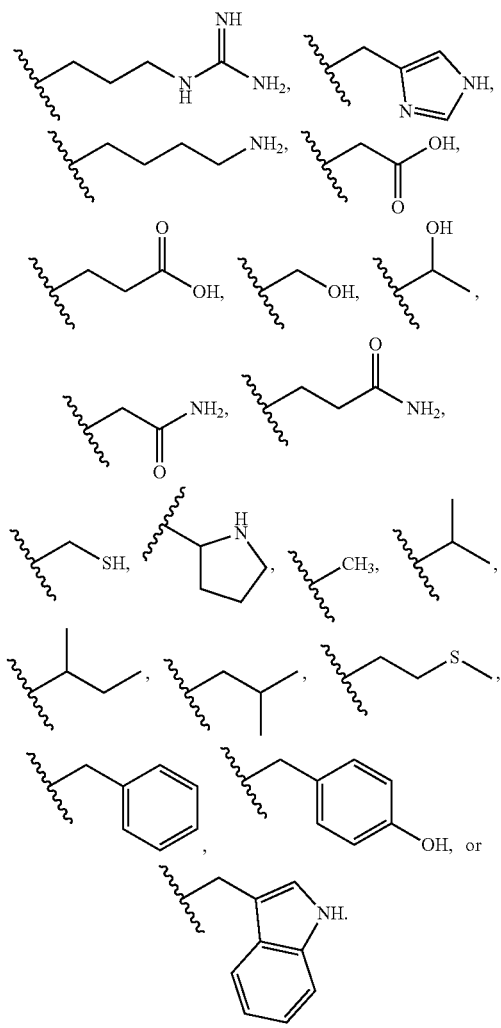

The term "non-natural amino acid side chain" refers to the functional substituent of compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium, allylalanine, 2-aminoisobutryric acid. Non-natural amino acids are non-proteinogenic amino acids that occur naturally or are chemically synthesized. Such analogs have modified R groups (e.g., norleucine) or modified peptide backbones, but retain the same basic chemical structure as a naturally occurring amino acid. Non-limiting examples include exo-cis-3-Aminobicyclo[2.2.1]hept-5-ene-2-carboxylic acid hydrochloride, cis-2-Aminocycloheptanecarboxylic acid hydrochloride, cis-6-Amino-3-cyclohexene-1-carboxylic acid hydrochloride, cis-2-Amino-2-methylcyclohexanecarboxylic acid hydrochloride, cis-2-Amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-β-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe(2-Br)-OH, Boc-Phe(4-Br)-OH, Boc-D-Phe(4-Br)-OH, Boc-D-Phe(3-Cl)—OH, Boc-Phe(4-NH$_2$)—OH, Boc-Phe(3-NO$_2$)—OH, Boc-Phe(3,5-F2)-OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-[4-Boc-piperazino) (trifluoromethyl)phenyl]acetic acid purum, Boc-β-(2-quinolyl)-Ala-OH, N—Boc-1,2,3,6-tetrahydro-2-pyridinecarboxylic acid, Boc-β-(4-thiazolyl)-Ala-OH, Boc-β-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)-OH, Fmoc-Phe(4-Br)-OH, Fmoc-Phe(3,5-F2)-OH, Fmoc-β-(4-thiazolyl)-Ala-OH, Fmoc-β-(2-thienyl)-Ala-OH, 4-(Hydroxymethyl)-D-phenylalanine.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST® or BLAST® 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST®, BLAST-2®, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 700, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The term "DNA polymerase" and "nucleic acid polymerase" are used in accordance with their plain ordinary meaning and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g. Therminator™ γ, 9°N™ polymerase (exo–), Therminator™ II, Therminator™ III, or Therminator™ IX).

The term "thermophilic nucleic acid polymerase" as used herein refers to a family of DNA polymerases (e.g., 9°N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. *PNAS.* 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator™ II enzyme from New England Biolabs with D141A/E143A/Y409V/A485L); 3'-amino-dNTPs, 3'-azido-dNTPs and other 3'-modified nucleotides (e.g., NEB Therminator™ III DNA Polymerase with D141A/E143A/L408S/Y409A/P410V mutations, NEB Therminator™ IX DNA polymerase), or γ-phosphate labeled nucleotides (e.g., Therminator™ γ: D141A/E143A/W355A/L408W/R460A/Q461S/K464E/D480V/R484W/A485L). Typically, these enzymes do not have 5'-3' exonuclease activity. Additional information about thermophilic nucleic acid polymerases may be found in (Southworth M W, et al. *PNAS.* 1996; 93(11):5281-5285; Bergen K, et al. *Chem Bio Chem.* 2013; 14(9):1058-1062; Kumar S, et al. *Scientific Reports.* 2012; 2:684; Fuller C W, et al. 2016; 113(19):5233-5238; Guo J, et al. *Proceedings of the National Academy of Sciences of the United States of America.* 2008; 105(27):9145-9150), which are incorporated herein in their entirety for all purposes.

The term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at either the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

The term "independently resolvable" means that the entity under study can be examined independent of other entities due to spatial separation, for example, one polymerase-template complex can be probed independent from another polymerase-template complex present at a different physical location, or "address", on the solid substrate.

The terms "measure", "measuring", "measurement" and the like refer not only to quantitative measurement of a particular variable, but also to qualitative and semi-quantitative measurements. Accordingly, "measurement" also includes detection, meaning that merely detecting a change, without quantification, constitutes measurement.

The term "population" refers to a collection of one or more entities, e.g., DNA molecules.

"Perfectly matched" in reference to a nucleic acid duplex means that the poly- or oligonucleotide strands making up the duplex form a double-stranded structure, or region of double-stranded structure, with one another such that every nucleotide (or nucleotide analogue) in each strand undergoes Watson-Crick base-pairing with a nucleotide in the other strand in the duplexed (i.e., hybridized) region. The term also comprehends the pairing of nucleoside analogues, such as deoxyinosine with deoxycytidine, and the like. Conversely, a "mismatch" in a nucleic acid duplex means that one or more pairs of nucleotides in the duplex fail to undergo Watson-Crick base-pairing.

A "polymerase-template complex" refers to functional complex between a DNA polymerase and a DNA primer-template molecule being sequenced.

The terms "sequencing", "sequence determination", "determining a nucleotide sequence", and the like include determination of partial as well as full sequence information of the polynucleotide being sequenced. That is, the term includes sequence comparisons, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide.

The term "sequencing reaction mixture" refers to an aqueous mixture that contains the reagents necessary to allow a dNTP or dNTP analogue to add a nucleotide to a DNA strand by a DNA polymerase.

The term "solid substrate" means any suitable medium present in the solid phase to which an antibody or an agent can be covalently or non-covalently affixed or immobilized. Preferred solid substrates are glass. Non-limiting examples include chips, beads and columns. The solid substrate can be non-porous or porous. Exemplary solid substrates include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides, etc.), nylon, ceramics, resins, Zeonor, silica or silica-based materials including silicon and modified silicon, carbon, metals, inorganic glasses, optical fiber bundles, and polymers.

The term "species", when used in the context of describing a particular compound or molecule species, refers to a population of chemically indistinct molecules. When used in the context of taxonomy, "species" is the basic unit of classification and a taxonomic rank. For example, in reference to the microorganism *Thermococcus* EP1, EP1 is a species of the genus *Thermococcus*.

The terms "position", "numbered with reference to" or "corresponding to," when used in the context of the numbering of a given amino acid or polynucleotide sequence, refer to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. One skilled in the art will immediately recognize the identity and location of residues corresponding to a specific position in a protein (e.g., polymerase) in other proteins with different numbering systems. For example, by performing a simple sequence alignment with a protein (e.g., polymerase) the identity and location of residues corresponding to specific positions of said protein are identified in other protein sequences aligning to said protein. For example, a selected residue in a selected protein corresponds to methionine at position 129 when the selected residue occupies the same essential spatial or other structural relationship as a methionine at position 129. In some embodiments, where a selected protein is aligned for maximum homology with a protein, the position in the aligned selected protein aligning with methionine 129 said to correspond to methionine 129. Instead of a primary sequence alignment, a three-dimensional structural alignment can also be used, e.g., where the structure of the selected protein is aligned for maximum correspondence with the methionine at position 129, and the overall structures compared. In this case, an amino acid that occupies the same essential position as methionine 129 in the structural model is said to correspond to the methionine 129 residue. For example, references to a TspEP1 polymerase amino acid position recited herein may refer to a numbered position set forth in SEQ ID NO:1, or the corresponding position in a polymerase homolog of SEQ ID NO:1. In embodiments, references to a polymerase amino acid position recited herein refers to a numbered position set forth in SEQ ID NO:1 which is the amino acid sequence of the wildtype TspEP1 polymerase. In embodiments, SEQ ID NO: 4, 5, 6, and 18, are all variants of TspEP1 polymerase with substitution, deletion, and/or addition mutations at amino acid positions referenced relative to wildtype TspEP1 polymerase with amino acid sequence of SEQ ID NO: 1. In embodiments, the polymerase provided herein may have one or more amino acid substitution mutations at position 129, 141, 142, 143, 144, 209, 210, 213, 214, 215, 276, 277, 313 and/or 317 where the numbering is in reference to the amino acid position as provided in SEQ ID NO: 1. In embodiments, the polymerase provided herein may have one or more amino acid substitution mutations at position 36, 93, 129, 141, 143, 144, 152, 153, 155, 157, 215, 303, 307, 317, 479, 480, 481, 488, 517, 593, 605, and/or 642 where the numbering is in reference to the amino acid position as provided in SEQ ID NO: 1. In embodiments, the polymerase includes an amino acid substitution mutation at more than one position compared to SEQ ID NO: 1. For example, in embodiments, the polymerase includes the following substitution mutations: M129A, D141A, T144A, E143A, L411A, Y412G, A488V, T517S, and T593I where the number refers to the corresponding position in SEQ ID NO: 1. One having skill in the art would understand the amino acid mutation nomenclature, such that M129A refers to methionine (single letter code is A), at position 129, is replaced with alanine (single letter code A).

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally non-adherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulate" is used in accordance with its plain ordinary meaning and refers to the act of changing or varying one or more properties. "Modulation" refers to the process of changing or varying one or more properties.

The term "kit" is used in accordance with its plain ordinary meaning and refers to any delivery system for delivering materials or reagents for carrying out a method of the invention. Such delivery systems include systems that allow for the storage, transport, or delivery of reaction reagents (e.g., nucleotides, enzymes, nucleic acid templates, etc. in the appropriate containers) and/or supporting materials (e.g., buffers, written instructions for performing the reaction, etc.) from one location to another location. For example, kits include one or more enclosures (e.g., boxes) containing the relevant reaction reagents and/or supporting materials. Such contents may be delivered to the intended recipient together or separately. For example, a first container may contain an enzyme, while a second container contains nucleotides. In embodiments, the kit includes vessels containing one or more enzymes, primers, adaptors, or other reagents as described herein. Vessels may include any structure capable of supporting or containing a liquid or solid material and may include, tubes, vials, jars, containers, tips, etc. In embodiments, a wall of a vessel may permit the transmission of light through the wall. In embodiments, the vessel may be optically clear. The kit may include the enzyme and/or nucleotides in a buffer. In embodiments, the buffer includes an acetate buffer, 3-(N-morpholino)propanesulfonic acid (MOPS) buffer, N-(2-Acetamido) aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

A "patentable" process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the unpatentable embodiment(s). In addition, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

The phrase "stringent hybridization conditions" refers to conditions under which a primer will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

II. Polymerases

Provided herein are, inter alia, are modified Archaea Family B DNA polymerases. Archaeal DNA polymerases are Family B polymerases that characteristically have separate domains for DNA polymerase activity and 3'-5' exonuclease activity. The exonuclease domain is characterized by as many as six and at least three conserved amino acid sequence motifs in and around a structural binding pocket. Examples of archaeal polymerases include polymerases obtained from species of *Thermococcus, Pyrococcus* and *Sulfolobus*. During polymerization, nucleotides are added to the 3' end of a primer strand and during the 3'-5' exonuclease reaction, the 3' terminus of the primer is shifted to the 3'-5' exonuclease domain and the one or more of the 3'-terminal nucleotides are hydrolyzed.

In embodiments, the variants of a *Thermococcus* sp. EP1 family B DNA polymerase provided herein have reduced exonuclease activity and are useful in methods of incorporating modified nucleotides in nucleic acid synthesis reactions. In embodiments, the polymerase is a thermophilic nucleic acid polymerase.

Parent archaeal polymerases may be DNA polymerases that are isolated from naturally occurring organisms. The parent DNA polymerases, also referred to as wild type polymerase, share the property of having a structural binding pocket that binds and hydrolyzes a substrate nucleic acid, producing 5'-dNMP. The structural binding pocket in this family of polymerases also shares the property of having sequence motifs that form the binding pocket, referred to as Exo Motifs I-VI. In embodiments, the parent or wild type TspEP1 polymerase has an amino acid sequence comprising SEQ ID NO: 1.

"Synthetic" DNA polymerases refer to non-naturally occurring DNA polymerases such as those constructed by synthetic methods, mutated parent DNA polymerases such as truncated DNA polymerases and fusion DNA polymerases (e.g. U.S. Pat. No. 7,541,170). Variants of the parent DNA polymerase have been engineered by mutating residues using site-directed or random mutagenesis methods known in the art. In embodiments, the mutations are in any of Motifs I-VI. The variant is expressed in an expression system such as *E. coli* by methods known in the art. The variant is then screened using the assays described herein to determine exonuclease activity.

In embodiments, the polymerase (a synthetic or variant DNA polymerase) provided herein may contain 1, 2, 3, 4, 5, 6, 7, 8, 9, 10, 11, 12 or more mutations as compared to the wild-type sequence of *Thermococcus* spEP1 family B DNA polymerase of SEQ ID NO: 1. The polymerase (a synthetic or variant DNA polymerase) may contain 10, 20, 30, 40, 50 or more mutations as compared to the wild-type sequence of *Thermococcus* spEP1 family B DNA polymerase of SEQ ID NO: 1. The polymerase (a synthetic or variant DNA polymerase) may contain between 10 and 20, between 20 and 30, between 30 and 40, or between 40 or 50 mutations as compared to the wild-type sequence of *Thermococcus* spEP1 family B DNA polymerase of SEQ ID NO: 1.

In an aspect, the polymerase (a synthetic or variant DNA polymerase) provided herein may have one or more amino acid substitution mutations between positions 129 and 318 inclusive of endpoint positions. In embodiments, the polymerase (a synthetic or variant DNA polymerase) provided herein may have one or more amino acid substitution mutations at position 129, 141, 142, 143, 144, 209, 210, 213, 214, 215, 276, 277, 313 and/or 317.

In an aspect is provided a polymerase including an amino acid sequence that is at least 80% identical to a continuous 500 amino acid sequence within SEQ ID NO: 1. In embodiments, the polymerase includes an amino acid sequence that is at least 85% identical to a continuous 500 amino acid sequence within SEQ ID NO: 1. In embodiments, the polymerase includes an amino acid sequence that is at least 90% identical to a continuous 500 amino acid sequence within SEQ ID NO: 1. In embodiments, the polymerase includes an amino acid sequence that is at least 95% identical to a continuous 500 amino acid sequence within SEQ ID NO: 1.

In an aspect is provided a polymerase including an amino acid sequence that is at least 95% identical to a continuous 500 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 96% identical to a continuous 500 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 97% identical to a continuous 500 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 98% identical to a continuous 500 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 99% identical to a continuous 500 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In an aspect is provided a polymerase including an amino acid sequence that is at least 95% identical to a continuous 600 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 96% identical to a continuous 600 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 97% identical to a continuous 600 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 98% identical to a continuous 600 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 99% identical to a continuous 600 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In an aspect is provided a polymerase including an amino acid sequence that is at least 95% identical to a continuous 700 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 96% identical to a continuous 700 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 97% identical to a continuous 700 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 98% identical to a continuous 700 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 99% identical to a continuous 700 amino acid sequence within SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In an aspect is provided a polymerase including an amino acid sequence that is at least 95% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 96% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 97% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 98% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In an aspect is provided a polymerase including an amino acid sequence that is at least 99% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In embodiments, the polymerase includes an alanine or serine at amino acid position 411 or an amino acid functionally equivalent to amino acid position 411. In embodiments, the polymerase includes an alanine at amino acid position 411 or an amino acid functionally equivalent to amino acid position 411. In embodiments, the polymerase includes a serine at amino acid position 411 or an amino acid functionally equivalent to amino acid position 411. In embodiments, the polymerase includes a glycine or alanine at amino acid position 412 or an amino acid functionally equivalent to amino acid position 412. In embodiments, the polymerase includes a glycine at amino acid position 412 or an amino acid functionally equivalent to amino acid position 412. In embodiments, the polymerase includes an alanine at amino acid position 412 or an amino acid functionally equivalent to amino acid position 412. In embodiments, the polymerase includes a proline, valine, or isoleucine at amino acid position 413 or an amino acid functionally equivalent to amino acid position 413. In embodiments, the polymerase includes a proline at amino acid position 413 or an amino acid functionally equivalent to amino acid position 413. In embodiments, the polymerase includes a valine at amino acid position 413 or an amino acid functionally equivalent to amino acid position 413. In embodiments, the polymerase includes an isoleucine at amino acid position 413 or an amino acid functionally equivalent to amino acid position 413.

In embodiments, the polymerase includes a serine at amino acid position 411 or an amino acid functionally equivalent to amino acid position 411; an alanine at amino acid position 412 or an amino acid functionally equivalent to amino acid position 412; and a valine at amino acid position 413 or an amino acid functionally equivalent to amino acid position 413. In embodiments, the polymerase includes a serine at amino acid position 411; an alanine at amino acid position 412; and a valine at amino acid position 413.

In embodiments, the polymerase includes an alanine at amino acid position 411 or an amino acid functionally equivalent to amino acid position 411; an alanine at amino acid position 412 or an amino acid functionally equivalent to amino acid position 412; and an isoleucine at amino acid position 413 or an amino acid functionally equivalent to amino acid position 413. In embodiments, the polymerase includes an alanine at amino acid position 411; an alanine at amino acid position 412; and an isoleucine at amino acid position 413.

In embodiments, the polymerase includes an alanine at amino acid position 411 or an amino acid functionally equivalent to amino acid position 411; a glycine at amino acid position 412 or an amino acid functionally equivalent to amino acid position 412; and a proline at amino acid position 413 or an amino acid functionally equivalent to amino acid position 413. In embodiments, the polymerase includes an alanine at amino acid position 411; a glycine at amino acid position 412; and a proline at amino acid position 413. At position 413, proline is not a mutation, rather it is the amino acid present in the wild-type enzyme.

In embodiments, the polymerase further includes an amino acid substitution mutation at position 36, or an amino acid functionally equivalent to amino acid position 36, or 93, or an amino acid functionally equivalent to amino acid position 93, of SEQ ID NO:1. In embodiments, the polymerase further includes an alanine or histidine amino acid substitution mutation at position 36, or an amino acid functionally equivalent to amino acid position 36. In embodiments, the polymerase further includes an alanine, glycine, or glutamine acid substitution mutation at position 93, or an amino acid functionally equivalent to amino acid position 93, of SEQ ID NO:1.

In embodiments, the polymerase further includes an amino acid substitution mutation at position 36, 93, 129, 141, 143, 144, 152, 153, 155, 157, 215, 303, 307, 317, 479, 480, 481, 488, 517, 593, 605, or 642 of SEQ ID NO:1. In embodiments, the polymerase further includes a conservative an amino acid substitution at position 36, 93, 129, 141, 143, 144, 152, 153, 155, 157, 215, 303, 307, 317, 479, 480, 481, 488, 517, 593, 605, or 642 of SEQ ID NO:1.

In embodiments, the polymerase includes an amino acid substitution mutation at position 129, 141, 143, 144, 209, 210, 213, 214, 215, 276, 277, 313 and/or 317 of SEQ ID NO: 1. In embodiments, the polymerase include a conservative amino acid substitution mutation at position 129, 141, 143, 144, 209, 210, 213, 214, 215, 276, 277, 313 and/or 317 of SEQ ID NO: 1.

In embodiments, the polymerase includes an amino acid substitution at position 129. The amino acid substitution at position 129 may be an alanine substitution, a glycine substitution, a valine substitution, a leucine substitution or an isoleucine substitution. In embodiments, the amino acid substitution at position 129 is an alanine substitution. In embodiments, the polymerase includes an alanine substitution mutation at position 129.

In embodiments, the polymerase includes an alanine substitution mutation at position 141. In embodiments, the polymerase includes an alanine substitution mutation at position 143. In embodiments, the polymerase includes an alanine substitution mutation at position 141 and an alanine substitution mutation at position 143.

In embodiments, the polymerase includes an amino acid substitution at position 141. The amino acid substitution at position 141 may be an alanine substitution, a glycine substitution, a methionine substitution, a valine substitution, a leucine substitution or an isoleucine substitution. In embodiments, the amino acid substitution at position 141 is an alanine substitution.

In embodiments, the amino acid substitution at position 143 is an alanine substitution. In embodiments, the polymerase includes an amino acid substitution at position 143. The amino acid substitution at position 143 may be an alanine substitution, a glycine substitution, a methionine substitution, a valine substitution, a leucine substitution or an isoleucine substitution. In embodiments, the amino acid substitution at position 143 is an alanine substitution.

In embodiments, the polymerase includes an alanine substitution mutation at position 144.

In embodiments, the polymerase includes a threonine at position 153. In embodiments, the polymerase includes an aspartic acid at position 155. In embodiments, the polymerase includes a threonine at position 153 and an aspartic acid at position 155 of SEQ ID NO:1.

In embodiments, the polymerase includes a glutamic acid at position 152. In embodiments, the polymerase includes a threonine at position 153. In embodiments, the polymerase includes a glutamic acid at position 152 and a threonine at position 153 of SEQ ID NO:1.

In embodiments, the polymerase includes an isoleucine at position 303. In embodiments, the polymerase includes an methionine at position 307. In embodiments, the polymerase includes an isoleucine at position 303 and a methionine at position 307 of SEQ ID NO:1.

In embodiments, the polymerase includes an amino acid substitution mutation at amino acid position 517 of SEQ ID NO:1. In embodiments, the polymerase includes a serine or threonine at amino acid position 517 of SEQ ID NO:1. In embodiments, the polymerase includes a serine at amino acid position 517 of SEQ ID NO:1.

In embodiments, the polymerase includes an alanine or histidine at amino acid position 36 or an amino acid position functionally equivalent to amino acid position 36. In embodiments, the polymerase includes an alanine, glycine, or glutamine at amino acid position 93 or an amino acid position functionally equivalent to amino acid position 93. In embodiments, the polymerase includes an alanine at amino acid position 129 or an amino acid position functionally equivalent to amino acid position 129. In embodiments, the polymerase includes an alanine at amino acid position 141 or an amino acid position functionally equivalent to amino acid position 141. In embodiments, the polymerase includes an alanine at amino acid position 143 or an amino acid position functionally equivalent to amino acid position 143. In embodiments, the polymerase includes an alanine at amino acid position 144 or an amino acid position functionally equivalent to amino acid position 144. In embodiments, the polymerase includes a glutamic acid at amino acid position 152 or an amino acid position functionally equivalent to amino acid position 152. In embodiments, the polymerase includes a glutamic acid or threonine at amino acid position 153. In embodiments, the polymerase includes or an amino acid position functionally equivalent to amino acid position 153. In embodiments, the polymerase includes a threonine at amino acid position 155 or an amino acid position functionally equivalent to amino acid position 155. In embodiments, the polymerase includes an aspartic acid at amino acid position 157 or an amino acid position functionally equivalent to amino acid position 157. In embodiments, the polymerase includes an alanine at amino acid position 215 or an amino acid position functionally equivalent to amino acid position 215. In embodiments, the polymerase includes an isoleucine at amino acid position 303 or an amino acid position functionally equivalent to amino acid position 303. In embodiments, the polymerase includes a methionine at amino acid position 307 or an amino acid position functionally equivalent to amino acid position 307.

In embodiments, the polymerase includes an alanine or histidine at amino acid position 36. In embodiments, the polymerase includes an alanine at amino acid position 36. In embodiments, the polymerase includes a histidine at amino acid position 36. In embodiments, the polymerase includes an alanine, glycine, or glutamine at amino acid position 93. In embodiments, the polymerase includes an alanine at amino acid position 93. In embodiments, the polymerase includes a glycine at amino acid position 93. In embodiments, the polymerase includes a glutamine at amino acid position 93. In embodiments, the polymerase includes an alanine at amino acid position 129. In embodiments, the polymerase includes an alanine at amino acid position. In embodiments, the polymerase includes an alanine at amino acid position 143. In embodiments, the polymerase includes an alanine at amino acid position 144. In embodiments, the polymerase includes a glutamic acid at amino acid position 152. In embodiments, the polymerase includes a glutamic acid at amino acid position 153. In embodiments, the polymerase includes a threonine at amino acid position 153. In embodiments, the polymerase includes a threonine at amino acid position 155. In embodiments, the polymerase includes an aspartic acid at amino acid position. In embodiments, the polymerase includes an alanine at amino acid position 215. In embodiments, the polymerase includes an isoleucine at amino acid position 303. In embodiments, the polymerase includes a methionine at amino acid position 307.

In embodiments, the polymerase further includes at least one of the following: an alanine or histidine at amino acid position 36 or an amino acid position functionally equivalent to amino acid position 36; an alanine, glycine, or glutamine at amino acid position 93 or an amino acid position functionally equivalent to amino acid position 93; an alanine at amino acid position 129 or an amino acid position functionally equivalent to amino acid position 129; an alanine at amino acid position 141 or an amino acid position functionally equivalent to amino acid position 141; an alanine at amino acid position 143 or an amino acid position functionally equivalent to amino acid position 143; an alanine at amino acid position 144 or an amino acid position functionally equivalent to amino acid position 144; a glutamic acid at amino acid position 152 or an amino acid position functionally equivalent to amino acid position 152; a glutamic acid or threonine at amino acid position 153 or an amino acid position functionally equivalent to amino acid position 153; a threonine at amino acid position 155 or an amino acid position functionally equivalent to amino acid position 155; an aspartic acid at amino acid position 157 or an amino acid position functionally equivalent to amino acid position 157; an alanine at amino acid position 215 or an amino acid position functionally equivalent to amino acid position 215; an isoleucine at amino acid position 303 or an amino acid position functionally equivalent to amino acid position 303; or a methionine at amino acid position 307 or an amino acid position functionally equivalent to amino acid position 307.

In embodiments, the polymerase includes an alanine at amino acid position 317 or an amino acid position functionally equivalent to amino acid position 317. In embodiments, the polymerase includes a phenylalanine at amino acid position 381 or an amino acid position functionally equivalent to amino acid position 381. In embodiments, the polymerase includes a tryptophan at amino acid position 479 or an amino acid position functionally equivalent to amino acid position 479. In embodiments, the polymerase includes an alanine at amino acid position 480 or an amino acid position functionally equivalent to amino acid position 480. In embodiments, the polymerase includes an alanine at amino acid position 481 or an amino acid position functionally equivalent to amino acid position 481. In embodiments, the polymerase includes a valine at amino acid position 488 or an amino acid position functionally equivalent to amino acid position 488. In embodiments, the polymerase includes a serine at amino acid position 517 or an amino acid position functionally equivalent to amino acid position 517. In embodiments, the polymerase includes an isoleucine at amino acid position 593 or an amino acid position functionally equivalent to amino acid position 593. In embodiments, the polymerase includes an alanine at amino acid position 605 or an amino acid position functionally equivalent to amino acid position 605. In embodiments, the polymerase includes a leucine at amino acid position 642 or an amino acid position functionally equivalent to amino acid position 642.

In embodiments, the polymerase includes an alanine at amino acid position 317. In embodiments, the polymerase includes a phenylalanine at amino acid position 381. In embodiments, the polymerase includes a tryptophan at amino acid position 479. In embodiments, the polymerase includes an alanine at amino acid position 480. In embodiments, the polymerase includes an alanine at amino acid position 481. In embodiments, the polymerase includes a valine at amino acid position 488. In embodiments, the polymerase includes a serine at amino acid position 517. In embodiments, the polymerase includes an isoleucine at amino acid position 593. In embodiments, the polymerase includes an alanine at amino acid position. In embodiments, the polymerase includes a leucine at amino acid position 642.

In embodiments, the polymerase further includes at least one of the following: an alanine at amino acid position 317 or an amino acid position functionally equivalent to amino acid position 317; a phenylalanine at amino acid position 381 or an amino acid position functionally equivalent to amino acid position 381; a tryptophan at amino acid position 479 or an amino acid position functionally equivalent to amino acid position 479; an alanine at amino acid position 480 or an amino acid position functionally equivalent to amino acid position 480; an alanine at amino acid position 481 or an amino acid position functionally equivalent to amino acid position 481; a valine at amino acid position 488 or an amino acid position functionally equivalent to amino acid position 488; a serine at amino acid position 517 or an amino acid position functionally equivalent to amino acid position 517; an isoleucine at amino acid position 593 or an amino acid position functionally equivalent to amino acid position 593; an alanine at amino acid position 605 or an amino acid position functionally equivalent to amino acid position 605; or a leucine at amino acid position 642 or an amino acid position functionally equivalent to amino acid position 642.

In embodiments, the polymerase is capable of incorporating modified nucleotides at reaction temperatures across the range of 40° C. to 80° C. In embodiments, the polymerase is capable of incorporating modified nucleotides at reaction temperatures across the range of 60° C. to 80° C. In embodiments, the polymerase is capable of incorporating modified nucleotides at reaction temperatures across the range of 80° C. to 90° C.

In embodiments, the polymerase includes an amino acid substitution at position 142. The amino acid substitution at position 142 may be an alanine substitution, a glycine substitution, a methionine substitution, a valine substitution, or a leucine substitution. In embodiments, the amino acid substitution at position 142 is a glycine substitution. In embodiments, the polymerase includes an amino acid substitution at position 144. The amino acid substitution at position 144 may be a lysine substitution or an arginine substitution. In embodiments, the amino acid substitution at position 144 is an arginine substitution. In embodiments, the polymerase includes an amino acid substitution at 209. The amino acid substitution at position 209 may be an alanine substitution, a glycine substitution, a methionine substitution, a valine substitution, a leucine substitution, or an isoleucine substitution. In embodiments, the amino acid substitution at position 209 is a glycine substitution. In embodiments, the polymerase includes an amino acid substitution at position 210. The amino acid substitution at position 210 may be an alanine substitution, a glycine substitution, a methionine substitution, a valine substitution, a leucine substitution, or an isoleucine substitution. In embodiments, the amino acid substitution at position 210 is a glycine substitution. In embodiments, the polymerase includes an amino acid substitution at position 213. The amino acid substitution at position 213 may be an alanine substitution, a glycine substitution, a methionine substitution, a valine substitution, a leucine substitution, or an isoleucine substitution. In embodiments, the amino acid substitution at position 213 is a glycine substitution. In embodiments, the polymerase includes an amino acid substitution at position 214. The amino acid substitution at position 214 may be an alanine substitution, a glycine substitution, a methionine substitution, a valine substitution, a leucine substitution, or an isoleucine substitution. In embodiments, the amino acid substitution at position 214 is a glycine substitution. In embodiments, the polymerase includes an amino acid substitution at position 215. The amino acid substitution at position 215 may be an alanine substitution, a glycine substitution, a methionine substitution, a valine substitution, a leucine substitution, or an isoleucine substitution. In embodiments, the amino acid substitution at position 215 is an alanine substitution. In embodiments, the polymerase includes an amino acid substitution at position 276. The amino acid substitution at position 276 may be lysine substitution or an arginine substitution. In embodiments, the amino acid substitution at position 276 is an arginine substitution. In embodiments, the polymerase includes an amino acid substitution at position 277. The amino acid substitution at position 277 may be an aspartic acid substitution or a glutamic acid substitution. In embodiments, the amino acid substitution at position 277 is glutamic acid. In embodiments, the polymerase includes an amino acid substitution at position 313. The amino acid substitution at position 313 may be an alanine substitution, a glycine substitution, a methionine substitution, a valine substitution, a leucine substitution, or an isoleucine substitution. In embodiments, the amino acid substitution at position 313 is a glycine substitution. In embodiments, the polymerase includes an amino acid substitution at position 317. The amino acid substitution at position 317 may be an alanine substitution, a glycine substitution, a methionine substitution, a valine substitution, a leucine substitution, or an isoleucine substitution. In embodiments, the amino acid substitution at position 317 is an alanine substitution.

In embodiments, the polymerase (a synthetic or variant DNA polymerase) provided herein may further include one or more amino acid substitution mutations between position 318 and 774, inclusive of endpoint positions. In embodiments, the polymerase (a synthetic or variant DNA polymerase) provided herein may have one or more amino acid substitution mutations at position 407, 410, 411, 412, 413, 463, 486, 488, 490, 494, 497, 498, 499, 543, 545, and/or 546.

In embodiments, the polymerase includes an amino acid substitution at position 411. The amino acid substitution at position 411 may be a serine substitution, a threonine substitution, an asparagine substation, or a glutamine substitution. In embodiments, the amino acid substitution at position 411 is a serine substitution. In embodiments, the amino acid substitution at position 411 may be an alanine substitution, a glycine substitution, a valine substitution, a methionine substitution, a leucine substitution or an isoleucine substitution. In embodiments, the amino acid substitution at position 411 is an alanine substitution.

In embodiments, the polymerase includes an amino acid substitution at position 412. The amino acid substitution at position 412 may be an alanine substitution, a glycine substitution, a valine substitution, a methionine substitution, a leucine substitution or an isoleucine substitution. In embodiments, the amino acid substitution at position 412 is an alanine substitution.

In embodiments, the polymerase includes an amino acid substitution at position 413. The amino acid substitution at position 413 may be an alanine substitution, a glycine substitution, a valine substitution, a leucine substitution or an isoleucine substitution. In embodiments, the amino acid substitution at position 413 is a valine substitution, a leucine substitution or an isoleucine substitution. In embodiments, the amino acid substitution at position 413 is a valine substitution or an isoleucine substitution. In embodiments, the amino acid substitution at position 413 is a valine substitution. In embodiments, the amino acid substitution at position 413 is an isoleucine substitution.

In embodiments, the polymerase includes an alanine at amino acid position 411; a glycine at amino acid position 412; and an isoleucine or proline at amino acid position 413.

In embodiments, the polymerase includes a serine at amino acid position 411; an alanine or glycine at amino acid position 412; and a valine, isoleucine, or proline at amino acid position 413.

In embodiments, the polymerase includes a serine at amino acid position 411; an alanine at amino acid position 412; and a valine, isoleucine, or proline at amino acid position 413.

In embodiments, the polymerase includes an amino acid substitution mutation between position 129 and 318 of SEQ ID NO: 1, inclusive of position endpoints (i.e., 129 and 318).

In embodiments, the polymerase further includes an amino acid substitution mutation at positions 129, 141, and 143. In embodiments, the polymerase further includes an amino acid substitution mutation at positions 129, 141, or 143. In embodiments, the polymerase further includes an amino acid substitution mutation at positions 141 and 143.

In embodiments, the polymerase includes an amino acid substitution at position 488. The amino acid substitution at position 488 may be a glycine substitution, methionine substitution, a valine substitution, a leucine substitution or an isoleucine substitution. In embodiments, the amino acid substitution at position 488 is a valine substitution.

In embodiments, the polymerase further includes an amino acid substitution mutation at position 517. In embodiments, the polymerase includes a serine, alanine, asparagine, or threonine at position 517. In embodiments, the polymerase includes a serine at position 517.

In embodiments, the polymerase further includes an amino acid substitution mutation at position 593. In embodiments, the polymerase includes an isoleucine, valine, leucine, or methionine at position 593. In embodiments, the polymerase includes an isoleucine at position 593.

In embodiments, the polymerase includes the following mutations: D141A, E143A, L411S, Y412A, and P413V. In embodiments, the polymerase includes the following mutations: D141A, E143A, L411S, Y412A, P413V, and A488V. In embodiments, the polymerase includes the following mutations: D141A, E143A, L411A, Y412G, and A488V. In embodiments, the polymerase includes the following mutations: M129A, D141A, E143A, L411A, Y412A, P413I, and A488V. In embodiments, the polymerase includes the following mutations: D141A, E143A, and A485L.

In embodiments, the polymerase exhibits an increased rate of incorporation of modified nucleotides into a nucleic acid (e.g., a nucleic acid primer), relative to a control (e.g., wild-type TspEP1 DNA polymerase or SG2000). In embodiments, the rate of incorporation is increased 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0-fold relative to a control (e.g., wild-type TspEP1 or SG2000). In embodiments, the rate of incorporation is increased 1-fold, 2-fold, 3-fold, 4-fold, 5-fold, or 6.0-fold relative to a control (e.g., wild-type TspEP1 or SG2000). In embodiments, the rate of incorporation of a modified nucleotide is increased 1.1-fold relative to a control (e.g., wild-type TspEP1 or SG2000). In embodiments, the rate of incorporation of a modified nucleotide is increased 1.2-fold relative to a control (e.g., wild-type TspEP1 or SG2000). In embodiments, the rate of incorporation of a modified nucleotide is increased 1.3-fold relative to a control (e.g., wild-type TspEP1 or SG2000). In embodiments, the rate of incorporation of a modified nucleotide is increased 1.4-fold relative to a control (e.g., wild-type TspEP1 or SG2000). In embodiments, the rate of incorporation of a modified nucleotide is increased 1.5-fold relative to a control (e.g., wild-type TspEP1 or SG2000). In embodiments, the rate of incorporation of a modified nucleotide is increased 1.6-fold relative to a control (e.g., wild-type TspEP1 or SG2000). In embodiments, the rate of incorporation of a modified nucleotide is increased 1.7-fold relative to a control (e.g., wild-type TspEP1 or SG2000). In embodiments, the rate of incorporation of a modified nucleotide is increased 1.8-fold relative to a control (e.g., wild-type TspEP1 or SG2000). In embodiments, the rate of incorporation of a modified nucleotide is increased 1.9-fold relative to a control (e.g., wild-type TspEP1 or SG2000). In embodiments, the rate of incorporation of a modified nucleotide is increased 2.0-fold relative to a control (e.g., wild-type TspEP1 or SG2000). In embodiments, the rate of incorporation of a modified nucleotide is increased 2.1-fold relative to a control (e.g., wild-type TspEP1 or SG2000). In embodiments, the rate of incorporation of a modified nucleotide is increased 2.2-fold relative to a control (e.g., wild-type TspEP1 or SG2000). In embodiments, the rate of incorporation of a modified nucleotide is increased 2.3-fold relative to a control (e.g., wild-type TspEP1 or SG2000). In embodiments, the rate of incorporation of a modified nucleotide is increased 2.4-fold relative to a control (e.g., wild-type TspEP1 or SG2000). In embodiments, the rate of incorporation of a modified nucleotide is increased 2.5-fold relative to a control (e.g., wild-type TspEP1 or SG2000). In embodiments, the rate of incorporation of a modified nucleotide is increased 2.6-fold relative to a control (e.g., wild-type TspEP1 or SG2000). In embodiments, the rate of incorporation of a modified nucleotide is increased 2.7-fold relative to a control (e.g., wild-type TspEP1 or SG2000). In embodiments, the rate of incorporation of a modified nucleotide is increased 2.8-fold relative to a control (e.g., wild-type TspEP1 or SG2000). In embodiments, the rate of incorporation of a modified nucleotide is increased 2.9-fold relative to a control (e.g., wild-type TspEP1 or SG2000). In embodiments, the rate of incorporation of a modified nucleotide is increased 3.0-fold relative to a control (e.g., wild-type TspEP1 or SG2000). In embodiments, the rate of incorporation of a modified nucleotide is increased 3.1-fold relative to a control (e.g., wild-type TspEP1 or SG2000). In embodiments, the rate of incorporation of a modified nucleotide is increased 3.2-fold relative to a control (e.g., wild-type TspEP1 or SG2000). In embodiments, the rate of incorporation of a modified nucleotide is increased 3.3-fold relative to a control (e.g., wild-type TspEP1 or SG2000). In embodiments, the rate of incorporation of a modified nucleotide is increased 3.4-fold relative to a control (e.g., wild-type TspEP1 or SG2000). In embodiments, the rate of incorporation of a modified nucleotide is increased 3.5-fold relative to a control (e.g., wild-type TspEP1 or SG2000). In embodiments, the rate of incorporation of a modified nucleotide is increased 3.6-fold relative to a control (e.g., wild-type TspEP1 or SG2000). In embodiments, the rate of incorporation of a modified nucleotide is increased 3.7-fold relative to a control (e.g., wild-type TspEP1 or SG2000). In embodiments, the rate of incorporation of a modified nucleotide is increased 3.8-fold relative to a control (e.g., wild-type TspEP1 or SG2000). In embodiments, the rate of incorporation of a modified nucleotide is increased 3.9-fold relative to a control (e.g., wild-type TspEP1 or SG2000). In embodiments, the rate of incorporation of a modified nucleotide is increased 4.0-fold relative to a control (e.g., wild-type TspEP1 or SG2000). In embodiments, the rate of incorporation of a modified nucleotide is increased 4.1-fold relative to a control (e.g., wild-type TspEP1 or SG2000). In embodiments, the rate of incorporation of a modified nucleotide is increased 4.2-fold relative to a control (e.g., wild-type TspEP1 or SG2000). In embodiments, the rate of incorporation of a modified nucleotide is increased 4.3-fold relative to a control (e.g., wild-type TspEP1 or SG2000). In embodiments, the rate of incorporation of a modified nucleotide is increased 4.4-fold relative to a control (e.g., wild-type TspEP1 or SG2000). In embodiments, the rate of incorporation of a modified nucleotide is increased 4.5-fold relative to a control (e.g., wild-type TspEP1 or SG2000). In embodiments, the rate of incorporation of a modified nucleotide is increased 4.6-fold relative to a control (e.g., wild-type TspEP1 or SG2000). In embodiments, the rate of incorporation of a modified nucleotide is increased 4.7-fold relative to a control (e.g., wild-type TspEP1 or SG2000). In embodiments, the rate of incorporation of a modified nucleotide is increased 4.8-fold relative to a control (e.g., wild-type TspEP1 or SG2000). In embodiments, the rate of incorporation of a modified nucleotide is increased 4.9-fold relative to a control (e.g., wild-type TspEP1 or SG2000). In embodiments, the rate of incorporation of a modified nucleotide is increased 5.0-fold relative to a control (e.g., wild-type TspEP1 or SG2000). In embodiments, the rate of incorporation of a modified nucleotide is increased 5.1-fold relative to a control (e.g., wild-type TspEP1 or SG2000). In embodiments, the rate of incorporation of a modified nucleotide is increased 5.2-fold relative to a control (e.g., wild-type TspEP1 or SG2000). In embodiments, the rate of incorporation of a modified nucleotide is increased 5.3-fold relative to a control (e.g., wild-type TspEP1 or SG2000). In embodiments, the rate of incorporation of a modified nucleotide is increased 5.4-fold relative to a control (e.g., wild-type TspEP1 or SG2000). In embodiments, the rate of incorporation of a modified nucleotide is increased 5.5-fold relative to a control (e.g., wild-type TspEP1 or SG2000). In embodiments, the rate of incorporation of a modified nucleotide is increased 5.6-fold relative to a control (e.g., wild-type TspEP1 or SG2000). In embodiments, the rate of incorporation of a modified nucleotide is increased 5.7-fold relative to a control (e.g., wild-type TspEP1 or SG2000). In embodiments, the rate of incorporation of a modified nucleotide is increased 5.8-fold relative to a control (e.g., wild-type TspEP1 or SG2000). In embodiments, the rate of incorporation of a modified nucleotide is increased 5.9-fold relative to a control (e.g., wild-type TspEP1 or SG2000). In embodiments, the rate of incorporation of a modified nucleotide is increased 6.0-fold relative to a control (e.g., wild-type TspEP1 or SG2000). In embodiments, the rate of incorporation of a modified nucleotide is increased 6.1-fold relative to a control (e.g., wild-type TspEP1 or SG2000). In embodiments, the rate of incorporation of a modified nucleotide is increased 6.2-fold relative to a control (e.g., wild-type TspEP1 or SG2000). In embodiments, the rate of incorporation of a modified nucleotide is increased 6.3-fold relative to a control (e.g., wild-type TspEP1 or SG2000). In embodiments, the rate of incorporation of a modified nucleotide is increased 6.4-fold relative to a control (e.g., wild-type TspEP1 or SG2000). In embodiments, the rate of incorporation of a modified nucleotide is increased 6.5-fold relative to a control (e.g., wild-type TspEP1 or SG2000). In embodiments, the rate of incorporation of a modified nucleotide is increased 6.6-fold relative to a control (e.g., wild-type TspEP1 or SG2000). In embodiments, the rate of incorporation of a modified nucleotide is increased 6.7-fold relative to a control (e.g., wild-type TspEP1 or SG2000). In embodiments, the rate of incorporation of a modified nucleotide is increased 6.8-fold relative to a control (e.g., wild-type TspEP1 or SG2000). In embodiments, the rate of incorporation of a modified nucleotide is increased 6.9-fold relative to a control (e.g., wild-type TspEP1 or SG2000). In embodiments, the rate of incorporation of a modified nucleotide is increased about 2-fold relative to a control (e.g., wild-type TspEP1 or SG2000). In embodiments, the rate of incorporation of a modified nucleotide is increased about 3-fold relative to a control (e.g., wild-type TspEP1 or SG2000). In embodiments, the rate of incorporation of a modified nucleotide is increased about 4-fold relative to a control (e.g., wild-type TspEP1 or SG2000). In embodiments, the rate of incorporation of a modified nucleotide is increased about 5-fold relative to a control (e.g., wild-type TspEP1 or SG2000). In embodiments, the rate of incorporation of a modified nucleotide is increased about 6-fold relative to a control (e.g., wild-type TspEP1 or SG2000). In embodiments, the rate of incorporation of a modified nucleotide is increased about 7-fold relative to a control (e.g., wild-type TspEP1 or SG2000). In embodiments, the rate of incorporation of a modified nucleotide is increased about 8-fold relative to a control (e.g., wild-type TspEP1 or SG2000). In embodiments, the rate of incorporation of a modified nucleotide is increased about 9-fold relative to a control (e.g., wild-type TspEP1 or SG2000). In embodiments, the rate of incorporation of a modified nucleotide is increased about 10-fold relative to a control (e.g., wild-type TspEP1 or SG2000). In embodiments, the rate of incorporation of a modified nucleotide is increased 2-fold relative to a control (e.g., wild-type TspEP1 or SG2000). In embodiments, the rate of incorporation of a modified nucleotide is increased 3-fold relative to a control (e.g., wild-type TspEP1 or SG2000). In embodiments, the rate of incorporation of a modified nucleotide is increased 4-fold relative to a control (e.g., wild-type TspEP1 or SG2000). In embodiments, the rate of incorporation of a modified nucleotide is increased 5-fold relative to a control (e.g., wild-type TspEP1 or SG2000). In embodiments, the rate of incorporation of a modified nucleotide is increased 6-fold relative to a control (e.g., wild-type TspEP1 or SG2000). In embodiments, the rate of incorporation of a modified nucleotide is increased 7-fold relative to a control (e.g., wild-type TspEP1 or SG2000). In embodiments, the rate of incorporation of a modified nucleotide is increased 8-fold relative to a control (e.g., wild-type TspEP1 or SG2000). In embodiments, the rate of incorporation of a modified nucleotide is increased 9-fold relative to a control (e.g., wild-type TspEP1 or SG2000). In embodiments, the rate of incorporation of a modified nucleotide is increased 10-fold relative to a control (e.g., wild-type TspEP1 or SG2000).

In embodiments, the polymerase includes the mutation A488L. In embodiments, the polymerase includes the mutation A642L. In embodiments, the polymerase includes the mutation D215A. In embodiments, the polymerase includes the mutation D317A. In embodiments, the polymerase includes the mutation E721A. In embodiments, the polymerase includes the mutation G153E. In embodiments, the polymerase includes the mutation I524L. In embodiments, the polymerase includes the mutation K479A. In embodiments, the polymerase includes the mutation K479A, K480A, and L481S. In embodiments, the polymerase includes the mutation K480A. In embodiments, the polymerase includes the mutation K605A. In embodiments, the polymerase includes the mutation K715E. In embodiments, the polymerase includes the mutation L481S. In embodiments, the polymerase includes the mutation N738A. In embodiments, the polymerase includes the mutation R708A. In embodiments, the polymerase includes the mutation R716A.

In embodiments, the polymerase (a synthetic or variant DNA polymerase) provided herein may further include one or more amino acid substitution mutations between position 319 and 774, inclusive of endpoint positions (i.e., 319 and 774). In embodiments, the polymerase (a synthetic or variant DNA polymerase) provided herein may have one or more amino acid substitution mutations at position 407, 410, 411, 412, 413, 463, 486, 488, 490, 494, 497, 498, 499, 543, 545, and/or 546.

In embodiments, the polymerase includes an amino acid substitution at position 411. The amino acid substitution at position 411 may be a serine substitution, a threonine substitution, an asparagine substation, or a glutamine substitution. In embodiments, the amino acid substitution at position 411 is a serine substitution. In embodiments, the amino acid substitution at position 411 may be an alanine substitution, a glycine substitution, a valine substitution, a methionine substitution, a leucine substitution or an isoleucine substitution. In embodiments, the amino acid substitution at position 411 is an alanine substitution.

In embodiments, the polymerase includes an amino acid substitution at position 412. The amino acid substitution at position 412 may be an alanine substitution, a glycine substitution, a valine substitution, a methionine substitution, a leucine substitution or an isoleucine substitution. In embodiments, the amino acid substitution at position 412 is an alanine substitution.

In embodiments, the polymerase includes an amino acid substitution at position 413. The amino acid substitution at position 413 may be an alanine substitution, a glycine substitution, a valine substitution, a methionine substitution, a leucine substitution or an isoleucine substitution. In embodiments, the amino acid substitution at position 413 is a valine substitution or an isoleucine substitution. In embodiments, the amino acid substitution at position 413 is a valine substitution. In embodiments, the amino acid substitution at position 413 is an isoleucine substitution.

In embodiments, the polymerase includes an amino acid substitution at position 488. The amino acid substitution at position 488 may be a glycine substitution, methionine substitution, a valine substitution, a leucine substitution or an isoleucine substitution. In embodiments, the amino acid substitution at position 488 is a valine substitution.

In embodiments, the polymerase includes an amino acid substitution at position at position 407, 410, 411, 412, 413, 463, 486, 488, 490, 494, 497, 498, 499, 543, 545, and/or 546. In embodiments, the polymerase includes an amino acid substitution at position 407. The amino acid substitution at position 407 may be aspartic acid. In embodiments, the polymerase includes an amino acid substitution at position 410. The amino acid substitution at position 410 may be an alanine substitution, glycine substitution, methionine substitution, a valine substitution, a leucine substitution or an isoleucine substitution. In embodiments, the amino acid substitution at position 410 is an alanine substitution. In embodiments, the polymerase includes an amino acid substitution at position 486. The amino acid substitution at position 486 may be a serine substitution, a threonine substitution, or an asparagine substitution. In embodiments, the amino acid substitution at position 486 is an asparagine substitution. In embodiments, the polymerase includes an amino acid substitution at position 490. The amino acid substitution at position 490 may be an arginine substitution or a lysine substitution. In embodiments, the amino acid substitution at position 490 is an arginine substitution. In embodiments, the polymerase includes an amino acid substitution at position 494. The amino acid substitution at position 494 may be a serine substitution, a threonine substitution, or a glutamine substitution. In embodiments, the amino acid substitution at position 494 is a glutamine substitution. In embodiments, the polymerase includes an amino acid substitution at position 497. The amino acid substitution at position 497 may be phenylalanine substitution, a tryptophan substitution, or a histidine substitution. In embodiments, the substitution at position 497 is a phenylalanine substitution. In embodiments, the polymerase includes an amino acid substitution at position 498. In embodiments, the amino acid substitution at position 498 may be an alanine substitution, a methionine substitution, a valine substitution, a leucine substitution or an isoleucine substitution. In embodiments, the amino acid substitution at position 498 is an alanine substitution. In embodiments, the polymerase includes an amino acid substitution at position 499. The amino acid substitution at position 499 may be phenylalanine substitution, a tryptophan substitution, or a histidine substitution. In embodiments, the substitution at position 499 is a phenylalanine substitution. In embodiments, the polymerase includes an amino acid substitution at position 543. The amino acid substitution at position 543 may be a glutamic acid substitution. In embodiments, the polymerase includes an amino acid substitution at position 545. The amino acid substitution at position 545 may be a glutamic acid substitution. In embodiments, the polymerase includes an amino acid substitution at position 546. The amino acid substitution at position 546 may be an alanine substitution, methionine substitution, a valine substitution, a leucine substitution or an isoleucine substitution. In embodiments, the amino acid substitution at position 546 is an alanine substitution.

In an aspect, the polymerase (a synthetic or variant DNA polymerase) provided herein may have one or more amino acid substitution mutations at position 129, 141, 143, 411, 412, 413, and/or 488.

In embodiments, the polymerase includes an amino acid sequence that is at least 80% identical to a continuous 500 amino acid sequence within SEQ ID NO: 1. The polymerase includes substitution mutations at positions 141 and 143 of SEQ ID NO: 1. The polymerase further includes at least one amino acid substitution mutation at a position selected from positions 129, 411, 412, 413 and/or 488 of SEQ ID NO: 1.

In embodiments, the polymerase includes an amino acid sequence that is at least 85%, at least 90%, or at least 95% identical to a continuous 500 amino acid sequence within SEQ ID NO: 1. In embodiments, the polymerase includes an amino acid sequence that is at least 80%, at least 85%, at least 90%, or at least 95% identical to a continuous 600 amino acid sequence within SEQ ID NO: 1. In embodiments, the polymerase includes an amino acid sequence that is at least 80%, at least 85%, at least 90%, or at least 95% identical to a continuous 700 amino acid sequence within SEQ ID NO: 1. In embodiments, the polymerase includes an amino acid sequence that is at least 85% identical to a continuous 500 amino acid sequence within SEQ ID NO: 1. In embodiments, the polymerase includes an amino acid sequence that is at least 90% identical to a continuous 500 amino acid sequence within SEQ ID NO: 1. In embodiments, the polymerase includes an amino acid sequence that is at least 95% identical to a continuous 500 amino acid sequence within SEQ ID NO: 1. In embodiments, the polymerase includes an amino acid sequence that is at least 85% identical to a continuous 600 amino acid sequence within SEQ ID NO: 1. In embodiments, the polymerase includes an amino acid sequence that is at least 90% identical to a continuous 600 amino acid sequence within SEQ ID NO: 1. In embodiments, the polymerase includes an amino acid sequence that is at least 95% identical to a continuous 600 amino acid sequence within SEQ ID NO: 1. In embodiments, the polymerase includes an amino acid sequence that is at least 85% identical to a continuous 700 amino acid sequence within SEQ ID NO: 1. In embodiments, the polymerase includes an amino acid sequence that is at least 90% identical to a continuous 700 amino acid sequence within SEQ ID NO: 1. In embodiments, the polymerase includes an amino acid sequence that is at least 95% identical to a continuous 700 amino acid sequence within SEQ ID NO: 1.

In embodiments, the polymerase includes alanine substitution mutations at positions 141 and 143 of SEQ ID NO: 1. In embodiments, the polymerase further includes at least one amino acid substitution mutation at a position selected from positions 129, 411, 412, 413, and/or 488 of SEQ ID NO: 1. In embodiments, the polymerase further includes at least one amino acid substitution at a position selected from an alanine, glycine, leucine, isoleucine, or valine at position 129, a serine, threonine, an asparagine, a glutamine, an alanine, a glycine, an isoleucine, a valine, or a methionine at position 411, an alanine, a glycine, an isoleucine, a valine, or a methionine at position 412, a valine, isoleucine, leucine, or methionine at position 413, and a valine, isoleucine, leucine, or methionine at position 488. In embodiments, the polymerase further includes one amino acid substitution mutation selected from a serine at position 411, an alanine at position 412, a valine at position 413, and a valine at position 488. In embodiments, the polymerase further includes one amino acid substitution mutation selected from an alanine at position 129, a serine at position 409, an alanine at position 412, an isoleucine at position 413, and a valine at position 488.

In embodiments, the polymerase includes alanine substitution mutations at positions 141 and 143 of SEQ ID NO: 1 and further includes a serine at position 411, an alanine at position 412, and a valine at position 413 as exemplified by SEQ ID NO: 4. In embodiments, the polymerase includes alanine substitution mutations at positions 141 and 143 of SEQ ID NO: 1 and further includes a serine at position 411, an alanine at position 412, a valine at position 413 and a valine at position 488 as exemplified by SEQ ID NO: 5. In embodiments, the polymerase includes alanine substitution mutations at positions 141 and 143 of SEQ ID NO: 1 and further includes an alanine at position 129, an alanine at position 411, an alanine at position 412, an isoleucine at position 413 and a valine at position 488 as exemplified by SEQ ID NO: 6.

The synthetic or variant DNA polymerases may have a sequence that is at least 60%, at least 65%, at least 70%, at least 75%, at least 80%, at least 85%, at least 90%, or at least 95% identical to the wild-type sequence of *Thermococcus* spEP1 family B DNA polymerase of SEQ ID NO: 1. In embodiments, the synthetic or variant DNA polymerases may have a sequence that is 60%, 61%, 62%, 63%, 64%, 65%, 66%, 67%, 68%, or 69% identical to the wild-type sequence of *Thermococcus* spEP1 family B DNA polymerase of SEQ ID NO: 1. The synthetic or variant DNA polymerases may have a sequence that is 70%, 71%, 72%, 73%, 74%, 75%, 76%, 77%, 78%, or 79% identical to the wild-type sequence of *Thermococcus* spEP1 family B DNA polymerase of SEQ ID NO: 1. The synthetic or variant DNA polymerases may have a sequence that is 80%, 81%, 82%, 83%, 84%, 85%, 86%, 87%, 88%, or 89% identical to the wild-type sequence of *Thermococcus* spEP1 family B DNA polymerase of SEQ ID NO: 1. The synthetic or variant DNA polymerases may have a sequence that is 90%, 91%, 92%, 93%, 94%, 95%, 96%, 97%, 98%, or 99% identical to the wild-type sequence of *Thermococcus* spEP1 family B DNA polymerase of SEQ ID NO: 1.

The synthetic or variant DNA polymerases may have a sequence that is identical to a continuous 500, 600, or 700 continuous amino acids of SEQ ID NO: 1. In embodiments, the synthetic or variant DNA polymerases may have a sequence that is identical to a continuous 500, 505, 510, 515, 520, 525, 530, 535, 540, 545, 550, 555, 560, 565, 570, 575, 580, 585, 590, or 595 continuous amino acids of SEQ ID NO: 1. In embodiments, the synthetic or variant DNA polymerases may have a sequence that is identical to a continuous 600, 605, 610, 615, 620, 625, 630, 635, 640, 645, 650, 655, 660, 665, 670, 675, 680, 685, 690, or 695 continuous amino acids of SEQ ID NO: 1.

Examples of mutations giving rise to an exo⁻/exo⁻ variants include mutations at positions in a parent polymerase corresponding to positions in SEQ ID NO: 1 identified as follows: 141 and 143.

In embodiments, mutations may include substitution of the amino acid in the parent amino acid sequences with an amino acid, which is not the parent amino acid. In embodiments, the mutations may result in conservative amino acid changes. In embodiments, non-polar amino acids may be converted into polar amino acids (threonine, asparagine, glutamine, cysteine, tyrosine, aspartic acid, glutamic acid or histidine) or the parent amino acid may be changed to an alanine.

Alternatively, mutations may be randomly generated within the various motifs (within or outside the highly conserved sequences described) using standard techniques known in the art and the resultant enzymes can be tested using the sensitive assays described in the Examples to determine whether they have substantially no exonuclease activity.

Functionally equivalent, positionally equivalent and homologous amino acids within the wild type amino acid sequences of two different polymerases do not necessarily have to be the same type of amino acid residue, although functionally equivalent, positionally equivalent and homologous amino acids are commonly conserved. By way of example, the motif A region of 9°N polymerase has the sequence LYP, the functionally homologous region of Vent™ polymerase also has sequence LYP. In the case of these two polymerases the homologous amino acid sequences are identical, however homologous regions in other polymerases may have different amino acid sequence. The LYP amino acids are located at 408, 409, 410 of a 9°N polymerase, 409, 410, and 411 of a *Pyrococcus abyssi* polymerase and the functional equivalent amino acid positions in the wild-type enzyme of *Thermococcus* EP1 are located at 411, 412, and 413.

In embodiments, the polymerase is capable of incorporating an A-Term, S-Term, or i-term (e.g., i-term1 or item2) reversible terminator moiety. In embodiments, the polymerase incorporates an A-Term, S-Term, or i-term (e.g., i-term1 or item2) reversible terminator moiety. A-Term refers to azide-containing terminators (Guo J, et al. PNAS 2008); for example having the formula:

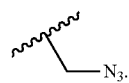

S-Term refers to sulfide-containing terminators (WO 2017/058953); for example having the formula

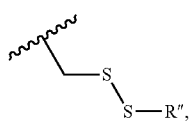

wherein R" is unsubstituted $C_1$-$C_4$ alkyl. The i-term probe refers to an isomeric reversible terminator For example, an i-term probe has the formula:

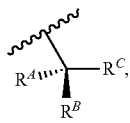

wherein $R^A$ and $R^B$ are hydrogen or alkyl, wherein at least one of $R^A$ or $R^B$ are hydrogen to yield a stereoisomeric probe, and $R^C$ is the remainder of the reversible terminator.

Certain mutations in the polymerase favor the incorporation of one isomer, thus creating optimized polymerases for a unique class of reversible terminators (i.e., isomeric reversible terminators). In embodiments, the polymerase exhibits isomeric preference (i.e. it incorporates a modified nucleotide of one isomer (e.g., i-term1) at a faster rate than it incorporates a modified nucleotide of a different isomer (e.g., i-term2).

In embodiments, the nucleotide is

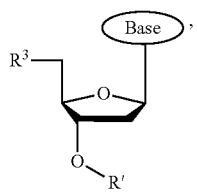

wherein Base is a Base as described herein, $R^3$ is —OH, monophosphate, or polyphosphate or a nucleic acid, and R' is a reversible terminator having the formula:

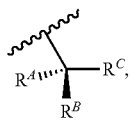

wherein $R^A$ and $R^B$ are hydrogen or alkyl and $R^C$ is the remainder of the reversible terminator. In embodiments, $R^A$ is methyl, $R^B$ is hydrogen, and $R^C$ is the remainder of the reversible terminator moiety. In embodiments, R' has the formula

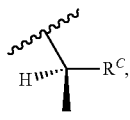

wherein $R^C$ is the remainder of the reversible terminator moiety. In embodiments, i-term1 has the formula

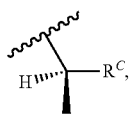

and i-term 2 has the formula:

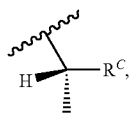

wherein $R^C$ is the remainder of the reversible terminator moiety.

In embodiments, the polymerase (e.g., a polymerase as described herein) is truncated at the C-terminus. In embodiments, the polymerase (e.g., a polymerase as described herein) is truncated at the C-terminus and retains the ability to incorporate a modified nucleotide. In embodiments, the polymerase (e.g., a polymerase as described herein) is truncated at the C-terminus, wherein the polymerase is truncated to remove at least 20 amino acids from the C-terminus. In embodiments, the polymerase (e.g., a polymerase as described herein) is truncated at the C-terminus, wherein the polymerase is truncated to remove at least 10 amino acids from the C-terminus. In embodiments, the polymerase (e.g., a polymerase as described herein) is truncated at the C-terminus, wherein the polymerase is truncated to remove at least 5 amino acids from the C-terminus. In embodiments, the polymerase (e.g., a polymerase as described herein) is truncated at the C-terminus, wherein the truncation removes 5 to 16 amino acids from the C-terminus. In embodiments, the polymerase (e.g., a polymerase as described herein) is truncated at the C-terminus, wherein the truncation removes 5 amino acids from the C-terminus. In embodiments, the polymerase (e.g., a polymerase as described herein) is truncated at the C-terminus, wherein the truncation removes 10 amino acids from the C-terminus. In embodiments, the polymerase (e.g., a polymerase as described herein) is truncated at the C-terminus, wherein the truncation removes 13 amino acids from the C-terminus. In embodiments, the polymerase (e.g., a polymerase as described herein) is truncated at the C-terminus, wherein the truncation removes 16 amino acids from the C-terminus.

In another aspect is provided a nucleic acid encoding a mutant or improved DNA polymerase as described herein, a vector comprising the recombinant nucleic acid, and/or a host cell transformed with the vector. In certain embodiments, the vector is an expression vector. Host cells comprising such expression vectors are useful in methods of the invention for producing the mutant or improved polymerase by culturing the host cells under conditions suitable for expression of the recombinant nucleic acid. The polymerases of the invention may be contained in reaction mixtures and/or kits. The embodiments of the recombinant nucleic acids, host cells, vectors, expression vectors, reaction mixtures and kits are as described above and herein. The full plasmid nucleic acid sequence used to generate *Thermococcus* spEP1 protein SG2000 is provided in SEQ ID NO: 17.

In an aspect is provided a kit. Generally, the kit includes at least one container providing a mutant or improved DNA polymerase as described herein. In embodiments, the kit further includes one or more additional containers providing one or more additional reagents. For example, the one or more additional containers provide nucleoside triphosphates; a buffer suitable for polynucleotide extension; and/or a primer hybridizable, under polynucleotide extension conditions, to a predetermined polynucleotide template. The kit may also include a template nucleic acid (DNA and/or RNA), one or more primer or probe polynucleotides, nucleoside triphosphates (including, e.g., deoxyribonucleotides, ribonucleotides, labelled nucleotides, modified nucleotides), buffers, salts, labels (e.g., fluorophores). In embodiments, the kit includes a nucleotide solution as described herein. In embodiments, the kit further includes instructions.

III. Methods of Use

In an aspect, a method of incorporating a modified nucleotide into a nucleic acid sequence is provided. The method includes allowing the following components to interact: (i) a nucleic acid template, (ii) a primer that has an extendible 3' end (iii) a nucleotide solution, and (iv) a polymerase (e.g., a DNA polymerase or a thermophilic nucleic acid polymerase as described here). The polymerase used in the method includes an amino acid sequence that is at least 80% identical to a continuous 500 amino acid sequence within SEQ ID NO: 1. In embodiments, the polymerase has exonuclease activity that is reduced at least 80% relative to the exonuclease activity of a polymerase of SEQ ID NO: 1. The polymerase used in the method includes substitution mutations at positions 141 and 143 of SEQ ID NO: 1. The polymerase used in the method further includes at least one amino acid substitution mutation at a position selected from position 129, 411, 412, 413 and 488 of SEQ ID NO: 1. In embodiments, the polymerase is a polymerase as described herein, including embodiments.

In an aspect, a method of preparing a growing polynucleotide complementary to a target single-stranded polynucleotide in a sequencing reaction is provided. The method incudes incorporating a modified nucleotide molecule into a growing complementary polynucleotide, where the incorporation of the modified nucleotide prevents the introduction of any subsequent nucleotide into the growing complementary polynucleotide and wherein the incorporation of the modified nucleotide molecule is accomplished by a polymerase as described herein.

In an aspect, a method for performing a primer extension reaction is provided. The method incudes contacting a modified polymerase comprising the amino acid sequence of any one of SEQ ID NO: 1-10, with a nucleic acid molecule and a modified nucleotide under conditions where the modified nucleotide is incorporated into the nucleic acid molecule by the polymerase.

In embodiments, the nucleic acid template is DNA, RNA, or analogs thereof. In embodiments, the nucleic acid template is a primer. Primers are usually single-stranded for maximum efficiency in amplification, but may alternatively be double-stranded. If double-stranded, the primer is usually first treated to separate its strands before being used to prepare extension products. This denaturation step is typically affected by heat, but may alternatively be carried out using alkali, followed by neutralization. Thus, a "primer" is complementary to a nucleic acid template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

In embodiments, the nucleotide solution includes modified nucleotides. It is understood that a modified nucleotide and a nucleotide analogue are interchangeable terminology in this context. In embodiments, the nucleotide solution includes labelled nucleotides. In embodiments, the nucleotides include synthetic nucleotides. In embodiments, the nucleotide solution includes modified nucleotides that independently have different reversible terminating moieties (e.g., nucleotide A has an A-term reversible terminator, nucleotide G has an S-term reversible terminator, nucleotide C has an S-term reversible terminator, and nucleotide T has an i-term 1 reversible terminator). In embodiments the nucleotide solution contains native nucleotides. In embodiments the nucleotide solution contains labelled nucleotides.

In embodiments, the modified nucleotide has a removable group, for example a label, a blocking group, or protecting group. The removable group includes a chemical group that can be removed from a dNTP analogue such that a DNA polymerase can extend the nucleic acid (e.g., a primer or extension product) by the incorporation of at least one additional nucleotide. In embodiments, the removal group is a reversible terminator.

In embodiments, the modified nucleotide includes a blocking moiety and/or a label moiety. The blocking moiety on a nucleotide can be reversible, whereby the blocking moiety can be removed or modified to allow the 3' hydroxyl to form a covalent bond with the 5' phosphate of another nucleotide. The blocking moiety can be effectively irreversible under particular conditions used in a method set forth herein. A label moiety of a nucleotide can be any moiety that allows the nucleotide to be detected, for example, using a spectroscopic method. In embodiments, one or more of the above moieties can be absent from a nucleotide used in the methods and compositions set forth herein. For example, a nucleotide can lack a label moiety or a blocking moiety or both.

In embodiments, the blocking moiety can be located, for example, at the 3' position of the nucleotide and may be a chemically cleavable moiety such as an allyl group, an azidomethyl group or a methoxymethyl group, or may be an enzymatically cleavable group such as a phosphate. Suitable nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465, the contents of which are incorporated herein by reference in their entirety. The nucleotides may be labelled or unlabeled. In embodiments, the modified nucleotides with reversible terminators useful in methods provided herein may be 3'-O-blocked reversible or 3'-unblocked reversible terminators. The 3'-O-blocked reversible terminators are known in the art, and may be, for instance, a 3'-ONH$_2$ reversible terminator, a 3'-O-allyl reversible terminator, or a 3'-O-azidomethyl reversible terminator.

In embodiments, the modified nucleotides useful in methods provided herein can include 3'-unblocked reversible terminators. The 3'-unblocked reversible terminators are known in the art and include for example, the "virtual terminator" as described in U.S. Pat. No. 8,114,973 and the "lightening terminator" as described in U.S. Pat. No. 10,041,115, the contents of which are incorporated herein by reference in their entirety.

In embodiments, the modified nucleotide (also referred to herein as a nucleotide analogue) has the formula:

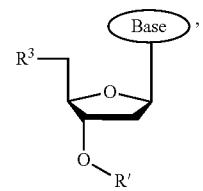

wherein Base is a Base as described herein (e.g., B of Formula Ia or Ib), $R^3$ is —OH, monophosphate, or polyphosphate or a nucleic acid, and R' is a reversible terminator having the formula:

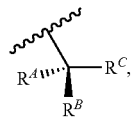

wherein $R^A$ and $R^B$ are hydrogen or alkyl and $R^C$ is the remainder of the reversible terminator. In embodiments, the reversible terminator is

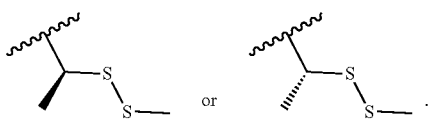

In embodiments, the reversible terminator is

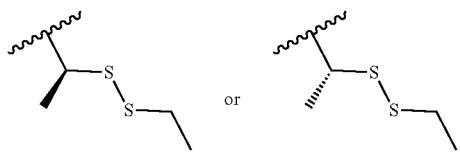

In embodiments, the reversible terminator is

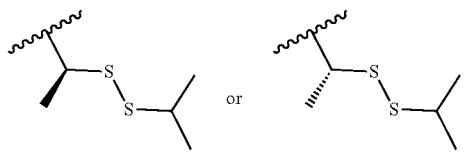

In embodiments, the reversible terminator is

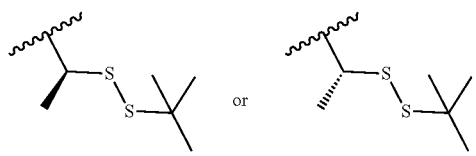

In embodiments, the reversible terminator is

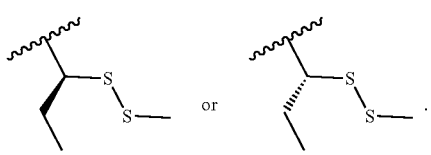

In embodiments, the reversible terminator is

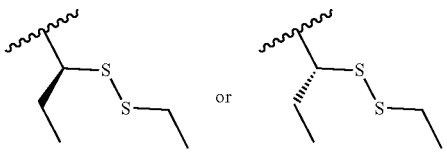

In embodiments, the reversible terminator is

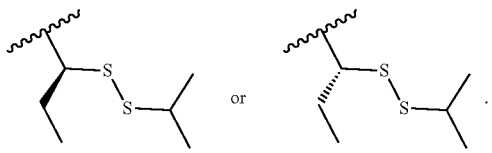

In embodiments, the reversible terminator is

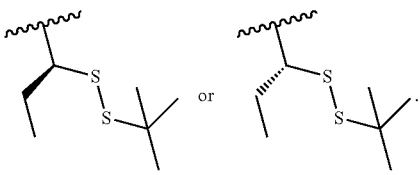

In embodiments, the reversible terminator is

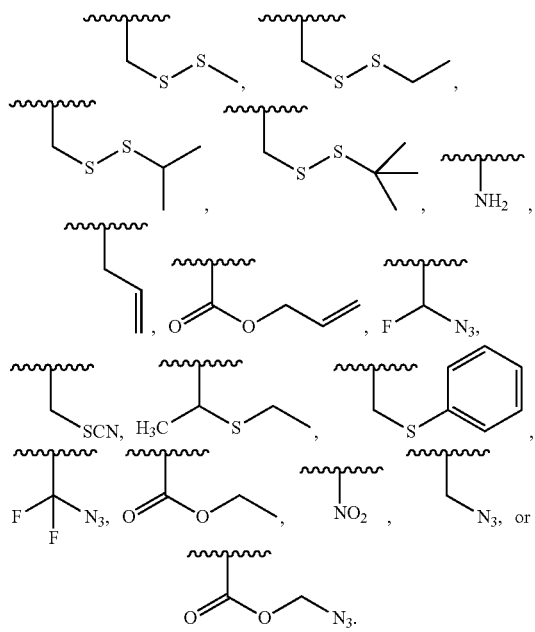

In embodiments, the reversible terminator is

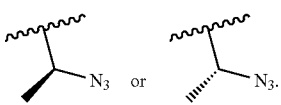

In embodiments, the reversible terminator is

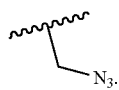

In embodiments, the modified nucleotide (e.g., also referred to herein as a nucleotide analogue) has the formula:

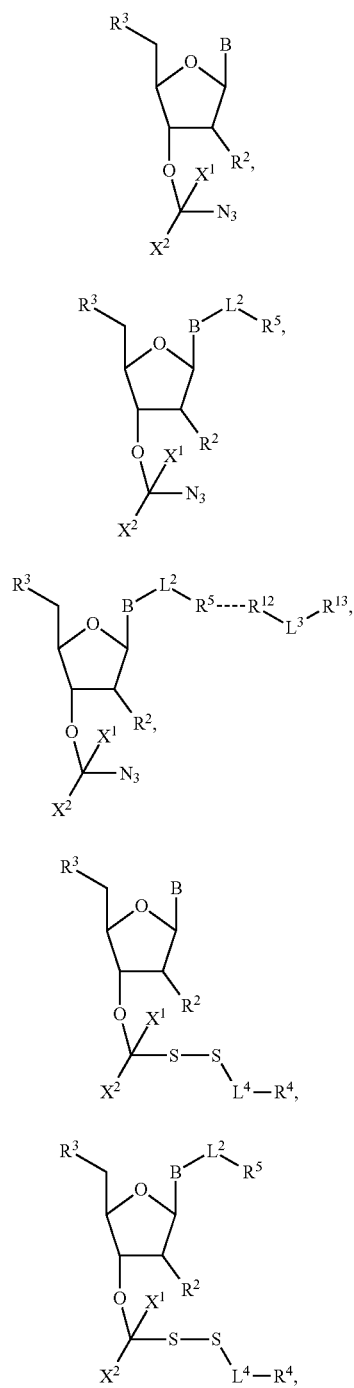

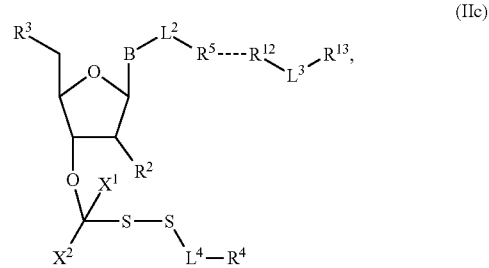

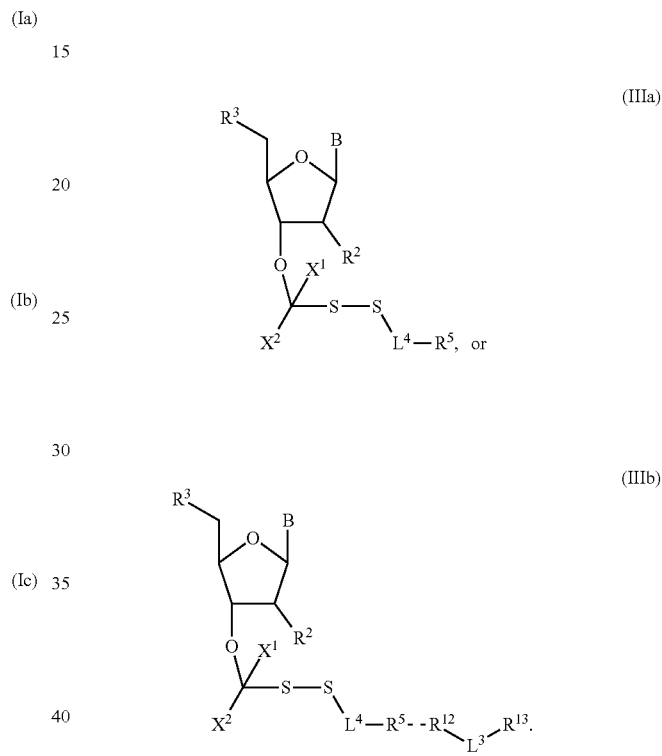

The symbol "----" is a non-covalent bond. The symbol B is a base or analogue thereof. $L^2$ is a covalent linker (e.g., a cleavable linker). $L^3$ is a covalent linker. $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^2$ is hydrogen or —$OR^{2A}$, wherein $R^{2A}$ is hydrogen, polymerase-compatible moiety, or polymerase-compatible cleavable moiety. $R^3$ is —OH, monophosphate, or polyphosphate or a nucleic acid. $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is a detectable label, an anchor moiety, or affinity anchor moiety. $R^{12}$ is a complementary affinity anchor moiety binder. $R^{13}$ is a detectable label. The symbols $X^1$ and $X^2$ are independently hydrogen, halogen, —$N_3$, or —CN, wherein at least wherein at least one of $X^1$ or $X^2$ is halogen, —$N_3$, or —CN. In embodiments, at least one of $X^1$ or $X^2$ is halogen. In embodiments, if $X^1$ is —$N_3$ then $X^2$ is not —$N^3$ for formula (Ia), (Ib), and (Ic).

In embodiments, the nucleotide analogue has the formula:

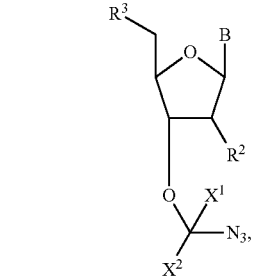
(Ia)

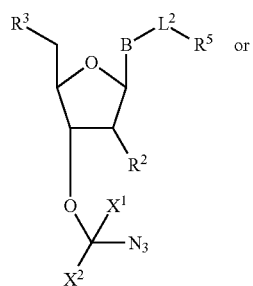
(Ib)

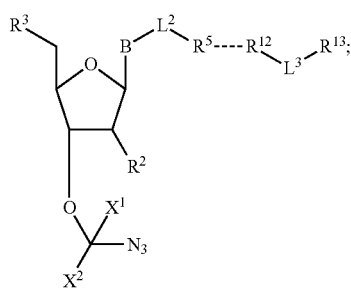
(Ic)

wherein $R^3$, B, $R^2$, $X^1$, $X^2$, $L^2$, $R^5$, $R^{12}$, $L^3$, and $R^{13}$ are as described herein, including embodiments.

In embodiments, the nucleotide analogue has the formula:

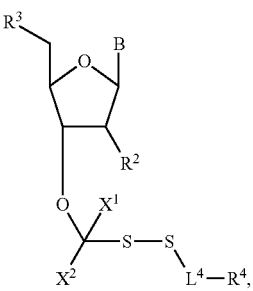
(IIa)

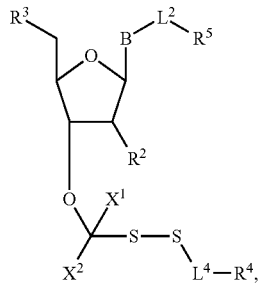
(IIb)

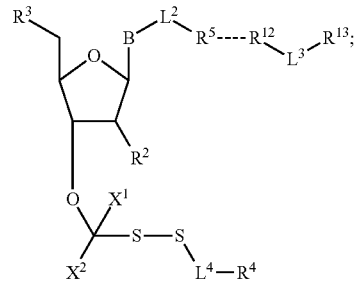
(IIc)

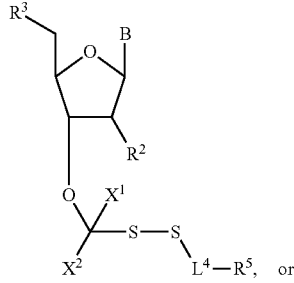
(IIIa)

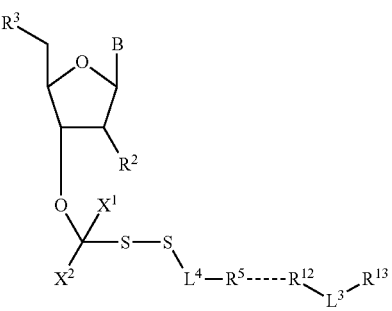
(IIIb)

wherein $R^3$, B, $R^2$, $X^1$, $X^2$, $L^2$, $L^4$, $R^4$, $R^5$, $R^{12}$, $L^3$, and $R^{13}$ are as described herein, including embodiments.

In embodiments, the nucleotide analogue has the formula:

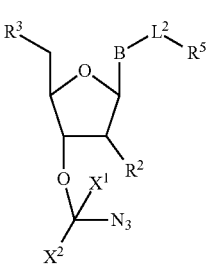
(Ib)

-continued (Ic)
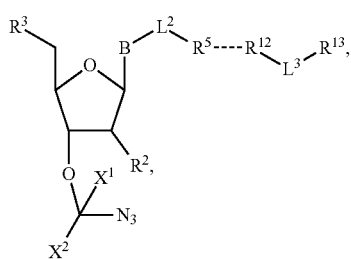

(IIb)
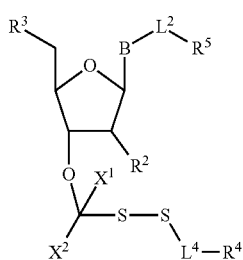

(IIc)
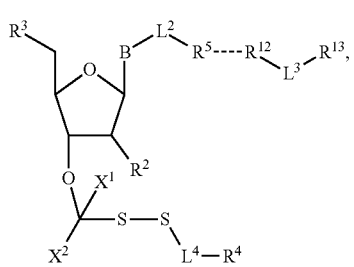

(IIIa)
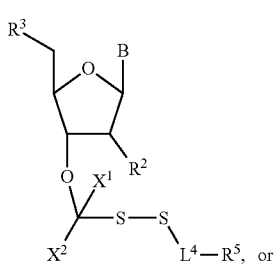

(IIIb)
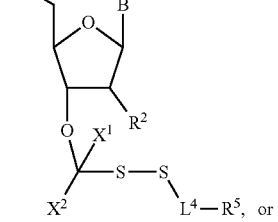
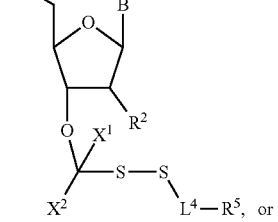

wherein $R^3$, B, $R^2$, $X^1$, $X^2$, $L^2$, $L^4$, $R^4$, $R^5$, $R^{12}$, $L^3$, and $R^{13}$ are as described herein, including embodiments.

In embodiments, the nucleotide analogue has the formula:

(Ia)
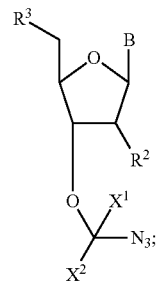

wherein $R^3$, B, $R^2$, $X^1$, and $X^2$ are as described herein, including embodiments. In embodiments, the nucleotide analogue has the formula:

(Ib)
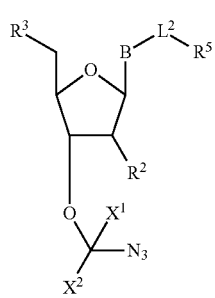

wherein $R^3$, B, $L^2$, $R^5$, $R^2$, $X^1$, and $X^2$ are as described herein, including embodiments. In embodiments, the nucleotide analogue has the formula:

(Ic)
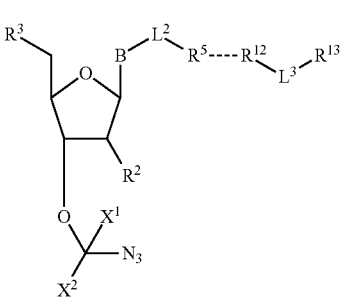

wherein $R^3$, B, $L^2$, $R^5$, $R^{12}$, $L^3$, $R^{13}$, $R^2$, $X^1$, and $X^2$ are as described herein, including embodiments. In embodiments, the nucleotide analogue has the formula:

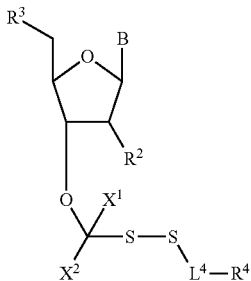

(IIa)

wherein $R^3$, B, $R^2$, $X^1$, $X^2$, L4, and R4 are as described herein, including embodiments. In embodiments, the nucleotide analogue has the formula:

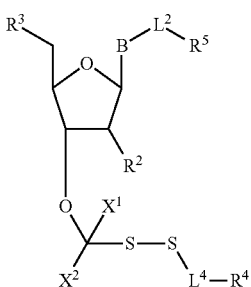

(IIb)

wherein $R^3$, B, $L^2$, $R^5$, $R^2$, $X^1$, $X^2$, $L^4$, and $R^4$ are as described herein, including embodiments. In embodiments, the nucleotide analogue has the formula:

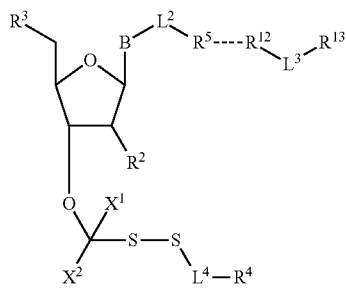

(IIc)

wherein $R^3$, B, $L^2$, $R^5$, $R^{12}$, $L^3$, $R^{13}$, $R^2$, $x^1$, $X^2$, $L^4$ and $R^4$ are as described herein, including embodiments. In embodiments, the nucleotide analogue has the formula:

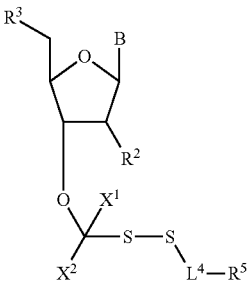

(IIIa)

wherein $R^3$, B, $R^2$, $X^1$, $X^2$, $L^4$ and $R^5$ are as described herein, including embodiments. In embodiments, the nucleotide analogue has the formula:

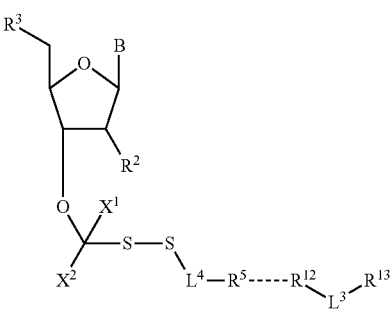

(IIIb)

wherein $R^3$, B, $R^2$, $X^1$, $X^2$, $L^4$, $R^5$, $R^{12}$, $L^3$, and $R^{13}$ are as described herein, including embodiments.

In embodiments, B is

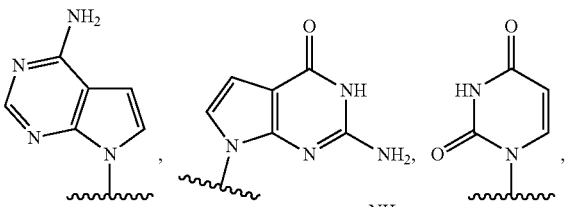

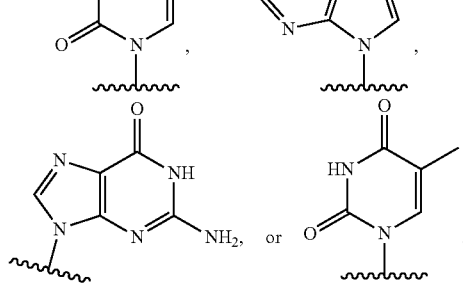

In embodiments, B is
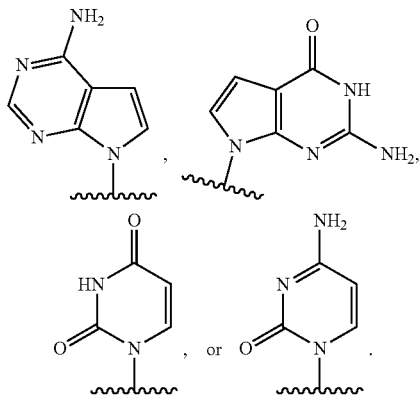
In embodiments, B is
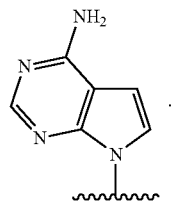 [SMILES: *n1ccc2c(N)ncnc21 ; "."]
In embodiments, B is
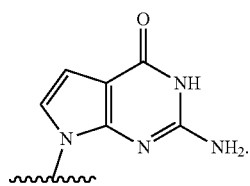 [SMILES: *n1ccc2c(=O)[nH]c(N)nc21]
In embodiments, B is
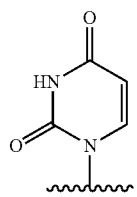
In embodiments, B¹ is
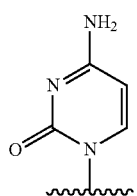
In embodiments, B is
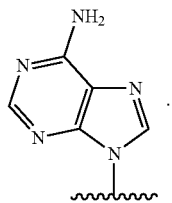 [SMILES: *n1cnc2c(N)ncnc21 ; "."]
In embodiments, B is
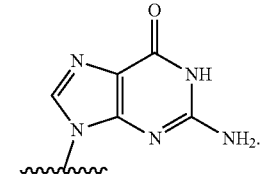 [SMILES: *n1cnc2c(=O)[nH]c(N)nc21]
In embodiments, B is
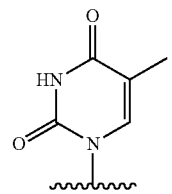
In embodiments, B is -continued

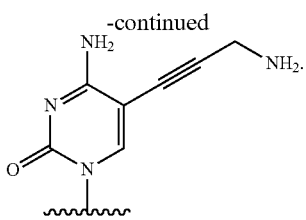

In embodiments, B is

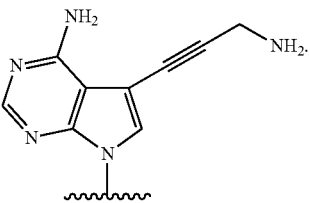 [SMILES: *n1cc(C#CCN)c2c(N)ncnc21]

In embodiments, B is

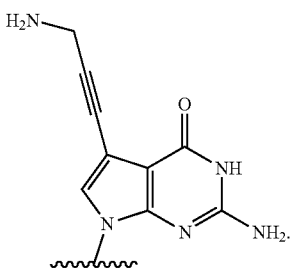 [SMILES: *n1cc(C#CCN)c2c(=O)[nH]c(N)nc21]

In embodiments, B is

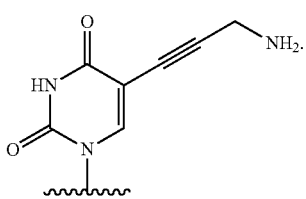 [SMILES: *n1cc(C#CCN)c(=O)[nH]c1=O]

In embodiments, B is

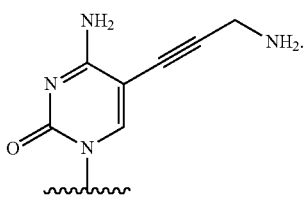 [SMILES: *n1cc(C#CCN)c(N)nc1=O]

In embodiments, $R^3$ is a monophosphate moiety. In embodiments, $R^3$ is a triphosphate moiety.

In embodiments, $X^1$ is hydrogen. In embodiments, $X^1$ is halogen (e.g., —F). In embodiments, $X^1$ is —CN. In embodiments, $X^1$ is —$N_3$. In embodiments, $X^2$ is hydrogen. In embodiments, $X^2$ is halogen (e.g., —F). In embodiments, $X^2$ is —CN. In embodiments, $X^2$ is —$N_3$.

In embodiments, $X^1$ is hydrogen, and $X^2$ is halogen. In embodiments, $X^1$ is hydrogen, and $X^2$ is —CN. In embodiments, $X^1$ is hydrogen, and $X^2$ is —$N_3$. In embodiments, $X^1$ is halogen, and $X^2$ is hydrogen. In embodiments, $X^1$ is halogen, and $X^2$ is halogen. In embodiments, $X^1$ is halogen, and $X^2$ is —CN. In embodiments, $X^1$ is halogen, and $X^2$ is —$N_3$. In embodiments, $X^1$ is —CN, and $X^2$ is hydrogen. In embodiments, $X^1$ is —CN, and $X^2$ is halogen. In embodiments, $X^1$ is —CN, and $X^2$ is —CN. In embodiments, $X^1$ is —CN, and $X^2$ is —$N_3$. In embodiments, $X^1$ is —$N_3$, and $X^2$ is hydrogen. In embodiments, $X^1$ is —$N_3$, and $X^2$ is halogen. In embodiments, $X^1$ is —$N_3$, and $X^2$ is —CN. In embodiments, $X^1$ is —$N_3$, and $X^2$ is —$N_3$.

In embodiments, $X^1$ is hydrogen, and $X^2$ is —F. In embodiments, $X^1$ is hydrogen, and $X^2$ is —CN. In embodiments, $X^1$ is hydrogen, and $X^2$ is —$N_3$. In embodiments, $X^1$ is —F, and $X^2$ is hydrogen. In embodiments, $X^1$ is —F, and $X^2$ is —F. In embodiments, $X^1$ is —F, and $X^2$ is —CN. In embodiments, $X^1$ is —F, and $X^2$ is —$N_3$. In embodiments, $X^1$ is —CN, and $X^2$ is hydrogen. In embodiments, $X^1$ is —CN, and $X^2$ is —F. In embodiments, $X^1$ is —CN, and $X^2$ is —CN. In embodiments, $X^1$ is —CN, and $X^2$ is —$N_3$. In embodiments, $X^1$ is —$N_3$, and $X^2$ is hydrogen. In embodiments, $X^1$ is —$N_3$, and $X^2$ is —F. In embodiments, $X^1$ is —$N_3$, and $X^2$ is —CN. In embodiments, $X^1$ is —$N_3$, and $X^2$ is —$N_3$.

In embodiments, $X^1$ is H and $X^2$ is —$N_3$. In embodiments, $X^1$ is H and $X^2$ is —CN. In embodiments, $X^1$ is H and $X^2$ is —F. In embodiments, $X^1$ is —F and $X^2$ is —F. In embodiments, $X^1$ is —$N_3$ and $X^2$ is —$N_3$. In embodiments, $X^1$ is —$N_3$ and $X^2$ is —$N_3$. In embodiments, $X^1$ is —$N_3$ and $X^2$ is —CN. In embodiments, $X^1$ is —CN and $X^2$ is —CN.

In embodiments, $X^1$ is H and $X^2$ is —$N_3$ for formula (Ia), (Ib), and (Ic). In embodiments, $X^1$ is H and $X^2$ is —CN for formula (Ia), (Ib), and (Ic). In embodiments, $X^1$ is H and $X^2$ is —F for formula (Ia), (Ib), and (Ic). In embodiments, $X^1$ is —F and $X^2$ is —F for formula (Ia), (Ib), and (Ic). In embodiments, $X^1$ is —$N_3$ and $X^2$ is —$N_3$ for formula (Ia), (Ib), and (Ic). In embodiments, $X^1$ is —$N_3$ and $X^2$ is —$N_3$ for formula (Ia), (Ib), and (Ic). In embodiments, $X^1$ is —$N_3$ and $X^2$ is —CN for formula (Ia), (Ib), and (Ic). In embodiments, $X^1$ is —CN and $X^2$ is —CN for formula (Ia), (Ib), and (Ic).

In embodiments, $X^1$ is not —$N_3$ and $X^2$ is not —$N_3$ for formula (Ia), (Ib), and (Ic). In embodiments, $X^1$ is not —CN and $X^2$ is not —$N_3$ for formula (Ia), (Ib), and (Ic). In embodiments, $X^1$ is not —CN and $X^2$ is not —CN for formula (Ia), (Ib), and (Ic).

In embodiments, $X^1$ is not —$N_3$ and $X^2$ is not —$N_3$ for formula (IIa), (IIb), (IIc), (IIIa), or (IIIb). In embodiments, $X^1$ is not —$N_3$ and $X^2$ is not —CN for formula (IIa), (IIb), (IIc), (IIIa), or (IIIb). In embodiments, $X^1$ is not —CN and $X^2$ is not —CN for formula (IIa), (IIb), (IIc), (IIIa), or (IIIb).

In embodiments, $L^2$ is a cleavable linker. In embodiments, $L^2$ is a non-cleavable linker. In embodiments, $L^2$ is a chemically cleavable linker. In embodiments, $L^2$ is a photocleavable linker, an acid-cleavable linker, a base-cleavable linker, an oxidant-cleavable linker, a reductant-cleavable linker, or a fluoride-cleavable linker. In embodiments, $L^2$ is a cleavable linker comprising a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

In embodiments, $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, L² is
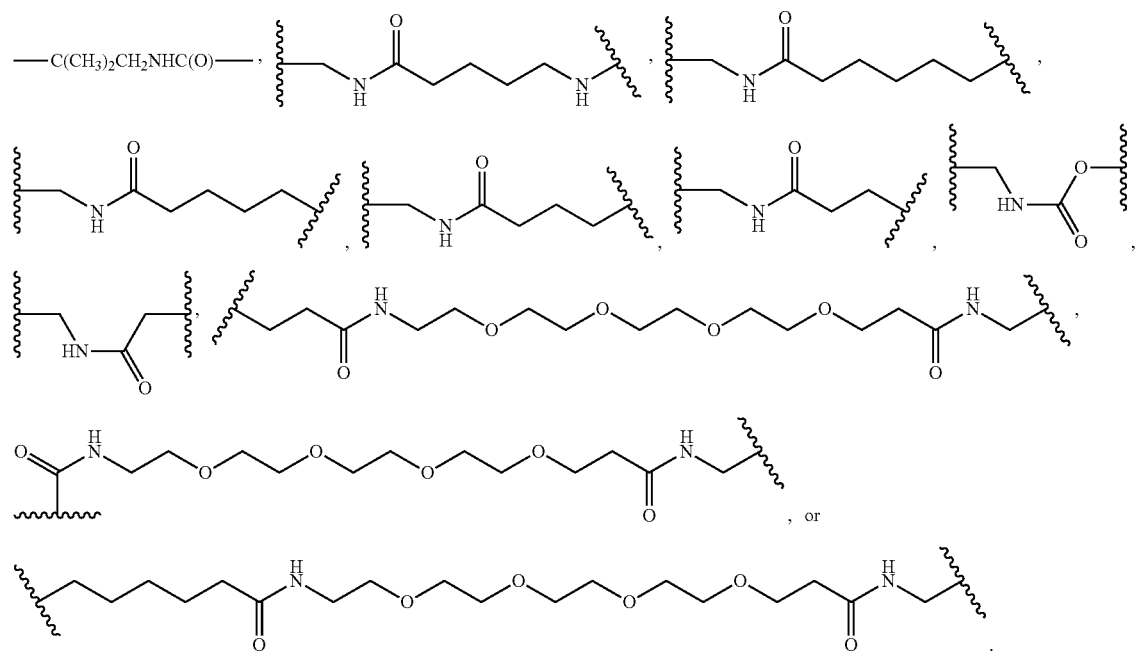
In embodiments, L² is
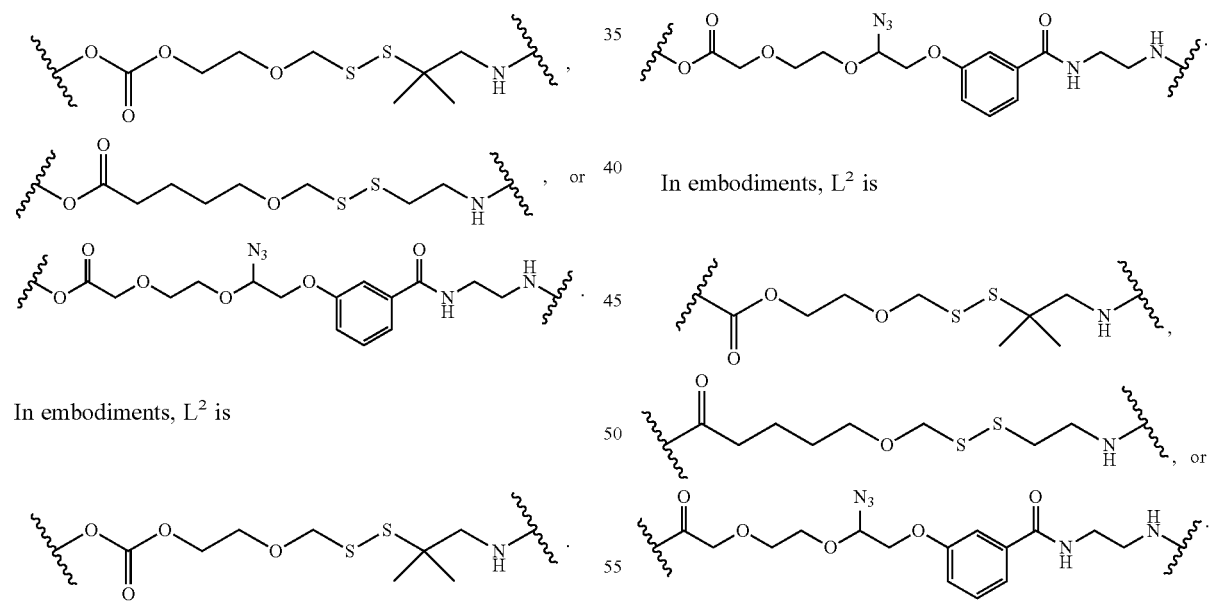
In embodiments, L² is
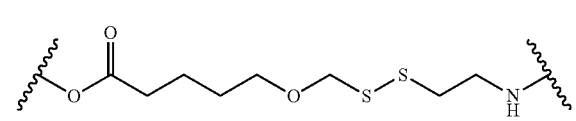
In embodiments, L² is
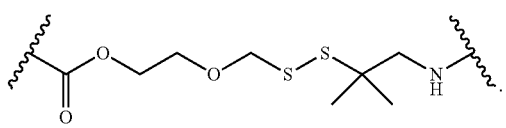 [SMILES: *NCC(C)(C)SSCOCCOC(*)=O]

In embodiments, L² is
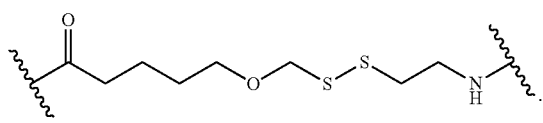 [SMILES: *NCCSSCOCCCCC(*)=O]
In embodiments, L² is
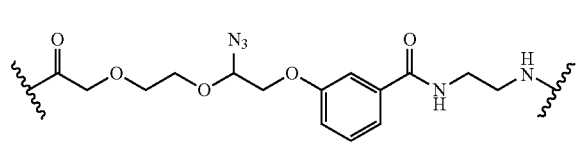
In embodiments, L² is
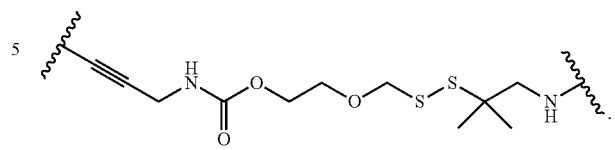
In embodiments, L² is
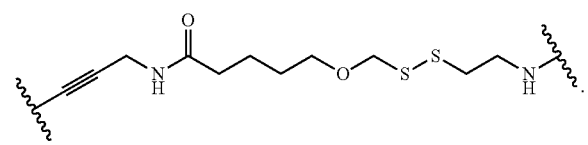 [SMILES: *C#CCNC(=O)CCCCOCSSCCN*]
In embodiments, L² is
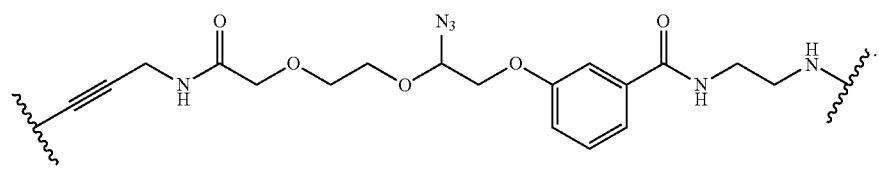 [SMILES: *C#CCNC(=O)COCCOC(COc1cccc(C(=O)NCCN*)c1)N=[N+]=[N-]]
In embodiments, L² is
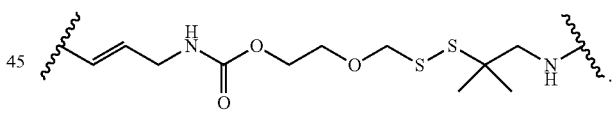
In embodiments, L² is
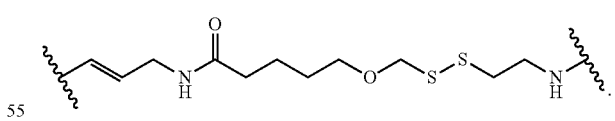
In embodiments, L² is
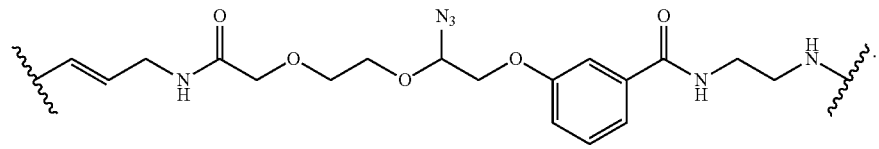 [SMILES: */C=C/CNC(=O)COCCOC(COc1cccc(C(=O)NCCN*)c1)N=[N+]=[N-]]

In embodiments, L² is
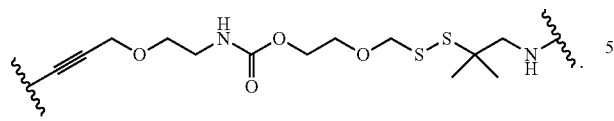.
In embodiments, L² is
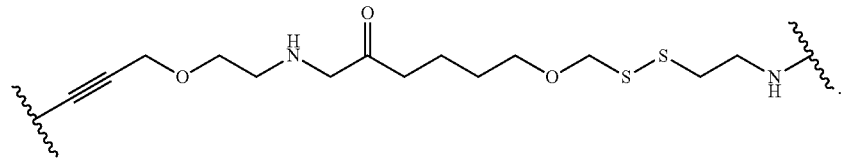 [SMILES: *C#CCOCCNCC(=O)CCCCOCSSCCN*].
In embodiments, L² is
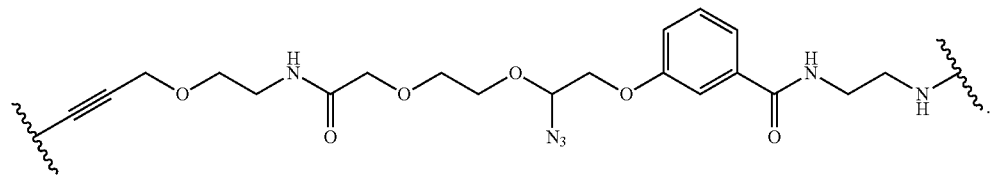 [SMILES: *C#CCOCCNC(=O)COCCOC(COc1cccc(C(=O)NCCN*)c1)N=[N+]=[N-]].
In embodiments, L² is
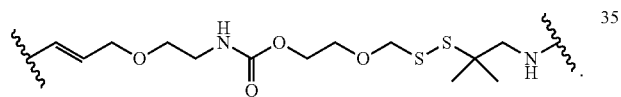.
In embodiments, L² is
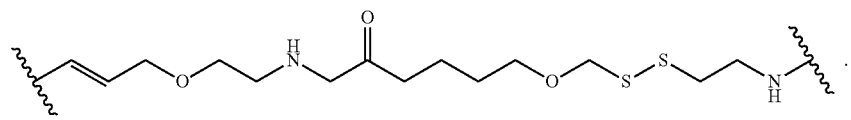 [SMILES: */C=C/COCCNCC(=O)CCCCOCSSCCN* ; "."].
In embodiments, L² is
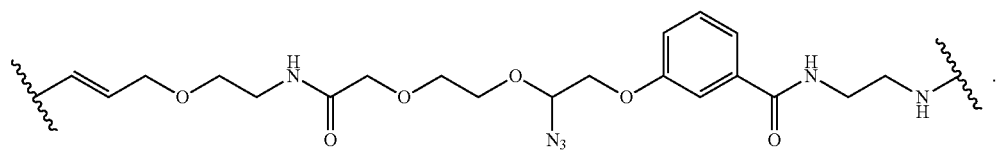 [SMILES: */C=C/COCCNC(=O)COCCOC(COc1cccc(C(=O)NCCN*)c1)N=[N+]=[N-] ; "."].

In embodiments, $L^2$ is
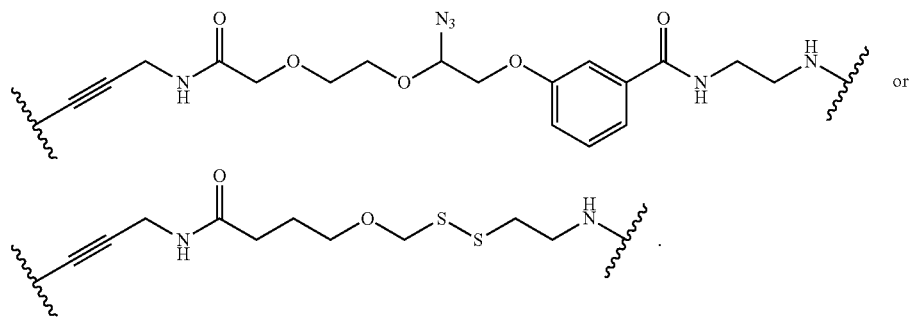
or
In embodiments, $L^2$ is
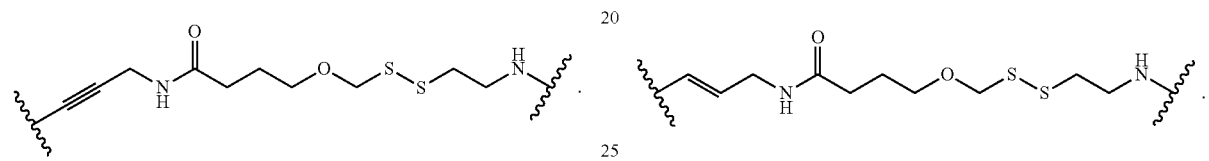
In embodiments, $L^2$ is
In embodiments, $L^2$ is
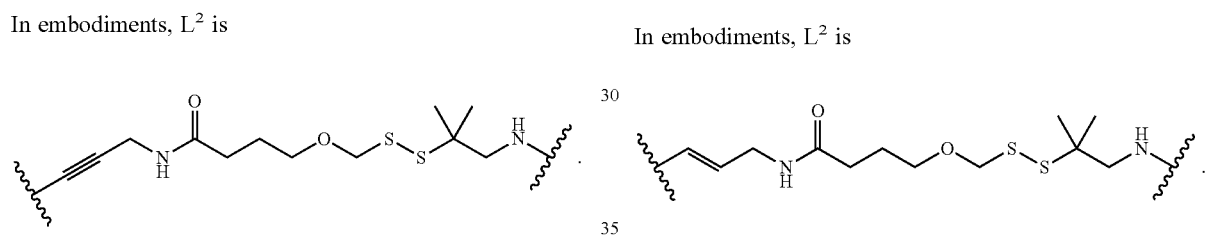
In embodiments, $L^2$ is
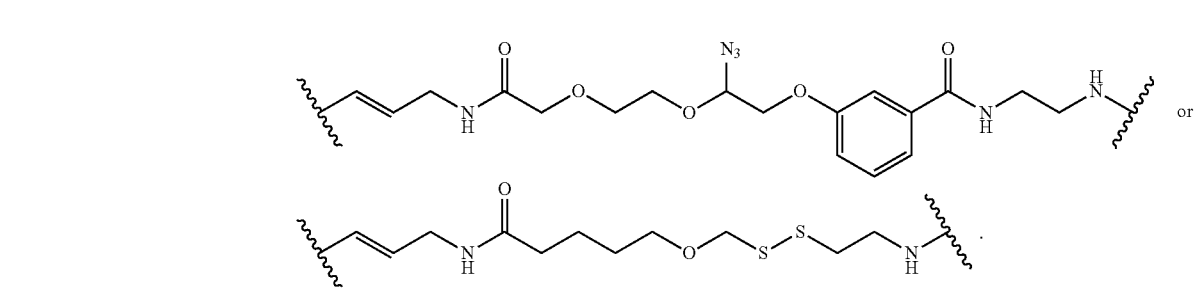
or
In embodiments, $L^2$ is
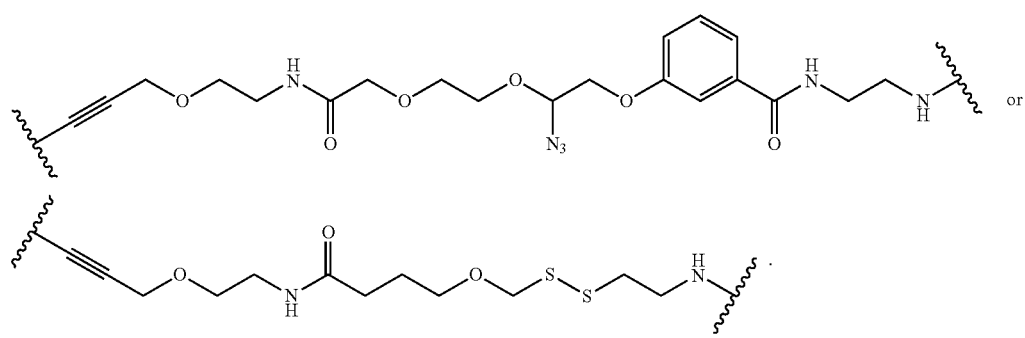
or In embodiments, L² is
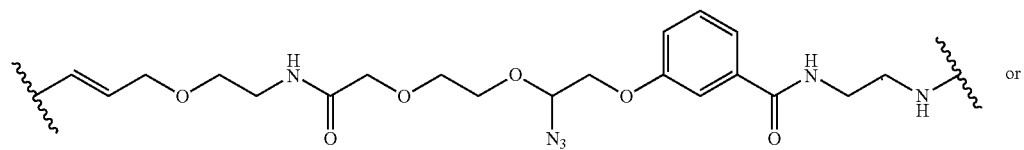 or
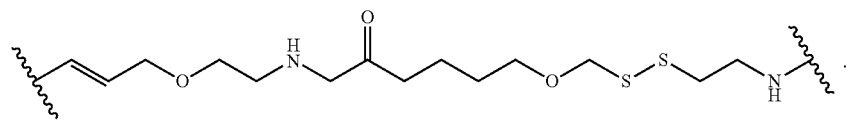
In embodiments, L² is
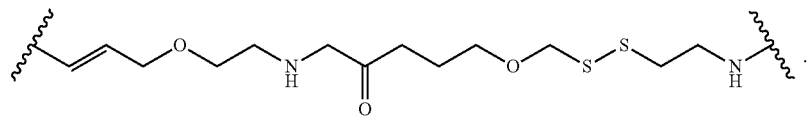 [SMILES: */C=C/COCCNCC(=O)CCCOCSSCCN* ; "."]
In embodiments, L² is
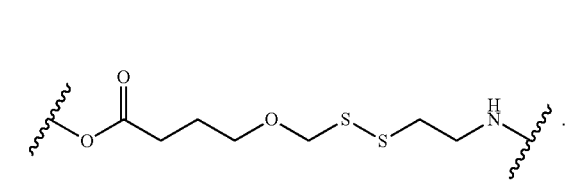 [SMILES: *NCCSSCOCCCC(=O)O* ; "."]
In embodiments, L² is
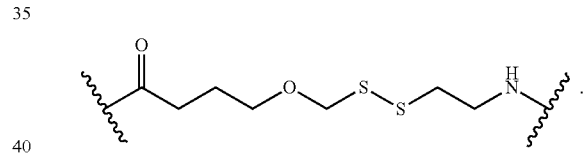
In embodiments, -L²-R⁵ is
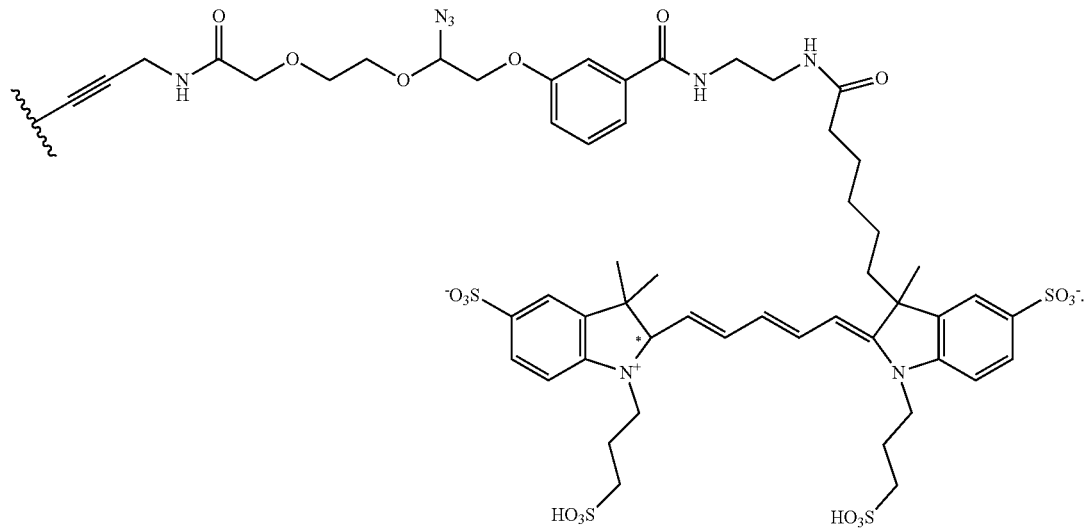

In embodiments, -L²-R⁵ is
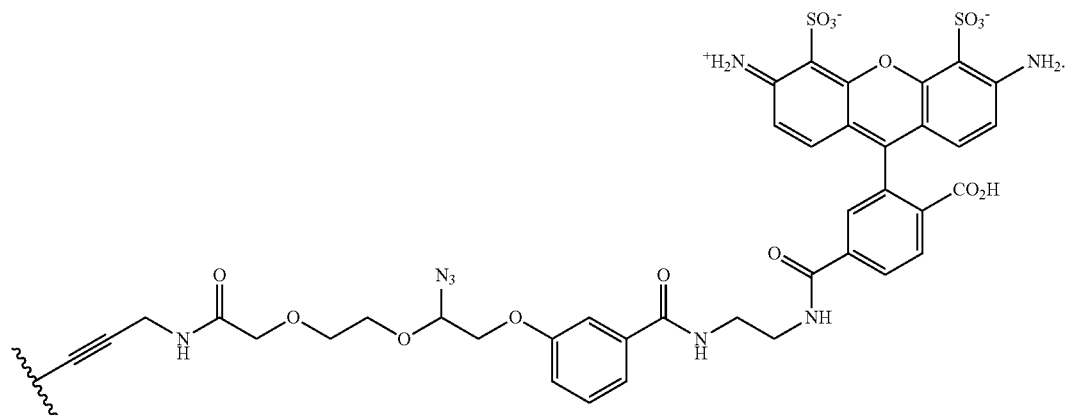
20
In embodiments, -L²-R⁵ is
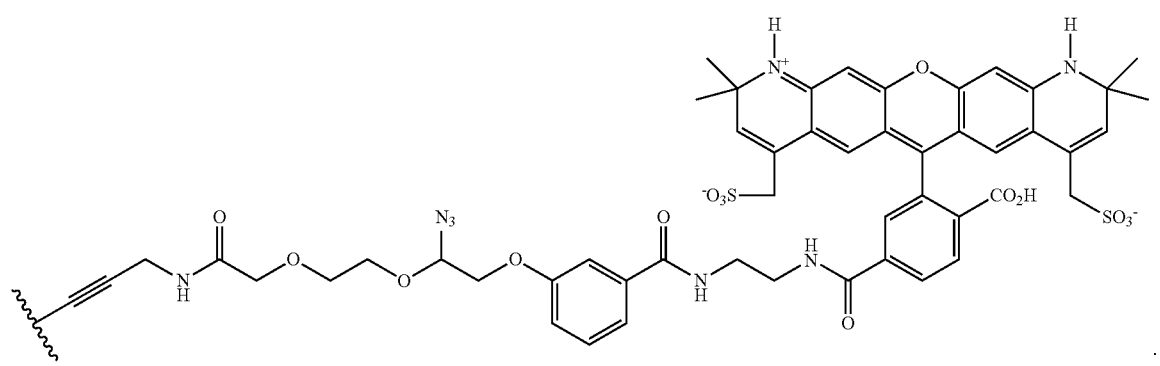
In embodiments, -L²-R⁵ is
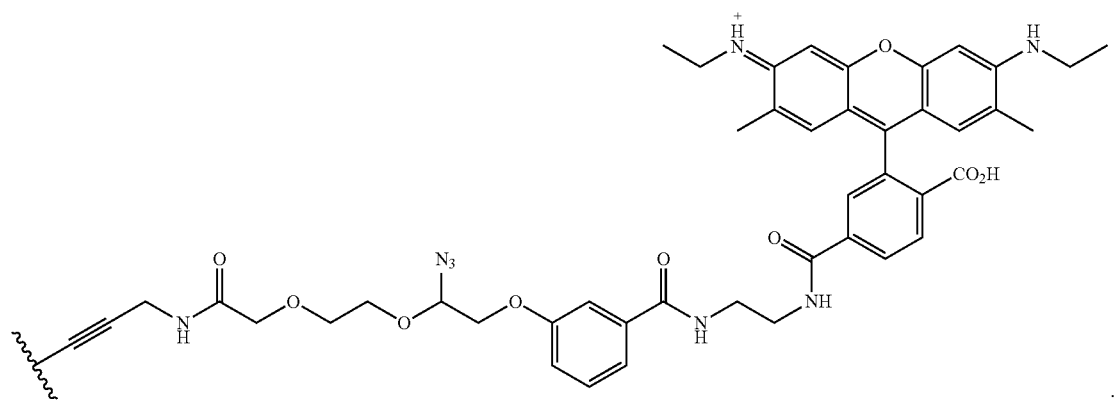

In embodiments, -L²-R⁵ is
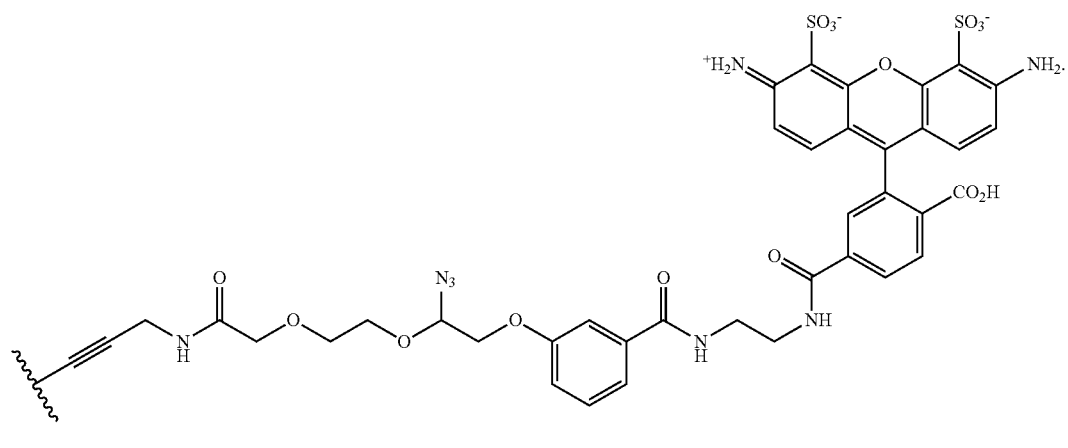
In embodiments, R⁵ is a streptavidin moiety. In embodiments, R⁵ is an anchor moiety, or affinity anchor moiety. In embodiments, R⁵ is an anchor moiety. In embodiments, R⁵ is an affinity anchor moiety.
In embodiments, R⁵ is
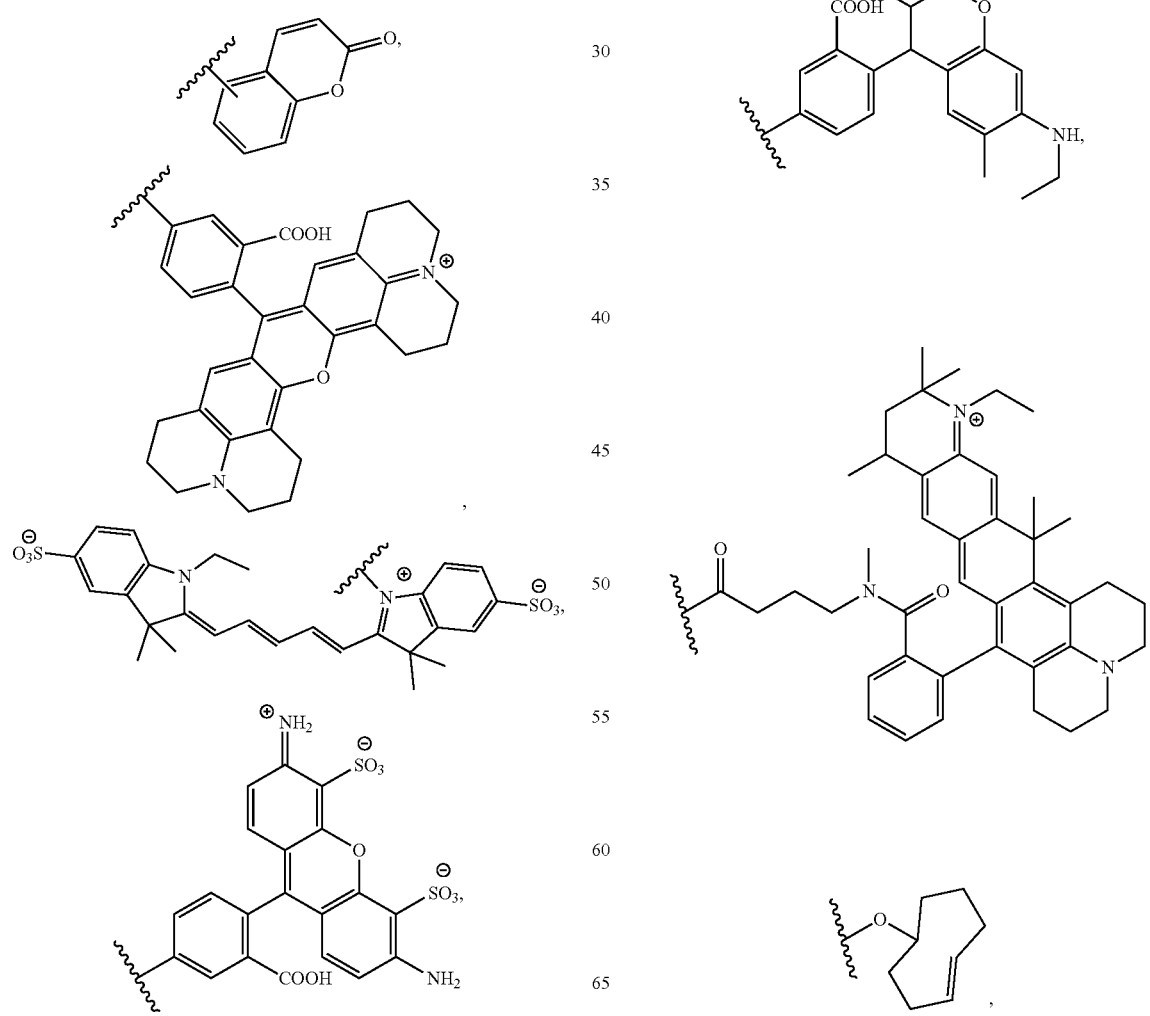

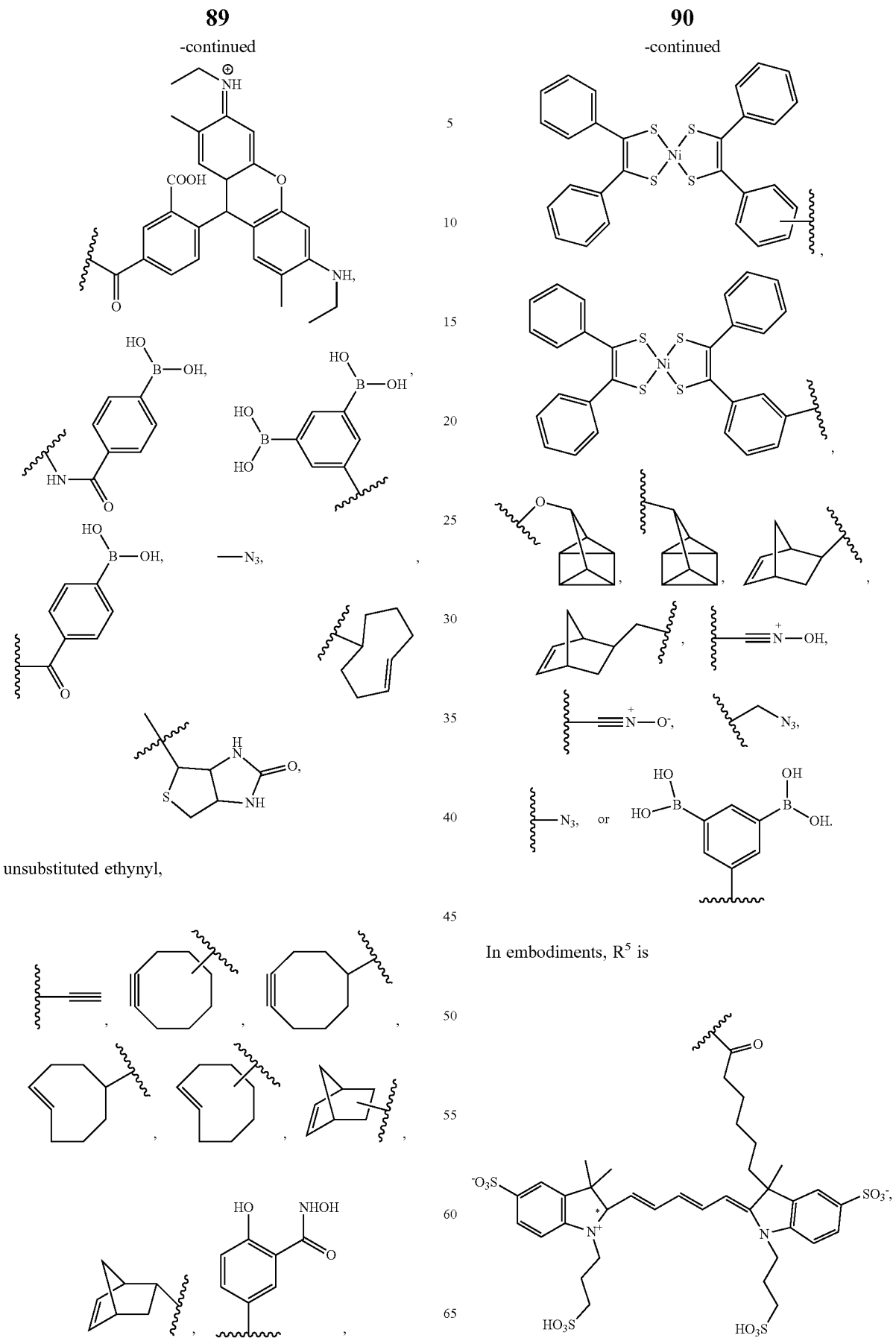

-continued

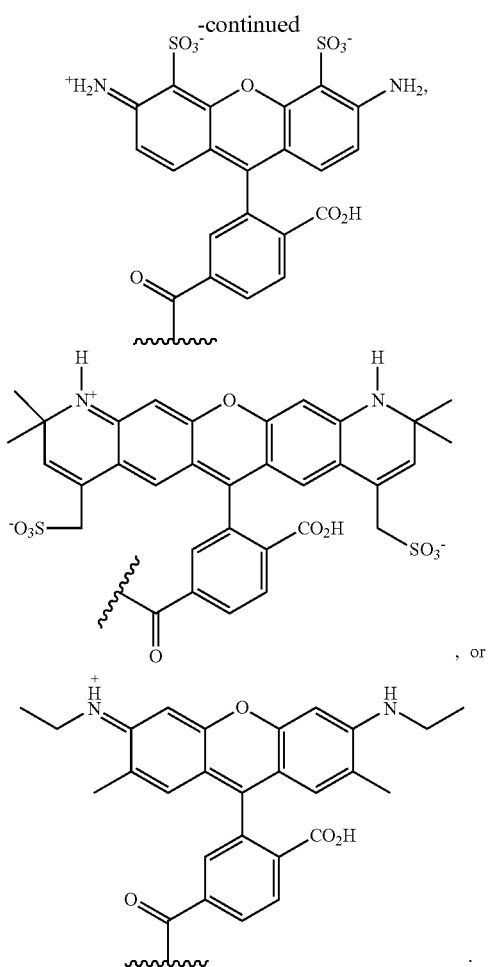

, or

In embodiments, $R^5$ is a biotin moiety. In embodiments, $R^5$ is a biotin moiety and $R^{12}$ is a streptavidin moiety.

In embodiments, $R^5$ is

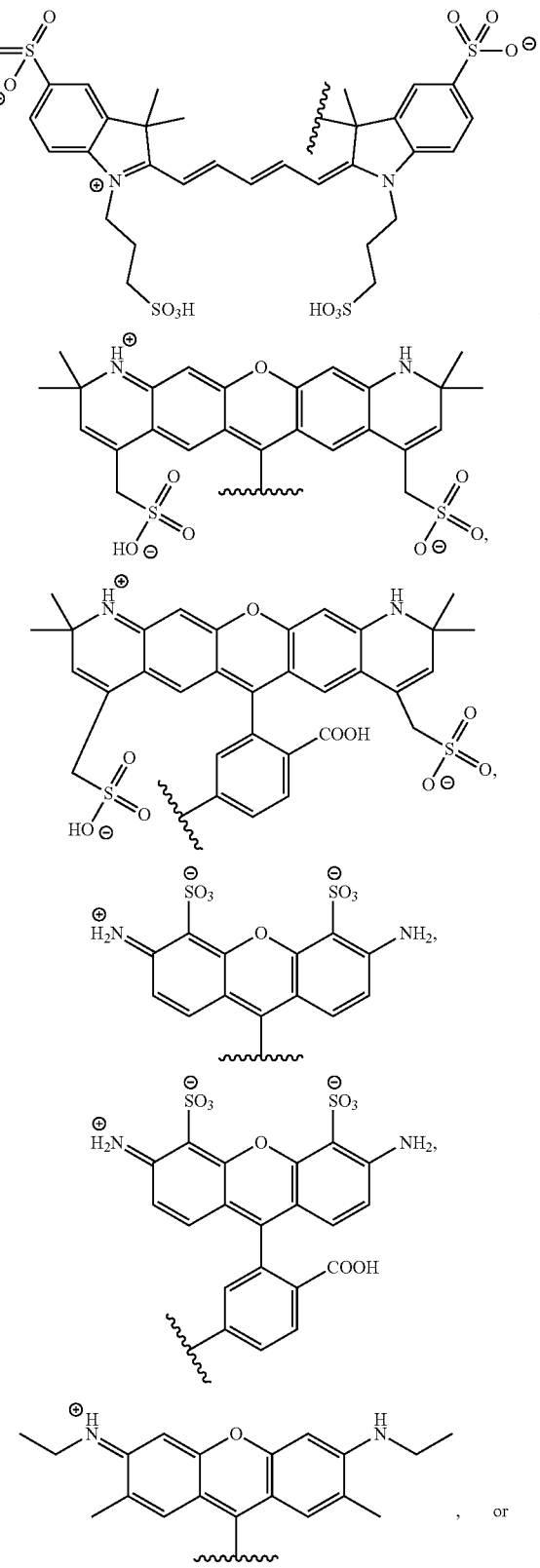

In embodiments, $R^5$ is a detectable label. In embodiments, $R^5$ is a fluorescent dye. In embodiments, $R^5$ is an anchor moiety. In embodiments, $R^5$ is a click chemistry reactant moiety. In embodiments, $R^5$ is a trans-cyclooctene moiety or azide moiety. In embodiments, $R^5$ is an affinity anchor moiety. In embodiments, $R^5$ is a biotin moiety. In embodiments, $R^5$ is a reactant for a bioconjugate reaction that forms a covalent bond between $R^5$ and a second bioconjugate reaction reactant (e.g., $R^{12}$).

In embodiments, $R^5$ is a fluorescent dye. In embodiments $R^5$ is a Alexa Fluor® 350 moiety, Alexa Fluor® 405 moiety, Alexa Fluor® 430 moiety, Alexa Fluor® 488 moiety, Alexa Fluor® 532 moiety, Alexa Fluor® 546 moiety, Alexa Fluor® 555 moiety, Alexa Fluor® 568 moiety, Alexa Fluor® 594 moiety, Alexa Fluor® 610 moiety, Alexa Fluor® 633 moiety, Alexa Fluor® 635 moiety, Alexa Fluor® 647 moiety, Alexa Fluor® 660 moiety, Alexa Fluor® 680 moiety, Alexa Fluor® 700 moiety, Alexa Fluor® 750 moiety, or Alexa Fluor® 790 moiety. In embodiments the detectable moiety is a Alexa Fluor® 488 moiety, Rhodamine 6G (R6G) moiety, ROX Reference Dye (ROX) moiety, or Cy5 moiety.

In embodiments $R^5$ is a FAM™ moiety, TET™ moiety, JOE™ moiety, VIC® moiety, HEX™ moiety, NED™ moiety, PET® moiety, ROX™ moiety, TAMRA™ moiety, TET™ moiety, Texas Red® moiety, Alexa Fluor® 488 moiety, Rhodamine 6G (R6G) moiety, ROX Reference Dye (ROX) moiety, Sulfo-Cy5, or Cy5 moiety. In embodiments $R^5$ is a Rhodamine 6G (R6G) moiety, ROX Reference Dye (ROX) moiety, Sulfo-Cy5, or Cy5 moiety.

93
-continued
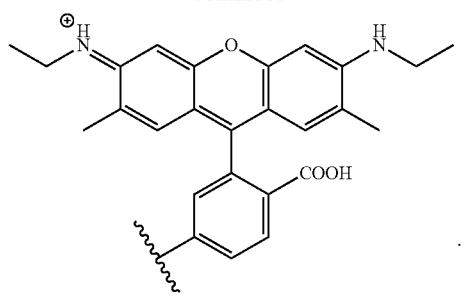
In embodiments, R⁵ is
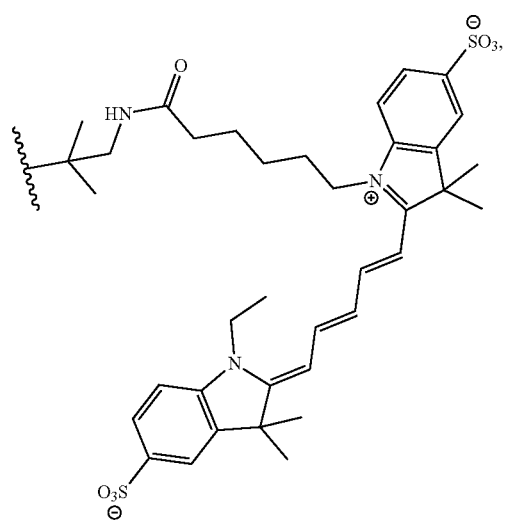
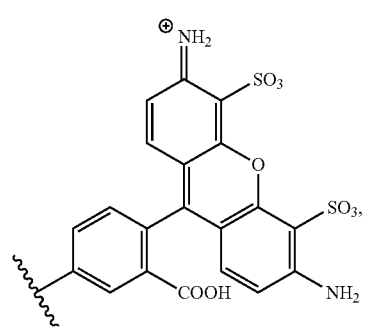
94
-continued
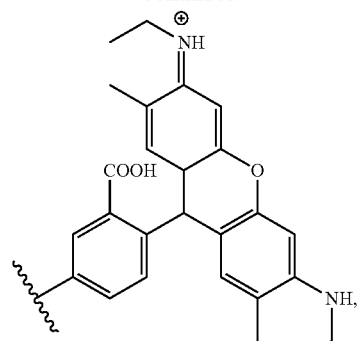
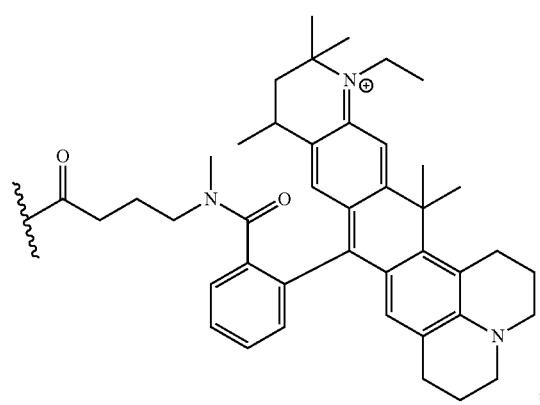
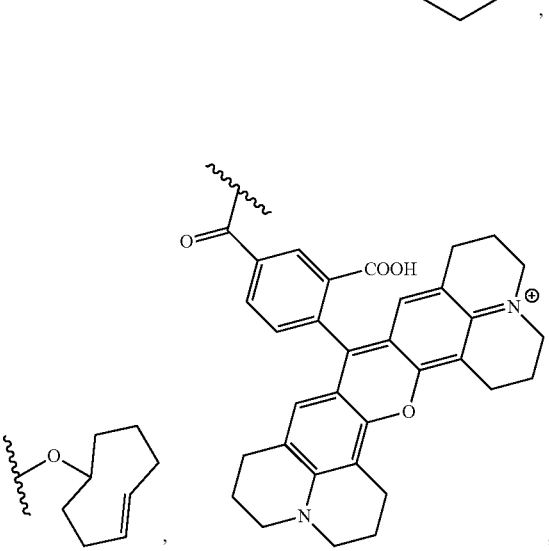
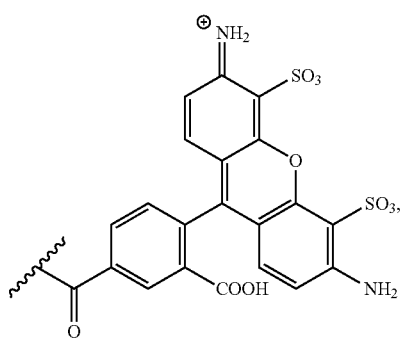

-continued

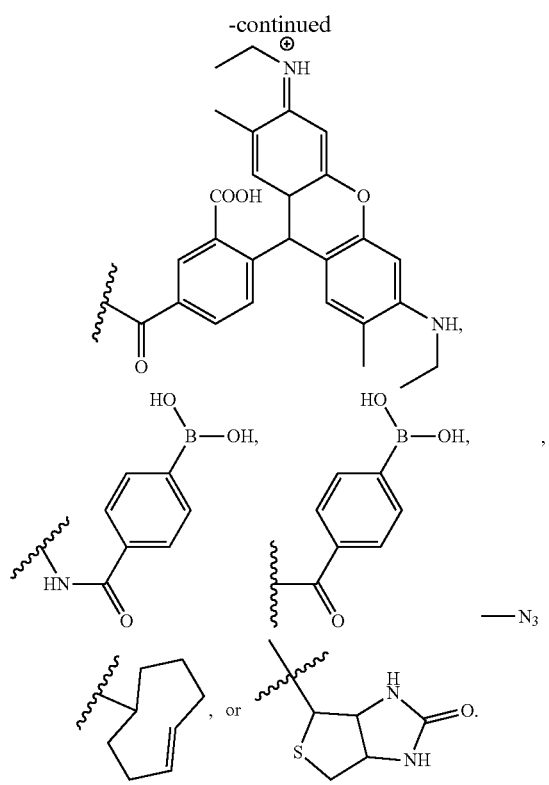

In embodiments, L⁴ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, L⁴ is a bond, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, L⁴ is a substituted or unsubstituted $C_1$-$C_6$ alkylene or substituted or unsubstituted 2 to 6 membered heteroalkylene. In embodiments, L⁴ is an unsubstituted $C_1$-$C_4$ alkylene. In embodiments, L⁴ is a bond.

In embodiments, L⁴ is a substituted or unsubstituted methylene. In embodiments, L⁴ is substituted with a substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene. In embodiments, L⁴ is a bond, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene.

In embodiments, L⁴ is substituted with a substituted or unsubstituted $C_1$-$C_6$ alkylene or substituted or unsubstituted 2 to 6 membered heteroalkylene. In embodiments, L⁴ is a substituted or unsubstituted $C_1$-$C_6$ alkylene or substituted or unsubstituted 2 to 6 membered heteroalkylene. In embodiments, L⁴ is substituted with a substituted or unsubstituted $C_1$-$C_6$ alkylene. In embodiments, L⁴ is an unsubstituted methylene.

In embodiments, R⁴ is substituted or unsubstituted C1-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, R⁴ is substituted or unsubstituted $C_1$-$C_6$ alkyl, or substituted or unsubstituted phenyl. In embodiments, R⁴ is an unsubstituted $C_1$-$C_6$ alkyl.

In embodiments, R⁴ is substituted (e.g., substituted with a substituent group, a size-limited substituent group, or lower substituent group) or unsubstituted alkyl. In embodiments, R⁴ is substituted (e.g., substituted with a substituent group, a size-limited substituent group, or lower substituent group) alkyl. In embodiments, R⁴ is unsubstituted alkyl. In embodiments, R⁴ is substituted or unsubstituted alkyl (e.g., $C_1$-$C_8$, $C_1$-$C_6$, $C_1$-$C_4$, or $C_1$-$C_2$). In embodiments, R⁴ is substituted alkyl (e.g., $C_1$-$C_8$, $C_1$-$C_6$, $C_1$-$C_4$, or $C_1$-$C_2$). In embodiments, R⁴ is unsubstituted alkyl (e.g., $C_1$-$C_8$, $C_1$-$C_6$, $C_1$-$C_4$, or $C_1$-$C_2$).

In embodiments, R⁴ is substituted (e.g., substituted with a substituent group, a size-limited substituent group, or lower substituent group) or unsubstituted heteroalkyl. In embodiments, R⁴ is substituted (e.g., substituted with a substituent group, a size-limited substituent group, or lower substituent group) heteroalkyl. In embodiments, R⁴ is unsubstituted heteroalkyl. In embodiments, R⁴ is substituted or unsubstituted heteroalkyl (e.g., 2 to 8 membered, 2 to 6 membered, 4 to 6 membered, 2 to 3 membered, or 4 to 5 membered). In embodiments, R⁴ is substituted heteroalkyl (e.g., 2 to 8 membered, 2 to 6 membered, 4 to 6 membered, 2 to 3 membered, or 4 to 5 membered). In embodiments, R⁴ is an unsubstituted heteroalkyl (e.g., 2 to 8 membered, 2 to 6 membered, 4 to 6 membered, 2 to 3 membered, or 4 to 5 membered).

In embodiments, R⁴ is substituted or unsubstituted alkyl (e.g., $C_1$-$C_8$ alkyl, $C_1$-$C_6$ alkyl, or $C_1$-$C_4$ alkyl). In embodiments, R⁴ is substituted alkyl (e.g., $C_1$-$C_8$ alkyl, $C_1$-$C_6$ alkyl, or $C_1$-$C_4$ alkyl). In embodiments, R⁴ is an unsubstituted alkyl (e.g., $C_1$-$C_8$ alkyl, $C_1$-$C_6$ alkyl, or $C_1$-$C_4$ alkyl). In embodiments, R⁴ is substituted or unsubstituted methyl. In embodiments, R⁴ is substituted or unsubstituted $C_2$ alkyl. In embodiments, R⁴ is substituted or unsubstituted $C_3$ alkyl. In embodiments, R⁴ is substituted or unsubstituted $C_4$ alkyl. In embodiments, R⁴ is substituted or unsubstituted $C_5$ alkyl. In embodiments, R⁴ is substituted or unsubstituted $C_6$ alkyl. In embodiments, R⁴ is substituted or unsubstituted $C_7$ alkyl. In embodiments, R⁴ is substituted or unsubstituted $C_8$ alkyl. In embodiments, R⁴ is substituted methyl. In embodiments, R⁴ is substituted $C_2$ alkyl. In embodiments, R⁴ is substituted $C_3$ alkyl. In embodiments, R⁴ is substituted $C_4$ alkyl. In embodiments, R⁴ is substituted $C_5$ alkyl. In embodiments, R⁴ is substituted $C_6$ alkyl. In embodiments, R⁴ is substituted $C_7$ alkyl. In embodiments, R⁴ is substituted $C_8$ alkyl. In embodiments, R⁴ is an unsubstituted methyl. In embodiments, R⁴ is an unsubstituted $C_2$ alkyl. In embodiments, R⁴ is an unsubstituted $C_3$ alkyl. In embodiments, R⁴ is an unsubstituted $C_4$ alkyl (e.g., t-butyl). In embodiments, R⁴ is an unsubstituted $C_5$ alkyl. In embodiments, R⁴ is an unsubstituted $C_6$ alkyl. In embodiments, R⁴ is an unsubstituted $C_7$ alkyl. In embodiments, R⁴ is an unsubstituted $C_8$ alkyl.

In embodiments, the nucleotide analogue has the formula:

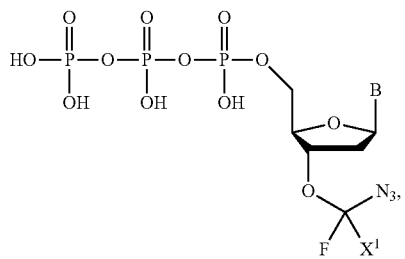

wherein B and X$^1$ are as described herein, including embodiments. In embodiments, the nucleotide analogue has the formula:

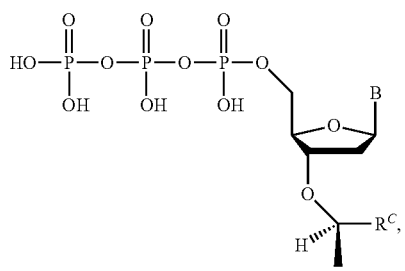

wherein B and R$^C$ are as described herein, including embodiments. In embodiments, the nucleotide analogue has the formula:

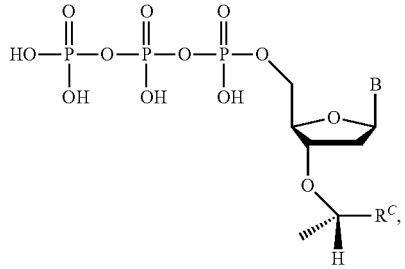

wherein B and R$^C$ are as described herein, including embodiments. In embodiments, the nucleotide analogue has the formula:

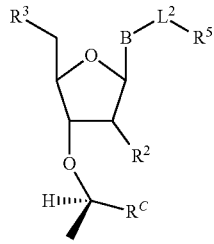

wherein R$^2$, R$^3$, B, L$^2$, L$^5$, and R$^C$ are as described herein.

In embodiments, the nucleotide analogue has the formula:

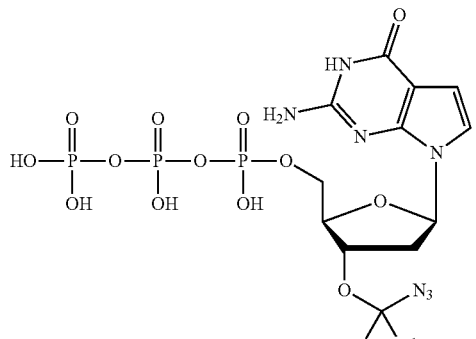

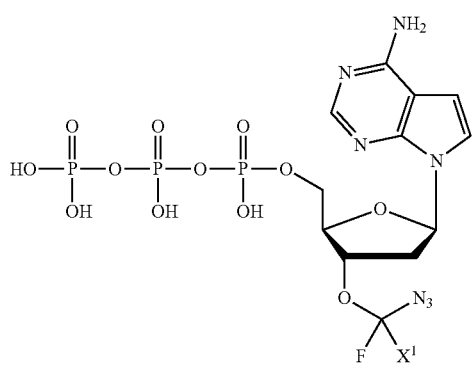

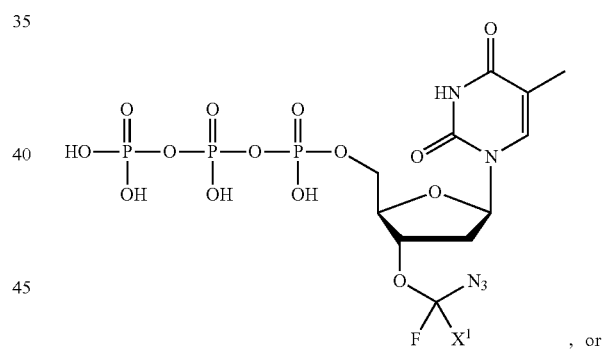

, or

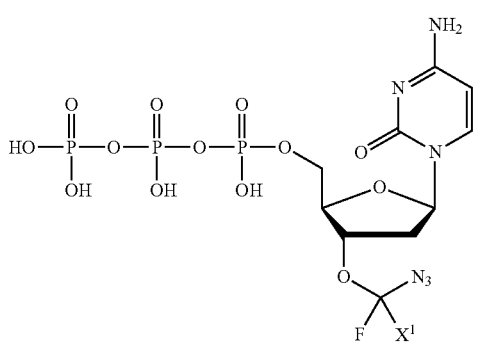

wherein X$^1$ is as described herein, including embodiments.

In embodiments, the nucleotide analogue has the formula:

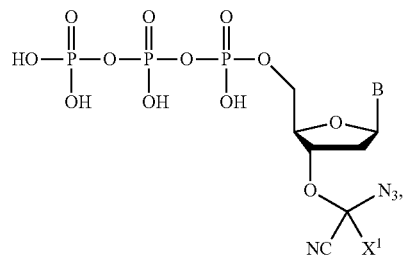

wherein B and X¹ are as described herein, including embodiments.

In embodiments, the nucleotide analogue has the formula:

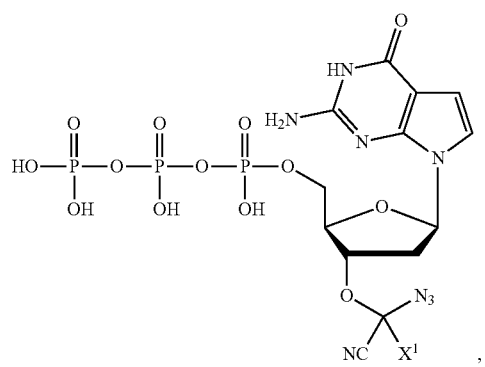

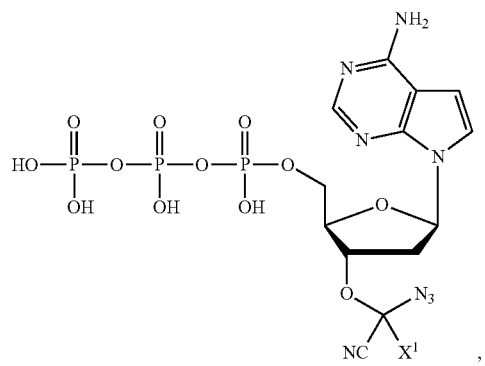

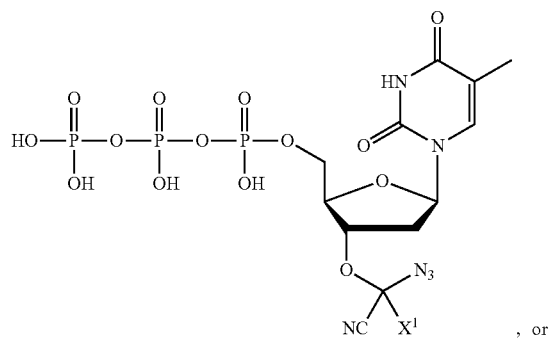

, or

-continued

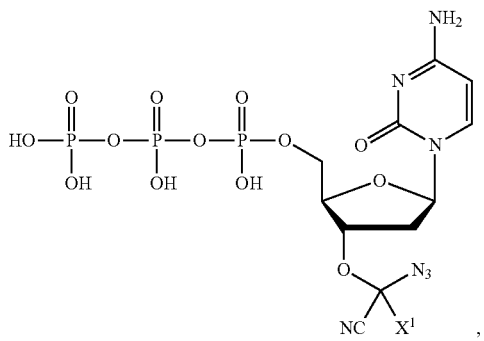

wherein X¹ is as described herein, including embodiments.

In embodiments, the nucleotide analogue has the formula:

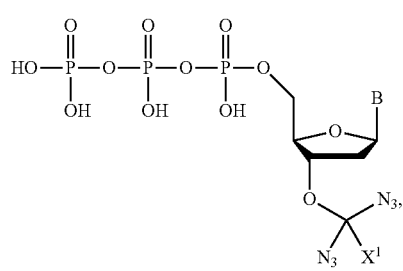

wherein B and X¹ are as described herein, including embodiments.

In embodiments, the nucleotide analogue has the formula:

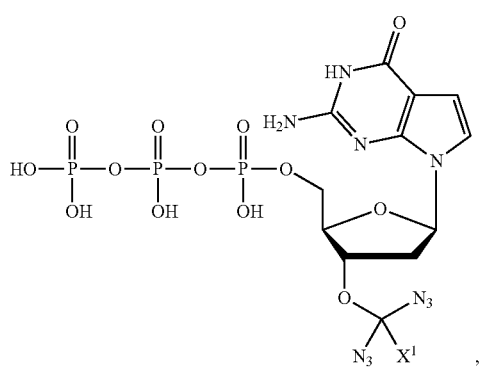

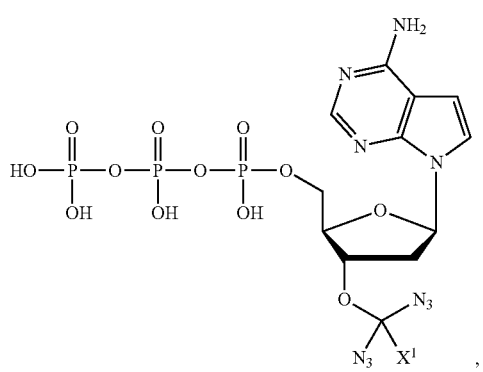

,

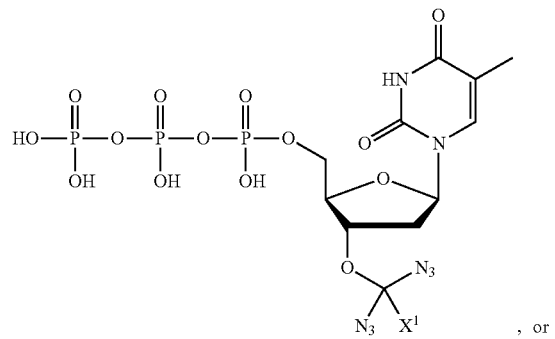

, or

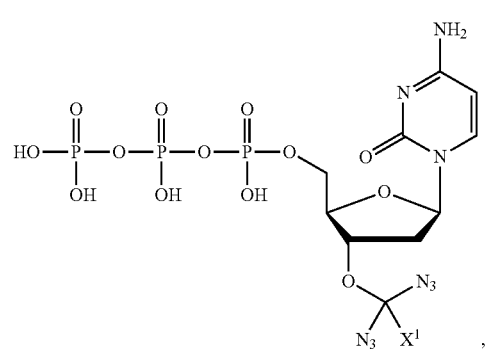

, wherein $X^1$ is as described herein, including embodiments.

In embodiments, the nucleotide analogue has the formula:

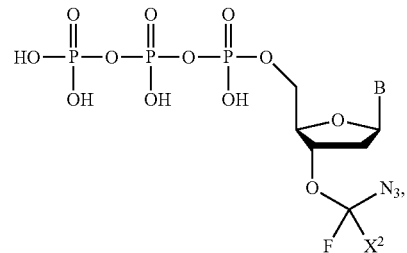

wherein B and $X^2$ are as described herein, including embodiments.

In embodiments, the nucleotide analogue has the formula:

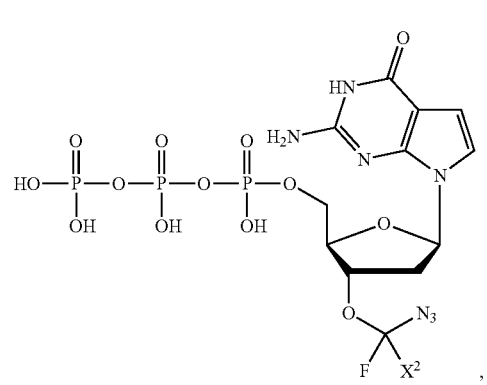

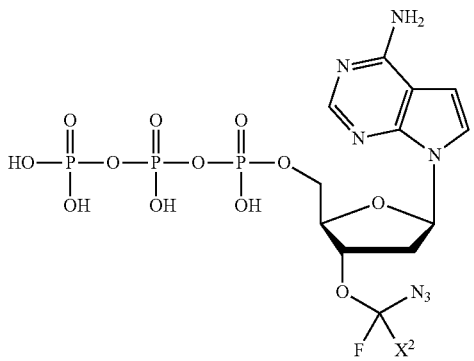

,

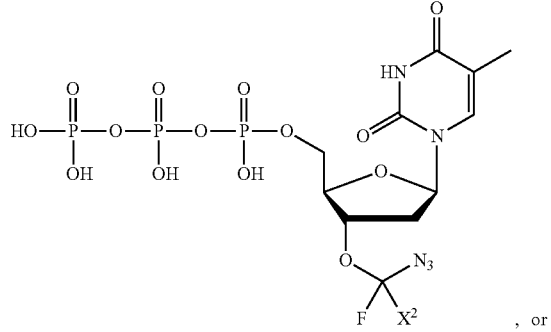

, or

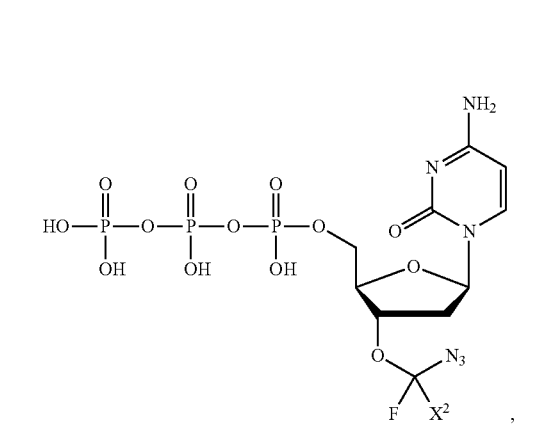

wherein $X^2$ is as described herein, including embodiments.

In embodiments, the nucleotide analogue has the formula:

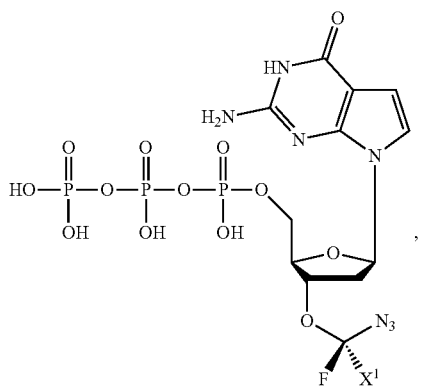

-continued
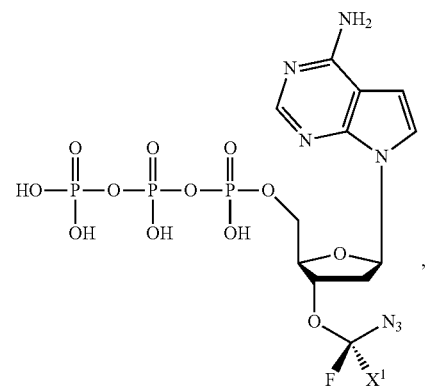
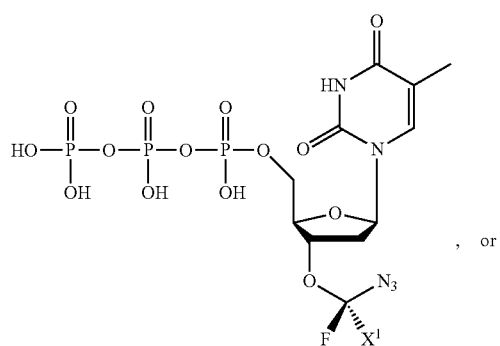
, or
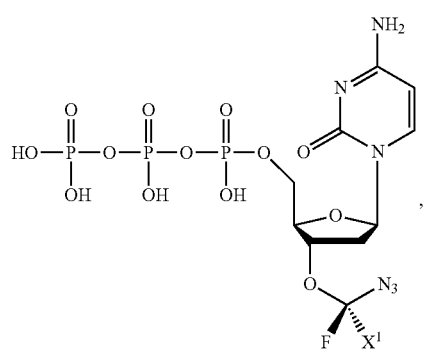
wherein $X^1$ is as described herein, including embodiments.
In embodiments, the nucleotide analogue has the formula:
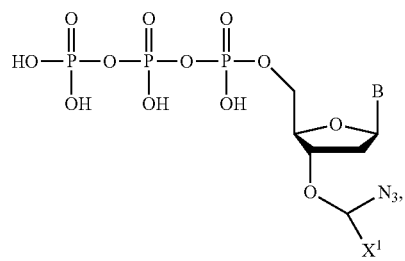
wherein B and $X^1$ are as described herein, including embodiments.
In embodiments, the nucleotide analogue has the formula:
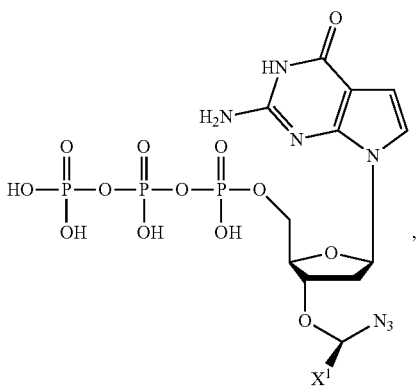
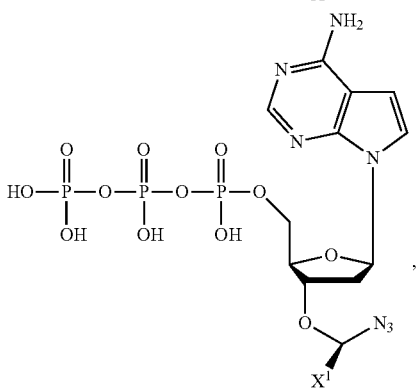
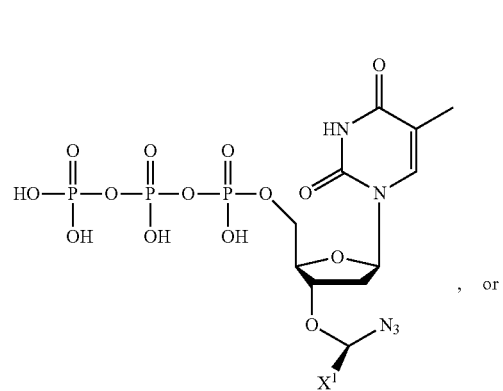
, or
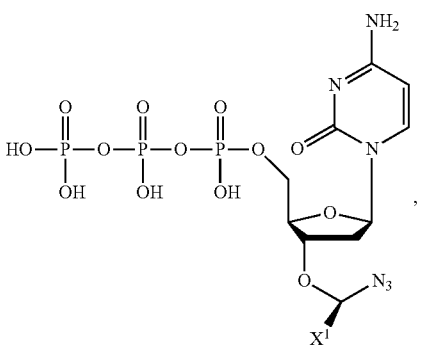
wherein $X^1$ is as described herein, including embodiments.

In embodiments, the nucleotide analogue has the formula:

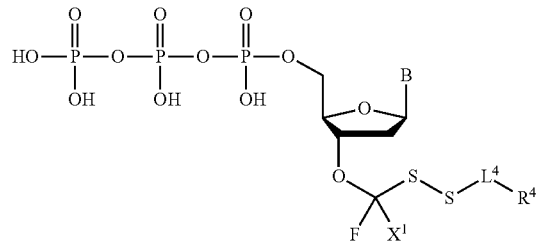

wherein $X^1$, B, $L^4$, and $R^4$ are as described herein, including embodiments.

In embodiments, the nucleotide analogue has the formula:

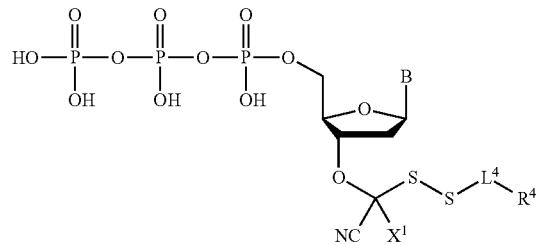

wherein $X^1$, B, $L^4$, and $R^4$ are as described herein, including embodiments.

In embodiments, the nucleotide analogue has the formula:

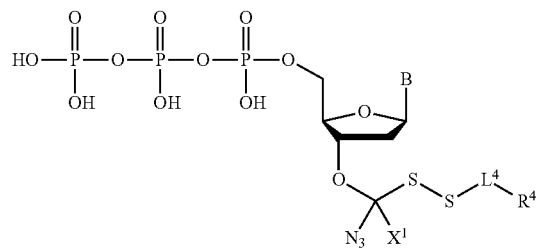

wherein $X^1$, B, $L^4$, and $R^4$ are as described herein, including embodiments.

In embodiments, the nucleotide analogue has the formula:

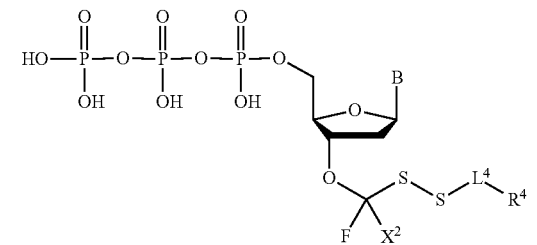

wherein $X^2$, B, $L^4$, and $R^4$ are as described herein, including embodiments.

In embodiments, the nucleotide analogue has the formula:

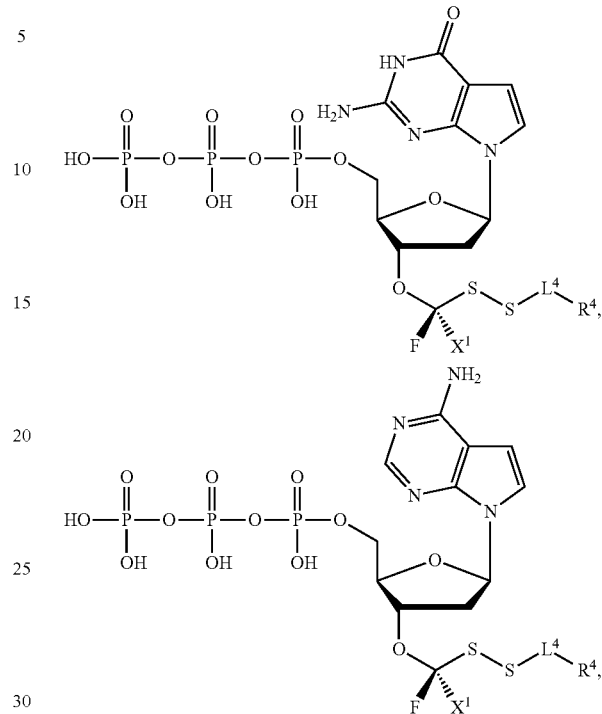

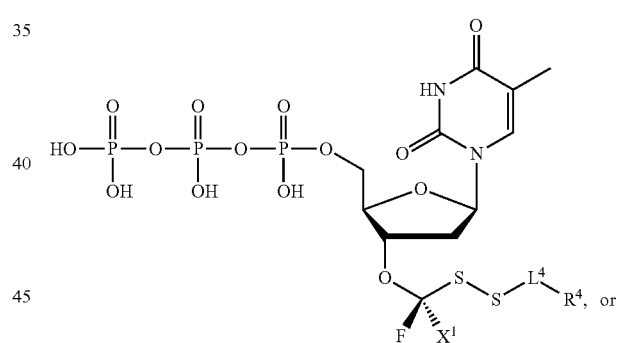

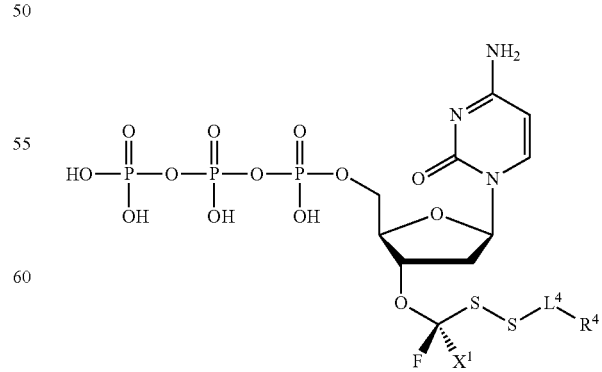

wherein $X^1$, $L^4$, and $R^4$ are as described herein, including embodiments.

In embodiments, the nucleotide analogue has the formula:

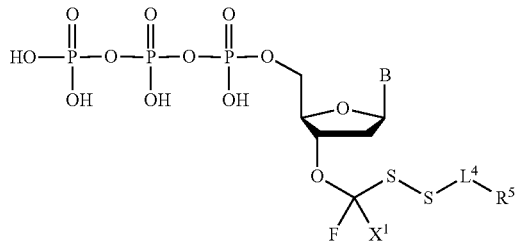

wherein $X^1$, B, $L^4$, and $R^5$ are as described herein, including embodiments.

In embodiments, the nucleotide analogue has the formula:

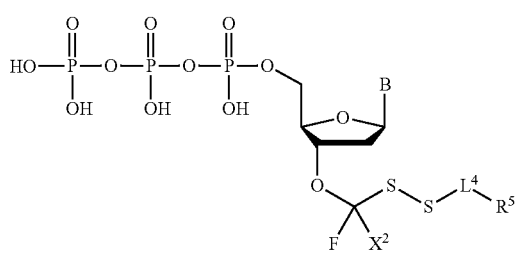

wherein $X^2$, B, $L^4$, and $R^5$ are as described herein, including embodiments.

In embodiments, the nucleotide analogue has the formula:

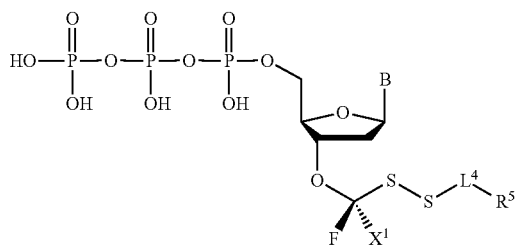

wherein $X^1$, B, $L^4$, and $R^5$ are as described herein, including embodiments.

In embodiments, the nucleotide analogue has the formula:

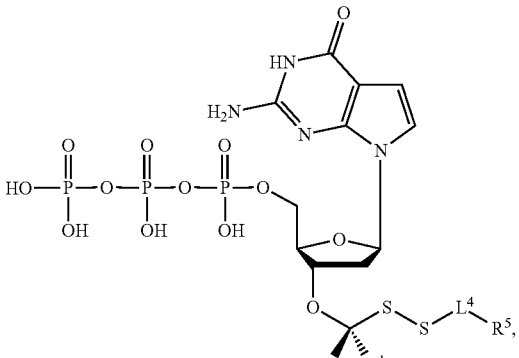

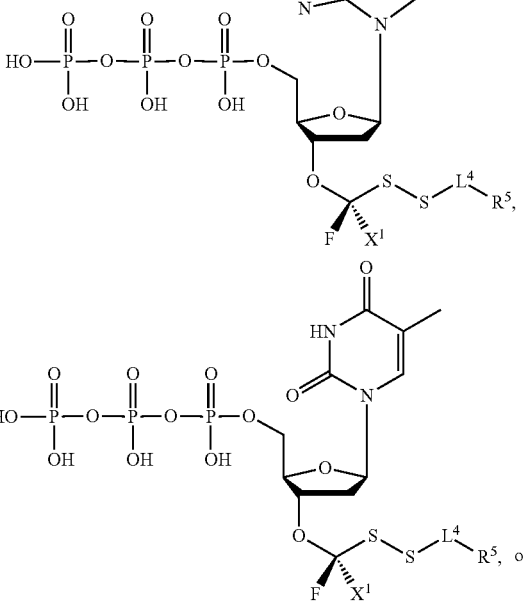

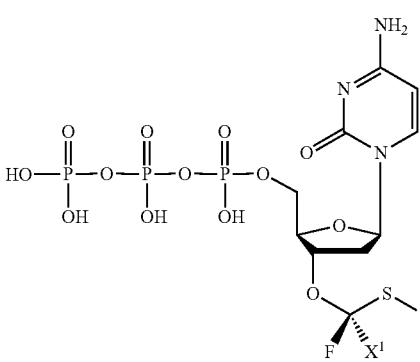

wherein $X^1$, $L^4$, and $R^5$ are as described herein, including embodiments.

In embodiments, the nucleotide analogue has the formula:
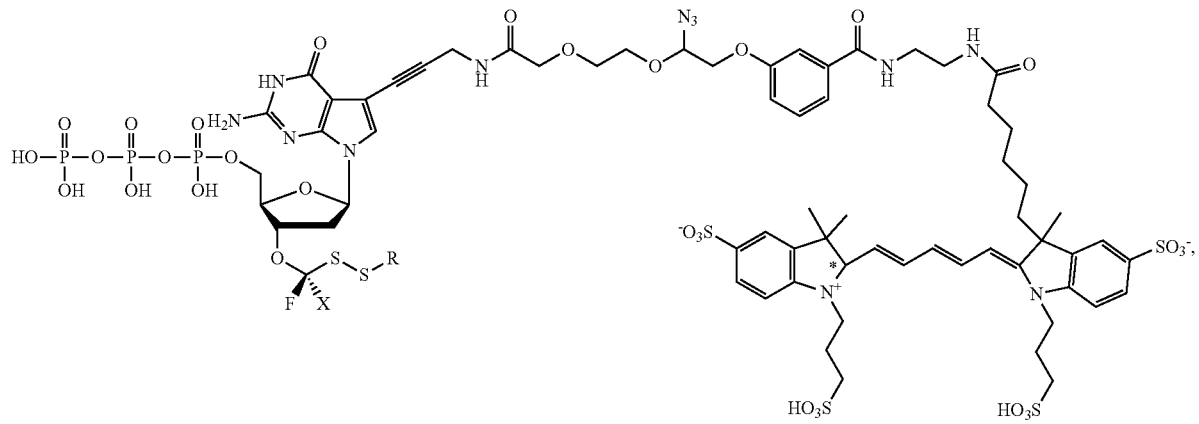
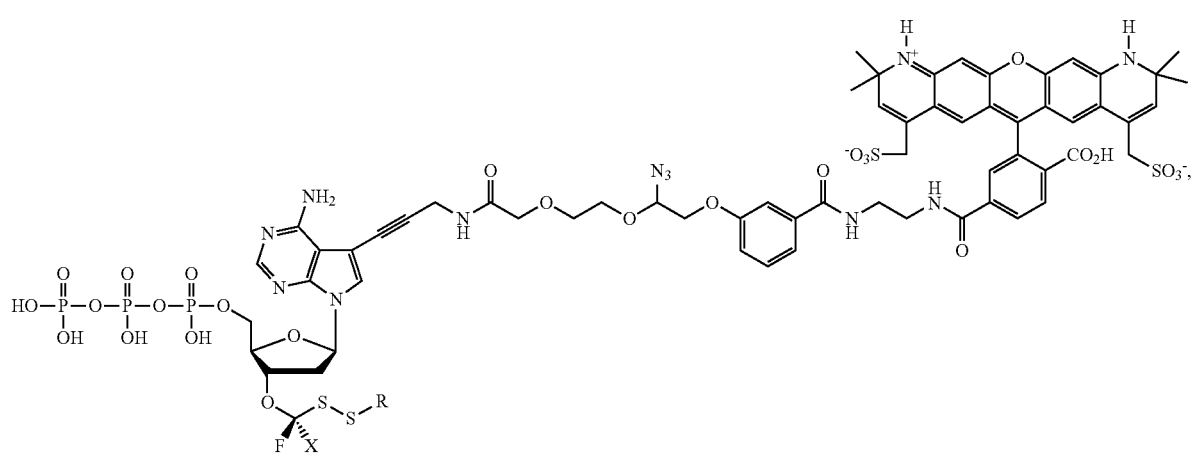
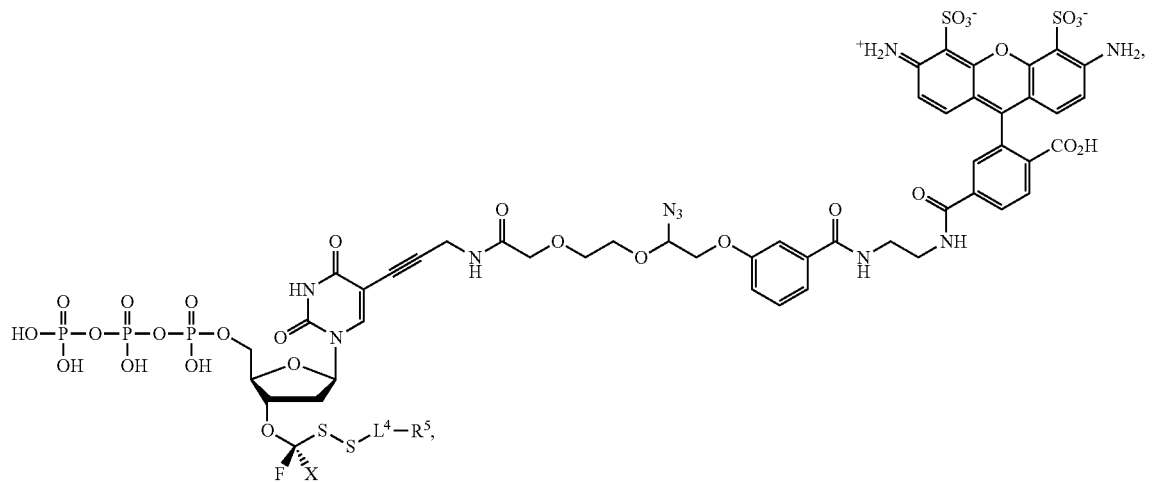

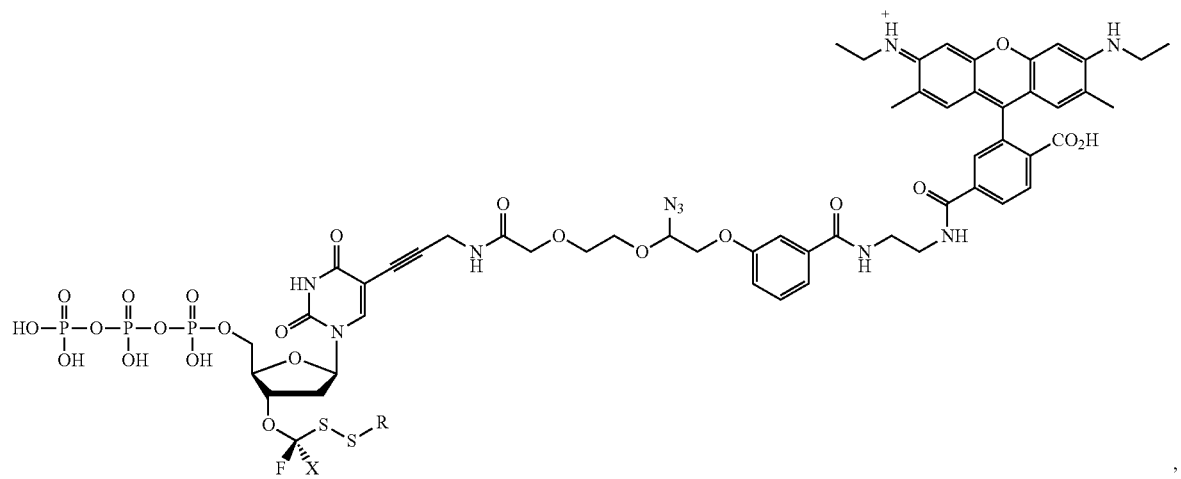
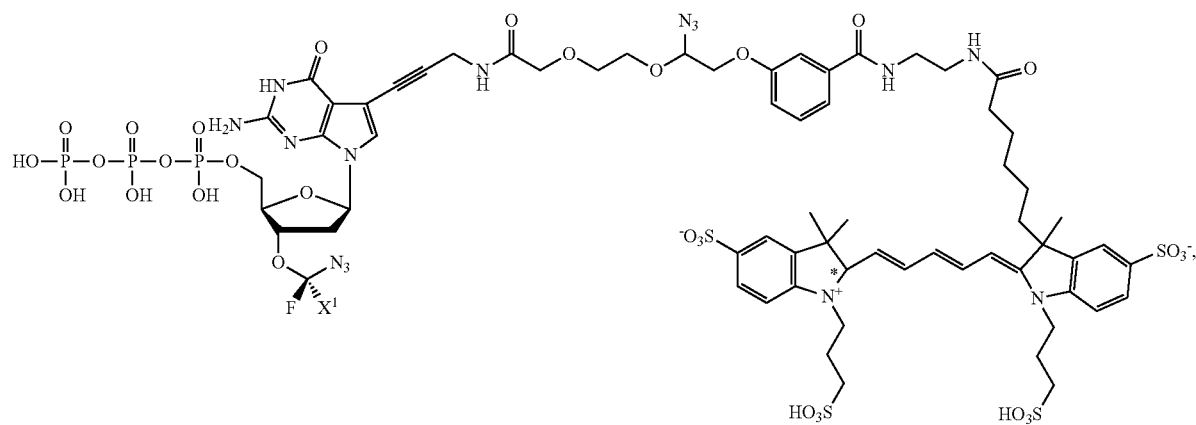
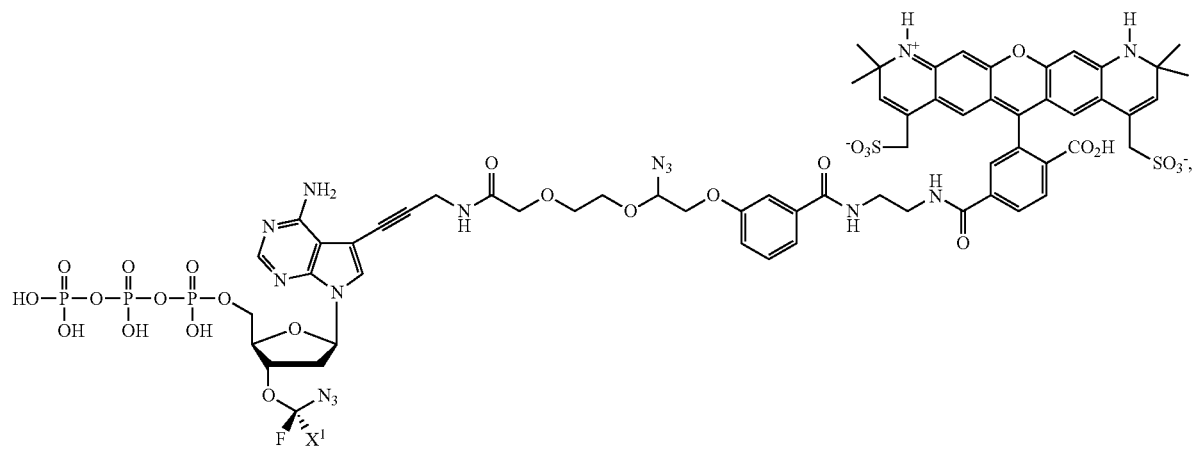

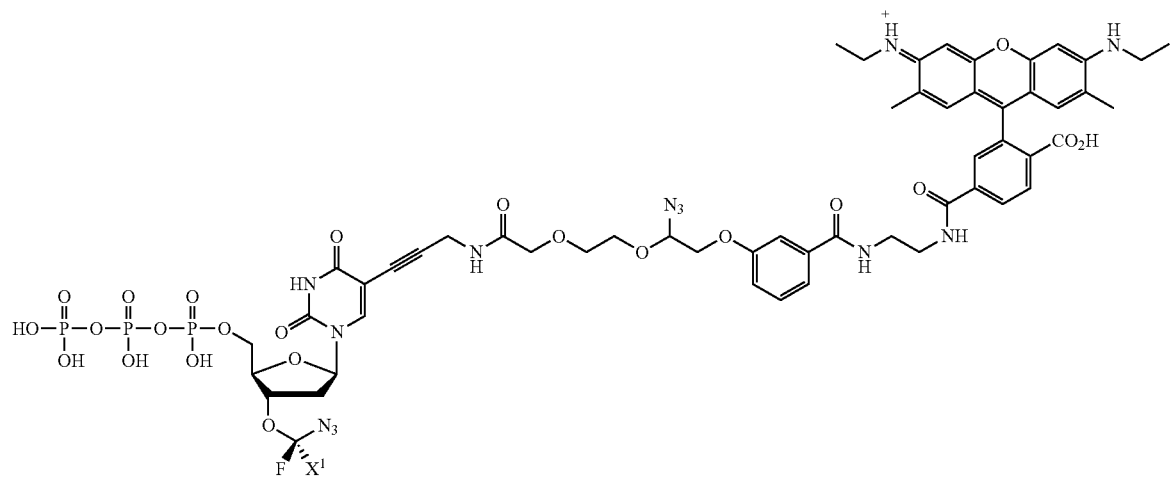
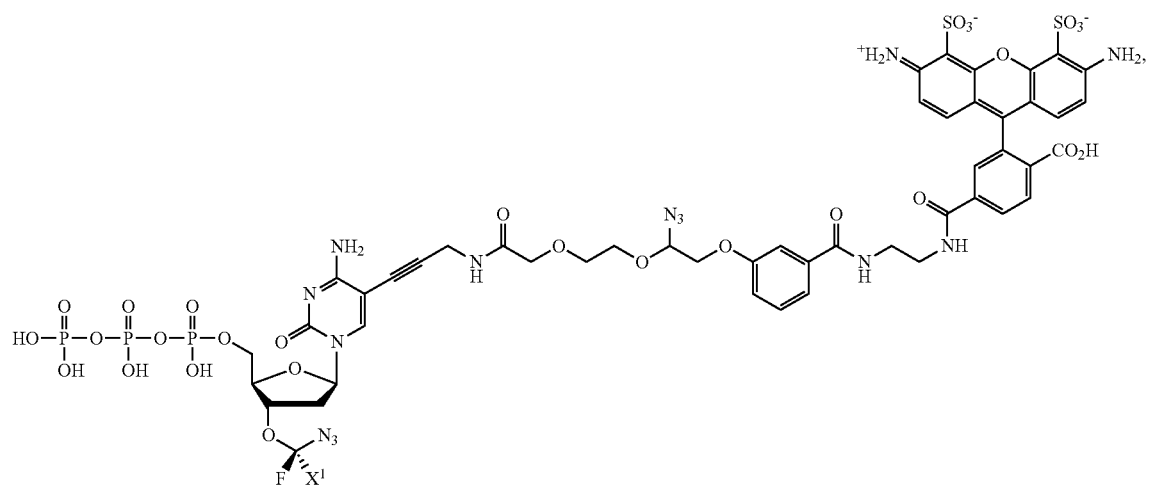
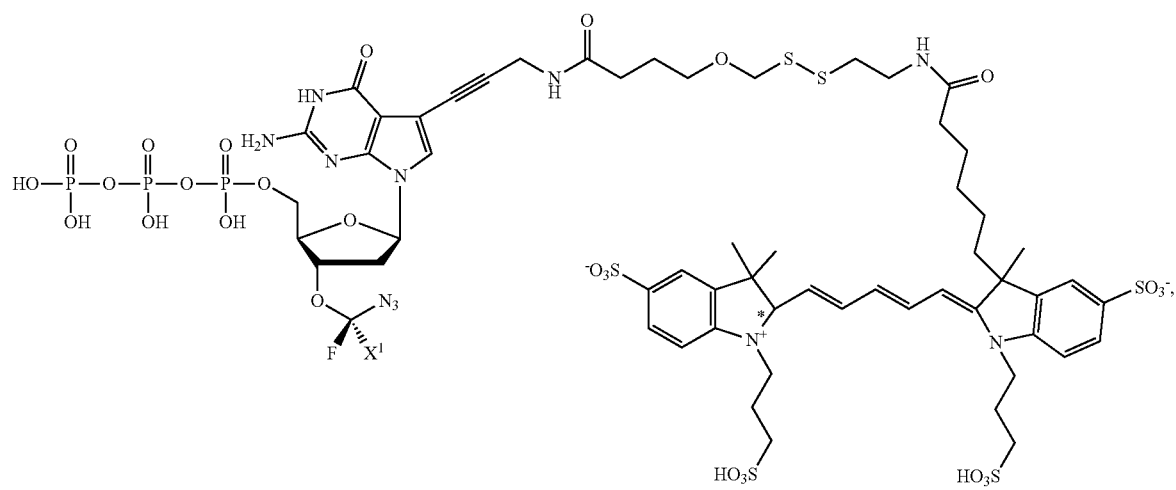

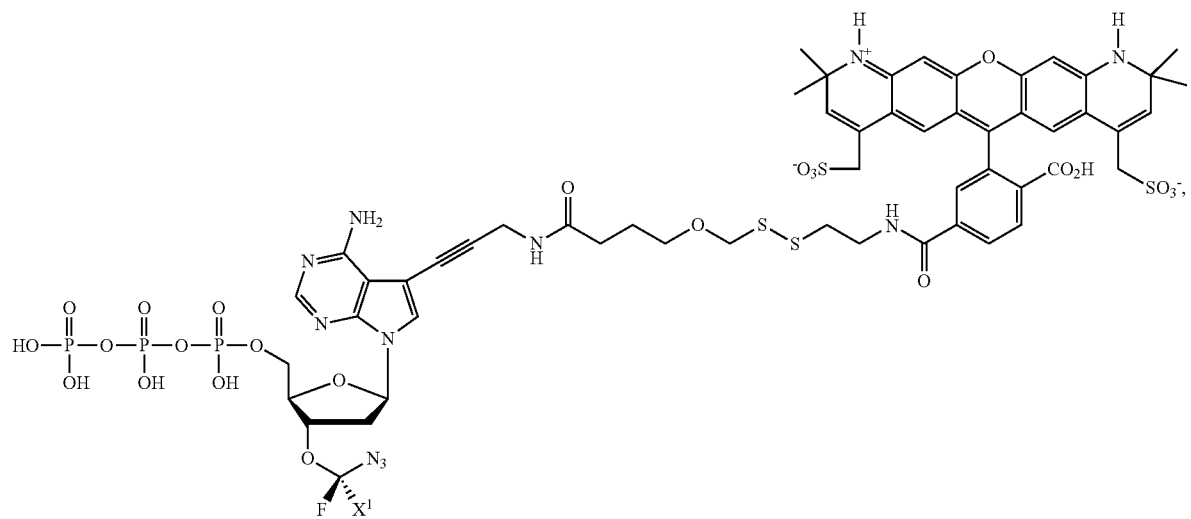
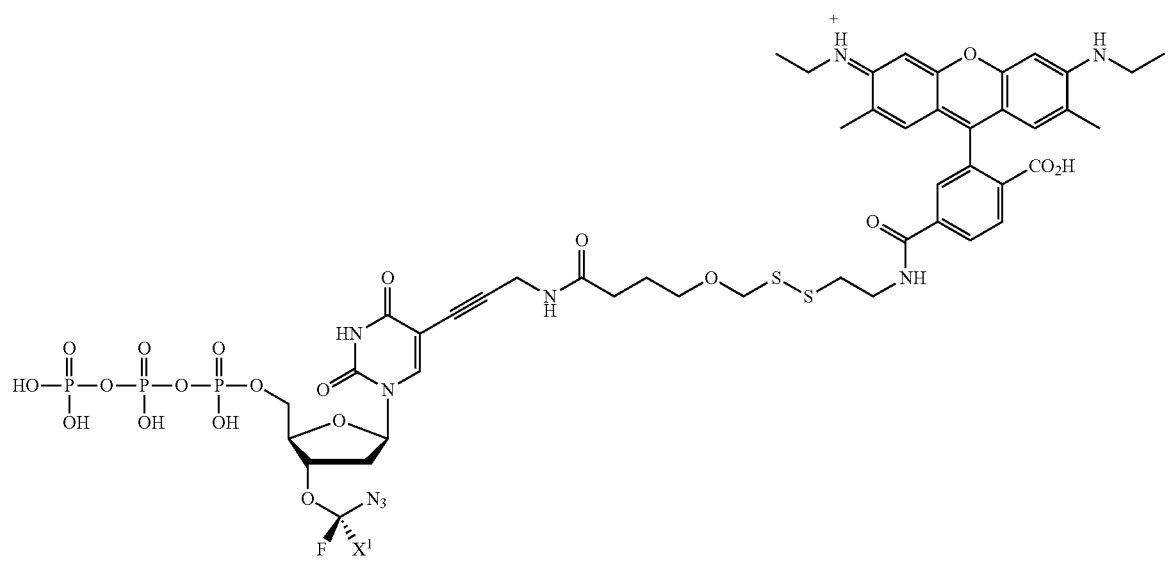
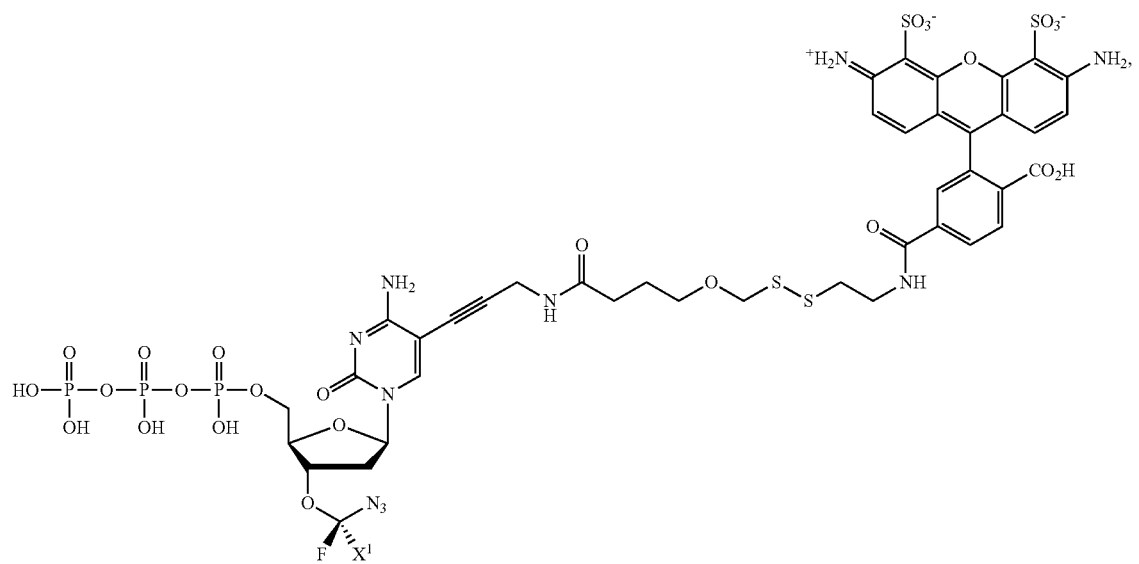

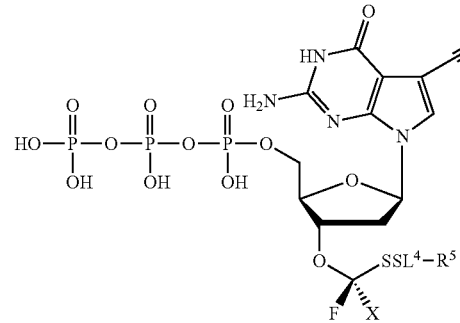
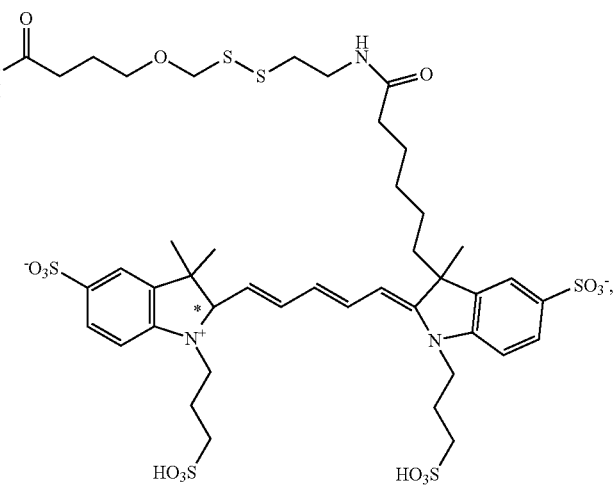
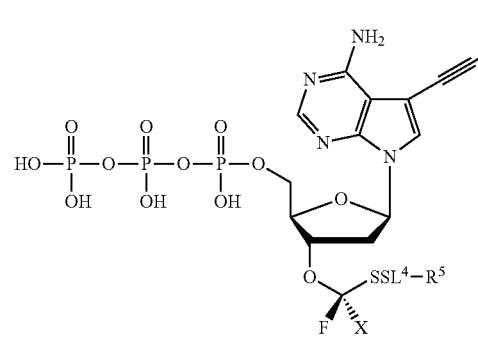
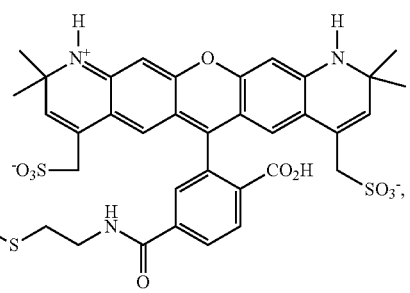
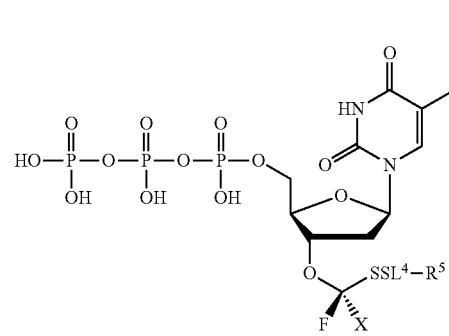
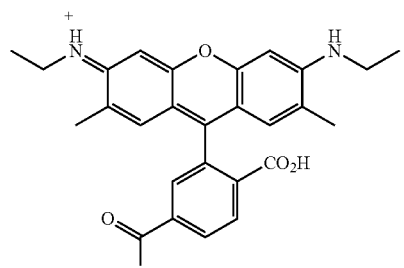
, or

-continued

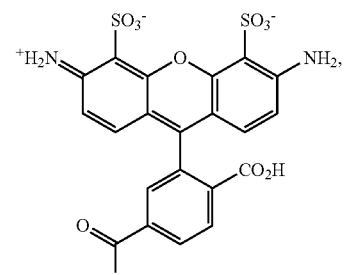
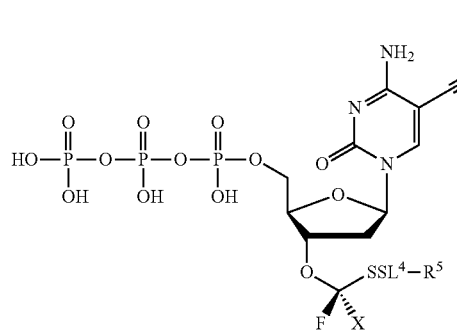

wherein X and $X^1$ are each independently a halogen, and $L^4$ and $R^4$ are as described herein.

In embodiments, the polymerases provided herein are used with modified nucleotides and nucleic acid synthesis methods as described in US 2018/0274024, WO/2017/058953, WO 2017/205336, or US 2019/0077726, the contents of which are incorporated by reference herein for all purposes.

In embodiments, methods of incorporating a modified nucleotide into a nucleic acid sequence provided herein includes a polymerase (a synthetic or variant DNA polymerase) with one or more amino acid substitution mutations at position 129, 141,143, 411, 412, 413 and/or 488. In embodiments, the polymerase includes an amino acid substitution at position 141. The amino acid substitution at position 141 may be an alanine substitution, a glycine substitution, a valine substitution, a methionine substitution, a leucine substitution or an isoleucine substitution. In embodiments, the amino acid substitution at position 141 is an alanine substitution. In embodiments, the polymerase includes an amino acid substitution at position 143. The amino acid substitution at position 143 may be an alanine substitution, a glycine substitution, a valine substitution, a methionine substitution, a leucine substitution or an isoleucine substitution. In embodiments, the amino acid substitution at position 143 is an alanine substitution.

In embodiments, the polymerase includes an amino acid substitution at position 129. The amino acid substitution at position 129 may be an alanine substitution, a glycine substitution, a valine substitution, a leucine substitution or an isoleucine substitution. In embodiments, the amino acid substitution at position 129 is an alanine substitution.

In embodiments, the polymerase includes an amino acid substitution at position 411. The amino acid substitution at position 411 may be a serine substitution or a threonine substitution. In embodiments, the amino acid substitution at position 411 is a serine substitution. In embodiments, the amino acid substitution at position 411 is an alanine substitution, a glycine substitution, a valine substitution, a methionine, a leucine substitution or an isoleucine substitution. In embodiments, the amino acid substitution at position 411 is an alanine substitution, a glycine substitution, a valine substitution, a leucine substitution or an isoleucine substitution.

In embodiments, the polymerase includes an amino acid substitution at position 412. The amino acid substitution at position 412 may be an alanine substitution, a glycine substitution, a valine substitution, a leucine substitution or an isoleucine substitution. In embodiments, the amino acid substitution at position 412 is an alanine substitution.

In embodiments, the polymerase includes an amino acid substitution at position 413. The amino acid substitution at position 413 may be an alanine substitution, a glycine substitution, a valine substitution, a leucine substitution or an isoleucine substitution. In embodiments, the amino acid substitution at position 413 is a valine substitution, a leucine substitution or an isoleucine substitution. In embodiments, the amino acid substitution at position 413 is a valine substitution or an isoleucine substitution. In embodiments, the amino acid substitution at position 413 is a valine substitution. In embodiments, the amino acid substitution at position 413 is an isoleucine substitution.

In embodiments, the polymerase includes an amino acid substitution at position 488. The amino acid substitution at position 488 may be an alanine substitution, a glycine substitution, a valine substitution, a leucine substitution or an isoleucine substitution. In embodiments, the amino acid substitution at position 488 is a valine substitution.

In embodiments, the polymerase includes an amino acid sequence that is at least 80% identical to a continuous 500 amino acid sequence within SEQ ID NO: 1. The polymerase includes substitution mutations at positions 141 and 143 of SEQ ID NO: 1. The polymerase further includes at least one amino acid substitution mutation at a position selected from positions 129, 411, 412, 413 and/or 488 of SEQ ID NO: 1.

In embodiments, the polymerase includes an amino acid sequence that is at least 85%, at least 90%, or at least 95% identical to a continuous 500 amino acid sequence within SEQ ID NO: 1. In embodiments, the polymerase includes an amino acid sequence that is at least 80%, at least 85%, at least 90%, or at least 95% identical to a continuous 600 amino acid sequence within SEQ ID NO: 1. In embodiments, the polymerase includes an amino acid sequence that is at least 80%, at least 85%, at least 90%, or at least 95% identical to a continuous 700 amino acid sequence within SEQ ID NO: 1.

In embodiments, the polymerase includes alanine substitution mutations at positions 141 and 143 of SEQ ID NO: 1. In embodiments, the polymerase further includes at least one amino acid substitution mutation at a position selected from positions 129, 411, 412, 413, and/or 488 of SEQ ID NO: 1. In embodiments, the polymerase further includes at least one amino acid substitution at a position selected from an alanine, glycine, leucine, isoleucine, or valine at position 129, a serine, threonine, an aspargine, a glutamine, an alanine, a glycine, an isoleucine, a valine, or a methionine at position 411, an alanine, a glycine, an isoleucine, a valine, or a methionine at position 412, a valine, isoleucine, leucine, or methionine at position 413, and a valine, isoleucine, leucine, or methionine at position 488. In embodiments, the polymerase further includes one amino acid substitution mutation selected from a serine at position 411, an alanine at position 412, a valine at position 413, and a valine at position 488. In embodiments, the polymerase further includes one amino acid substitution mutation selected from an alanine at position 129, a serine at position 409, an alanine at position 412, an isoleucine at position 413, and a valine at position 488.

In embodiments, the polymerase includes alanine substitution mutations at positions 141, 143, and 412 of SEQ ID NO: 1 and further includes a serine at position 411 and a valine at position 413 as exemplified by SEQ ID NO: 4. In embodiments, the polymerase includes alanine substitution mutations at positions 141, 143, and 412 of SEQ ID NO: 1 and further includes a serine at position 411, a valine at position 413 and a valine at position 488 as exemplified by SEQ ID NO: 5. In embodiments, the polymerase includes alanine substitution mutations at positions 141, 143, and 412 of SEQ ID NO: 1 and further includes an alanine at position 129, an alanine at position 411, an isoleucine at position 413 and a valine at position 488 as exemplified by SEQ ID NO: 6.

The polymerase (a synthetic or variant DNA polymerase) may have a sequence that is at least 60%, at least 65%, at least 70%, at least 75%, at least 80%, at least 85%, at least 90%, or at least 95% identical to the wild-type sequence of *Thermococcus* sp. EP1 family B DNA polymerase of SEQ ID NO: 1. In embodiments, the polymerase may have a sequence that is 60%, 61%, 62%, 63%, 64%, 65%, 66%, 67%, 68%, or 69% identical to the wild-type sequence of *Thermococcus* sp. EP1 family B DNA polymerase of SEQ ID NO: 1. The polymerase may have a sequence that is 70%, 71%, 72%, 73%, 74%, 75%, 76%, 77%, 78%, or 79% identical to the wild-type sequence of *Thermococcus* sp. EP1 family B DNA polymerase of SEQ ID NO: 1. The polymerase may have a sequence that is 80%, 81%, 82%, 83%, 84%, 85%, 86%, 87%, 88%, or 89% identical to the wild-type sequence of *Thermococcus* sp. EP1 family B DNA polymerase of SEQ ID NO: 1. The polymerase may have a sequence that is 90%, 91%, 92%, 93%, 94%, 95%, 96%, 97%, 98%, or 99% identical to the wild-type sequence of *Thermococcus* sp. EP1 family B DNA polymerase of SEQ ID NO: 1

The polymerase (a synthetic or variant DNA polymerase) may have a sequence that is identical to a continuous 500, 600, or 700 continuous amino acids of SEQ ID NO: 1. In embodiments, the polymerase may have a sequence that is identical to a continuous 500, 505, 510, 515, 520, 525, 530, 535, 540, 545, 550, 555, 560, 565, 570, 575, 580, 585, 590, or 595 continuous amino acids of SEQ ID NO: 1. In embodiments, the polymerase may have a sequence that is identical to a continuous 600, 605, 610, 615, 620, 625, 630, 635, 640, 645, 650, 655, 660, 665, 670, 675, 680, 685, 690, or 695 continuous amino acids of SEQ ID NO: 1.

Examples of mutations giving rise to an exo⁻/exo⁻ variants include mutations at positions in a parent polymerase corresponding to positions in SEQ ID NO: 1 identified as follows: 129, 141, 143, 411, 412, 413, and 488.

In embodiments, mutations may include substitution of the amino acid in the parent amino acid sequences with an amino acid, which is not the parent amino acid. In embodiments, the mutations may result in conservative amino acid changes. In embodiments, non-polar amino acids may be converted into polar amino acids (threonine, asparagine, glutamine, cysteine, tyrosine, aspartic acid, glutamic acid or histidine) or the parent amino acid may be changed to an alanine.

In embodiments, the method includes maintaining the temperature at about 55° C. In embodiments, the method includes maintaining the temperature at about 55° C. to about 80° C. In embodiments, the method includes maintaining the temperature at about 60° C. to about 70° C. In embodiments, the method includes maintaining the temperature at about 65° C. to about 75° C. In embodiments, the method includes maintaining the temperature at about 65° C. In embodiments, the method includes maintaining the temperature at a pH of 8.0 to 11.0. In embodiments, the pH is 9.0 to 11.0. In embodiments, the pH is 9.5. In embodiments, the pH is 10.0. In embodiments, the pH is 8.0, 8.5, 9.0, 9.5, 10.0, 10.5, or 11.0. In embodiments, the pH is from 9.0 to 11.0, and the temperature is about 60° C. to about 70° C.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: Development of Family B DNA Polymerase Variants

A number of Family B polymerases from Archaea that have sequences with a range of 30-80% identity to *Thermococcus* sp. 9°N amino acid sequence (SEQ ID NO: 2) were selected. One from *Thermococcus* sp. EP1 (as denoted in SEQ ID NO: 1 which has 80% identity to SEQ ID NO: 2) and a second from *Pyrobaculum calidifontis* JCM 11548 (as denoted in SEQ ID NO: 3 which has 35% identity to SEQ ID NO: 2) were chosen for evaluation. Expression constructs for these sequences, which correspond to wild type or parent polymerase were made and expressed in *E. coli*. The expressed proteins (polymerase) were purified from *E. coli* and tested for polymerase and exonuclease activity. For *Pyrobaculum calidifontis* JCM 11548, the purified polymerase exhibited less than 5% specific activity for both DNA polymerase and exonuclease activity compared with *Thermococcus* sp. 9°N. Due to the low activity, this polymerase was not analyzed further.

All polymerases used were expressed in *E. coli* BL21 STAR (DE3) (ThermoFisher) as follows. First the gene was synthesized (ATUM) in pD451-SR expression vector using codons selected for high-yield expression. Whenever needed, additional in vitro substitution mutagenesis was performed on the gene sequence using a Site Directed Mutagenesis Kit (New England Biolabs) and confirmed by Sanger sequencing. Clones for each variant were transformed into BL21 STAR (DE3) (ThermoFisher) and incubated at 37° C. with shaking in 2.0 L flasks until an OD600 of 0.6 was reached. Then iPTG (1 mM final concentration) was added to induce specific protein expression. The cells were incubated 3 hours at 37° C. and collected by centrifugation at 5000 rpm for 5 minutes. Cell pellets were stored at minus 80° C.

All purification steps were performed at 4° C. except as indicated. The frozen cell paste was resuspended in lysis buffer (20 mM Tris pH 7.5, 500 mM NaCl, 1 mM EDTA, 1 mM DTT, 10% Glycerol, 1 mM PMSF, and protease inhibitor cocktail, EDTA-free (Thermo Fisher). The suspended cells were subjected to sonication and centrifuged at 20,000 rpm for 20 min. Then the supernatant was heated to 80° C. for 30 min to inactivate host proteins. The mixture was again centrifuged at 20,000 rpm for 20 min and the pellet discarded.

The supernatant was collected and Poly(ethyleneimine) was added slowly to the supernatant to a final concentration of 0.4% with continued stirring for 30 minutes. The mixture was centrifuged at 20,000 rpm for 20 min and the pellet was discarded. Then solid ammonium sulfate was added to the supernatant to 65% saturation with stirring continued for 30 min. The mixture was centrifuged at 20,000 rpm for 20 min and the precipitated proteins were resuspended in 10 ml Buffer A (20 mM Tris pH 7.0, 50 mM KCl, 0.1 mM EDTA, 10% glycerol, 1 mM DTT, 1 mM PMSF). The protein was dialyzed overnight against 1 Liter Buffer A. The dialyzed sample was centrifuged at 20,000 rpm for 20 min to remove any precipitate and the supernatant was loaded onto a 5 ml Hi-Trap SP FF column (GE Healthcare) equilibrated with Buffer A. The polymerase was eluted using a 100 ml gradient from 50 to 800 mM KCl. Peak fractions were pooled and dialyzed overnight against Buffer B (20 mM Tris pH 7.5, 50 mM KCl, 0.1 mM EDTA, 10% glycerol, 1 mM DTT, 1 mM PMSF). The dialyzed sample was centrifuged at 20,000 rpm for 20 min to remove any precipitate and the supernatant was loaded onto a 5 ml Hi-Trap Heparin column (GE Healthcare) equilibrated with Buffer B. The polymerase was eluted using a 100 ml gradient from 50 to 800 mM KCl. Peak fractions were pooled and dialyzed overnight against storage buffer (20 mM Tris pH 7.5, 100 mM KCl, 0.1 mM EDTA, 50% glycerol, 1 mM DTT) and stored at −20° C.

Polymerase and exonuclease assays were done using a fluorescent primer/template as described elsewhere (see, for example, Nikiforov T T. et al. Anal Biochem. 2014 Sep. 15; 461:67-73; and Nikiforov T T. et al. *Anal Biochem.* 2011 May 15; 412(2):229-36). *Thermococcus* sp. EP1 wild type polymerase (SEQ ID NO.: 1) showed both polymerase and exonuclease activity. The full plasmid nucleic acid sequence of wild type *Thermococcus* sp. EP1 gene cloned in plasmid used to generate the *Thermococcus* sp. EP1 protein is provided in SEQ ID NO: 17. The nucleic acid sequence for wild type *Thermococcus* sp. EP1 gene is provided as SEQ ID NO: 16.

*Thermococcus* sp. EP1 wildtype polymerase showed both polymerase and exonuclease activity. Variants were constructed and tested for polymerase, exonuclease and for activity with nucleotide reversible terminators and for sequencing SBS. Alignment of the polymerase variant amino acid sequences against parental wild type (SG2000) and against variant *Thermococcus* sp. EP1 are shown in FIGS. 2A-2E. Variant SG2100 includes alanine at position 141, 143, and 412, a serine at position 411, a valine at position 413. Variant SG2105 includes alanine at position 141, 143, and 412, a serine at position 411, a valine at position 413 and a valine at position 488. SG2200 includes alanine at position 129, 141, 143, 411, 412, an isoleucine at position 413 and a valine at position 488. Additional variants comprising the mutations described herein, see for example Table 1, may be synthesized according to known techniques described herein.

TABLE 1

List of mutant polymerases. The mutations in this table are mutations relative to the wild type *Thermococcus* sp. EP1 (SEQ ID NO: 1). As described elsewhere here, P413P is not a mutation, rather specifying the particular amino acid, proline, at position 413 of SEQ ID NO: 1.

| Internal Ref # | Amino acids |
| --- | --- |
| SE-TEP-1 | L411A; Y412G; P413P; G153T; |
| SE-TEP-2 | L411A; Y412G; P413P; G157D; |
| SE-TEP-3 | L411A; Y412G; P413P; F152E; |
| SE-TEP-4 | L411A; Y412G; P413P; G155T; |
| SE-TEP-5 | L411A; Y412G; P413P; T301I; |
| SE-TEP-6 | L411A; Y412G; P413P; L305M; |
| SE-TEP-7 | L411A; Y412G; P413P; R379F; |
| SE-TEP-8 | L411A; Y412G; P413P; P36H; |
| SE-TEP-9 | L411A; Y412G; P413P; P36A; |
| SE-TEP-10 | L411A; Y412G; P413P; V93G; |
| SE-TEP-11 | L411A; Y412G; P413P; V93A; |
| SE-TEP-12 | L411A; Y412G; P413P; V93Q; |
| SE-TEP-13 | L411A; Y412G; P413P; M129A; |
| SE-TEP-14 | L411A; Y412G; P413P; D141A; |
| SE-TEP-15 | L411A; Y412G; P413P; E143A; |
| SE-TEP-16 | L411A; Y412G; P413P; T144A; |
| SE-TEP-17 | L411A; Y412G; P413P; G153E; |
| SE-TEP-18 | L411A; Y412G; P413P; D215A; |
| SE-TEP-19 | L411A; Y412G; P413P; D317A; |
| SE-TEP-20 | L411A; Y412G; P413P; K479W; |
| SE-TEP-21 | L411A; Y412G; P413P; K480A; |
| SE-TEP-22 | L411A; Y412G; P413P; L481A; |
| SE-TEP-23 | L411A; Y412G; P413P; A488V; |
| SE-TEP-24 | L411A; Y412G; P413P; T517S; |
| SE-TEP-25 | L411A; Y412G; P413P; T593I; |
| SE-TEP-26 | L411A; Y412G; P413P; K605A; |
| SE-TEP-27 | L411A; Y412G; P413P; A642L; |
| SE-TEP-28 | D141A; E143A; L411A; Y412G; P413P; G153T; |
| SE-TEP-29 | D141A; E143A; L411A; Y412G; P413P; G157D; |
| SE-TEP-30 | D141A; E143A; L411A; Y412G; P413P; F152E; |
| SE-TEP-31 | D141A; E143A; L411A; Y412G; P413P; G155T; |
| SE-TEP-32 | D141A; E143A; L411A; Y412G; P413P; T301I; |
| SE-TEP-33 | D141A; E143A; L411A; Y412G; P413P; L305M; |
| SE-TEP-34 | D141A; E143A; L411A; Y412G; P413P; R379F; |
| SE-TEP-35 | D141A; E143A; L411A; Y412G; P413P; P36H; |
| SE-TEP-36 | D141A; E143A; L411A; Y412G; P413P; P36A; |
| SE-TEP-37 | D141A; E143A; L411A; Y412G; P413P; V93G; |
| SE-TEP-38 | D141A; E143A; L411A; Y412G; P413P; V93A; |
| SE-TEP-39 | D141A; E143A; L411A; Y412G; P413P; V93Q; |
| SE-TEP-40 | D141A; E143A; L411A; Y412G; P413P; M129A; |
| SE-TEP-41 | D141A; E143A; L411A; Y412G; P413P; T144A; |
| SE-TEP-42 | D141A; E143A; L411A; Y412G; P413P; G153E; |
| SE-TEP-43 | D141A; E143A; L411A; Y412G; P413P; D215A; |
| SE-TEP-44 | D141A; E143A; L411A; Y412G; P413P; D317A; |
| SE-TEP-45 | D141A; E143A; L411A; Y412G; P413P; K479W; |
| SE-TEP-46 | D141A; E143A; L411A; Y412G; P413P; K480A; |
| SE-TEP-47 | D141A; E143A; L411A; Y412G; P413P; L481A; |
| SE-TEP-48 | D141A; E143A; L411A; Y412G; P413P; A488V; |
| SE-TEP-49 | D141A; E143A; L411A; Y412G; P413P; T517S; |
| SE-TEP-50 | D141A; E143A; L411A; Y412G; P413P; T593I; |
| SE-TEP-51 | D141A; E143A; L411A; Y412G; P413P; K605A; |
| SE-TEP-52 | D141A; E143A; L411A; Y412G; P413P; A642L; |
| SE-TEP-53 | L411A; Y412A; P413I; G153T; |
| SE-TEP-54 | L411A; Y412A; P413I; G157D; |
| SE-TEP-55 | L411A; Y412A; P413I; F152E; |
| SE-TEP-56 | L411A; Y412A; P413I; G155T; |
| SE-TEP-57 | L411A; Y412A; P413I; T301I; |
| SE-TEP-58 | L411A; Y412A; P413I; L305M; |
| SE-TEP-59 | L411A; Y412A; P413I; R379F; |
| SE-TEP-60 | L411A; Y412A; P413I; P36H; |

TABLE 1-continued

List of mutant polymerases. The mutations in this table are mutations relative to the wild type *Thermococcus* sp. EP1 (SEQ ID NO: 1). As described elsewhere here, P413P is not a mutation, rather specifying the particular amino acid, proline, at position 413 of SEQ ID NO: 1.

| Internal Ref # | Amino acids |
|---|---|
| SE-TEP-61 | L411A; Y412A; P413I; P36A; |
| SE-TEP-62 | L411A; Y412A; P413I; V93G; |
| SE-TEP-63 | L411A; Y412A; P413I; V93A; |
| SE-TEP-64 | L411A; Y412A; P413I; V93Q; |
| SE-TEP-65 | L411A; Y412A; P413I; M129A; |
| SE-TEP-66 | L411A; Y412A; P413I; D141A; |
| SE-TEP-67 | L411A; Y412A; P413I; E143A; |
| SE-TEP-68 | L411A; Y412A; P413I; T144A; |
| SE-TEP-69 | L411A; Y412A; P413I; G153E; |
| SE-TEP-70 | L411A; Y412A; P413I; D215A; |
| SE-TEP-71 | L411A; Y412A; P413I; D317A; |
| SE-TEP-72 | L411A; Y412A; P413I; K479W; |
| SE-TEP-73 | L411A; Y412A; P413I; K480A; |
| SE-TEP-74 | L411A; Y412A; P413I; L481A; |
| SE-TEP-75 | L411A; Y412A; P413I; A488V; |
| SE-TEP-76 | L411A; Y412A; P413I; T517S; |
| SE-TEP-77 | L411A; Y412A; P413I; T593I; |
| SE-TEP-78 | L411A; Y412A; P413I; K605A; |
| SE-TEP-79 | L411A; Y412A; P413I; A642L; |
| SE-TEP-80 | M129A; D141A; E143A; L411A; Y412A; P413I; G153T; |
| SE-TEP-81 | M129A; D141A; E143A; L411A; Y412A; P413I; G157D; |
| SE-TEP-82 | M129A; D141A; E143A; L411A; Y412A; P413I; F152E; |
| SE-TEP-83 | M129A; D141A; E143A; L411A; Y412A; P413I; G155T; |
| SE-TEP-84 | M129A; D141A; E143A; L411A; Y412A; P413I; T301I; |
| SE-TEP-85 | M129A; D141A; E143A; L411A; Y412A; P413I; L305M; |
| SE-TEP-86 | M129A; D141A; E143A; L411A; Y412A; P413I; R379F; |
| SE-TEP-87 | M129A; D141A; E143A; L411A; Y412A; P413I; P36H; |
| SE-TEP-88 | M129A; D141A; E143A; L411A; Y412A; P413I; P36A; |
| SE-TEP-89 | M129A; D141A; E143A; L411A; Y412A; P413I; V93G; |
| SE-TEP-90 | M129A; D141A; E143A; L411A; Y412A; P413I; V93A; |
| SE-TEP-91 | M129A; D141A; E143A; L411A; Y412A; P413I; V93Q; |
| SE-TEP-92 | M129A; D141A; E143A; L411A; Y412A; P413I; T144A; |
| SE-TEP-93 | M129A; D141A; E143A; L411A; Y412A; P413I; G153E; |
| SE-TEP-94 | M129A; D141A; E143A; L411A; Y412A; P413I; D215A; |
| SE-TEP-95 | M129A; D141A; E143A; L411A; Y412A; P413I; D317A; |
| SE-TEP-96 | M129A; D141A; E143A; L411A; Y412A; P413I; K479W; |
| SE-TEP-97 | M129A; D141A; E143A; L411A; Y412A; P413I; K480A; |
| SE-TEP-98 | M129A; D141A; E143A; L411A; Y412A; P413I; L481A; |
| SE-TEP-99 | M129A; D141A; E143A; L411A; Y412A; P413I; A488V; |
| SE-TEP-100 | M129A; D141A; E143A; L411A; Y412A; P413I; T517S; |
| SE-TEP-101 | M129A; D141A; E143A; L411A; Y412A; P413I; T593I; |
| SE-TEP-102 | M129A; D141A; E143A; L411A; Y412A; P413I; K605A; |
| SE-TEP-103 | M129A; D141A; E143A; L411A; Y412A; P413I; A642L; |
| SE-TEP-104 | L411S; Y412A; P413V; G153T; |
| SE-TEP-105 | L411S; Y412A; P413V; G157D; |
| SE-TEP-106 | L411S; Y412A; P413V; F152E; |
| SE-TEP-107 | L411S; Y412A; P413V; G155T; |
| SE-TEP-108 | L411S; Y412A; P413V; T301I; |
| SE-TEP-109 | L411S; Y412A; P413V; L305M; |
| SE-TEP-110 | L411S; Y412A; P413V; R379F; |
| SE-TEP-111 | L411S; Y412A; P413V; P36H; |
| SE-TEP-112 | L411S; Y412A; P413V; P36A; |
| SE-TEP-113 | L411S; Y412A; P413V; V93G; |
| SE-TEP-114 | L411S; Y412A; P413V; V93A; |
| SE-TEP-115 | L411S; Y412A; P413V; V93Q; |
| SE-TEP-116 | L411S; Y412A; P413V; M129A; |
| SE-TEP-117 | L411S; Y412A; P413V; D141A; |
| SE-TEP-118 | L411S; Y412A; P413V; E143A; |
| SE-TEP-119 | L411S; Y412A; P413V; T144A; |
| SE-TEP-120 | L411S; Y412A; P413V; G153E; |
| SE-TEP-121 | L411S; Y412A; P413V; D215A; |
| SE-TEP-122 | L411S; Y412A; P413V; D317A; |
| SE-TEP-123 | L411S; Y412A; P413V; K479W; |
| SE-TEP-124 | L411S; Y412A; P413V; K480A; |
| SE-TEP-125 | L411S; Y412A; P413V; L481A; |
| SE-TEP-126 | L411S; Y412A; P413V; A488V; |
| SE-TEP-127 | L411S; Y412A; P413V; T517S; |
| SE-TEP-128 | L411S; Y412A; P413V; T593I; |
| SE-TEP-129 | L411S; Y412A; P413V; K605A; |
| SE-TEP-130 | L411S; Y412A; P413V; A642L; |
| SE-TEP-131 | M129A; D141A; E143A; L411S; Y412A; P413V; G153T; |
| SE-TEP-132 | M129A; D141A; E143A; L411S; Y412A; P413V; G157D; |
| SE-TEP-133 | M129A; D141A; E143A; L411S; Y412A; P413V; F152E; |
| SE-TEP-134 | M129A; D141A; E143A; L411S; Y412A; P413V; G155T; |
| SE-TEP-135 | M129A; D141A; E143A; L411S; Y412A; P413V; T301I; |
| SE-TEP-136 | M129A; D141A; E143A; L411S; Y412A; P413V; L305M; |
| SE-TEP-137 | M129A; D141A; E143A; L411S; Y412A; P413V; R379F; |
| SE-TEP-138 | M129A; D141A; E143A; L411S; Y412A; P413V; P36H; |
| SE-TEP-139 | M129A; D141A; E143A; L411S; Y412A; P413V; P36A; |
| SE-TEP-140 | M129A; D141A; E143A; L411S; Y412A; P413V; V93G; |
| SE-TEP-141 | M129A; D141A; E143A; L411S; Y412A; P413V; V93A; |
| SE-TEP-142 | M129A; D141A; E143A; L411S; Y412A; P413V; V93Q; |
| SE-TEP-143 | M129A; D141A; E143A; L411S; Y412A; P413V; T144A; |
| SE-TEP-144 | M129A; D141A; E143A; L411S; Y412A; P413V; G153E; |
| SE-TEP-145 | M129A; D141A; E143A; L411S; Y412A; P413V; D215A; |
| SE-TEP-146 | M129A; D141A; E143A; L411S; Y412A; P413V; D317A; |
| SE-TEP-147 | M129A; D141A; E143A; L411S; Y412A; P413V; K479W; |
| SE-TEP-148 | M129A; D141A; E143A; L411S; Y412A; P413V; K480A; |
| SE-TEP-149 | M129A; D141A; E143A; L411S; Y412A; P413V; L481A; |
| SE-TEP-150 | M129A; D141A; E143A; L411S; Y412A; P413V; A488V; |
| SE-TEP-151 | M129A; D141A; E143A; L411S; Y412A; P413V; T517S; |
| SE-TEP-152 | M129A; D141A; E143A; L411S; Y412A; P413V; T593I; |
| SE-TEP-153 | M129A; D141A; E143A; L411S; Y412A; P413V; K605A; |
| SE-TEP-154 | M129A; D141A; E143A; L411S; Y412A; P413V; A642L; |

The aim of the general experimental plan was to produce an optimized *Thermococcus* sp. EP1 polymerase for nucleic acid sequencing methods. Over 150 variants of *Thermococcus* sp. EP1 are described herein. Variants are profiled against a variety of reverse terminators. Some of the better performing enzymes have between 7 and 12 mutations relative to the wild-type.

Example 2: Assay for Incorporation of Nucleotide Reversible Terminators

The rate of incorporation of a fluorescent NRT was measured using primer/templates attached to avidin-coated magnetic beads (MyOne C1, ThermoFisher). The 5'-biotinylated 160 primer is annealed to the appropriate 160-X template and bound to the beads along with a tethering oligo 5'-Biotin-CG(TAGCCG)$_6$TAGC-ddC (tether B) (SEQ ID NO: 20). The beads are then attached to the surface of 384-well streptavidin-coated plates (Greiner Bio-one) to which tether A (5'-Biotin-GC(TACGGC)$_6$TACG-ddC) (SEQ ID NO: 19) has previously been bound. Reactions are initiated in Thermopol buffer (New England Biolabs) by the addition of 200 nM NRT and 133 nM DNA polymerase at a temperature of 60° C. The reaction is stopped by flooding duplicate wells with room temperature wash buffer (1 mM EDTA, 20 mM Tris pH 8, 50 mM NaCl, 0.025% Triton™ X-100) after incubation for 30 sec and additional wells after 10 min. Blanks were also made without incubation. The wells were imaged under a fluorescence microscope, and the images analyzed using software that identifies fluorescent beads and calculates their average brightness. The blank was subtracted from the time points and the values at 30 sec and 10 min used to calculate the half-time of incorporation assuming first-order kinetics with completion in under 10 min.

TABLE 2

Template Sequences

| | |
|---|---|
| 160-1 (SEQ ID NO: 11) | 5'-GACTCACATGAATCAGTGCAGCAT CAGATGTATGACCGAAGCGGACGAAGG TGCGTGGA-3ddC |
| 160-2 (SEQ ID NO: 12) | 5'-GTGGTTCATCGCGTCCGATATCA AACTTCGTCAAGTCGAAGCGGACGAA GGTGCGTGGA-3ddC |
| 160-3 (SEQ ID NO: 13) | 5'-TACTAGGTTGTACGATCCCTGCA CTTCAGCTAAGCACGAAGCGGACGAA GGTGCGTGGA-3ddC |
| 160-4 (SEQ ID NO: 14) | 5'-AGCTACCAATATTTAGTTTCCGA GTCTCAGCTCATGCGAAGCGGACGAA GGTGCGTGGA-3ddC |
| 160 Primer (SEQ ID NO: 15) | 5'-Biotin-AAAAAAAAAAAGT CCACGCACCTTCGTCCGCTTCG |

The underlined nucleotide is the first one downstream from the 160 primer. The results as shown in Table 3 indicate that the new backbone polymerase from TspEP1 (SG2105) has activity with NRTs that is comparable, and in the case of SG2105 faster incorporation, than other polymerase species (e.g., *Thermococcus* 9N7 Therminator IX species).

TABLE 3

Assay Results

| | Half Time (sec) | |
|---|---|---|
| | S Term | A Term |
| SG2100 | 114 | 110 |
| SG2105 | 10 | 14 |
| SG2200 | 71 | 103 |
| Therm. IX | 20 | 17 |

Shown are average half-times for incorporation of NRTs by various polymerases. S-Term refers to sulfide-containing terminators (WO 2017/058953). A-Term refers to azide-containing terminators (Guo J, et al. PNAS 2008) Therminator IX (Therm. IX) is a *Thermococcus* 9N7 polymerase from New England Biolabs.

Example 3: Isomer Differentiation

Balancing incorporation kinetics and fidelity is a challenge. If the mutations in the polymerase result in a rapid average incorporation half time but are too promiscuous such that the inappropriate nucleotide is incorporated into the primer, this will result in a large source of error in sequencing applications. It is also desirable to design a polymerase capable to incorporating a variety of reversible terminators. Through rational design of the motif A region, a series of mutations that accelerate incorporation with an acceptable fidelity score were discovered. To explore the motif A region, three differently sized reversible terminator probes linked to the 3' oxygen were used: an A-Term, S-Term, and i-term. A-Term refers to azide-containing terminators (Guo J, et al. PNAS 2008); for example having the formula:

S-Term refers to sulfide-containing terminators (WO 2017/058953); for example having the formula

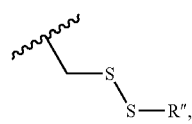

wherein R" is unsubstituted $C_1$-$C_4$ alkyl. The i-Term probe refers to an isomeric reversible terminator For example, an i-term probe has the formula:

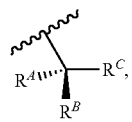

wherein $R^A$ and $R^B$ are hydrogen or alkyl, wherein at least one of $R^A$ or $R^B$ are hydrogen to yield a stereoisomeric probe, and $R^C$ is the remainder of the reversible terminator.

Certain mutations in the polymerase favor the incorporation of one isomer, thus creating optimized polymerases for a unique class of reversible terminators.

In embodiments, the nucleotide is

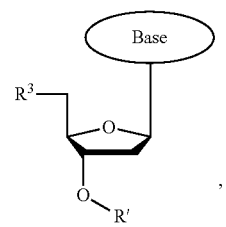

wherein Base is a Base as described herein, $R^3$ is —OH, monophosphate, or polyphosphate or a nucleic acid, and R' is a reversible terminator having the formula:

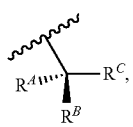

wherein $R^A$ and $R^B$ are hydrogen or alkyl and $R^C$ is the remainder of the reversible terminator. In embodiments, $R^A$ is methyl, $R^B$ is hydrogen, and $R^C$ is the remainder of the reversible terminator moiety. In embodiments, R' has the formula

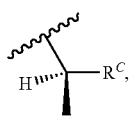

wherein $R^C$ is the remainder of the reversible terminator moiety. In embodiments, the nucleotide is

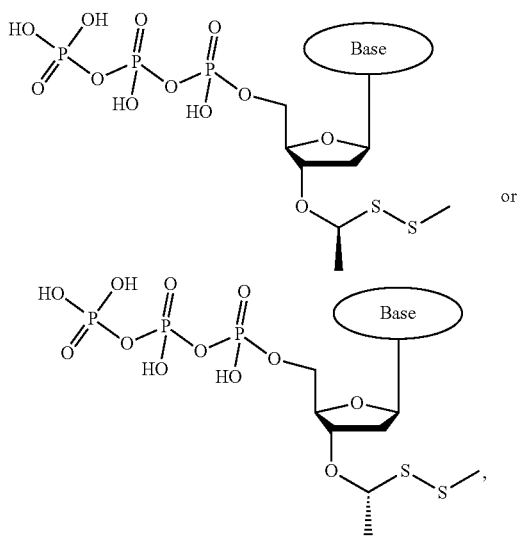

wherein the Base is cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), guanosine or a derivative thereof (e.g., 7-methylguanosine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is thymine, cytosine, uracil, adenine, guanine, hypoxanthine, xanthine, theobromine, caffeine, uric acid, or isoguanine.

One parameter, the average half time of nucleotide incorporation, is measured over all four nucleotides (A, T, C, and G), and serves as a useful indicator of the enzyme kinetics. The relative average halftime, At, is defined as the difference in the half time of incorporation for the mutant relative to the half time of incorporation using SG2100 for the same terminator moiety, or $\Delta t = t_{mutant} - t_{SG2100}$. Because i-term has two possible isomers, both i-term1 and i-term2 may be reported.

The initial screening assays employ a modified nucleotide without a fluorophore or cleavable linker. In nucleic acid sequencing applications that utilize reversible terminating nucleotides, the modified nucleotide typically has a modified base (e.g., a base linked to a fluorophore via a cleavable linker). When the linker attaching the fluorophore to the base is cleaved there is usually a residual spacer arm left after the cleavage. This residual modification may interfere with incorporation of subsequent nucleotides by polymerase. Therefore, we explore if these mutant polymerases are tolerable of these scars by measuring the incorporation rate of a fully modified nucleotide (i.e. a nucleotide comprising a reversible terminator, cleavable linker, and fluorophore).

A subsequent assay measures the average absolute half time of incorporation of a modified nucleotide containing a reversible terminator moiety (i-term 1 and i-term2), and a cleavable linker, where the cleavable linker is linking the fluorophore to the nucleotide. The average is the average half time of incorporation for four different nucleotides, A, T, C, and G.

Example 4: Measuring Enzyme Fidelity

The fidelity of a DNA polymerase is the result of accurate replication of a desired template. Specifically, this involves multiple steps, including the ability to read a template strand, select the appropriate nucleoside triphosphate and insert the correct nucleotide at the 3' primer terminus, such that Watson-Crick base pairing is maintained. In addition to effective discrimination of correct versus incorrect nucleotide incorporation, some DNA polymerases possess a 3'→5' exonuclease activity. This activity, known as "proofreading", is used to excise incorrectly incorporated mononucleotides that are then replaced with the correct nucleotide. In embodiments of the invention described herein, the exonuclease activity has been removed, therefore it is important to have a high fidelity enzyme.

High-fidelity DNA polymerases have safeguards to protect against both making and propagating mistakes while copying DNA. Such mutated polymerases have a significant binding preference for the correct versus the incorrect nucleoside triphosphate during polymerization. If an incorrect nucleotide does bind in the polymerase active site, incorporation is slowed due to the sub-optimal architecture of the active site complex (e.g., within motif A or the exonuclease domain). This lag time increases the opportunity for the incorrect nucleotide to dissociate before polymerase progression, thereby allowing the process to start again, with a correct nucleoside triphosphate. If an incorrect nucleotide is inserted, the perturbation caused by the mispaired bases is detected, and the polymerase moves the 3' end of the growing DNA chain into a proofreading 3'→5' exonuclease domain. There, the incorrect nucleotide is removed by the 3→5' exonuclease activity, whereupon the chain is moved back into the polymerase domain, where polymerization can continue.

Fidelity of the polymerase may be quantified using any suitable method known in the art. For example, to quantify the fidelity we do a single nucleotide extension where the next base to be incorporated is known (e.g., A) in the presence of excess incorrect nucleotide (e.g., G). For example, the enzyme, template, primer composition is mixed with 5 mM dATP and 500 mM dGTP (the most likely misincorporation), to probe nucleotide incorporation with 100-fold excess of the wrong nucleotide. The fidelity score is the signal (relative fluorescence units) from the correct base divided by the signal from the incorrect base. Therefore, a higher the fidelity score corresponds to a lower rate of misincorporation (i.e., incorporating the incorrect nucleotide).

Example 5: Rationale for Design of SG2100

In the context of nucleic acid sequencing, the use of nucleotides bearing a 3' reversible terminator allows successive nucleotides to be incorporated into a polynucleotide chain in a controlled manner. The DNA template for a sequencing reaction will typically comprise a double-stranded region having a free 3' hydroxyl group which serves as a primer or initiation point for the addition of further nucleotides in the sequencing reaction. The region of the DNA template to be sequenced will overhang this free 3' hydroxyl group on the complementary strand. The primer bearing the free 3' hydroxyl group may be added as a separate component (e.g. a short oligonucleotide) which hybridizes to a region of the template to be sequenced. Following the addition of a single nucleotide to the DNA template, the presence of the 3' reversible terminator prevents incorporation of a further nucleotide into the polynucleotide chain. While the addition of subsequent nucleotides is prevented, the identity of the incorporated is detected (e.g., exciting a unique detectable label that is linked to the incorporated nucleotide). The reversible terminator is then removed, leaving a free 3' hydroxyl group for addition of the next nucleotide. The sequencing cycle can then continue with the incorporation of the next blocked, labelled nucleotide.

Sequencing by synthesis of nucleic acids ideally requires the controlled (i.e. one at a time), yet rapid, incorporation of the correct complementary nucleotide opposite the oligonucleotide being sequenced. This allows for accurate sequencing by adding nucleotides in multiple cycles as each nucleotide residue is sequenced one at a time, thus preventing an uncontrolled series of incorporations occurring.

Figure 1A:
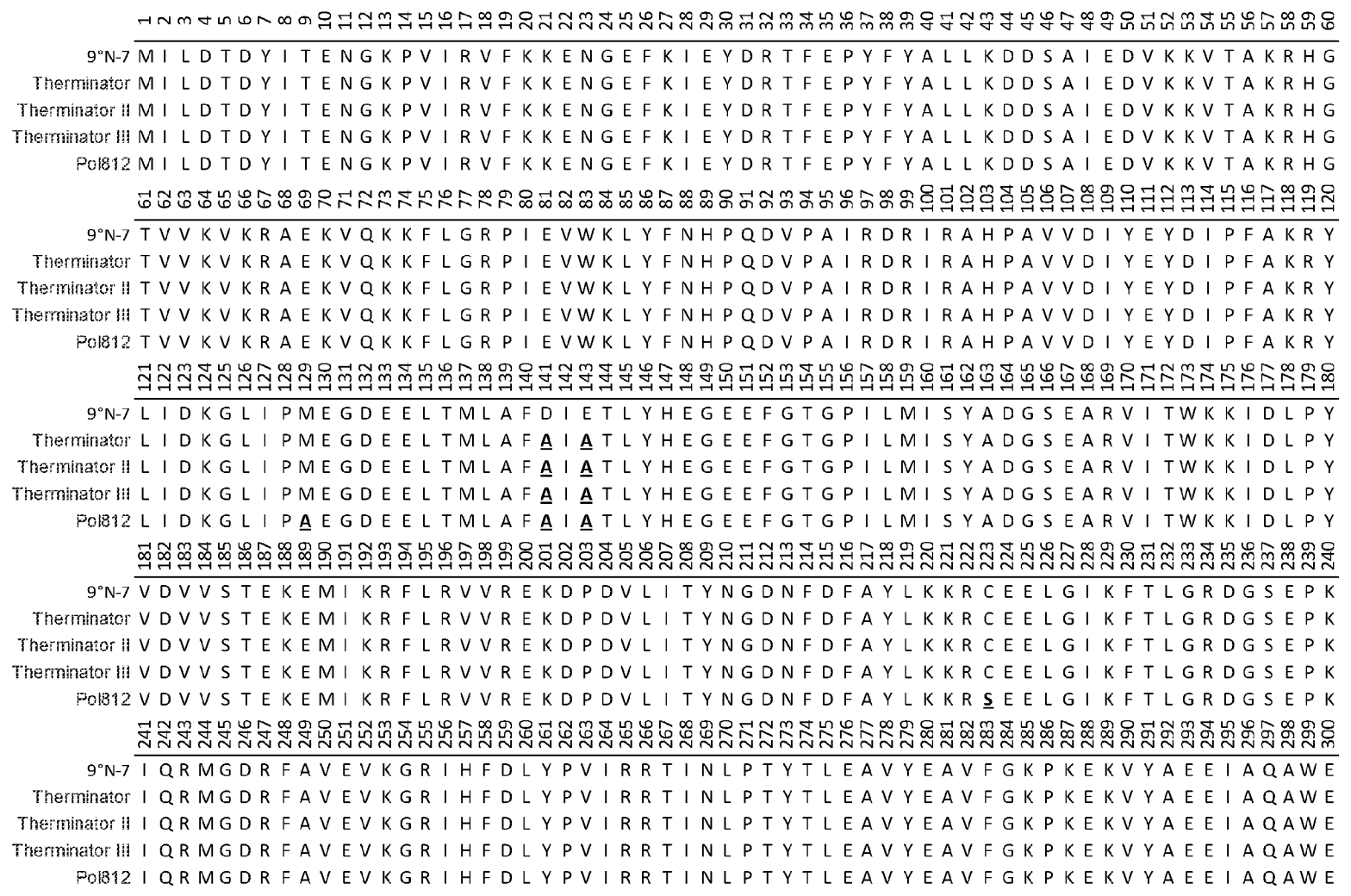
Figure 1B:
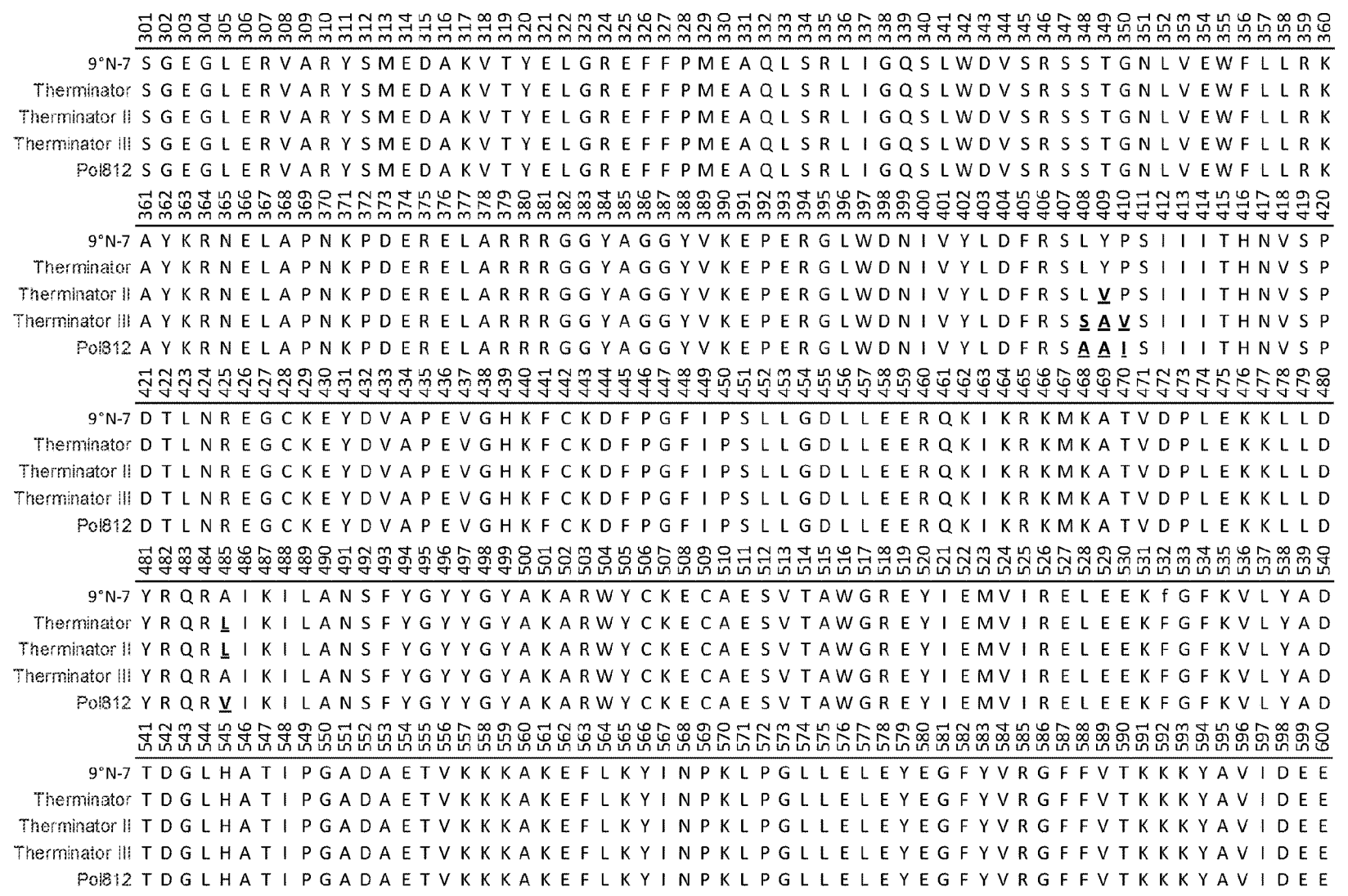

As described herein wild-type Thermococcus sp. EP1 has difficulty incorporating modified nucleotides (e.g., nucleotides including a reversible terminator and/or a cleavable linked base). A minimum set of mutations is necessary to modify the exonuclease activity and permit incorporation. For example, mutations at D141 and E143 which are known to affect exo activity (Southworth et al, 1996 Proc. Natl Acad. Sci USA 93:5281). As described in WO 2005/024010, modifications to the so-called motif A region, 408-410 of 9°N polymerases, exhibit improved incorporation of nucleotide analogues bearing substituents at the 3' position of the sugar. Note, amino acids at positions 408, 409, 410 in a 9°N polymerase are functionally equivalent to amino acids 411, 412, and 413 in wild type TspEP1. This trio of amino acids are in close proximity to the nucleotide that is being incorporated, and a change in the sequence or structure of this motif alters the incorporation kinetics. Moreover, this trio of amino acids is in the active site and is strictly conserved across the different types of polymerases, see for example FIG. 1 US 2017/0298327 showing wild-type 9°N, TGO, KOD1, Pfu, MmS2 and RB69 polymerases which all possess amino acids L, Y, and P in motif A.

For brevity, amino acid mutation nomenclature is used throughout this application. One having skill in the art would understand the amino acid mutation nomenclature, such that D141A refers to aspartic acid (single letter code is D), at position 141, is replaced with alanine (single letter code A). Likewise, it is understood that when an amino acid mutation nomenclature is used and the terminal amino acid code is missing, e.g., P411, it is understood that no mutation was made relative to the wild type.

While the aforementioned mutations were conducted in other thermostable enzymes (e.g., Thermococcus 9°N-7, Pfu, relying on the suggested mutation described above, the first mutated enzyme, SG2100, has the following mutations D141A, E143A, L411S, Y412A, and P413V which permits incorporation of modified nucleotides without exonuclease activity. Polymerase SG2100 has variations analogous to Terminator III. Additional research (e.g., Gardner, A. F. and Jack, W. E. (1999) Nucleic Acids Research 27, 2545-2555; Gardner and Jack, 2002. Nucl. Acids Res. 30:605; and Arezi et al., 2002. J. Mol. Biol. 322:719) suggested that mutations at 485 of a Thermococcus 9°N sequence enhanced the incorporation of nucleotide analogues that lack a 3' sugar hydroxyl moiety (acyNTPs and dideoxyNTPs).

Example 6: Mutational Analysis of Motif A

Through site directed mutagenesis and computational models, key mutations in the motif A region (i.e., the three amino acids functionally equivalent or homologous to amino acids 411, 412, and 413 in wild type TspEP1) were determined to include SAP, SAV, SGI, AGP, AAI, and AGI. Note when amino acid position 413 is proline, this corresponds to the wild-type amino acid. As described in WO 2005/024010, it was widely believed that modifications to the motif A region are required to incorporate nucleotide analogues; and so it was surprising to find that only modifying positions 411 and 412 in the motif A region not only resulted in the incorporation of a modified nucleotide, but significantly improved incorporation kinetics. Additional mutants with these motif A region modifications, as well as other modifications to the backbone, may improve DNA binding, improve modified nucleotide incorporation, deter exonuclease activity, and permit differentiation for isomeric reversible terminators.

Additional polymerase mutants with modifications to key mutations in the motif A region (i.e., the three amino acids functionally equivalent or homologous to amino acids 411, 412, and 413 in wild type TspEP1) include SAV, AAI, and AGP. Note, for example, AGI corresponds to the mutations L411A, Y412G, and P413I; when motif A is AGP this corresponds to mutations in amino acid positions 411 and 412 (i.e., L411A and Y412G) and amino acid position 413 is proline, the wild type amino acid denoted by the symbol P. TO be clear, when amino acid position 413 is proline (or a position functionally equivalent to 413), this corresponds to the wild-type amino acid and not a mutated amino acid. As described in Seo et al. J Org Chem 68(2): 609-12 (2003) and WO 2005/024010, it was widely believed that modifications to the motif A region are required to incorporate nucleotide analogues; and so it was surprising to find that only modifying positions 411 and 412 in the motif A region not only resulted in the incorporation of a modified nucleotide, but significantly improved incorporation kinetics. Table 1 includes additional mutants with these motif A region modifications, as well as other modifications to the backbone to improve DNA binding, increase fidelity, improve modified nucleotide incorporation, and deter exonuclease activity. Interestingly, particular combinations of mutations permit differentiation for isomeric reversible terminators.

| Amino Acid FASTA Sequences |
|---|

SG2000 [*Thermococcus* sp. EP1]

SEQ ID NO: 1

MILGADYITKDGKPIVRLFKKENGEFKIELDPHFRPYIYALLRDDSAIEEIMQIKGERHGKTVRIVDAIK
VKKKFLRRPVEVWKLIFEHPQDVPAMRGKIRSHPAVVDIYEYDIPFAKRYLIDKGLIPMEGEEDLKLLAF
DIETFYHEGDEFGKGEIIMISYADDEEAGVITWKRINLPYVHVVSNEREMIKRFVQIIKEKDPDVIITYN
GDNFDLPYIIKRAEKLGVRLLLGRDKEHPEPKIQRMGDSFAVEIKGRIHFDLFPVVRRTINLPTYTLEAV
YETVLGKQKTKLGAEEIAAIWETEEGMKKLAQYSMEDAKATYELGREFFPMEAELAKVIGQSVWDVSRSS
TGNLVEWYMLRVAYERNELAPNKPSDEEYKRRLRSTYLGGYVKEPERGLWGNIVYLDFRSLYPSIIVTHN
VSPDTLEREGCQDYEVAPIVGYRECKDFPGFIPSILENLIETRQEVKKRMKSTTDPVERKMLDYRQRALK
ILANSYYGYQGYPKARWYSKECAESVTAWGRHYIEMSIREIEEKFGEKVLYADTDGFYATLPGETPETIK
KKAKEFLDYINSKLPGLLELEYEGFYLRGFEVIKKRYAVIDEDGRITTRGLEVVRRDWSEIAKETQAKVL
EAILREGSVEKAVEIVKSVVERIAKYKVPLEKLVIHEQITRELKDYKAIGPHVAIAKRLAAKGIKVPGT
IISYIVLKGGGKISDRVVLLTEYDPRKHKYDPDYYIENQVLPAVLRILEAFGYKKEDLKYQRSKQTGLEA
WLRR

9oN-7 Wild Type

SEQ ID NO: 2

MILDTDYITENGKPVIRVFKKENGEFKIEYDRTFEPYFYALLKDDSAIEDVKKVTAKRHGTVVKVKRAEK
VQKKFLGRPIEVWKLYFNHPQDVPAIRDRIRAHPAVVDIYEYDIPFAKRYLIDKGLIPMEGDEELTMLAF
DIETLYHEGEEFGTGPILMISYADGSEARVITWKKIDLPYVDVVSTEKEMIKRFLRVVREKDPDVLITYN
GDNFDFAYLKKRCEELGIKFTLGRDGSEPKIQRMGDRFAVEVKGRIHFDLYPVIRRTINLPTYTLEAVYE
AVFGKPKEKVYAEEIAQAWESGEGLERVARYSMEDAKVTYELGREFFPMEAQLSRLIGQSLWDVSRSSTG
NLVEWELLRKAYKRNELAPNKPDERELARRRGGYAGGYVKEPERGLWDNIVYLDFRSLYPSIIITHNVSP
DTLNREGCKEYDVAPEVGHKECKDFPGFIPSLLGDLLEERQKIKRKMKATVDPLEKKLLDYRQRAIKILA
NSFYGYYGYAKARWYCKECAESVTAWGREYIEMVIRELEEKFGEKVLYADTDGLHATIPGADAETVKKKA
KEFLKYINPKLPGLLELEYEGFYVRGFEVIKKKYAVIDEEGKITTRGLEIVRRDWSEIAKETQARVLEAI
LKHGDVEEAVRIVKEVTEKLSKYEVPPEKLVIHEQITRDLRDYKATGPHVAVAKRLAARGVKIRPGTVIS
YIVLKGSGRIGDRAIPADEFDPTKHRYDAEYYIENQVLPAVERILKAFGYRKEDLRYQKTKQVGLGAWLK
VKGKK

SG3000 [*Pyrobaculum calidifontis*]

SEQ ID NO: 3

MRFWPLDATYSVVGGVPEVRVFGVDGEGRRVVLVDRRFRPYFYAKCDKCDASLAKSYLSRVAPVEAVEVV
ERRFFGRPTIFLKVVAKVPEDVRKLREAALGAPGVVDVYEADIRYYMRYMIDKGVVPCAWNVVEAREAGK
LGPLPLYEVVEWAGVEEGFPPPLRVLAFDIEVYNERGSPDPLRDPVVMLAVKTSDGREEVFEAEGRDDRR
VIRGFVDFVKEFDPDVIVGYNSNGFDWPYLSERAKALGVPLRVDRLGGVPQQSVYGHWSVVGRANVDLYN
IVDEFPEIKVKILDRVAEYEGVMKRSERVLIPGHKVYEYWNDPAKRPTLMRYVLDDVRSTLGLAEKLLPF
LIQLSSVSGLPLDQVAAASVGNRVEWMLLRYAYRMGEVAPNREEREYEPYKGAIVLEPKPGLYSDVLVLD
FSSMYPNIMMKYNLSPDTYLEPHEPDPPEGVVVAPEVGHRFRKAPTGFIPAVLKHLVELRRAVREEAKKY
PPDSPEYRLLDERQRALKVMANAMYGYLGWVGARWYKKEVAESVTAFARAILLDVVEYAKRLGIEVIYGD
TDSLFVKKSGAVDRLVKYVEERHGIEIKVDKDYERVLFTEAKKRYAGLLRDGRIDIVGFEVVRGDWCELA
KEVQLNVVELILKSKSVGEARERVVKYVREVVERLKAYKFDLDDLIIWKTLDKELDEYKAYGPHVHAALE
LKRRGYKVGKGTTVGYVIVRGPGKVSERAMPYIFVDDASKVDVDYYIEKQVIPAALRIAEVLGVKESDLK
TGRVEKSLLDFLG

| Amino Acid FASTA Sequences |
| --- |

SG2100 [*Thermococcus* sp. EP1]
SEQ ID NO: 4

MILGADYITKDGKPIVRLFKKENGEFKIELDPHFRPYIYALLRDDSAIEEIMQIKGERHGKTVRIVDAIK

VKKKFLRRPVEVWKLIFEHPQDVPAMRGKIRSHPAVVDIYEYDIPFAKRYLIDKGLIPMEGEEDLKLLAF

AIATFYHEGDEFGKGEIIMISYADDEEAGVITWKRINLPYVHVVSNEREMIKRFVQIIKEKDPDVIITYN

GDNFDLPYIIKRAEKLGVRLLLGRDKEHPEPKIQRMGDSFAVEIKGRIHFDLFPVVRRTINLPTYTLEAV

YETVLGKQKTKLGAEEIAAIWETEEGMKKLAQYSMEDAKATYELGREFFPMEAELAKVIGQSVWDVSRSS

TGNLVEWYMLRVAYERNELAPNKPSDEEYKRRLRSTYLGGYVKEPERGLWGNIVYLDFRSSAVSIIVTHN

VSPDTLEREGCQDYEVAPIVGYRECKDFPGFIPSILENLIETRQEVKKRMKSTTDPVERKMLDYRQRALK

ILANSYYGYQGYPKARWYSKECAESVTAWGRHYIEMSIREIEEKFGEKVLYADTDGFYATLPGETPETIK

KKAKEFLDYINSKLPGLLELEYEGFYLRGFEVIKKRYAVIDEDGRITTRGLEVVRRDWSEIAKETQAKVL

EAILREGSVEKAVEIVKSVVERIAKYKVPLEKLVIHEQITRELKDYKAIGPHVAIAKRLAAKGIKVKPGT

IISYIVLKGGGKISDRVVLLTEYDPRKHKYDPDYYIENQVLPAVLRILEAFGYKKEDLKYQRSKQTGLEA

WLRR

SG2105 [*Thermococcus* sp. EP1]
SEQ ID NO: 5

MILGADYITKDGKPIVRLFKKENGEFKIELDPHFRPYIYALLRDDSAIEEIMQIKGERHGKTVRIVDAIK

VKKKFLRRPVEVWKLIFEHPQDVPAMRGKIRSHPAVVDIYEYDIPFAKRYLIDKGLIPMEGEEDLKLLAF

AIATFYHEGDEFGKGEIIMISYADDEEAGVITWKRINLPYVHVVSNEREMIKRFVQIIKEKDPDVIITYN

GDNFDLPYIIKRAEKLGVRLLLGRDKEHPEPKIQRMGDSFAVEIKGRIHFDLFPVVRRTINLPTYTLEAV

YETVLGKQKTKLGAEEIAAIWETEEGMKKLAQYSMEDAKATYELGREFFPMEAELAKVIGQSVWDVSRSS

TGNLVEWYMLRVAYERNELAPNKPSDEEYKRRLRSTYLGGYVKEPERGLWGNIVYLDFRSSAVSIIVTHN

VSPDTLEREGCQDYEVAPIVGYRECKDFPGFIPSILENLIETRQEVKKRMKSTTDPVERKMLDYRQRVLK

ILANSYYGYQGYPKARWYSKECAESVTAWGRHYIEMSIREIEEKFGEKVLYADTDGFYATLPGETPETIK

KKAKEFLDYINSKLPGLLELEYEGFYLRGFEVIKKRYAVIDEDGRITTRGLEVVRRDWSEIAKETQAKVL

EAILREGSVEKAVEIVKSVVERIAKYKVPLEKLVIHEQITRELKDYKAIGPHVAIAKRLAAKGIKVKPGT

IISYIVLKGGGKISDRVVLLTEYDPRKHKYDPDYYIENQVLPAVLRILEAFGYKKEDLKYQRSKQTGLEA

WLRR

SG2200 [*Thermococcus* sp. EP1]
SEQ ID NO: 6

MILGADYITKDGKPIVRLFKKENGEFKIELDPHFRPYIYALLRDDSAIEEIMQIKGERHGKTVRIVDAIK

VKKKFLRRPVEVWKLIFEHPQDVPAMRGKIRSHPAVVDIYEYDIPFAKRYLIDKGLIPAEGEEDLKLLAF

AIATFYHEGDEFGKGEIIMISYADDEEAGVITWKRINLPYVHVVSNEREMIKRFVQIIKEKDPDVIITYN

GDNFDLPYIIKRAEKLGVRLLLGRDKEHPEPKIQRMGDSFAVEIKGRIHFDLFPVVRRTINLPTYTLEAV

YETVLGKQKTKLGAEEIAAIWETEEGMKKLAQYSMEDAKATYELGREFFPMEAELAKVIGQSVWDVSRSS

TGNLVEWYMLRVAYERNELAPNKPSDEEYKRRLRSTYLGGYVKEPERGLWGNIVYLDFRSAAISIIVTHN

VSPDTLEREGCQDYEVAPIVGYRECKDFPGFIPSILENLIETRQEVKKRMKSTTDPVERKMLDYRQRVLK

ILANSYYGYQGYPKARWYSKECAESVTAWGRHYIEMSIREIEEKFGEKVLYADTDGFYATLPGETPETIK

KKAKEFLDYINSKLPGLLELEYEGFYLRGFEVIKKRYAVIDEDGRITTRGLEVVRRDWSEIAKETQAKVL

| Amino Acid FASTA Sequences |
| --- |

EAILREGSVEKAVEIVKSVVERIAKYKVPLEKLVIHEQITRELKDYKAIGPHVAIAKRLAAKGIKVKPGT

IISYIVLKGGGKISDRVVLLTEYDPRKHKYDPDYYIENQVLPAVLRILEAFGYKKEDLKYQRSKQTGLEA

WLRR

*Thermococcus* 9N7 variant (D141A, E143A, A485L)
SEQ ID NO: 7

MILDTDYITENGKPVIRVFKKENGEFKIEYDRTFEPYFYALLKDDSAIEDVKKVTAKRHGTVVKVKRAEK

VQKKFLGRPIEVWKLYFNHPQDVPAIRDRIRAHPAVVDIYEYDIPFAKRYLIDKGLIPMEGDEELTMLAF

AIATLYHEGEEFGTGPILMISYADGSEARVITWKKIDLPYVDVVSTEKEMIKRFLRVVREKDPDVLITYN

GDNFDFAYLKKRCEELGIKFTLGRDGSEPKIQRMGDRFAVEVKGRIHFDLYPVIRRTINLPTYTLEAVYE

AVFGKPKEKVYAEEIAQAWESGEGLERVARYSMEDAKVTYELGREFFPMEAQLSRLIGQSLWDVSRSSTG

NLVEWELLRKAYKRNELAPNKPDERELARRRGGYAGGYVKEPERGLWDNIVYLDERSLYPSIIITHNVSP

DTLNREGCKEYDVAPEVGHKECKDFPGFIPSLLGDLLEERQKIKRKMKATVDPLEKKLLDYRQRLIKILA

NSFYGYYGYAKARWYCKECAESVTAWGREYIEMVIRELEEKFGEKVLYADTDGLHATIPGADAETVKKKA

KEFLKYINPKLPGLLELEYEGFYVRGFFVTKKKYAVIDEEGKITTRGLEIVRRDWSEIAKETQARVLEAI

LKHGDVEEAVRIVKEVTEKLSKYEVPPEKLVIHEQITRDLRDYKATGPHVAVAKRLAARGVKIRPGTVIS

YIVLKGSGRIGDRAIPADEFDPTKHRYDAEYYIENQVLPAVERILKAFGYRKEDLRYQKTKQVGLGAWLK

VKGKK

SG92 *Thermococcus* 9N7 variant
SEQ ID NO: 8

MILDTDYITENGKPVIRVFKKENGEFKIEYDRTFEPYFYALLKDDSAIEDVKKVTAKRHGTVVKVKRAEK

VQKKFLGRPIEVWKLYFNHPQDVPAIRDRIRAHPAVVDIYEYDIPFAKRYLIDKGLIPMEGDEELTMLAF

AIATLYHEGEEFGTGPILMISYADGSEARVITWKKIDLPYVDVVSTEKEMIKRFLRVVREKDPDVLITYN

GDNFDFAYLKKRCEELGIKFTLGRDGSEPKIQRMGDRFAVEVKGRIHFDLYPVIRRTINLPTYTLEAVYE

AVFGKPKEKVYAEEIAQAWESGEGLERVARYSMEDAKVTYELGREFFPMEAQLSRLIGQSLWDVSRSSTG

NLVEWFLLRKAYKRNELAPNKPDERELARRRGGYAGGYVKEPERGLWDNIVYLDFRSLVPSIIITHNVSP

DTLNREGCKEYDVAPEVGHKFCKDFPGFIPSLLGDLLEERQKIKRKMKATVDPLEKKLLDYRQRLIKILA

NSFYGYYGYAKARWYCKECAESVTAWGREYIEMVIRELEEKFGFKVLYADTDGLHATIPGADAETVKKKA

KEFLKYINPKLPGLLELEYEGFYVRGFFVTKKKYAVIDEEGKITTRGLEIVRRDWSEIAKETQARVLEAI

LKHGDVEEAVRIVKEVTEKLSKYEVPPEKLVIHEQITRDLRDYKATGPHVAVAKRLAARGVKIRPGTVIS

YIVLKGSGRIGDRAIPADEFDPTKHRYDAEYYIENQVLPAVERILKAFGYRKEDLRYQKTKQVGLGAWLK

VKGKK

SG100 *Thermococcus* 9N7 variant
SEQ ID NO: 9

MILDTDYITENGKPVIRVFKKENGEFKIEYDRTFEPYFYALLKDDSAIEDVKKVTAKRHGTVVKVKRAEK

VQKKFLGRPIEVWKLYFNHPQDVPAIRDRIRAHPAVVDIYEYDIPFAKRYLIDKGLIPMEGDEELTMLAF

AIATLYHEGEEFGTGPILMISYADGSEARVITWKKIDLPYVDVVSTEKEMIKRFLRVVREKDPDVLITYN

GDNFDFAYLKKRCEELGIKFTLGRDGSEPKIQRMGDRFAVEVKGRIHFDLYPVIRRTINLPTYTLEAVYE

AVFGKPKEKVYAEEIAQAWESGEGLERVARYSMEDAKVTYELGREFFPMEAQLSRLIGQSLWDVSRSSTG

NLVEWELLRKAYKRNELAPNKPDERELARRRGGYAGGYVKEPERGLWDNIVYLDFRSSAVSIIITHNVSP

DTLNREGCKEYDVAPEVGHKFCKDFPGFIPSLLGDLLEERQKIKRKMKATVDPLEKKLLDYRQRAIKILA

NSFYGYYGYAKARWYCKECAESVTAWGREYIEMVIRELEEKFGFKVLYADTDGLHATIPGADAETVKKKA

| Amino Acid FASTA Sequences |
|---|

KEFLKYINPKLPGLLELEYEGFYVRGFFVTKKKYAVIDEEGKITTRGLEIVRRDWSEIAKETQARVLEAI

LKHGDVEEAVRIVKEVTEKLSKYEVPPEKLVIHEQITRDLRDYKATGPHVAVAKRLAARGVKIRPGTVIS

YIVLKGSGRIGDRAIPADEFDPTKHRYDAEYYIENQVLPAVERILKAFGYRKEDLRYQKTKQVGLGAWLK

VKGKK

SG200 sequence Pol812

SEQ ID NO: 10

MILDTDYITENGKPVIRVFKKENGEFKIEYDRTFEPYFYALLKDDSAIEDVKKVTAKRHGTVVKVKRAEK

VQKKFLGRPIEVWKLYFNHPQDVPAIRDRIRAHPAVVDIYEYDIPFAKRYLIDKGLIPAEGDEELTMLAF

AIATLYHEGEEFGTGPILMISYADGSEARVITWKKIDLPYVDVVSTEKEMIKRFLRVVREKDPDVLITYN

GDNFDFAYLKKRSEELGIKFTLGRDGSEPKIQRMGDRFAVEVKGRIHFDLYPVIRRTINLPTYTLEAVYE

AVFGKPKEKVYAEEIAQAWESGEGLERVARYSMEDAKVTYELGREFFPMEAQLSRLIGQSLWDVSRSSTG

NLVEWFLLRKAYKRNELAPNKPDERELARRRGGYAGGYVKEPERGLWDNIVYLDFRSAAISIIITHNVSP

DTLNREGCKEYDVAPEVGHKFCKDFPGFIPSLLGDLLEERQKIKRKMKATVDPLEKKLLDYRQRVIKILA

NSFYGYYGYAKARWYCKECAESVTAWGREYIEMVIRELEEKFGFKVLYADTDGLHATIPGADAETVKKKA

KEFLKYINPKLPGLLELEYEGFYVRGFFVTKKKYAVIDEEGKITTRGLEIVRRDWSEIAKETQARVLEAI

LKHGDVEEAVRIVKEVTEKLSKYEVPPEKLVIHEQITRDLRDYKATGPHVAVAKRLAARGVKIRPGTVIS

YIVLKGSGRIGDRAIPADEFDPTKHRYDAEYYIENQVLPAVERILKAFGYRKEDLRYQKTKQVGLGAWLK

VKGKK

SEQ ID NO: 16

ATGATTCTGGGCGCCGACTATATCACCAAAGACGGTAAACCGATTGTTCGTCTGTTCAAAAAAGAAATGGTGAGT

TCAAGATCGAGCTGGACCCGCATTTCCGTCCGTACATTTACGCACTCTTGCGTGACGACAGCGCGATTGAAGAAAT

CATGCAGATCAAAGGTGAACGCCATGGCAAGACTGTCCGCATTGTCGATGCGATCAAGGTCAAGAAAAAGTTCCTG

CGTCGCCCTGTCGAAGTGTGGAAGCTGATTTTCGAGCACCCGCAAGACGTCCCGGCAATGCGTGGCAAGATTCGCA

GCCATCCGGCTGTGGTCGATATTTACGAGTACGACATCCCGTTCGCAAAGCGCTACCTGATTGACAAGGGCCTGAT

CCCGATGGAGGGTGAAGAAGATCTGAAGCTGTTAGCCTTTGACATCGAAACGTTCTATCACGAGGGCGATGAATTT

GGTAAAGGTGAGATTATCATGATTAGCTACGCGGACGACGAAGAGGCCGGTGTGATCACCTGGAAGCGCATCAATC

TGCCGTATGTTCATGTTGTGTCGAATGAACGCGAGATGATTAAGCGTTTCGTGCAAATCATCAAAGAAAAAGACCC

GGACGTTATCATTACCTACAATGGTGATAACTTTGATTTGCCGTACATCATTAAGCGCGCAGAAAAACTGGGTGTC

CGTCTGCTGCTGGGTCGCGACAAGAACACCCGGAGCCTAAGATCCAGCGTATGGGTGATAGCTTCGCGGTGGAAA

TTAAGGGTCGTATCCACTTTGATCTGTTCCCGGTCGTTCGCCGCACCATCAATCTGCCGACGTACACCCTGGAAGC

GGTTTACGAGACTGTGTTGGGTAAGCAAAAAACTAAACTGGGCGCTGAAGAAATCGCCGCCATTTGGGAAACCGAA

GAGGGCATGAAGAAACTGGCGCAATATAGCATGGAAGATGCGAAGGCTACCTATGAACTGGGTCGTGAGTTCTTCC

CGATGGAAGCTGAGCTGGCAAAGGTTATTGGTCAGAGCGTCTGGGACGTTTCTCGTTCTAGCACCGGCAACCTGGT

CGAGTGGTACATGCTGCGTGTGGCGTATGAGCGTAACGAACTGGCACCGAATAAGCCGAGCGACGAAGAGTACAAA

CGTCGTCTGCGCTCCACTTACTTGGGCGGCTACGTAAAAGAACCGGAGCGCGGTCTGTGGGTAACATTGTGTATC

TGGACTTTCGTAGCTTGTATCCAAGCATTATCGTGACGCACAACGTTAGCCCGGATACGTTGGAGCGCGAGGGCTG

CCAGGACTACGAGGTTGCCCCAATTGTGGGTTACCGCTTCTGCAAAGATTTTCCAGGTTTCATCCCTTCGATTCTG

GAGAATCTGATCGAAACCCGTCAAGAGGTTAAGAAACGCATGAAAAGCACCACGGATCCGGTCGAACGTAAAATGC

TGGACTATCGTCAGCGTGCGCTGAAAATCTTGGCTAATTCCTATTATGGTTACCAGGGCTACCCGAAAGCTCGTTG

GTATAGCAAAGAGTGTGCTGAGTCCGTGACGGCGTGGGGCCGTCACTACATTGAGATGAGCATTCGTGAGATTGAA

| Amino Acid FASTA Sequences |
| --- |
| GAGAAATTTGGTTTCAAGGTTCTGTATGCCGACACCGATGGTTTTTATGCGACCCTGCCGGGTGAAACGCCGGAAA |
| CGATTAAGAAAAAAGCAAAAGAATTTCTGGACTATATCAACTCCAAGTTACCGGGTCTGCTTGAGCTGGAGTATGA |
| GGGCTTTTACTTGCGTGGTTTCTTTGTCACCAAAAAAACGCTACGCAGTGATCGATGAAGATGGTCGTATTACCACC |
| CGCGGCCTGGAAGTCGTTCGTCGTGACTGGAGCGAAATCGCAAAAGAAACCCAAGCAAAGTCCTGGAAGCGATCC |
| TGCGTGAGGGCTCCGTTGAGAAAGCCGTGGAAATCGTTAAGAGCGTGGTCGAGCGCATTGCGAAGTATAAAGTTCC |
| ACTGGAGAAATTGGTCATTCACGAGCAAATTACGCGCGAACTGAAAGATTACAAGGCAATCGGTCCACATGTTGCG |
| ATCGCGAAGCGTCTGGCAGCCAAAGGTATCAAGGTTAAACCGGGTACCATTATCTCATATATTGTGCTGAAAGGCG |
| GCGGCAAGATCAGCGATCGTGTGGTTCTGCTGACCGAGTATGATCCGCGTAAGCACAAATACGATCCGGATTACTA |
| TATCGAGAATCAAGTGCTGCCGGCCGTTTTGAGAATTCTGGAAGCATTTGGCTACAAAAAAGAGGACCTGAAATAC |
| CAGCGTAGCAAGCAAACCGGCTTGGAAGCTTGGCTGCGTCGCTAATGA |

SEQ ID NO: 17

| |
| --- |
| CCCGTAGAAAAGATCAAAGGATCTTCTTGAGATCCTTTTTTTCTGCGCGTAATCTGCTGCTTGCAAACAAAAA |
| AACCACCGCTACCAGCGGTGGTTTGTTTGCCGGATCAAGAGCTACCAACTCTTTTTCCGAAGGTAACTGGCTT |
| CAGCAGAGCGCAGATACCAAATACTGTTCTTCTAGTGTAGCCGTAGTTAGCCCACCACTTCAAGAACTCTGTA |
| GCACCGCCTACATACCTCGCTCTGCTAATCCTGTTACCAGTGGCTGCTGCCAGTGGCGATAAGTCGTGTCTTA |
| CCGGGTTGGACTCAAGACGATAGTTACCGGATAAGGCGCAGCGGTCGGGCTGAACGGGGGGTTCGTGCACACA |
| GCCCAGCTTGGAGCGAACGACCTACACCGAACTGAGATACCTACAGCGTGAGCTATGAGAAAGCGCCACGCTT |
| CCCGAAGGGAGAAAGGCGGACAGGTATCCGGTAAGCGGCAGGGTCGGAACAGGAGAGCGCACGAGGGGAGCTTC |
| CAGGGGGAAACGCCTGGTATCTTTATAGTCCTGTCGGGTTTCGCCACCTCTGACTTGAGCGTCGATTTTTGTG |
| ATGCTCGTCAGGGGGGCGGAGCCTATGGAAAAACGCCAGCAACGCGGCCTTTTTACGGTTCCTGGCCTTTTGC |
| TGGCCTTTTGCTCACATGTTCTTTCCTGCGTTATCCCCTGATTCTGTGGATAACCGTATTACCGCCTTTGAGT |
| GAGCTGATACCGCTCGCCGCAGCCGAACGACCGAGCGCAGCGAGTCAGTGAGCGAGGAAGCGGAAGGCGAGAG |
| TAGGGAACTGCCAGGCATCAAACTAAGCAGAAGGCCCCTGACGGATGGCCTTTTTGCGTTTCTACAAACTCTT |
| TCTGTGTTGTAAAACGACGGCCAGTCTTAAGCTCGGGCCCCCTGGGCGGTTCTGATAACGAGTAATCGTTAAT |
| CCGCAAATAACGTAAAAACCCGCTTCGGCGGGTTTTTTTATGGGGGGAGTTTAGGGAAAGAGCATTTGTCAGA |
| ATATTTAAGGGCGCCTGTCACTTTGCTTGATATATGAGAATTATTTAACCTTATAAATGAGAAAAAAGCAACG |
| CACTTTAAATAAGATACGTTGCTTTTTCGATTGATGAACACCTATAATTAAACTATTCATCTATTATTTATGA |
| TTTTTTGTATATACAATATTTCTAGTTTGTTAAAGAGAATTAAGAAAATAAATCTCGAAAATAATAAAGGGAA |
| AATCAGTTTTTGATATCAAAATTATACATGTCAACGATAATACAAATATAATACAAACTATAAGATGTTATC |
| AGTATTTATTATGCATTTAGAATAAATTTTGTGTCGCCCTTCCGCGAAATTAATACGACTCACTATAGGGAA |
| TTGTGAGCGGATAACAATTCCCCTCTAGAAATAATTTTGTTTAACTTTTGAGACCTTAAGGAGGTAAAAAT |
| GATTCTGGGCGCCGACTATATCACCAAAGACGGTAAACCGATTGTTCGTCTGTTCAAAAAAGAAATGGTGAG |
| TTCAAGATCGAGCTGGACCCGCATTTCCGTCCGTACATTTACGCACTCTTGCGTGACGACAGCGCGATTGAAG |
| AAATCATGCAGATCAAAGGTGAACGCCATGGCAAGACTGTCCGCATTGTCGATGCGATCAAGGTCAAGAAAA |
| GTTCCTGCGTCGCCCTGTCGAAGTGTGGAAGCTGATTTTCGAGCACCCGCAAGACGTCCCGGCAATGCGTGGC |
| AAGATTCGCAGCCATCCGGCTGTGGTCGATATTTACGAGTACGACATCCCGTTCGCAAAGCGCTACCTGATTG |
| ACAAGGGCCTGATCCCGATGGAGGGTGAAGAAGATCTGAAGCTGTTAGCCTTTGACATCGAAACGTTCTATCA |
| CGAGGGCGATGAATTTGGTAAAGGTGAGATTATCATGATTAGCTACGCGGACGACGAAGAGGCCGGTGTGATC |
| ACCTGGAAGCGCATCAATCTGCCGTATGTTCATGTTGTGTCGAATGAACGCGAGATGATTAAGCGTTTCGTGC |

| Amino Acid FASTA Sequences |
|---|
| AAATCATCAAAGAAAAAGACCCGGACGTTATCATTACCTACAATGGTGATAACTTTGATTTGCCGTACATCAT |
| TAAGCGCGCAGAAAAACTGGGTGTCCGTCTGCTGCTGGGTCGCGACAAAGAACACCCGGAGCCTAAGATCCAG |
| CGTATGGGTGATAGCTTCGCGGTGGAAATTAAGGGTCGTATCCACTTTGATCTGTTCCCGGTCGTTCGCCGCA |
| CCATCAATCTGCCGACGTACACCCTGGAAGCGGTTTACGAGACTGTGTTGGGTAAGCAAAAAACTAAACTGGG |
| CGCTGAAGAAATCGCCGCCATTTGGGAAACCGAAGAGGGCATGAAGAAACTGGCGCAATATAGCATGGAAGAT |
| GCGAAGGCTACCTATGAACTGGGTCGTGAGTTCTTCCCGATGGAAGCTGAGCTGGCAAAGGTTATTGGTCAGA |
| GCGTCTGGGACGTTTCTCGTTCTAGCACCGGCAACCTGGTCGAGTGGTACATGCTGCGTGTGGCGTATGAGCG |
| TAACGAACTGGCACCGAATAAGCCGAGCGACGAAGAGTACAAACGTCGTCTGCGCTCCACTTACTTGGGCGGC |
| TACGTAAAAGAACCGGAGCGCGGTCTGTGGGGTAACATTGTGTATCTGGACTTTCGTAGCTTGTATCCAAGCA |
| TTATCGTGACGCACAACGTTAGCCCGGATACGTTGGAGCGCGAGGGCTGCCAGGACTACGAGGTTGCCCCAAT |
| TGTGGGTTACCGCTTCTGCAAAGATTTTCCAGGTTTCATCCCTTCGATTCTGGAGAATCTGATCGAAACCCGT |
| CAAGAGGTTAAGAAACGCATGAAAAGCACCACGGATCCGGTCGAACGTAAAATGCTGGACTATCGTCAGCGTG |
| CGCTGAAAATCTTGGCTAATTCCTATTATGGTTACCAGGGCTACCCGAAAGCTCGTTGGTATAGCAAAGAGTG |
| TGCTGAGTCCGTGACGGCGTGGGGCCGTCACTACATTGAGATGAGCATTCGTGAGATTGAAGAGAAATTTGGT |
| TTCAAGGTTCTGTATGCCGACACCGATGGTTTTTATGCGACCCTGCCGGGTGAAACGCCGGAAACGATTAAGA |
| AAAAAGCAAAAGAATTTCTGGACTATATCAACTCCAAGTTACCGGGTCTGCTTGAGCTGGAGTATGAGGGCTT |
| TTACTTGCGTGGTTTCTTTGTCACCAAAAAACGCTACGCAGTGATCGATGAAGATGGTCGTATTACCACCCGC |
| GGCCTGGAAGTCGTTCGTCGTGACTGGAGCGAAATCGCAAAAGAAACCCAAGCAAAAGTCCTGGAAGCGATCC |
| TGCGTGAGGGCTCCGTTGAGAAAGCCGTGGAAATCGTTAAGAGCGTGGTCGAGCGCATTGCGAAGTATAAAGT |
| TCCACTGGAGAAATTGGTCATTCACGAGCAAATTACGCGCGAACTGAAAGATTACAAGGCAATCGGTCCACAT |
| GTTGCGATCGCGAAGCGTCTGGCAGCCAAAGGTATCAAGGTTAAACCGGGTACCATTATCTCATATATTGTGC |
| TGAAAGGCGGCGGCAAGATCAGCGATCGTGTGGTTCTGCTGACCGAGTATGATCCGCGTAAGCACAAATACGA |
| TCCGGATTACTATATCGAGAATCAAGTGCTGCCGGCCGTTTTGAGAATTCTGGAAGCATTTGGCTACAAAAAA |
| GAGGACCTGAAATACCAGCGTAGCAAGCAAACCGGCTTGGAAGCTTGGCTGCGTCGCTAATGAGGTTGAGGTC |
| TCACCCCCTAGCATAACCCCTTGGGGCCTCTAAACGGGTCTTGAGGGGTTTTTGCCCCTGAGACGCGTCAAT |
| CGAGTTCGTACCTAAGGGCGACACCCCCTAATTAGCCCGGGCGAAAGGCCCAGTCTTTCGACTGAGCCTTTCG |
| TTTTATTTGATGCCTGGCAGTTCCCTACTCTCGCATGGGGAGTCCCCACACTACCATCGGCGCTACGGCGTTT |
| CACTTCTGAGTTCGGCATGGGGTCAGGTGGGACCACCGCGCTACTGCCGCCAGGCAAACAAGGGGTGTTATGA |
| GCCATATTCAGGTATAAATGGGCTCGCGATAATGTTCAGAATTGGTTAATTGGTTGTAACACTGACCCCTATT |
| TGTTTATTTTTCTAAATACATTCAAATATGTATCCGCTCATGAGACAATAACCCTGATAAATGCTTCAATAAT |
| ATTGAAAAGGAAGAATATGAGCCATATTCAACGGGAAACGTCGAGGCCGCGATTAAATTCCAACATGGATGC |
| TGATTTATATGGGTATAAATGGGCTCGCGATAATGTCGGGCAATCAGGTGCGACAATCTATCGCTTGTATGGG |
| AAGCCCGATGCGCCAGAGTTGTTTCTGAAACATGGCAAAGGTAGCGTTGCCAATGATGTTACAGATGAGATGG |
| TCAGACTAAACTGGCTGACGGAATTTATGCCACTTCCGACCATCAAGCATTTTATCCGTACTCCTGATGATGC |
| ATGGTTACTCACCACTGCGATCCCCGGAAAAACAGCGTTCCAGGTATTAGAAGAATATCCTGATTCAGGTGAA |
| AATATTGTTGATGCGCTGGCAGTGTTCCTGCGCCGGTTGCACTCGATTCCTGTTTGTAATTGTCCTTTTAACA |
| GCGATCGCGTATTTCGCCTCGCTCAGGCGCAATCACGAATGAATAACGGTTTGGTTGATGCGAGTGATTTTGA |
| TGACGAGCGTAATGGCTGGCCTGTTGAACAAGTCTGGAAAGAAATGCATAAACTTTTGCCATTCTCACCGGAT |
| TCAGTCGTCACTCATGGTGATTTCTCACTTGATAACCTTATTTTTGACGAGGGGAAATTAATAGGTTGTATTG |

-continued

Amino Acid FASTA Sequences

```
ATGTTGGACGAGTCGGAATCGCAGACCGATACCAGGATCTTGCCATCCTATGGAACTGCCTCGGTGAGTTTTC

TCCTTCATTACAGAAACGGCTTTTTCAAAAATATGGTATTGATAATCCTGATATGAATAAATTGCAGTTTCAT

TTGATGCTCGATGAGTTTTTCTAAGCGGCGCGCCATCGAATGGCGCAAAACCTTTCGCGGTATGGCATGATAG

CGCCCGGAAGAGAGTCAATTCAGGGTGGTGAATATGAAACCAGTAACGTTATACGATGTCGCAGAGTATGCCG

GTGTCTCTTATCAGACCGTTTCCCGCGTGGTGAACCAGGCCAGCCACGTTTCTGCGAAAACGCGGGAAAAAGT

GGAAGCGGCGATGGCGGAGCTGAATTACATTCCCAACCGCGTGGCACAACAACTGGCGGGCAAACAGTCGTTG

CTGATTGGCGTTGCCACCTCCAGTCTGGCCCTGCACGCGCCGTCGCAAATTGTCGCGGCGATTAAATCTCGCG

CCGATCAACTGGGTGCCAGCGTGGTGGTGTCGATGGTAGAACGAAGCGGCGTCGAAGCCTGTAAAGCGGCGGT

GCACAATCTTCTCGCGCAACGCGTCAGTGGGCTGATCATTAACTATCCGCTGGATGACCAGGATGCCATTGCT

GTGGAAGCTGCCTGCACTAATGTTCCGGCGTTATTTCTTGATGTCTCTGACCAGACACCCATCAACAGTATTA

TTTTCTCCCATGAGGACGGTACGCGACTGGGCGTGGAGCATCTGGTCGCATTGGGTCACCAGCAAATCGCGCT

GTTAGCGGGCCCATTAAGTTCTGTCTCGGCGCGTCTGCGTCTGGCTGGCTGGCATAAATATCTCACTCGCAAT

CAAATTCAGCCGATAGCGGAACGGGAAGGCGACTGGAGTGCCATGTCCGGTTTTCAACAAACCATGCAAATGC

TGAATGAGGGCATCGTTCCCACTGCGATGCTGGTTGCCAACGATCAGATGGCGCTGGGCGCAATGCGCGCCAT

TACCGAGTCCGGGCTGCGCGTTGGTGCGGATATCTCGGTAGTGGGATACGACGATACCGAAGATAGCTCATGT

TATATCCCGCCGTTAACCACCATCAAACAGGATTTTCGCCTGCTGGGGCAAACCAGCGTGGACCGCTTGCTGC

ACTCTCTCAGGGCCAGGCGGTGAAGGGCAATCAGCTGTTGCCAGTCTCACTGGTGAAAAGAAAAACCACCCT

GGCGCCCAATACGCAAACCGCCTCTCCCCGCGCGTTGGCCGATTCATTAATGCAGCTGGCACGACAGGTTTCC

CGACTGGAAAGCGGGCAGTGACTCATGACCAAAATCCCTTAACGTGAGTTACGCGCGCGTCGTTCCACTGAGC

GTCAGAC
```

SG2210

SEQ ID NO: 18

```
MILGADYITKDGKPIVRLFKKENGEFKIELDPHFRPYIYALLRDDSAIEEIMQIKGERHGKTVRIVDAIKVKK

KFLRRPVEVWKLIFEHPQDVPAMRGKIRSHPAVVDIYEYDIPFAKRYLIDKGLIPAEGEEDLKLLAFAIATFY

HEGDEFGKGEIIMISYADDEEAGVITWKRINLPYVHVVSNEREMIKRFVQIIKEKDPDVIITYNGDNFDLPYI

IKRAEKLGVRLLLGRDKEHPEPKIQRMGDSFAVEIKGRIHFDLFPVVRRTINLPTYTLEAVYETVLGKQKTKL

GAEEIAAIWETEEGMKKLAQYSMEDAKATYELGREFFPMEAELAKVIGQSVWDVSRSSTGNLVEWYMLRVAYE

RNELAPNKPSDEEYKRRLRSTYLGGYVKEPERGLWGNIVYLDFRSAGPSIIVTHNVSPDTLEREGCQDYEVAP

IVGYRFCKDFPGFIPSILENLIETRQEVKKRMKSTTDPVERKMLDYRQRVLKILANSYYGYQGYPKARWYSKE

CAESVTAWGRHYIEMSIREIEEKFGFKVLYADTDGFYATLPGETPETIKKKAKEFLDYINSKLPGLLELEYEG

FYLRGFFVTKKRYAVIDEDGRITTRGLEVVRRDWSEIAKETQAKVLEAILREGSVEKAVEIVKSVVERIAKYK

VPLEKLVIHEQITRELKDYKAIGPHVAIAKRLAAKGIKVKPGTIISYIVLKGGGKISDRVVLLTEYDPRKHKY

DPDYYIENQVLPAVLRILEAFGYKKEDLKYQRSKQTGLEAWLRR
```

REFERENCES

1. Carl W. Fuller. November 2011. *Nature BioTechnology.*
2. Stanley Tabor and Charles C. Richardson, April 1989. *Journal of Biological Chemistry.*
3. Steven J. Evans and Mark J. Fogg et al., 2000. *Oxford University Press.*
4. Andrew F. Gardner and William E. Jack, 1997. *Nucleic Acids Research.* Vol. 27 No. 3
5. Diana C. Knapp et al., 2011. *Chem. Eur. J.* 17.
6. Michael L. Metzker et al., Jul. 25, 1994. *Oxford University Press.*
7. Bruno Canard and Robert S. Sarfati, 1994. Elsevier Science B.V.
8. Bruno Canard, Bruno Cardona, and Robert S. Sarfati, November 1995. *Proc. Natl. Acad. Sci. USA.*
9. Mike B. Welch and Kevin Burgess, 1999. *Nucleosides & Nucleotides.*
10. Mike B. Welch and Carlos I. Martinez et al., 1999. *Chem, Eur. J.* No. 3.

11. Jingyue Ju and Dae Hyun Kim et al., Oct. 26, 2006. Columbia Genome Center.
12. Taek-Soo Kim and Da-Rae Kim et al., 2010. *Chem Bio Chem* Volume 11.
13. Jia Guo and Ning Xu et al., Apr. 28, 2008. Columbia Genome Center.
    a. Published Application [Ju et al.] U.S. Pat. No. 6,664,079. Dec. 16, 2003.
    b. Supporting Information [Guo et al.]. *PNAS*.
14. Jia Guo and Lin Yu et al., Apr. 20, 2010. NIH-PA.
15. Bentley et al. *NATURE*. Volume 456. 6 Nov. 2008.
    a. Supplement to Bentley et al. *NATURE*. Volume 456. 6 Nov. 2008.
16. [Milton et al.] U.S. Pat. No. 7,541,444B2. Jun. 6, 2009.
17. Fei Chen and Eric A. Gaucher, Dec. 1, 2009. *PANS*.
18. Foldesi and Keller, 2007. *Nucleosides, Nucleotides, and Nucleic Acids*, Volume 26.
19. [Kwiatowski] U.S. Pat. No. 6,255,475B1. Jul. 3, 2001.
20. Jian Wu and Shenglong Zhang, Aug. 10, 2007. *PNAS*.
21. Hameer Ruparel and Lanrong Bi, Mar. 10, 2005. *PNAS*.
22. Jonathan Filee et al., 27 Nov. 2001. *Journal of Molecular Evolution*.
23. Diana C. Knapp et al., 2011. *Chem. Eur. J.*
24. Georges N. Cohen et al., 2003. *Molecular Microbiology*, Volume 47.
25. Yannick Gueguen et al., 2001. *Eur. J Biochem.*
26. Sonoko Ishino and Yoshizumi Ishino, 29 Aug. 2014. *Frontiers in Microbiology*.
27. Jack et al. Patent US2006/0199214-A1. Sep. 7, 2006.
28. Perler et al. U.S. Pat. No. 5,756,334. May 26, 1998.
29. Allen Horhota et al., Nov. 29, 2004. *JACS Articles*.
30. Andrew F. Gardner and William E. Jack, Oct. 31, 2001. Oxford University Press.
31. Jacques Dietrich et al., 22 Oct. 2002. *FEMS Microbiology Letters*.
32. Nikiforov TT. et al. *Anal Biochem.* 2014 Sep. 15; 461:67-73
33. Nikiforov TT. et al. *Anal Biochem.* 2011 May 15; 412(2):229-36.

P-EMBODIMENTS

Embodiment P1. A polymerase comprising an amino acid sequence that is at least 80% identical to a continuous 500 amino acid sequence within SEQ ID NO: 1, wherein the exonuclease activity of the polymerase is reduced at least 80% relative to the exonuclease activity of a polymerase of SEQ ID NO: 1.

Embodiment P2. The polymerase of Embodiment P1 wherein the polymerase comprises an amino acid sequence that is at least 95% identical to a continuous 500 amino acid sequence within SEQ ID NO: 1.

Embodiment P3. The polymerase of Embodiment P1 wherein the polymerase comprises an amino acid sequence that is at least 80% identical to a continuous 700 amino acid sequence within SEQ ID NO: 1.

Embodiment P4. The polymerase of Embodiment P3, wherein the polymerase comprises an amino acid sequence that is at least 95% identical to a continuous 700 amino acid sequence within SEQ ID NO: 1.

Embodiment P5. The polymerase of one of Embodiment P1 to Embodiment P4, wherein the reduction in exonuclease activity of the polymerase results from one or more amino acid mutations in SEQ ID NO: 1.

Embodiment P6. The polymerase of one of Embodiment P1 to Embodiment P5, wherein the polymerase comprises an amino acid substitution mutation between position 129 and 318 of SEQ ID NO: 1, inclusive of position endpoints.

Embodiment P7. The polymerase of one of Embodiment P1 to Embodiment P6, wherein the polymerase comprises an amino acid substitution mutation at position 129, 141, 143, 144, 209, 210, 213, 214, 215, 276, 277, 313 and/or 317 of SEQ ID NO: 1.

Embodiment P8. The polymerase of one of Embodiment P1 to Embodiment P7, wherein the polymerase comprises an alanine substitution mutation at position 141 and/or 143 of SEQ ID NO: 1.

Embodiment P9. The polymerase of one of Embodiment P1 to Embodiment P8, wherein the polymerase activity of the polymerase is altered relative to the polymerase activity of a polymerase of SEQ ID NO: 1.

Embodiment P10. The polymerase of Embodiment P9, wherein the altered polymerase activity of the polymerase results from one or more amino acid mutations in SEQ ID NO: 1, and wherein the altered polymerase activity is the capability of incorporating modified nucleotides during nucleic acid synthesis.

Embodiment P11. The polymerase of one of Embodiment P1 to Embodiment P10, wherein the polymerase comprises an amino acid substitution mutation after position 393 of SEQ ID NO: 1, inclusive of position endpoints.

Embodiment P12. The polymerase of one of Embodiment P1 to Embodiment P11, where the polymerase comprises an amino acid substitution mutation at position 408, 411, 412, 413, 414, 487, 489, 491, 495, 498, 499, 500, 543, 545, and/or 546 of SEQ ID NO: 1.

Embodiment P13. The polymerase of one of Embodiment P1 to Embodiment P12, wherein the polymerase comprises substitution mutations at position 129, 141, 143, 411, 412, 413, and/or 488 of SEQ ID NO: 1.

Embodiment P14. The polymerase of Embodiment 13 wherein the amino acid substitution mutation at position 129 is an alanine substitution, a glycine substitution, a valine substitution, a leucine substitution, or an isoleucine substitution; the amino acid substitution mutation at position 141 is an alanine substitution, a glycine substitution, a valine substitution, a methionine substitution, a leucine substitution, or an isoleucine substitution; the amino acid substitution mutation at position 143 is an alanine substitution, a glycine substitution, a valine substitution, a methionine substitution, a leucine substitution, or an isoleucine substitution; the amino acid substitution at position 411 is a serine substitution, a threonine substitution, an asparagine substitution, a glutamine substitution, alanine substitution, a glycine substitution, a valine substitution, a methionine substitution, a leucine substitution, or an isoleucine substitution; the amino acid substitution at position 412 is an alanine substitution, a glycine substitution, a valine substitution, a methionine substitution, a leucine substitution, or an isoleucine substitution; the amino acid substitution at position 413 is an alanine substitution, a glycine substitution, an isoleucine substitution, a leucine substitution, a methionine substitution, or a valine substitution; the amino acid substitution at position 488 an alanine substitution, a glycine substitution, an isoleucine substitution, a leucine substitution, a methionine substitution, or a valine substitution.

Embodiment P15. The polymerase of one of Embodiment P1 to Embodiment P14, wherein the amino acid substitution mutation is an alanine at position 129, an alanine at position 141, an alanine at position 143, a serine at position 411, alanine at position 411, an alanine at position 412, a valine at position 413, an isoleucine at position 413, and/or a valine at position 488.

Embodiment P16. The polymerase of one of Embodiment P1 to Embodiment P15, wherein the polymerase comprises an alanine at position 141, an alanine at position 143, serine at position 411, an alanine at position 412, and a valine at position 413.

Embodiment P17. The polymerase of one of Embodiment P1 to Embodiment P16, wherein the polymerase comprises an alanine at position 141, an alanine at position 143, a serine at position 411, an alanine at position 412, a valine at position 413 and a valine at position 489.

Embodiment P18. The polymerase of one of Embodiment P1 to Embodiment P17, wherein the polymerase comprises an alanine at position 129, an alanine at position 141, an alanine at position 143, an alanine at position 411, an alanine at position 412, an isoleucine at position 413 and a valine at position 489.

Embodiment P19. The polymerase of one of Embodiment P1 to Embodiment P18, wherein the exonuclease activity of the polymerase is reduced at least 90% relative to the exonuclease activity of a polymerase of SEQ ID NO: 1.

Embodiment P20. The polymerase of one of Embodiment P1 to Embodiment P19, wherein the exonuclease activity of the polymerase is reduced at least 99% relative to the exonuclease activity of a polymerase of SEQ ID NO: 1.

Embodiment P21. A method of incorporating a modified nucleotide into a nucleic acid sequence comprising allowing the following components to interact: (i) a DNA template, (ii) a nucleotide solution, and (iii) a polymerase, wherein the polymerase comprises an amino acid sequence that is at least 80% identical to a continuous 500 amino acid sequence within SEQ 1, and wherein the exonuclease activity of the polymerase is reduced at least 80% relative to the exonuclease activity of a polymerase of SEQ ID NO: 1.

Embodiment P22. The method of Embodiment P21, wherein the reduction in exonuclease activity of the polymerase results from one or more amino acid mutations in SEQ ID NO: 1.

Embodiment P23. The method of one of Embodiment P21 and Embodiment P22, wherein the polymerase activity of the polymerase is altered relative to the polymerase activity of a polymerase of SEQ ID NO: 1.

Embodiment P24. The method of one of Embodiment P21 to Embodiment P23, wherein the altered polymerase activity of the polymerase results from one or more amino acid mutations in SEQ ID NO: 1, and wherein the altered polymerase activity is the capability of incorporating modified nucleotides during nucleic acid synthesis.

Embodiment P25. The method of one of Embodiment P21 to Embodiment P24, wherein the polymerase comprises substitution mutations at position 129, 141, 143, 411, 412, 413, and/or 489 of SEQ ID NO: 1.

Embodiment P26. The method of one of Embodiment P21 to Embodiment P25, wherein the polymerase comprises an alanine at position 141, an alanine at position 143, serine at position 411, an alanine at position 412, and a valine at position 413.

ADDITIONAL EMBODIMENTS

Embodiment 1. A polymerase comprising an amino acid sequence that is at least 80% identical to SEQ ID NO: 1; comprising the following amino acids:
an alanine or serine at amino acid position 411 or an amino acid functionally equivalent to amino acid position 411;
a glycine or alanine at amino acid position 412 or an amino acid functionally equivalent to amino acid position 412; and
a proline, valine, or isoleucine at amino acid position 413 or an amino acid functionally equivalent to amino acid position 413.

Embodiment 2. The polymerase of Embodiment 1, comprising a serine at amino acid position 411 or an amino acid functionally equivalent to amino acid position 411; an alanine at amino acid position 412 or an amino acid functionally equivalent to amino acid position 412; and a valine at amino acid position 413 or an amino acid functionally equivalent to amino acid position 413.

Embodiment 3. The polymerase of Embodiments 1, comprising an alanine at amino acid position 411 or an amino acid functionally equivalent to amino acid position 411; an alanine at amino acid position 412 or an amino acid functionally equivalent to amino acid position 412; and an isoleucine at amino acid position 413 or an amino acid functionally equivalent to amino acid position 413.

Embodiment 4. The polymerase of any one of Embodiments 1, comprising an alanine at amino acid position 411 or an amino acid functionally equivalent to amino acid position 411; a glycine at amino acid position 412 or an amino acid functionally equivalent to amino acid position 412; and a proline at amino acid position 413 or an amino acid functionally equivalent to amino acid position 413.

Embodiment 5. The polymerase of any one of Embodiments 1 to 4, further comprising an amino acid substitution mutation at position 36, or an amino acid functionally equivalent to amino acid position 36, or 93, or an amino acid functionally equivalent to amino acid position 93, of SEQ ID NO:1.

Embodiment 6. The polymerase of any one of Embodiments 1 to 4, further comprising an amino acid substitution mutation at position 36, 93, 129, 141, 143, 144, 152, 153, 155, 157, 215, 303, 307, 317, 479, 480, 481, 488, 517, 593, 605, or 642 of SEQ ID NO:1.

Embodiment 7. The polymerase of any one of Embodiments 1 to 4, wherein the polymerase comprises an amino acid substitution mutation at position 129, 141, 143, 144, 209, 210, 213, 214, 215, 276, 277, 313 and/or 317 of SEQ ID NO: 1.

Embodiment 8. The polymerase of any one of Embodiments 1 to 4, wherein the polymerase comprises an alanine substitution mutation at position 129.

Embodiment 9. The polymerase of any one of Embodiments 1 to 4, wherein the polymerase comprises an alanine substitution mutation at position 141 and an alanine substitution mutation at position 143.

Embodiment 10. The polymerase of any one of Embodiments 1 to 4, wherein the polymerase comprises an alanine substitution mutation at position 144.

Embodiment 11. The polymerase of any one of Embodiments 1 to 10, wherein the polymerase comprises a threonine at position 153 and an aspartic acid at position 155 of SEQ ID NO:1.

Embodiment 12. The polymerase of any one of Embodiments 1 to 10, wherein the polymerase comprises a glutamic acid at position 152 and a threonine at position 153 of SEQ ID NO:1.

Embodiment 13. The polymerase of any one of Embodiments 1 to 10, wherein the polymerase comprises an isoleucine at 303 and a methionine at position 307 of SEQ ID NO:1.

Embodiment 14. The polymerase of any one of Embodiments 1 to 13, wherein the polymerase comprises a serine at amino acid position 517 of SEQ ID NO:1.

Embodiment 15. The polymerase of any one of Embodiments 1 to 4, further comprising at least one of the following:
an alanine or histidine at amino acid position 36 or an amino acid position functionally equivalent to amino acid position 36; an alanine, glycine, or glutamine at amino acid position 93 or an amino acid position functionally equivalent to amino acid position 93; an alanine at amino acid position 129 or an amino acid position functionally equivalent to amino acid position 129; an alanine at amino acid position 141 or an amino acid position functionally equivalent to amino acid position 141; an alanine at amino acid position 143 or an amino acid position functionally equivalent to amino acid position 143; an alanine at amino acid position 144 or an amino acid position functionally equivalent to amino acid position 144; a glutamic acid at amino acid position 152 or an amino acid position functionally equivalent to amino acid position 152; a glutamic acid or threonine at amino acid position 153 or an amino acid position functionally equivalent to amino acid position 153; a threonine at amino acid position 155 or an amino acid position functionally equivalent to amino acid position 155; an aspartic acid at amino acid position 157 or an amino acid position functionally equivalent to amino acid position 157; an alanine at amino acid position 215 or an amino acid position functionally equivalent to amino acid position 215; an isoleucine at amino acid position 303 or an amino acid position functionally equivalent to amino acid position 303; or a methionine at amino acid position 307 or an amino acid position functionally equivalent to amino acid position 307.

Embodiment 16. The polymerase of any one of Embodiments 1 to 15, further comprising at least one of the following: an alanine at amino acid position 317 or an amino acid position functionally equivalent to amino acid position 317; a phenylalanine at amino acid position 381 or an amino acid position functionally equivalent to amino acid position 381; a tryptophan at amino acid position 479 or an amino acid position functionally equivalent to amino acid position 479; an alanine at amino acid position 480 or an amino acid position functionally equivalent to amino acid position 480; an alanine at amino acid position 481 or an amino acid position functionally equivalent to amino acid position 481; a valine at amino acid position 488 or an amino acid position functionally equivalent to amino acid position 488; a serine at amino acid position 517 or an amino acid position functionally equivalent to amino acid position 517; an isoleucine at amino acid position 593 or an amino acid position functionally equivalent to amino acid position 593; an alanine at amino acid position 605 or an amino acid position functionally equivalent to amino acid position 605; or a leucine at amino acid position 642 or an amino acid position functionally equivalent to amino acid position 642.

Embodiment 17. The polymerase of any one of Embodiments 1 to 16, which exhibits an increased rate of incorporation of modified nucleotides, relative to a control.

Embodiment 18. The polymerase according to any one of Embodiments 1 to 17, which is capable of incorporating modified nucleotides at reaction temperatures across the range of 40° C. to 80° C.

Embodiment 19. A method of incorporating a modified nucleotide into a nucleic acid sequence comprising allowing the following components to interact: (i) a nucleic acid template, (ii) a nucleotide solution, and (iii) a polymerase, wherein the polymerase is a polymerase of any one of Embodiments 1 to 18.

Embodiment 20. A method of sequencing a nucleic acid sequence comprising:
a. hybridizing a nucleic acid template with a primer to form a primer-template hybridization complex;
b. contacting the primer-template hybridization complex with a DNA polymerase and nucleotides, wherein the DNA polymerase is a polymerase of any one of Embodiments 1 to 18 and the nucleotides comprise a modified nucleotide, wherein the modified nucleotide comprises a detectable label;
c. subjecting the primer-template hybridization complex to conditions which enable the polymerase to incorporate the modified nucleotide into the primer-template hybridization complex to form a modified primer-template hybridization complex; and
d. detecting the detectable label; thereby sequencing the nucleic acid sequence.

What is claimed is:

1. A method of extending a primer, said method comprising contacting a primer hybridized to a template polynucleotide with a nucleotide and extending said primer with a polymerase by incorporating the modified nucleotide to form an extended primer, wherein the polymerase comprises an amino acid sequence that is at least 90% identical to SEQ ID NO: 1; and further comprises:
   an alanine at amino acid position 411 or an amino acid functionally equivalent to amino acid position 411;
   a glycine at amino acid position 412 or an amino acid functionally equivalent to amino acid position 412; and
   a proline at amino acid position 413 or an amino acid functionally equivalent to amino acid position 413; and
   an alanine or glycine at amino acid position 93 or an amino acid functionally equivalent to amino acid position 93.

2. The method of claim 1, wherein the polymerase further comprises an alanine substitution mutation at position 141 and an alanine substitution mutation at position 143.

3. The method of claim 1, wherein the polymerase further comprises an alanine substitution mutation at position 144.

4. The method of claim 1, wherein the polymerase further comprises at least one of the following:
   an alanine or histidine at amino acid position 36 or an amino acid position functionally equivalent to amino acid position 36;
   an alanine at amino acid position 129 or an amino acid position functionally equivalent to amino acid position 129;
   an alanine at amino acid position 141 or an amino acid position functionally equivalent to amino acid position 141;
   an alanine at amino acid position 143 or an amino acid position functionally equivalent to amino acid position 143;
   an alanine at amino acid position 144 or an amino acid position functionally equivalent to amino acid position 144;
   a glutamic acid at amino acid position 152 or an amino acid position functionally equivalent to amino acid position 152;
   a glutamic acid or threonine at amino acid position 153 or an amino acid position functionally equivalent to amino acid position 153;
   a threonine at amino acid position 155 or an amino acid position functionally equivalent to amino acid position 155;
   an aspartic acid at amino acid position 157 or an amino acid position functionally equivalent to amino acid position 157;
   an alanine at amino acid position 215 or an amino acid position functionally equivalent to amino acid position 215;

an isoleucine at amino acid position 303 or an amino acid position functionally equivalent to amino acid position 303; or a methionine at amino acid position 307 or an amino acid position functionally equivalent to amino acid position 307.

5. The method of claim 1, wherein the polymerase further comprises at least one of the following:

an alanine at amino acid position 317 or an amino acid position functionally equivalent to amino acid position 317;

a phenylalanine at amino acid position 381 or an amino acid position functionally equivalent to amino acid position 381;

a tryptophan at amino acid position 479 or an amino acid position functionally equivalent to amino acid position 479;

an alanine at amino acid position 480 or an amino acid position functionally equivalent to amino acid position 480;

an alanine at amino acid position 481 or an amino acid position functionally equivalent to amino acid position 481;

a valine at amino acid position 488 or an amino acid position functionally equivalent to amino acid position 488;

a serine at amino acid position 517 or an amino acid position functionally equivalent to amino acid position 517;

an isoleucine at amino acid position 593 or an amino acid position functionally equivalent to amino acid position 593;

an alanine at amino acid position 605 or an amino acid position functionally equivalent to amino acid position 605;

or a leucine at amino acid position 642 or an amino acid position functionally equivalent to amino acid position 642.

6. The method of claim 1, wherein template polynucleotide comprises DNA.

7. The method of claim 1, wherein the nucleotide comprises a detectable label and a reversible terminator moiety.

8. The method of claim 1, wherein nucleotide does not include a detectable label.

9. The method of claim 7, wherein the reversible terminator moiety comprises an azido moiety or a disulfide moiety.

10. The method of claim 7, wherein the nucleotide has the formula

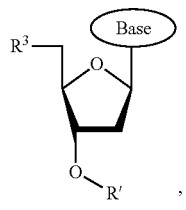

wherein the Base is a nucleobase, $R^3$ is a polyphosphate, and R' is a reversible terminator having the formula:

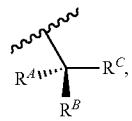

wherein $R^A$ and $R^B$ are hydrogen or alkyl and $R^C$ is the remainder of the reversible terminator.

11. The method of claim 7, wherein the reversible terminator moiety comprises

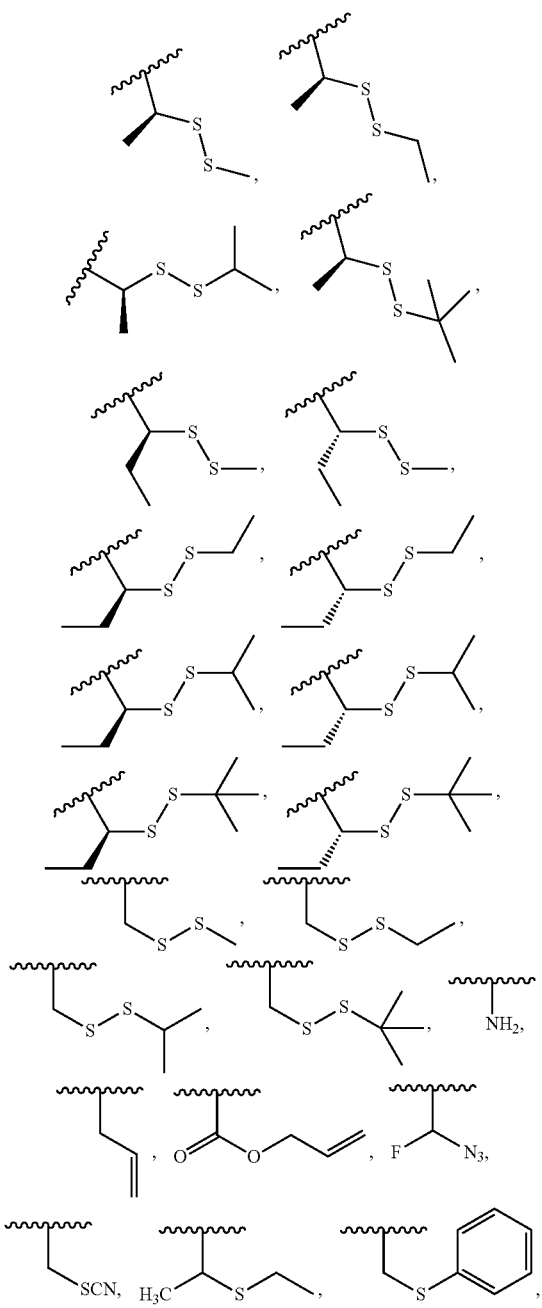

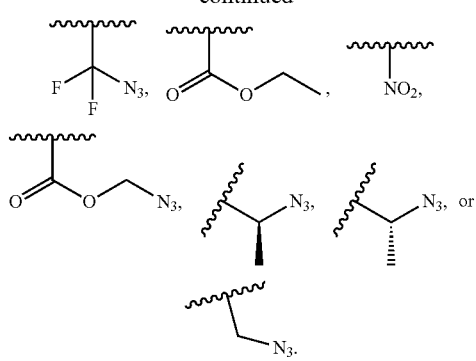

12. The method of claim 7, wherein the reversible terminator moiety comprises

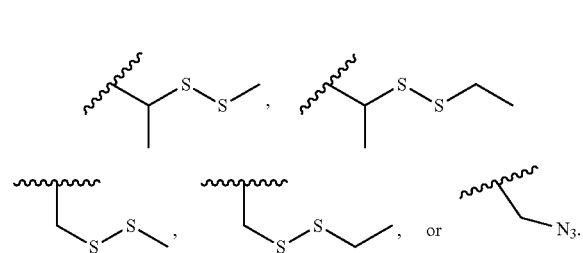

13. The method of claim 1, wherein the nucleotide has the formula:

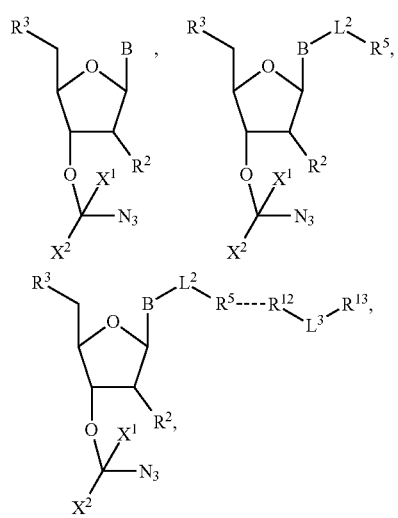

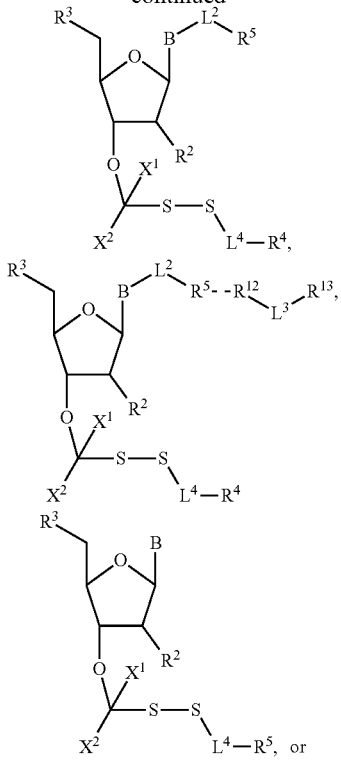

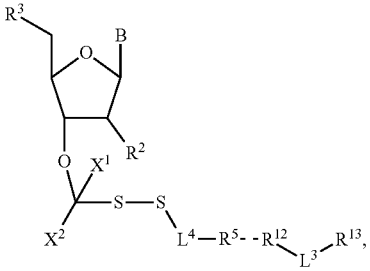

wherein
B is a nucleobase;
$L^2$ and $L^3$ are independently cleavable linker;
$L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^2$ is hydrogen or —OH;
$R^3$ is a polyphosphate;
$R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is a detectable label, an anchor moiety, or affinity anchor moiety;
$R^{12}$ is a complementary affinity anchor moiety binder;
$R^{13}$ is a detectable label;
$X^1$ and $X^2$ are independently hydrogen, halogen, —N$_3$, or —CN, wherein at least wherein at least one of $X^1$ or $X^2$ is halogen, —N$_3$, or —CN; and
the symbol "----" is a non-covalent bond.

14. The method of claim 1, wherein contacting the primer occurs at about 40° C. to about 80° C.

15. The method of claim 1, wherein contacting the primer occurs at about 50° C. to about 70° C.

16. The method of claim 1, wherein contacting the primer occurs at about 55° C. to about 65° C.

17. The method of claim 1, wherein the polymerase further comprises an amino acid substitution mutation at position 36, 129, 141, 143, 144, 152, 153, 155, 157, 209, 210, 213, 214, 215, 276, 277, 303, 307, 313, 317, 479, 480, 481, 488, 517, 593, 605, or 642 of SEQ ID NO: 1.

18. The method of claim 1, wherein the polymerase is capable of incorporating modified nucleotides at an increased rate of 1-fold to 10-fold relative to the rate of incorporation of its wild type polymerase.

* * * * *